(12) United States Patent
Lin et al.

(10) Patent No.: US 10,183,981 B2
(45) Date of Patent: Jan. 22, 2019

(54) INSULIN RECEPTOR PARTIAL AGONISTS

(71) Applicant: Merck Sharp & Dohme Corp., Rahway, NJ (US)

(72) Inventors: Songnian Lin, Holmdel, NJ (US); Lin Yan, East Brunswick, NJ (US); Pei Huo, Millburn, NJ (US); Dmitri Pissarnitski, Scotch Plains, NJ (US); Danqing Feng, Green Brook, NJ (US); Ravi Nargund, East Brunswick, NJ (US); Yuping Zhu, Edison, NJ (US); Ahmet Kekec, Hoboken, NJ (US); Christina B. Madsen-Duggan, Scotch Plains, NJ (US); Zhi-Cai Shi, Monmouth Junction, NJ (US); Zhicai Wu, Kenilworth, NJ (US); Yingjun Mu, Kenilworth, NJ (US)

( * ) Notice: Subject to any disclaimer, the term of this patent is extended or adjusted under 35 U.S.C. 154(b) by 0 days.

(21) Appl. No.: 16/007,046

(22) Filed: Jun. 13, 2018

(65) Prior Publication Data

US 2018/0291078 A1    Oct. 11, 2018

Related U.S. Application Data

(62) Division of application No. 14/945,461, filed on Nov. 19, 2015, now Pat. No. 10,017,556.

(60) Provisional application No. 62/242,503, filed on Oct. 16, 2015, provisional application No. 62/082,857, filed on Nov. 21, 2014.

(51) Int. Cl.
| | |
|---|---|
| *C07K 14/62* | (2006.01) |
| *A61K 38/28* | (2006.01) |
| *A61K 47/55* | (2017.01) |
| *A61K 47/60* | (2017.01) |
| *A61K 38/00* | (2006.01) |

(52) U.S. Cl.
CPC .............. *C07K 14/62* (2013.01); *A61K 38/28* (2013.01); *A61K 47/55* (2017.08); *A61K 47/60* (2017.08); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 3,907,763 A | 9/1975 | Brandenburg et al. | |
| 6,852,694 B2 | 2/2005 | Van Antwerp et al. | |
| 6,908,897 B2 | 6/2005 | Brandenburg et al. | |
| 10,017,556 B2 * | 7/2018 | Lin | A61K 38/28 |
| 2002/0160938 A1 | 10/2002 | Brandenburg et al. | |
| 2009/0197800 A1 | 8/2009 | Schaffe et al. | |
| 2015/0274802 A1 | 10/2015 | Dimarchi et al. | |
| 2016/0279272 A1 * | 9/2016 | Valliant | A61K 51/088 |
| 2017/0355743 A1 * | 12/2017 | Lin | A61K 38/28 |

FOREIGN PATENT DOCUMENTS

| | | |
|---|---|---|
| WO | WO200050456 | 8/2000 |
| WO | WO2008145721 A2 | 12/2008 |
| WO | WO2011059895 | 12/2011 |
| WO | WO2014052451 | 4/2014 |
| WO | WO2014141165 | 9/2014 |
| WO | WO2016081670 | 5/2016 |

OTHER PUBLICATIONS

Deppe et al. Naunyn-Schmiedeberg's Archives of Pharmacology, Springer, DE, vol. 350, No. 2, Aug. 1, 1994, pp. 213-217.*
Brandt, Sara J., Synthesis and Characterization of Insulin Receptor Partial Agonists as a Route to improved Diabetes Therapy, PhD Dissertation, Indiana University, 2015, pp. 1-207, NA.
Breiner et al., Heterogeneity of Insulin Receptors in Rat Tissues as Detected with the Partial Agonist, Molecular Pharmacology, 1993, Issue 2, pp. 271-276, 44.
Deppe et al., Structure activity relationship of covalently dimerized insulin derivatives: correlation of partial agonist efficacy with cross linkage at lysine B29, Archives of Pharmacology, Springer, DE, 1994, pp. 213-217, 350.
International Search Report of PCT/US2015/061445 dated Jun. 17, 2016.
Joost et al., Quantitative Dissociation of Glucose Transport Stimulation and Insulin Receptor Tyrosine Kinase Activation in Isolated Adipocytes with a Covalent Insulin Dimer, Biochemical Pharmacology, 1989, vol. 14, pp. 2269-2277, 38.
Knudsen et al., Agonism and Antagonism at the Insulin Receptor, PLos ONE, 2012, pp. 1-10, 7.
Mayer et al., Insulin Structure and Function, Biopolymers, 2007, No. 5, pp. 687-713, 88.
Oimomi et al., Carbamylation of Insulin and its Biological Activity, Nephron, 1987, pp. 63-66, 46.
Roth et al., Effects of Covalently Linked Insulin Dimers on Receptor Kinase Activity and Receptor down Regulation, Febs Letters, 1984, Issue 2, pp. 360-364, 170.
Schuettler et al., Preparation and Properties of Covalently Linked Insulin Dimers, Biopolymers, 1982, pp. 317-330, 363.
Shojaee-Moradie et al., Demonstration of a relatively hepatoselective effect of covalent insulin dimers on glucose metabolism in dogs, Diabetologia, 1995, pp. 1007-1013, 38.
Tatnell et al., Covalently Linked Insulin Dimers—Their Metabolism and Biological Effects Invivo as Partial Competitive Antagonists of Insulin Clearance, Diabetologia, 1984, Issue 1, pp. 27-31, 27.
Tatnell et al., Evidence concerning the mechanism of insulin receptor interaction and the structure of teh insulin receptor from biological properties of covalently linked insulin dimers, Biochem. J., 1983, pp. 687-694, 216.

(Continued)

*Primary Examiner* — Maury A Audet
(74) *Attorney, Agent, or Firm* — Janet E. Fair; Catherine D. Fitch

(57) ABSTRACT

Insulin dimers and insulin analog dimers that act as partial agonists at the insulin receptor are disclosed.

6 Claims, 20 Drawing Sheets

Specification includes a Sequence Listing.

(56) References Cited

OTHER PUBLICATIONS

Vinther et al., Novel Covalently Linked Insulin Dimer Engineered to Investigate teh Function of Insulin Dimerization, PLos ONE, 2012, pp. 1-9, 7.
Neiland et al., Antagonistic Effects of a Covalently Dimerized Insulin Derivative on Insulin Receptors in 3T3-L1 Adipocytes, Proc. Natl. Acad. Sci. USA, 1990, pp. 1154-1158, 87.
Written Opinion of PCT/US2015/061445 dated Jun. 17, 2016.
Zaykov et al., Poster P212—Exploration of the Structural and Mechanistic Basis for Partial Agonism of Insulin Dimers, American Peptide Symposium—Poster, Orlando Florida, 2015, Poster, NA.
U.S. Appl. No. 15/527,363, filed May 17, 2017.

* cited by examiner

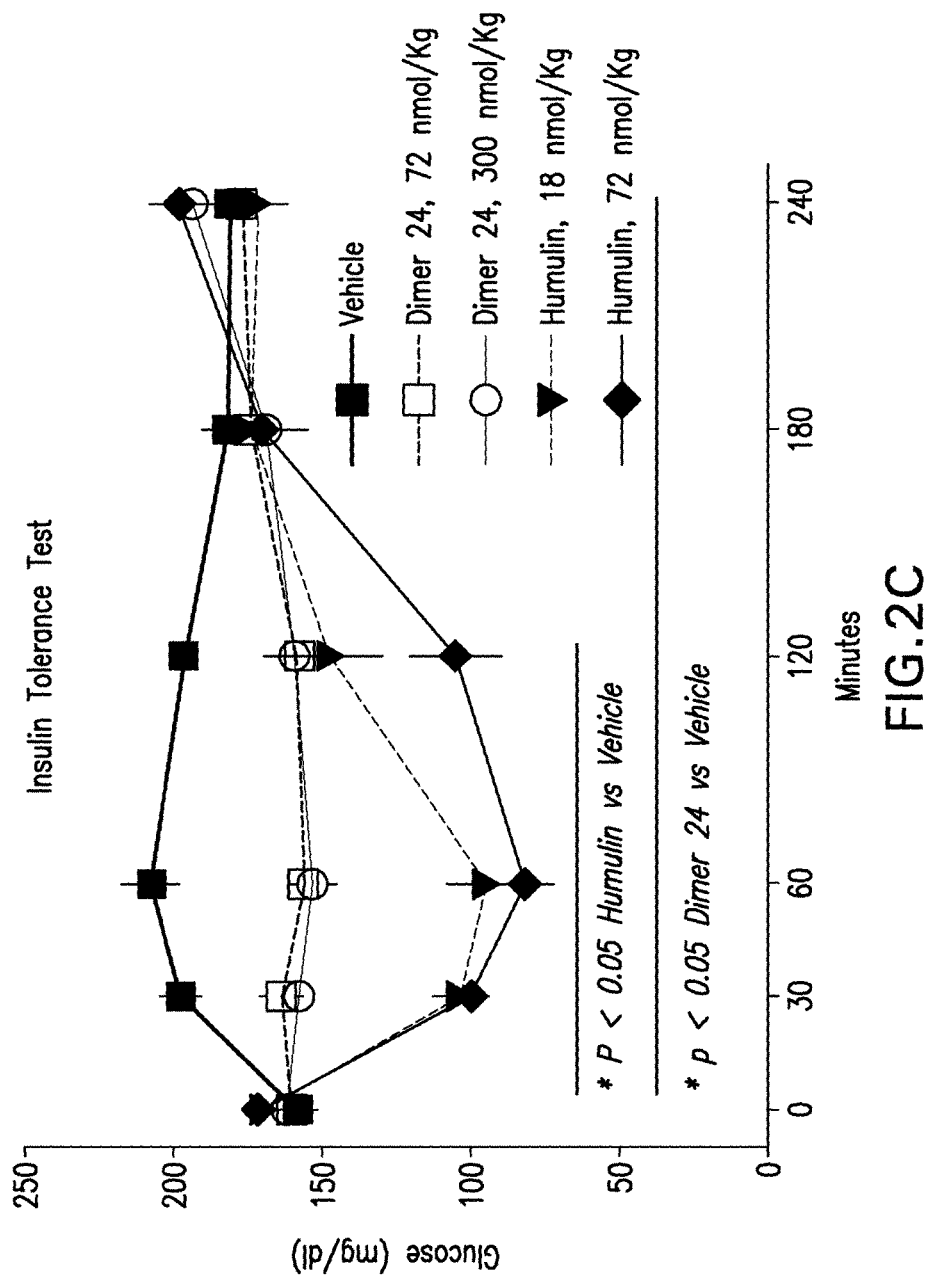

INSULIN RECEPTOR PARTIAL AGONISTS

CROSS-REFERENCE TO RELATED APPLICATIONS

This application is a divisional of U.S. patent application Ser. No. 14/945,461, which is a United States non provisional and claims priority from United States provisional applications No. 62/242,503, filed Oct. 16, 2015and No. 62/082,857, filed Nov. 21, 2014.

REFERENCE TO SEQUENCE LISTING SUBMITTED ELECTRONICALLY

The sequence listing of the present application is submitted electronically via EFS-Web as an ASCII formatted sequence listing with a file name "23876USDIV-SEQLIST-13JUN2018.TXT", creation date of Jun. 13, 2018, and a size of 6.59 KB. This sequence listing submitted EFS-Web is part of the specification and is herein incorporated by reference in its entirety.

BACKGROUND OF THE INVENTION (1) Field of the Invention

The present invention relates to insulin dimers and insulin analog dimers that act as partial agonists at the insulin receptor.

(2) Description of Related Art

Insulin is an essential therapy for type 1 diabetes mellitus (T1DM) patients and many type 2 mellitus diabetics (T2DMs), prescribed to close to one third of U.S. patients among all anti-diabetic drug users in the past decade. The worldwide market for insulins was US$20.4 billion in 2013 and is growing at a faster rate than all other anti-diabetic agents combined. However, challenges of current insulin therapies, including narrow TI to hypoglycemia and body weight gain, limit their wider adoption and potential for patients to achieve ideal glycemic control.

In addition to prandial insulin secretion in response to meals, the pancreas releases insulin at a "basal" rate, governed largely by plasma glucose levels to maintain appropriate fasting glucose regulation. This is achieved mainly by controlling hepatic glucose release, through endogenous insulin's hepato-preferring action. Modern insulin analogs include rapid acting and basal insulins, as well as mixtures of these two. Rapid-acting insulin analogs (RAA) are developed to control post-prandial hyperglycemia while insulins with extended duration of action regulate basal glucose levels. Long-acting insulins are used by all T1DM (in combination with prandial injections) and the majority of T2DM patients start their insulin therapy from a basal product. Basal insulin consumption is growing rapidly as the worldwide diabetes population (particularly T2DM) soars.

Despite continuous development efforts over the past several decades, available long-acting insulins are still not optimized compared to physiological basal insulin. This is partially because major focus was on improving PK flatness of these analogs but not fixing the relative over-insulinization of peripheral tissues, which contributes to increased hypoglycemia risk. As a result, hypoglycemia remains a key medical risk with huge burden on patients and causes significant morbidity and mortality.

BRIEF SUMMARY OF THE INVENTION

The present invention provides compounds comprising to two insulin molecules covalently linked to form an insulin molecule dimer that may activate the insulin receptor with regular insulin-like potency but with reduced maximum activity. These compounds are insulin receptor partial agonists (IPRAs): they behave like other insulin analogs to lower glucose effectively but with lower risk of hypoglycemia.

Provided are insulin receptor partial agonist covalent insulin dimers formulated as novel and transformative basal insulins (once daily administration) that manifest an improved therapeutic index (TI) over current standard of care (SOC) basal insulins. In one embodiment, the IPRAs of the present invention may lower glucose effectively with reduced risk of hypoglycemia in diabetic minipig and has the property of a once daily (QD) basal insulin. The improved TI may empower practitioners to more aggressively dose IRPAs of the present invention to achieve target goals for control of fasting glucose. Tight control of fasting glucose and HbA1c by an IRPA may allow it to serve as 1) a stand-alone long-acting insulin with an enhanced efficacy and safety profile in T2DM and 2) an improved foundational basal insulin in T1DM (and some T2DM) for use with additional prandial rapid-acting insulin analogs (RAA) doses. Thus, the present invention provides the following embodiments.

The present invention provides an insulin receptor partial agonist or insulin dimer comprising a first insulin or insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides; and wherein at least one amino terminus of the A-chain polypeptides and the B-chain polypeptides is covalently linked to a substituent, with the proviso that the linking moiety does not include a disulfide bond. In particular aspects, at least the amino terminus of the A-chain polypeptide and the B-chain polypeptide of the first insulin or insulin analog are covalently linked to a substituent.

In particular aspects of the insulin receptor partial agonist or insulin dimer, the amino terminus of each A-chain polypeptide and each B-chain polypeptide is covalently linked to a substituent. In particular aspects, the amino terminus of the A-chain polypeptide and the B-chain polypeptide of the first insulin or insulin analog and the amino terminus of the A-chain polypeptide and B-chain polypeptide of the second insulin or insulin analog are each covalently linked to a substituent. In embodiments in which the amino termini of the first and second insulin or insulin analogs are covalently linked to a substituent, the substituent on the amino termini of the A-chain and B-chain polypeptides of the first insulin or insulin analog may be the same as the substituent on the amino termini of the A-chain and B-chain polypeptides of the second insulin or insulin analog. In embodiments in which the amino termini of the first and second insulin or insulin analogs are covalently linked to a substituent, the substituent on the amino termini of the A-chain and B-chain polypeptides of the first insulin or insulin analog may be different from the sub stituent on the amino termini of the A-chain and B-chain polypeptides of the second insulin or insulin analog.

In a further aspect of the insulin receptor partial agonist or insulin dimer, the first and second insulin or insulin analog heterodimers are the same or wherein the first and second insulin or insulin analog heterodimers are different.

In a further still aspect of the insulin receptor partial agonist or insulin dimer, the linking moiety covalently links the first insulin or insulin analog heterodimer and the second insulin or insulin analog heterodimer via the epsilon amino group of a lysine residue at or near the carboxy terminus of their respective B-chain polypeptides.

In a further still aspect of the insulin receptor partial agonist or insulin dimer, the substituent has a general formula RC(O)—, where R can be R'CH2, R'NH, R'O, and R' can be H, linear alkyl chain, amino acid, peptide, PEG, saccharides, which in particular aspects RC(O)— may be acetyl, phenylacetyl, carbamoyl, N-alkyl carbamoyl, or alkoxycarbonyl. In particular aspects, the substituent is selected from the group consisting of acetyl, phenylacetyl, carbamoyl, N-alkyl carbamoyl, isobutyl, methoxy acetyl, glycine, aminoethylglucose (AEG), AEG-C6, PEG1, PEG2, N-dimethyl, and alkoxycarbonyl.

In particular aspects of the insulin receptor partial agonist or insulin dimer, each A-chain polypeptide independently comprises the amino acid sequence $GX_2X_3EQCCX_8SICSLYQLX_{17}NX_{19}CX_{23}$ (SEQ ID NO:3) and each B-chain polypeptide independently comprises the amino acid sequence $X_{25}LCGX_{29}X_{30}LVEALYLVCGERGFX27YTX_{31}X_{32}$ (SEQ ID NO:4) or $X_{22}VNQX_{25}X_{26}CGX_{29}X_{30}LVEALYLVCGERGFX_{27}YTX_{31}X_{32}X_{33}X_{34}X_{35}$ (SEQ ID NO:5) wherein $X_2$ is isoleucine or threonine; $X_3$ is valine, glycine, or leucine; $X_8$ is threonine or histidine; $X_{17}$ is glutamic acid or glutamine; $X_{19}$ is tyrosine, 4-methoxyphenylalanine, alanine, or 4-amino phenylalanine; $X_{23}$ is asparagine or glycine; $X_{22}$ is or phenylalanine and desamino-phenylalanine; $X_{25}$ is histidine or threonine; $X_{26}$ is leucine or glycine; $X_{27}$ is phenylalanine or aspartic acid; $X_{29}$ is alanine, glycine, or serine; $X_{30}$ is histidine, aspartic acid, glutamic acid, homocysteic acid, or cysteic acid; $X_{31}$ is aspartic acid, proline, or lysine; $X_{32}$ is lysine or proline; $X_{33}$ is threonine, alanine, or absent; $X_{34}$ is arginine or absent; and $X_{35}$ is arginine or absent; with the proviso at least one of $X_{31}$ or $X_{32}$ is lysine.

In particular aspects of the insulin receptor partial agonist or insulin dimer, the first and second insulins or insulin analogs are independently native human insulin, insulin lispro, insulin aspart, desB30 insulin, or insulin glargine.

In particular aspects of the insulin receptor partial agonists or insulin dimers, the linking moiety may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-C20 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In a further still aspect of the insulin receptor partial agonist or insulin dimer, the linking moiety is an acyl moiety, —C(O)RC(O)—, where R is alkyl chain, poly (ethylene glycol) (PEG) chain, amide-containing chain, triazole(s)-containing chain, cyclooctyne-containing moiety, a substituted acyl chain, or a polyethylene glycol (PEG) chain.

In a further aspect, the linking moiety is an alkyldioyl, —C(O)(CH$_2$)$_n$C(O)—, wherein n=0-45, including but not limited to an oxalyl (C2) moiety, a succinyl (C4) moiety, an adipoyl (C6) moiety, a suberyol (C8) moiety, a decanedioyl (C10) moiety, a dodecanedioyl (C12) moiety, a tetradecanedioyl (C14) moiety, or a hexadecanedioyl (C16) moiety.

The present invention further provides an insulin receptor partial agonist or insulin dimer comprising the formula $D^1$-L-$D^2$ wherein $D^1$ and $D^2$ are each independently an insulin or insulin analog polypeptide, wherein each insulin polypeptide is a heterodimer comprising an A-chain polypeptide and a B-chain polypeptide linked together through interchain disulfide bonds; L is a linking moiety wherein one end of the linker moiety is attached to an amino acid residue at or near the carboxyl group of $D^1$ and the other end of the linker moiety is attached to an amino acid residue at or near the carboxyl end of $D^2$ with the proviso that L does not include a disulfide linkage; and wherein the first and second insulin or insulin analog polypeptides include a substituent attached to the amino terminus of the A-chain polypeptide and the B-chain polypeptide.

In a further aspect of the insulin receptor partial agonist or insulin dimer, $D^1$ and $D^2$ are the same or wherein $D^1$ and $D^2$ are different.

In a further aspect of the insulin receptor partial agonist or insulin dimer, the linking moiety covalently links $D^1$ and $D^2$ via the epsilon amino group of a lysine residue at or near the carboxy terminus of $D^1$ and $D^2$.

In a further still aspect of the insulin receptor partial agonist or insulin dimer, the substituent has a general formula RC(O)—, where R can be R'CH2, R'NH, R'O, and R' can be H, linear alkyl chain, amino acid, peptide, PEG, saccharides, which in particular aspects RC(O)— may be acetyl, phenylacetyl, carbamoyl, N-alkyl carbamoyl, or alkoxycarbonyl. In particular aspects, the substituent is selected from the group consisting of acetyl, phenylacetyl, carbamoyl, N-alkyl carbamoyl, isobutyl, methoxy acetyl, glycine, aminoethylglucose (AEG), AEG-C6, PEG1, PEG2, N-dimethyl, and alkoxycarbonyl.

In particular aspects of the insulin receptor partial agonist or insulin dimer, each A-chain polypeptide independently comprises the amino acid sequence $GX_2X_3EQCCX_8SICSLYQLX_{17}NX_{19}CX_{23}$ (SEQ ID NO:3) and each B-chain polypeptide independently comprises the amino acid sequence $X_{25}LCGX_{29}X_{30}LVEALYLVCGERGFX27YTX_{31}X_{32}$ (SEQ ID NO:4) or $X_{22}VNQX_{25}X_{26}CGX_{29}X_{30}LVEALYLVCGERGFX_{27}YTX_{31}X_{32}X_{33}X_{34}X_{35}$ (SEQ ID NO:5) wherein $X_2$ is isoleucine or threonine; $X_3$ is valine, glycine, or leucine; $X_8$ is threonine or histidine; $X_{17}$ is glutamic acid or glutamine; $X_{19}$ is tyrosine, 4-methoxyphenylalanine, alanine, or 4-amino phenylalanine; $X_{23}$ is asparagine or glycine; $X_{22}$ is or phenylalanine and desamino-phenylalanine; $X_{25}$ is histidine or threonine; X26 is leucine or glycine; $X_{27}$ is phenylalanine or aspartic acid; $X_{29}$ is alanine, glycine, or serine; $X_{30}$ is histidine, aspartic acid, glutamic acid, homocysteic acid, or cysteic acid; $X_{31}$ is aspartic acid, proline, or lysine; $X_{32}$ is lysine or proline; $X_{33}$ is threonine, alanine, or absent; $X_{34}$ is arginine or absent; and $X_{35}$ is arginine or absent; with the proviso at least one of $X_{31}$ or $X_{32}$ is lysine.

In a further aspect of the insulin receptor partial agonist or insulin dimer, wherein $D^1$ and $D^2$ are independently native human insulin, insulin lispro, insulin aspart, desB30 insulin, or insulin glargine.

In particular aspects of the insulin receptor partial agonists or insulin dimers, the linking moiety may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-C20 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In a further still aspect of the insulin receptor partial agonist or insulin dimer, the linking moiety is an acyl moiety, —C(O)RC(O)—, where R is alkyl chain, poly(ethylene glycol) (PEG) chain, amide-containing chain, triazole(s)-containing chain, cyclooctyne-containing moiety, a substituted acyl chain, or a polyethylene glycol (PEG) chain.

In a further aspect of the insulin receptor partial agonist or insulin dimer, the linking moiety is an alkyldioyl, —C(O)(CH$_2$)$_n$C(O)—, wherein n=0-45, including but not limited to an oxalyl (C2) moiety, a succinyl (C4) moiety, an adipoyl (C6) moiety, a suberyol (C8) moiety, a decanedioyl (C10) moiety, a dodecanedioyl (C12) moiety, a tetradecanedioyl (C14) moiety, or a hexadecanedioyl (C16) moiety.

Further provided are compositions comprising any one of the aforementioned insulin receptor partial agonists or insulin dimer and a pharmaceutically acceptable carrier.

The present invention further provides an insulin receptor partial agonist or insulin dimer comprising a first insulin or insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides; and optionally wherein the amino terminus of at least one of the A-chain polypeptides and the B-chain polypeptides of the first insulin polypeptide or second insulin polypeptide is covalently linked to a substituent, with the proviso that (1) the linking moiety does not include a disulfide bond and (2) when the insulin or insulin analog is not a human insulin or insulin analog and the amino terminus of the A-chain polypeptide and the B-chain polypeptide do not include a substituent then the linking moiety is not an oxalyl (C2) moiety, a suberyol (C8) moiety, or a dodecanedioyl (C12) moiety.

In a further aspect of the insulin receptor partial agonist or insulin dimer, the first and second insulin or insulin analog heterodimers are the same or wherein the first and second insulin or insulin analog heterodimers are different.

In a further aspect of the insulin receptor partial agonist or insulin dimer, the linking moiety covalently links the first insulin or insulin analog heterodimer and the second insulin or insulin analog heterodimer via the epsilon amino group of a lysine residue at or near the carboxy terminus of their respective B-chain polypeptides.

In a further still aspect of the insulin receptor partial agonist or insulin dimer, the substituent has a general formula RC(O)—, where R can be R'CH2, R'NH, R'O, and R' can be H, linear alkyl chain, amino acid, peptide, PEG, saccharides, which in particular aspects RC(O)— may be acetyl, phenylacetyl, carbamoyl, N-alkyl carbamoyl, or alkoxycarbonyl. In particular aspects, the substituent is selected from the group consisting of acetyl, phenylacetyl, carbamoyl, N-alkyl carbamoyl, isobutyl, methoxy acetyl, glycine, aminoethylglucose (AEG), AEG-C6, PEG1, PEG2, N-dimethyl, and alkoxycarbonyl.

In a further aspect of the insulin receptor partial agonist or insulin dimer, the first and second insulins or insulin analogs are independently native human insulin, insulin lispro, insulin aspart, desB30 insulin, or insulin glargine.

In particular aspects of the insulin receptor partial agonist or insulin dimer, each A-chain polypeptide independently comprises the amino acid sequence GX$_2$X$_3$EQCCX$_8$SICSLYQLX$_{17}$NX$_{19}$CX$_{23}$ (SEQ ID NO:3) and each B-chain polypeptide independently comprises the amino acid sequence X$_{25}$LCGX$_{29}$X$_{30}$LVEALYLVCGERGFX27YTX$_{31}$X$_{32}$ (SEQ ID NO:4) or X$_{22}$VNQX$_{25}$X$_{26}$CGX$_{29}$X$_{30}$LVEALYLVCGERGFX$_{27}$YTX$_{31}$X$_{32}$X$_{33}$X$_{34}$X$_{35}$ (SEQ ID NO:5) wherein X$_2$ is isoleucine or threonine; X$_3$ is valine, glycine, or leucine; X$_8$ is threonine or histidine; X$_{17}$ is glutamic acid or glutamine; X$_{19}$ is tyrosine, 4-methoxyphenylalanine, alanine, or 4-amino phenylalanine; X$_{23}$ is asparagine or glycine; X$_{22}$ is or phenylalanine and desamino-phenylalanine; X$_{25}$ is histidine or threonine; X26 is leucine or glycine; X$_{27}$ is phenylalanine or aspartic acid; X$_{29}$ is alanine, glycine, or serine; X$_{30}$ is histidine, aspartic acid, glutamic acid, homocysteic acid, or cysteic acid; X$_{31}$ is aspartic acid, proline, or lysine; X$_{32}$ is lysine or proline; X$_{33}$ is threonine, alanine, or absent; X$_{34}$ is arginine or absent; and X$_{35}$ is arginine or absent; with the proviso at least one of X$_{31}$ or X$_{32}$ is lysine.

In particular aspects of the insulin receptor partial agonists or insulin dimers, the linking moiety may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-C20 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In a further still aspect of the insulin receptor partial agonist or insulin dimer, the linking moiety is an acyl moiety, —C(O)RC(O)—, where R is alkyl chain, poly(ethylene glycol) (PEG) chain, amide-containing chain, triazole(s)-containing chain, cyclooctyne-containing moiety, a substituted acyl chain, or a polyethylene glycol (PEG) chain.

In a further aspect of the insulin receptor partial agonist or insulin dimer, the linking moiety is a C2-C20 acyl moiety.

In particular aspects, the linking moiety is an alkyldioyl, —C(O)(CH$_2$)$_n$C(O)—, wherein n=0-45, including but not limited to an oxalyl (C2) moiety, a succinyl (C4) moiety, an adipoyl (C6) moiety, a suberyol (C8) moiety, a decanedioyl (C10) moiety, a dodecanedioyl (C12) moiety, a tetradecanedioyl (C14) moiety, or a hexadecanedioyl (C16) moiety.

Further provided are compositions comprising any one of the aforementioned insulin receptor partial agonists or insulin dimers and a pharmaceutically acceptable carrier.

The present invention further provides an insulin receptor partial agonist or insulin dimer comprising the formula $$D^1\text{-L-}D^2$$

wherein $D^1$ and $D^2$ are each independently an insulin or insulin analog polypeptide, wherein each insulin polypeptide is a heterodimer comprising an A-chain polypeptide and a B-chain polypeptide linked together through interchain disulfide bonds; L is a linking moiety wherein one end of the linker moiety is attached to an amino acid residue at or near the carboxyl group of $D^1$ and the other end of the linker moiety is attached to an amino acid residue at or near the carboxyl end of $D^2$ with the proviso that L does not include a disulfide linkage; and optionally, wherein at least one of $D^1$ or $D^2$ includes a substituent attached to the amino terminus of the A-chain polypeptide or the B-chain polypeptide of $D^1$ or $D^2$; with the proviso that (1) the linking moiety does not include a disulfide bond and (2) when the amino terminus of the A-chain polypeptide and the B-chain polypeptide do not include a substituent then the linking moiety is not an oxalyl (C2) moiety, a suberyol (C8) moiety, or a dodecanedioyl (C12) moiety.

In a further aspect of the insulin receptor partial agonist or insulin dimer, $D^1$ and $D^2$ are the same or wherein $D^1$ and $D^2$ are different.

In a further aspect of the insulin receptor partial agonist or insulin dimer, the linking moiety covalently links $D^1$ and $D^2$ via the epsilon amino group of a lysine residue at or near the carboxy terminus of $D^1$ and $D^2$.

In a further still aspect of the insulin receptor partial agonist or insulin dimer, the substituent has a general formula RC(O)—, where R can be R'CH2, R'NH, R'O, and R' can be H, linear alkyl chain, amino acid, peptide, PEG, saccharides, which in particular aspects RC(O)— may be acetyl, phenylacetyl, carbamoyl, N-alkyl carbamoyl, or alkoxycarbonyl. In particular aspects, the substituent is selected from the group consisting of acetyl, phenylacetyl, carbamoyl, N-alkyl carbamoyl, isobutyl, methoxy acetyl, glycine, aminoethylglucose (AEG), AEG-C6, PEG1, PEG2, N-dimethyl, and alkoxycarbonyl.

In a further aspect of the insulin receptor partial agonist or insulin dimer, $D^1$ and $D^2$ are independently native human insulin, insulin lispro, insulin aspart, desB30 insulin, or insulin glargine.

In particular aspects of the insulin receptor partial agonist or insulin dimer, each A-chain polypeptide independently comprises the amino acid sequence $GX_2X_3EQCCX_8SICSLYQLX_{17}NX_{19}CX_{23}$ (SEQ ID NO:3) and each B-chain polypeptide independently comprises the amino acid sequence $X_{25}LCGX_{29}X_{30}LV$-$EALYLVCGERGFX27YTX_{31}X_{32}$ (SEQ ID NO:4) or $X_{22}VNQX_{25}X_{26}CGX_{29}X_{30}LVEALYLVCGERGFX_{27}Y$-$TX_{31}X_{32}X_{33}X_{34}X_{35}$ (SEQ ID NO:5) wherein $X_2$ is isoleucine or threonine; $X_3$ is valine, glycine, or leucine; $X_8$ is threonine or histidine; $X_{17}$ is glutamic acid or glutamine; $X_{19}$ is tyrosine, 4-methoxy-phenylalanine, alanine, or 4-amino phenylalanine; $X_{23}$ is asparagine or glycine; $X_{22}$ is or phenylalanine and desamino-phenylalanine; $X_{25}$ is histidine or threonine; X26 is leucine or glycine; $X_{27}$ is phenylalanine or aspartic acid; $X_{29}$ is alanine, glycine, or serine; $X_{30}$ is histidine, aspartic acid, glutamic acid, homocysteic acid, or cysteic acid; $X_{31}$ is aspartic acid, proline, or lysine; $X_{32}$ is lysine or proline; $X_{33}$ is threonine, alanine, or absent; $X_{34}$ is arginine or absent; and $X_{35}$ is arginine or absent; with the proviso at least one of $X_{31}$ or $X_{32}$ is lysine.

In particular aspects of the insulin receptor partial agonists or insulin dimers, the linking moiety may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-C20 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In a further still aspect of the insulin receptor partial agonist or insulin dimer, the linking moiety is an acyl moiety, —C(O)RC(O)—, where R is alkyl chain, poly(ethylene glycol) (PEG) chain, amide-containing chain, triazole(s)-containing chain, cyclooctyne-containing moiety, a substituted acyl chain, or a polyethylene glycol (PEG) chain.

In a further aspect of the insulin receptor partial agonist or insulin dimer, the linking moiety is a C2-C20 acyl moiety.

In particular aspects, the linking moiety is an alkyldioyl, —C(O)(CH$_2$)$_n$C(O)—, wherein n=0-45, including but not limited to an oxalyl (C2) moiety, a succinyl (C4) moiety, an adipoyl (C6) moiety, a suberyol (C8) moiety, a decanedioyl (C10) moiety, a dodecanedioyl (C12) moiety, a tetradecanedioyl (C14) moiety, or a hexadecanedioyl (C16) moiety.

The present invention further provides an insulin analog dimer comprising:

a first insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides; wherein the insulin analog is selected from insulin lispro, insulin aspart, and insulin glargine; and optionally wherein the amino terminus of at least one of the A-chain polypeptides and the B-chain polypeptides of the first insulin polypeptide or second insulin polypeptide is covalently linked to a substituent, with the proviso that the linking moiety does not include a disulfide bond.

In a further aspect of the insulin receptor partial agonist, the first and second insulin or insulin analog heterodimers are the same or wherein the first and second insulin or insulin analog heterodimers are different.

In a further aspect of the insulin receptor partial agonist, the linking moiety covalently links the first insulin or insulin analog heterodimer and the second insulin or insulin analog heterodimer via the epsilon amino group of a lysine residue at or near the carboxy terminus of their respective B-chain polypeptides.

In a further still aspect of the insulin receptor partial agonist, the substituent has a general formula RC(O)—, where R can be R'CH2, R'NH, R'O, and R' can be H, linear alkyl chain, amino acid, peptide, PEG, saccharides, which in particular aspects RC(O)— may be acetyl, phenylacetyl, carbamoyl, N-alkyl carbamoyl, or alkoxycarbonyl. In particular aspects, the substituent is selected from the group consisting of acetyl, phenylacetyl, carbamoyl, N-alkyl carbamoyl, isobutyl, methoxy acetyl, glycine, aminoethylglucose (AEG), AEG-C6, PEG1, PEG2, N-dimethyl, and alkoxycarbonyl.

In a further aspect of the insulin receptor partial agonist, at least one of the first and second insulin or insulin analog is further conjugated to polyethylene glycol, a sugar moiety, or a heterocycle.

In particular aspects of the insulin receptor partial agonists, the linking moiety may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-C20 hydrocarbon chain wherein one or more methylene units are optionally and independently replaced by —O—, —S—, —N(R)—, —C(O)—, C(O)O—, OC(O)—, —N(R)C(O)—, —C(O)N (R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In a further still aspect of the insulin receptor partial agonist, the linking moiety is an acyl moiety, —C(O)RC(O)—, where R is alkyl chain, poly(ethylene glycol) (PEG) chain, amide-containing chain, triazole(s)-containing chain, cyclooctyne-containing moiety, a substituted acyl chain, or a polyethylene glycol (PEG) chain.

In a further aspect of the insulin receptor partial agonist, the linking moiety is a C2-C20 acyl moiety.

In particular aspects, the linking moiety is an alkyldioyl, —C(O)(CH$_2$)$_n$C(O)—, wherein n=0-45, including but not limited to an oxalyl (C2) moiety, a succinyl (C4) moiety, an adipoyl (C6) moiety, a suberyol (C8) moiety, a decanedioyl (C10) moiety, a dodecanedioyl (C12) moiety, a tetradecanedioyl (C14) moiety, or a hexadecanedioyl (C16) moiety.

The present invention further provides an insulin analog dimer comprising the formula

wherein $D^1$ and $D^2$ are each independently an insulin or insulin analog polypeptide, wherein each insulin polypeptide is a heterodimer comprising an A-chain polypeptide and a B-chain polypeptide linked together through interchain disulfide bonds; L is a linking moiety wherein one end of the linker moiety is attached to an amino acid residue at or near the carboxyl group of $D^1$ and the other end of the linker moiety is attached to an amino acid residue at or near the carboxyl end of $D^2$ with the proviso that L does not include a disulfide linkage; wherein the insulin analog is selected from insulin lispro, insulin aspart, and insulin glargine; and optionally, wherein at least one of $D^1$ or $D^2$ includes a substituent attached to the amino terminus of the A-chain polypeptide or the B-chain polypeptide of $D^1$ or $D^2$; with the proviso that the linking moiety does not include a disulfide bond.

In a further aspect of the insulin receptor partial agonist, $D^1$ and $D^2$ are the same or wherein $D^1$ and $D^2$ are different.

In a further aspect of the insulin receptor partial agonist, the linking moiety covalently links $D^1$ and $D^2$ via the epsilon amino group of a lysine residue at or near the carboxy terminus of $D^1$ and $D^2$.

In a further still aspect of the insulin receptor partial agonist, the substituent has a general formula RC(O)—, where R can be R'CH2, R'NH, R'O, and R' can be H, linear alkyl chain, amino acid, peptide, PEG, saccharides, which in particular aspects RC(O)— may be acetyl, phenylacetyl, carbamoyl, N-alkyl carbamoyl, or alkoxycarbonyl. In particular aspects, the substituent is selected from the group consisting of acetyl, phenylacetyl, carbamoyl, N-alkyl carbamoyl, isobutyl, methoxy acetyl, glycine, aminoethylglucose (AEG), AEG-C6, PEG1, PEG2, N-dimethyl, and alkoxycarbonyl.

In particular aspects of the insulin receptor partial agonists, the linking moiety may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-C20 hydrocarbon chain wherein one or more methylene units are optionally and independently replaced by —O—, —S—, —N(R)—, —C(O)—, C(O)O—, OC(O)—, —N(R)C(O)—, —C(O)N (R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In a further still aspect of the insulin receptor partial agonist, the linking moiety is an acyl moiety, —C(O)RC(O)—, where R is alkyl chain, poly(ethylene glycol) (PEG) chain, amide-containing chain, triazole(s)-containing chain, cyclooctyne-containing moiety, a substituted acyl chain, or a polyethylene glycol (PEG) chain.

In a further aspect of the insulin receptor partial agonist, the linking moiety is a C2-C20 acyl moiety.

In particular aspects, the linking moiety is an alkyldioyl, —C(O)(CH$_2$)$_n$C(O)—, wherein n=0-45, including but not limited to an oxalyl (C2) moiety, a succinyl (C4) moiety, an adipoyl (C6) moiety, a suberyol (C8) moiety, a decanedioyl (C10) moiety, a dodecanedioyl (C12) moiety, a tetradecanedioyl (C14) moiety, or a hexadecanedioyl (C16) moiety.

The present invention provides an insulin receptor partial agonist, comprising
a first insulin or insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides; optionally wherein the amino terminus of at least one of the A-chain polypeptides and the B-chain polypeptides of the first insulin polypeptide or second insulin polypeptide is covalently linked to a substituent; and wherein the insulin receptor partial agonist has a maximal response towards the human insulin receptor (IR) that is about 20%, 25%, 30%, 35%, 40%, 45%, 50%, 55%, 60%, 65%, or 70% of the maximal response of native human insulin towards the IR as determined by a functional phosphorylation assay; or
a first insulin or insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides; optionally wherein the amino terminus of at least one of the A-chain polypeptides and the B-chain polypeptides of the first insulin polypeptide or second insulin polypeptide is covalently linked to a substituent; and wherein the insulin receptor partial agonist has a maximal response towards the human insulin receptor (IR) that is between 20% and 70%, 40% and 70%, 50% and 70%, 40% and 60%, or 20% and 40% of the maximal response of native human insulin towards the IR as determined by a functional phosphorylation assay; or a first insulin or insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides; optionally wherein the amino terminus of at least one of the A-chain polypeptides and the B-chain polypeptides of the first insulin polypeptide or second insulin polypeptide is covalently linked to a substituent; and wherein the insulin receptor partial agonist has a maximal response towards the human insulin receptor (IR) that is at least 20%, 25%, 30%, 35%, 40%, 45%, 50%, 55%, 60%, 65%, or 70% of the maximal response of native human insulin towards the IR as determined by a functional phosphorylation assay; or a first insulin or insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides; optionally wherein the amino terminus of at least one of the A-chain polypeptides and the B-chain polypeptides of the first insulin polypeptide or second insulin polypeptide is covalently linked to a substituent; and wherein the insulin receptor partial agonist has a maximal response towards the human insulin receptor (IR) that is less than 70% of the maximal response of native human insulin towards the IR as determined by a functional phosphorylation assay; or a first insulin or insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides; optionally wherein the amino terminus of at least one of the A-chain polypeptides and the B-chain polypeptides of the first insulin polypeptide or second insulin polypeptide is covalently linked to a substituent; and wherein the insulin receptor partial agonist has a maximal response towards the human insulin receptor (IR) that is about 20%, 25%, 30%, 35%, 40%, 45%, 50%, 55%, 60%, 65%, or 70% of the maximal response of native human insulin towards the IR as determined by a functional phosphorylation assay.

In the above embodiments, the functional phosphorylation assay may be an Insulin Receptor (IR) AKT-Phosphorylation assay.

In a further aspect of the insulin receptor partial agonist, the linking moiety does not include a disulfide bond and when the amino terminus of the A-chain polypeptide and the B-chain polypeptide do not include a substituent the linking moiety is not an oxalyl (C2) moiety, a suberyol (C8) moiety, or a dodecanedioyl (C12) moiety.

In a further aspect of the insulin receptor partial agonist, the first and second insulin or insulin analog heterodimers are the same or wherein the first and second insulin or insulin analog heterodimers are different.

In a further aspect of the insulin receptor partial agonist, wherein the linking moiety covalently links the first insulin or insulin analog heterodimer and the second insulin or insulin analog heterodimer via the epsilon amino group of a lysine residue at or near the carboxy terminus of their respective B-chain polypeptides.

In a further still aspect of the insulin receptor partial agonist, the substituent has a general formula RC(O)—, where R can be R'CH2, R'NH, R'O, and R' can be H, linear alkyl chain, amino acid, peptide, PEG, saccharides, which in particular aspects RC(O)— may be acetyl, phenylacetyl, carbamoyl, N-alkyl carbamoyl, or alkoxycarbonyl. In particular aspects, the substituent is selected from the group consisting of acetyl, phenylacetyl, carbamoyl, N-alkyl carbamoyl, isobutyl, methoxy acetyl, glycine, aminoethylglucose (AEG), AEG-C6, PEG1, PEG2, N-dimethyl, and alkoxycarbonyl.

In a further aspect of the insulin receptor partial agonist, the first and second insulins or insulin analogs are independently native human insulin, insulin lispro, insulin aspart, desB30 insulin, or insulin glargine.

In particular aspects of the insulin receptor partial agonist, each A-chain polypeptide independently comprises the amino acid sequence $GX_2X_3EQCCX_8SICSLYQLX_{17}NX_{19}CX_{23}$ (SEQ ID NO:3) and each B-chain polypeptide independently comprises the amino acid sequence $X_{25}LCGX_{29}X_{30}LVEALYLVCGERGFX27YTX_{31}X_{32}$ (SEQ ID NO:4) or $X_{22}VNQX_{25}X_{26}CGX_{29}X_{30}LVEALYLVCGERGFX_{27}YTX_{31}X_{32}X_{33}X_{34}X_{35}$ (SEQ ID NO:5) wherein $X_2$ is isoleucine or threonine; $X_3$ is valine, glycine, or leucine; $X_8$ is threonine or histidine; $X_{17}$ is glutamic acid or glutamine; $X_{19}$ is tyrosine, 4-methoxyphenylalanine, alanine, or 4-amino phenylalanine; $X_{23}$ is asparagine or glycine; $X_{22}$ is or phenylalanine and desamino-phenylalanine; $X_{25}$ is histidine or threonine; X26 is leucine or glycine; $X_{27}$ is phenylalanine or aspartic acid; $X_{29}$ is alanine, glycine, or serine; $X_{30}$ is histidine, aspartic acid, glutamic acid, homocysteic acid, or cysteic acid; $X_{31}$ is aspartic acid, proline, or lysine; $X_{32}$ is lysine or proline; $X_{33}$ is threonine, alanine, or absent; $X_{34}$ is arginine or absent; and $X_{35}$ is arginine or absent; with the proviso at least one of $X_{31}$ or $X_{32}$ is lysine.

In particular aspects of the insulin receptor partial agonists, the linking moiety may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-20 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In a further still aspect of the insulin receptor partial agonist, the linking moiety is an acyl moiety, —C(O)RC(O)—, where R is alkyl chain, poly(ethylene glycol) (PEG) chain, amide-containing chain, triazole(s)-containing chain, cyclooctyne-containing moiety, a substituted acyl chain, or a polyethylene glycol (PEG) chain.

In a further aspect of the insulin receptor partial agonist, the linking moiety is a C2-C20 acyl moiety.

In particular aspects, the linking moiety is an alkyldioyl, —C(O)(CH$_2$)$_n$C(O)—, wherein n=0-45, including but not limited to an oxalyl (C2) moiety, a succinyl (C4) moiety, an adipoyl (C6) moiety, a suberyol (C8) moiety, a decanedioyl (C10) moiety, a dodecanedioyl (C12) moiety, a tetradecanedioyl (C14) moiety, or a hexadecanedioyl (C16) moiety.

The present invention further provides an insulin dimer comprising a first B29 or B28 Lys of a first insulin heterodimer molecule having a first A-chain polypeptide and first B-chain polypeptide and a second B29 or B28 Lys of a second insulin heterodimer having a second A-chain polypeptide and second B-chain polypeptide conjugated together by a bifunctional linker selected from the group consisting of Linker 1, Linker 2, Linker 3, Linker 10, Linker 11, Liner 12, Linker 13, Linker 14, Linker 15, Linker 16, Linker 17, Linker 18, Linker 19, Linker 20, Linker 21, Linker 22, Linker 23, Linker 24, Linker 25, Linker 26, Linker 27, Linker 28, Linker 29, Linker 30, Linker 31, Linker 32, Linker 33, Linker 34, Linker 35, Linker 36, Linker 37, Linker 38, Linker 39, Linker 40, Linker 41, Linker 42, Linker 43, Linker 44, Linker 45, Linker 46, Linker 47, Linker 48, Linker 49, and Linker 50 with the proviso that when the bifunctional linker is Linker 10, Linker 11, Linker 12, Linker 13, or Linker 14, at least one of the first or second A-chain or B-chain polypeptides is conjugated at its N-terminal amino acid to a substituent or at least the N-terminal amino acids of the first insulin heterodimer molecule are conjugated to a substituent or the N-terminal amino acids of both the first insulin heterodimer and second insulin heterodimer are conjugated to a substituent.

In particular embodiments, the substituent comprises an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides. In particular embodiments, the substituent is a carbamoyl group, acetyl group, glycine, methyl group, methoxy group, dimethyl group, isobutyl group, PEG1 group, AEG group, AEG-C6 alkyl group, or PEG2 group.

The present invention further provides an insulin dimer comprising a first B29 or B28 Lys of a first insulin heterodimer molecule having a first A-chain polypeptide and first B-chain polypeptide is conjugated to a first linker selected from the group consisting of Linker 5 and Linker 7 and a second B29 or B28 Lys of a second insulin heterodimer having a second A-chain polypeptide and second B-chain polypeptide conjugated to a second linker selected from the group consisting of Linker 4, Linker 6, Linker 8, and Linker 9 conjugated together via the first linker and the second linker.

In a further embodiment, the present invention provides an insulin analog dimer, comprising a first B29 or B28 Lys of a first insulin heterodimer molecule having a first A-chain polypeptide and first B-chain polypeptide conjugated to a first linker selected from the group consisting of Linker 5 and Linker 7 and a second B29 or B28 Lys of a second insulin heterodimer having a second A-chain polypeptide and second B-chain polypeptide conjugated to a second linker selected from the group consisting of Linker 5 and Linker 7, wherein the first and second linkers are conjugated together via a bridging linker having a structure

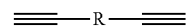

wherein R is a covalent bond, a carbon atom, a phenyl, a heteroatom, or an optionally substituted group selected from the group consisting of acyl, aliphatic, heteroaliphatic, aryl, heteroaryl, and heterocyclic. In particular aspects R is a C2, C3, C4, C6, C7, C8, C9 or C10 acyl group or a PEG2, PEG3, PEG4, PEG5, PEG6, PEG7, PEG8, PEG9, PEG10, PEG11, PEG12, PEG13, or PEG25.

In particular embodiments, the substituent comprises an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides. In particular embodiments, the substituent is a carbamoyl group, acetyl group, glycine, methyl group, methoxy group, dimethyl group, isobutyl group, PEG1 group, AEG group, AEG-C6 alkyl group, or PEG2 group.

In a further rembodiment, the present invention provides an insulin analog dimer, comprising a first B29 or B28 Lys of a first insulin heterodimer molecule having a first A-chain polypeptide and first B-chain polypeptide conjugated to a first linker selected from the group consisting of Linker 4, Linker 6, Linker 8, and Linker 9 and a second B29 or B28 Lys of a second insulin heterodimer having a second A-chain polypeptide and second B-chain polypeptide conjugated to a second linker selected from the group consisting of Linker 4, Linker 6, Linker 8, and Linker 9, wherein the first and second linkers are conjugated together via a bridging linker having a structure

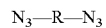

$N_3$—R—$N_3$ wherein R is a covalent bond, a carbon atom, a phenyl, a heteroatom, or an optionally substituted group selected from the group consisting of acyl, aliphatic, heteroaliphatic, aryl, heteroaryl, and heterocyclic. In particular aspects R is a C2, C3, C4, C6, C7, C8, C9 or C10 acyl group or a PEG2, PEG3, PEG4, PEG5, PEG6, PEG7, PEG8, PEG9, PEG10, PEG11, PEG12, PEG13, or PEG 25.

In particular embodiments, the substituent comprises an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides. In particular embodiments, the substituent is a carbamoyl group, acetyl group, glycine, methyl group, methoxy group, dimethyl group, isobutyl group, PEG1 group, AEG group, AEG-C6 alkyl group, or PEG2 group.

The present invention further provides compositions comprising any one of the insulin receptor partial agonists disclosed herein and a pharmaceutically acceptable salt.

The present invention provides a method for treating diabetes comprising administering to an individual with diabetes a therapeutically effective amount of a composition comprising any one of the aforementioned insulin receptor partial agonists. In particular aspects the diabetes is Type 1 diabetes, Type 2 diabetes, or gestational diabetes.

The present invention provides for the use of a composition for the treatment of diabetes comprising any one of the aforementioned insulin receptor partial agonists. In particular aspects the diabetes is Type 1 diabetes, Type 2 diabetes, or gestational diabetes.

The present invention provides for the use of any one of the insulin receptor partial agonists disclosed herein for the manufacture of a medicament for the treatment of diabetes. In particular aspects the diabetes is Type 1 diabetes, Type 2 diabetes, or gestational diabetes.

Definitions

Insulin—as used herein, the term means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus. The term is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

Insulin analog or analogue—the term as used herein includes any heterodimer analogue or single-chain analogue that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; deleting any or all of positions B1-4 and B26-30; or conjugating directly or by a polymeric or non-polymeric linker one or more acyl, polyethylglycine (PEG), or saccharide moiety (moieties); or any combination thereof. As exemplified by the N-linked glycosylated insulin analogues disclosed herein, the term further includes any insulin heterodimer and single-chain analogue that has been modified to have at least one N-linked glycosylation site and in particular, embodiments in which the N-linked glycosylation site is linked to or occupied by an N-glycan. Examples of insulin analogues include but are not limited to the heterodimer and single-chain analogues disclosed in published international application WO20100080606, WO2009/099763, and WO2010080609, the disclosures of which are incorporated herein by reference. Examples of single-chain insulin analogues also include but are not limited to those disclosed in published International Applications WO9634882, WO95516708, WO2005054291, WO2006097521, WO2007104734, WO2007104736, WO2007104737, WO2007104738, WO2007096332, WO2009132129; U.S. Pat. Nos. 5,304,473 and 6,630,348; and Kristensen et al., Biochem. J. 305: 981-986 (1995), the disclosures of which are each incorporated herein by reference.

The term further includes single-chain and heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin and which further includes at least one N-linked glycosylation site. In particular aspects, the insulin analogue is a partial agonist that has less than 80% (or 70%) activity at the insulin receptor as does native insulin. These insulin analogues, which have reduced activity at the insulin growth hormone receptor and enhanced activity at the insulin receptor, include both heterodimers and single-chain analogues.

Single-chain insulin or single-chain insulin analog—as used herein, the term encompasses a group of structurally-related proteins wherein the A-chain peptide or functional analogue and the B-chain peptide or functional analogue are covalently linked by a peptide or polypeptide of 2 to 35 amino acids or non-peptide polymeric or non-polymeric linker and which has at least 1%, 10%, 50%, 75%, or 90% of the activity of insulin at the insulin receptor as compared to native insulin. The single-chain insulin or insulin analogue further includes three disulfide bonds: the first disulfide bond is between the cysteine residues at positions 6 and 11 of the A-chain or functional analogue thereof, the second disulfide bond is between the cysteine residues at position 7 of the A-chain or functional analogue thereof and position 7 of the B-chain or functional analogue thereof, and the third disulfide bond is between the cysteine residues at position 20 of the A-chain or functional analogue thereof and position 19 of the B-chain or functional analogue thereof.

Connecting peptide or C-peptide—as used herein, the term refers to the connection moiety "C" of the α-C-A polypeptide sequence of a single chain preproinsulin-like molecule. Specifically, in the natural insulin chain, the C-peptide connects the amino acid at position 30 of the B-chain and the amino acid at position 1 of the A-chain. The term can refer to both the native insulin C-peptide, the monkey C-peptide, and any other peptide from 3 to 35 amino acids that connects the B-chain to the A-chain thus is meant to encompass any peptide linking the B-chain peptide to the A-chain peptide in a single-chain insulin analogue (See for example, U.S. Published application Nos. 20090170750 and 20080057004 and WO9634882) and in insulin precursor molecules such as disclosed in WO9516708 and U.S. Pat. No. 7,105,314.

Amino acid modification—as used herein, the term refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

Amino acid substitution—as used herein refers to the replacement of one amino acid residue by a different amino acid residue.

Conservative amino acid substitution—as used herein, the term is defined herein as exchanges within one of the following five groups:

I. Small aliphatic, nonpolar or slightly polar residues:
   Ala, Ser, Thr, Pro, Gly;
II. Polar, negatively charged residues and their amides:
   Asp, Asn, Glu, Gln, cysteic acid and homocysteic acid;
III. Polar, positively charged residues:
   His, Arg, Lys; Ornithine (Orn)

IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine Treat—As used herein, the term "treat" (or "treating", "treated", "treatment", etc.) refers to the administration of an IRPA of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition. For example, as used herein the term "treating diabetes" will refer in general to maintaining glucose blood levels near normal levels and may include increasing or decreasing blood glucose levels depending on a given situation.

Pharmaceutically acceptable carrier—as used herein, the term includes any of the standard pharmaceutical carriers, such as a phosphate buffered saline solution, water, emulsions such as an oil/water or water/oil emulsion, and various types of wetting agents suitable for administration to or by an individual in need. The term also encompasses any of the agents approved by a regulatory agency of the US Federal government or listed in the US Pharmacopeia for use in animals, including humans.

Pharmaceutically acceptable salt—as used herein, the term refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium, zinc, and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Effective or therapeutically effective amount—as used herein refers to a nontoxic but sufficient amount of an insulin analog to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." It is not always possible to determine the optimal effective amount prior to administration to or by an individual in need thereof. However, an appropriate "effective" amount in any individual case may be determined by one of ordinary skill in the art using routine experimentation.

Parenteral—as used herein, the term means not through the alimentary canal but by some other route such as intranasal, inhalation, subcutaneous, intramuscular, intraspinal, or intravenous.

BRIEF DESCRIPTION OF THE DRAWINGS

FIG. 2C shows the results of an Insulin Tolerance Test (ITT) in mice comparing Dimer 24 with RHI (Humulin). Dimer 24 was administered at a dose of 72 U/kg and a dose of 300 U/kg and Humulin was administered at a dose of 18 U/kg and a dose of 72 U/kg.

DETAILED DESCRIPTION OF THE INVENTION

Figure 1:
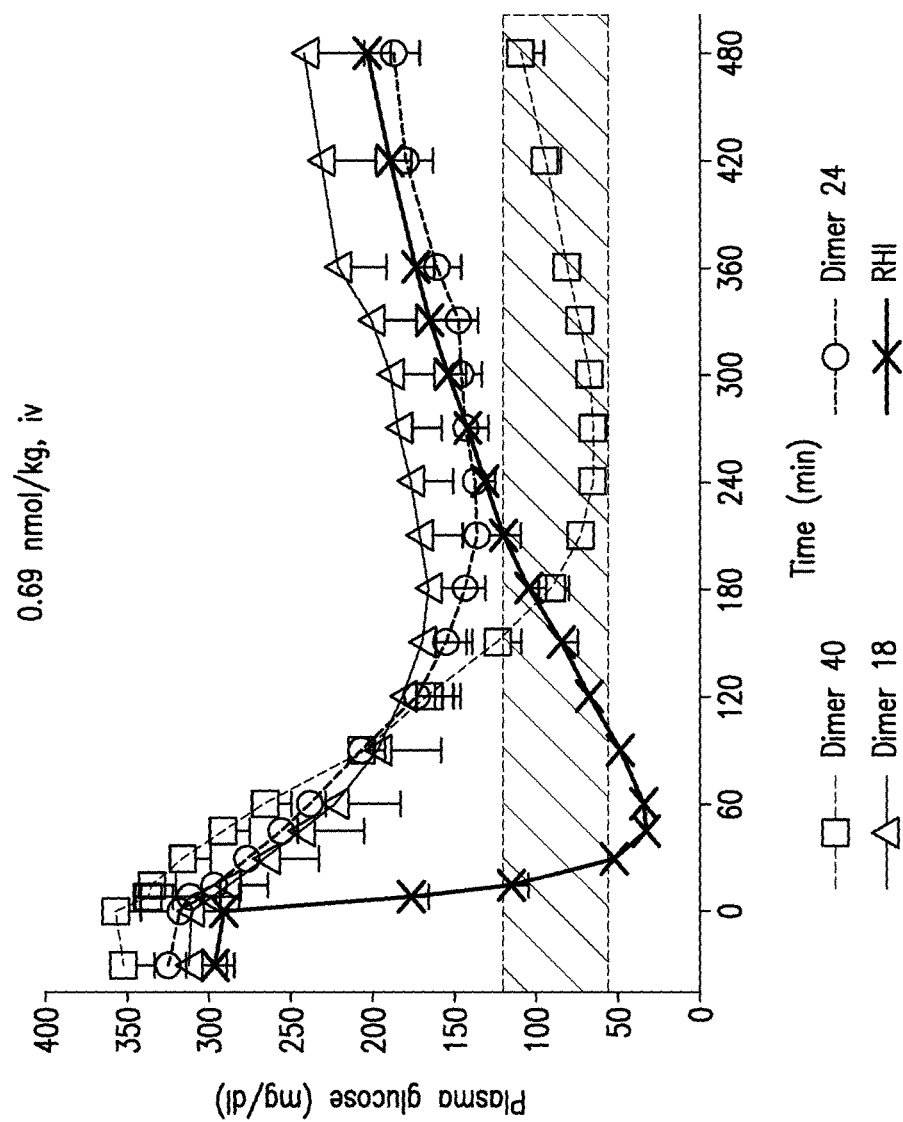
FIG. 1 shows the glucose lowering effect of Dimers 24, 18, and 40 compared to RHI when administered to diabetic minipigs at 0.69 nmol/kg.
Figure 2A:
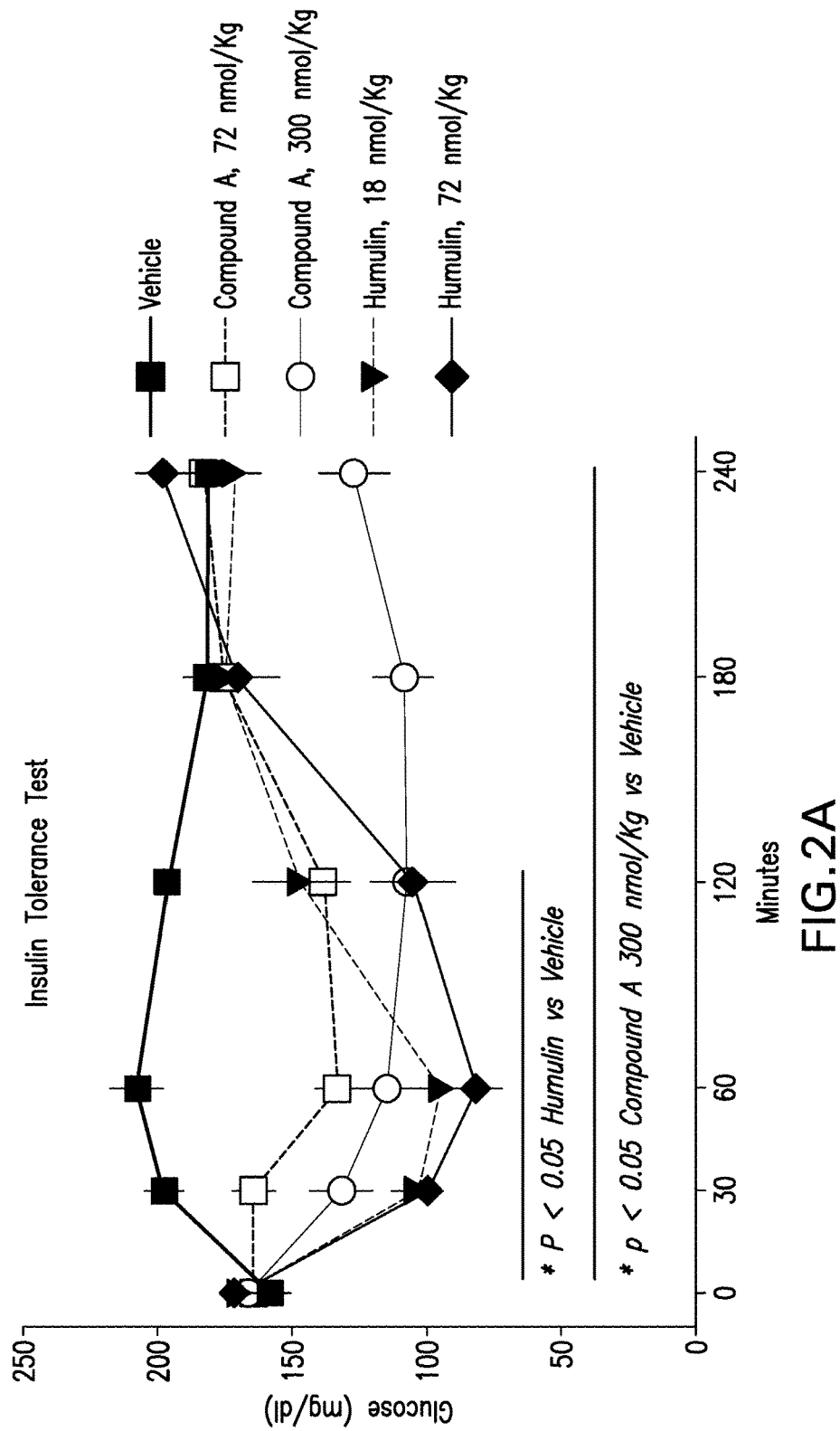
FIG. 2A shows the results of an Insulin Tolerance Test (ITT) in mice comparing compound A with RHI (Humulin). Compound A was administered at a dose of 72 U/kg and a dose of 300 U/kg and Humulin was administered at a dose of 18 U/kg and a dose of 72 U/kg.
Figure 2B:
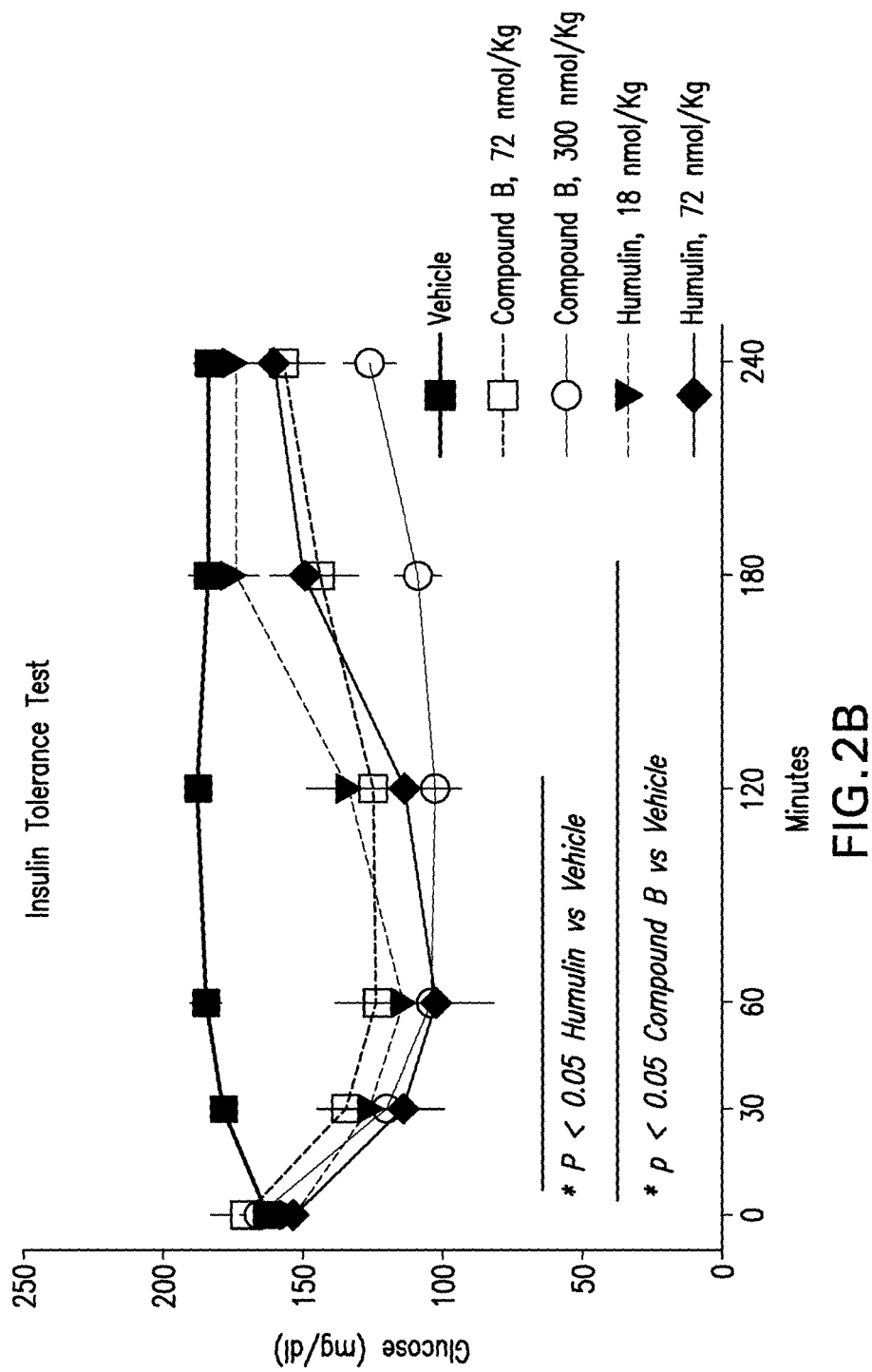
FIG. 2B shows the results of an Insulin Tolerance Test (ITT) in mice comparing compound B with RHI (Humulin). Compound B was administered at a dose of 72 U/kg and a dose of 300 U/kg and Humulin was administered at a dose of 18 U/kg and a dose of 72 U/kg.
Figure 2D:
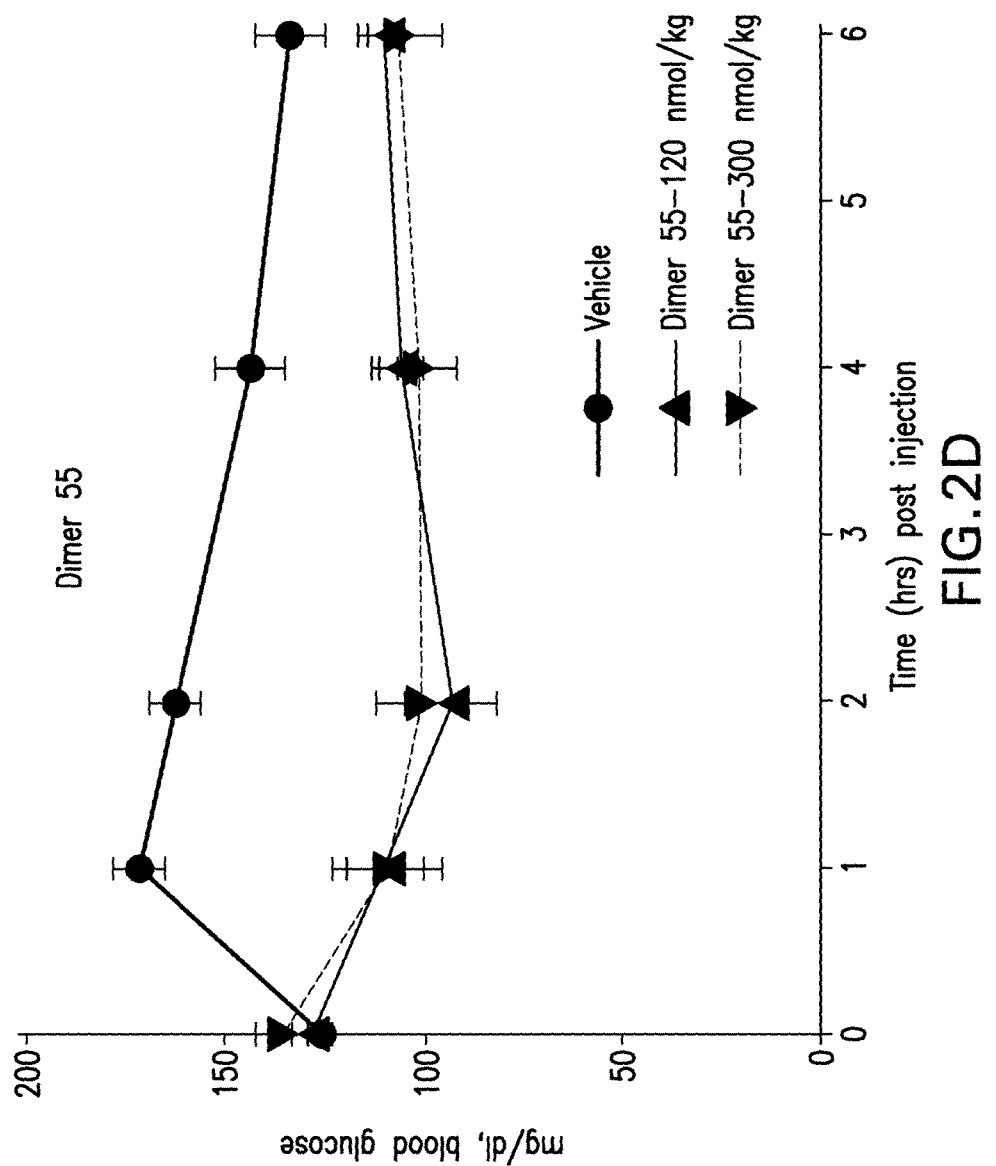
FIG. 2D shows the results of Dimer 55 in an Insulin Tolerance Test (ITT) in mice. Dimer 55 was administered at a dose of 120 nmol/kg and a dose of 300 nmol/kg.
Figure 2E:
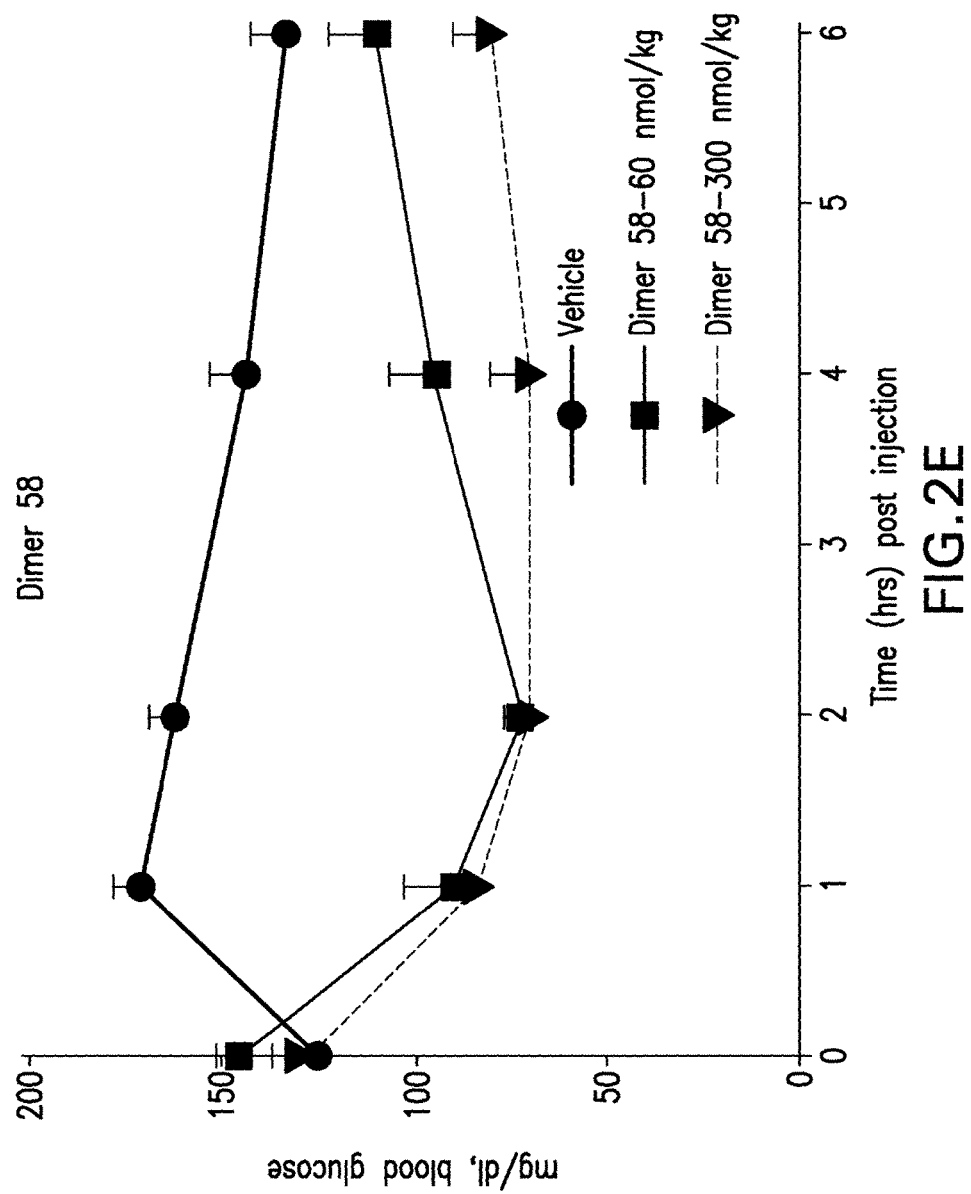
FIG. 2E shows the results of Dimer 58 in an Insulin Tolerance Test (ITT) in mice. Dimer 58 was administered at a dose of 60 nmol/kg and a dose of 300 nmol/kg.
Figure 2F:
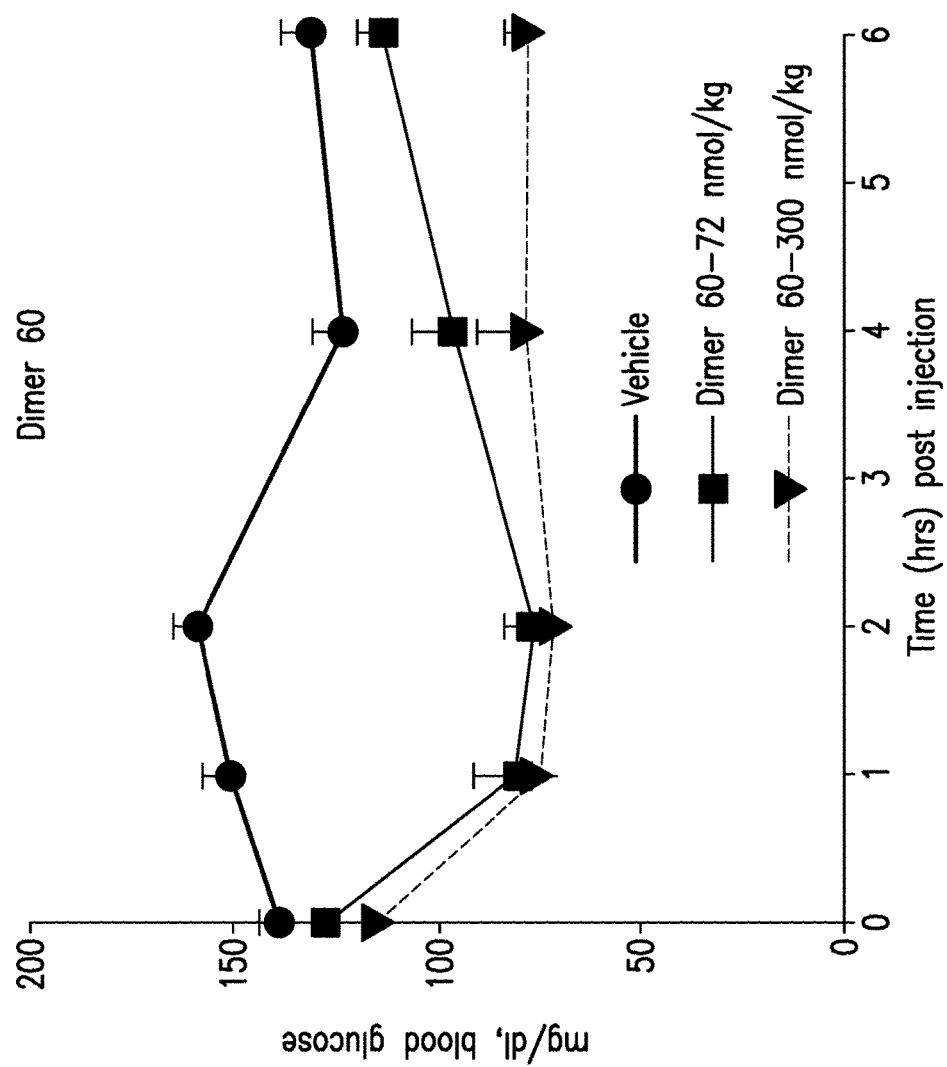
FIG. 2F shows the results of Dimer 60 in an Insulin Tolerance Test (ITT) in mice. Dimer 60 was administered at a dose of 72 nmol/kg and a dose of 300 nmol/kg.
Figure 2G:
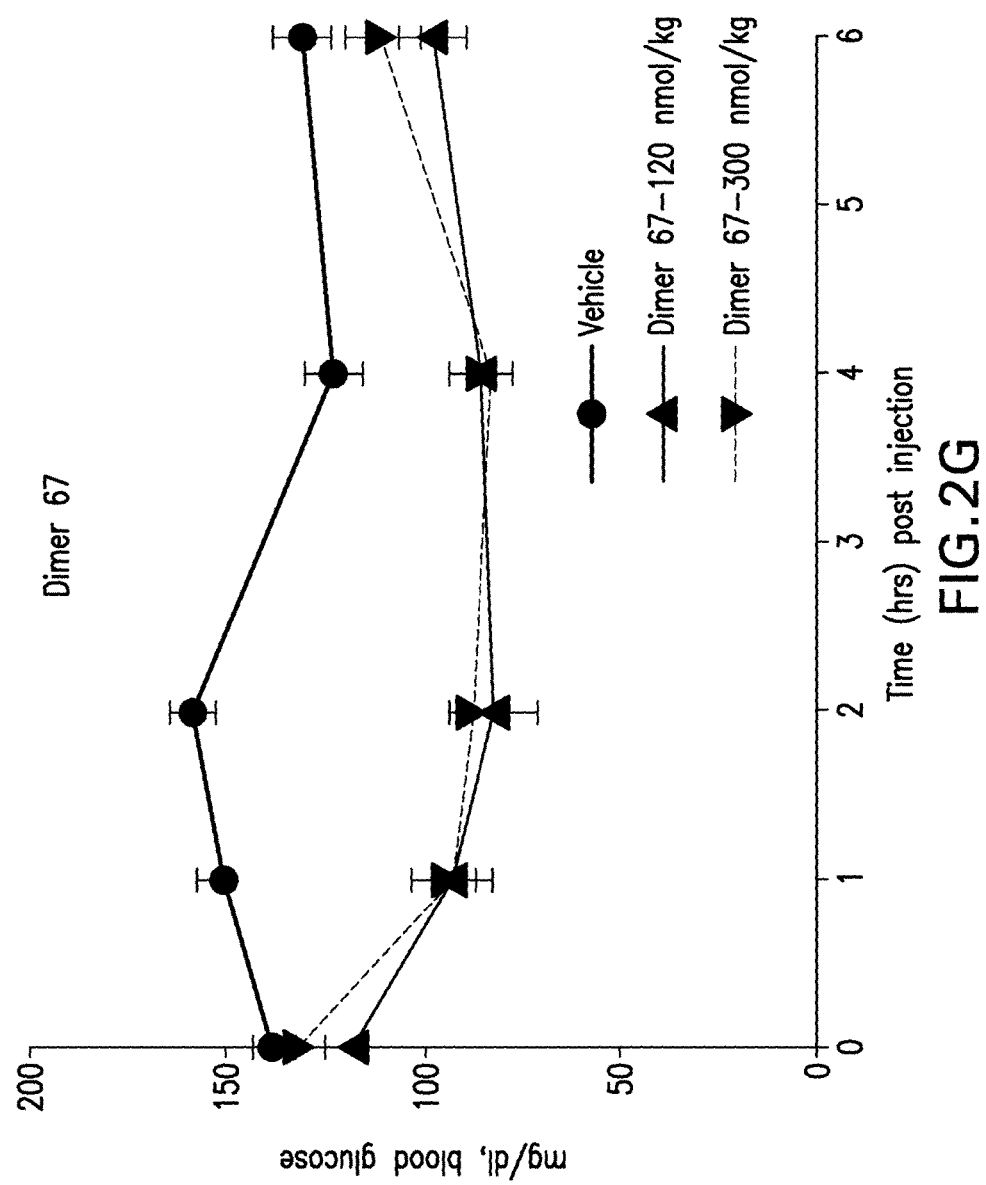
FIG. 2G shows the results of Dimer 67 in an Insulin Tolerance Test (ITT) in mice. Dimer 67 was administered at a dose of 120 nmol/kg and a dose of 300 nmol/kg.

The present invention provides compounds comprising two insulin molecules covalently linked to form a covalently-linked insulin dimer that may activate the insulin receptor with regular insulin-like potency and reduced maximum activity. These compounds are insulin receptor partial agonists (IRPA): they behave like other insulin analogs to lower glucose effectively but with lower risk of hypoglycemia.

Insulin dimers have been disclosed in Brandenburg et al. in U.S. Pat. No. 3,907,763 (1973); Tatnell et al., Biochem J. 216: 687-694 (1983); Shüttler and Brandenburg, Hoppe-Seyler's Z. Physiol. Chem, 363, 317-330, 1982; Weiland et al., Proc Natl. Acad. Sci. (USA) 87: 1154-1158 (1990); Deppe et al., Naunyn-Schmiedeberg's Arch Pharmacol (1994) 350:213-217; Brandenburg and Havenith in U.S. Pat. No. 6,908,897(B2) (2005); Knudsen et al., PLOS ONE 7: e51972 (2012); DiMarchi et al in WO2011/159895; DiMarchi et al. in WO 2014/052451; and Herrera et al., WO2014141165. More recently, insulin dimers have been described in Brant—*Synthesis and Characterization of Insulin Receptor Partial Agonists as a Route to Improved Diabetes Therapy*, Ph.D. Dissertation, Indiana University (April 2015) and Zaykov and DiMarchi, Poster P212—*Exploration of the structural and mechanical basis for partial agonism of insulin dimers*, American Peptide Symposium, Orlando Fla. (June 20-25 (2015). However, the inventors of the instant invention have discovered that the level of insulin activity and partial agonist activity of the dimers is a function of the dimeric structure, the sequence of the insulin analog, the length of the dimerization linker, and the site of dimerization that connects the two insulin polypeptides. The inventors have discovered that the insulin dimers of the present invention have reduced risk of promoting hypoglycemia when administered in high doses than native insulin or other insulin analogs when administered at high doses.

The present invention provides partial agonist covalently-linked insulin dimers formulated as a novel and transformative basal insulin (once daily administration) that manifests improved therapeutic index (TI) over current standard of care (SOC) basal insulins. These molecules may lower glucose effectively with reduced risk of hypoglycemia in diabetic minipig and have the property of a once daily (QD) basal insulin. The improved TI may enable practitioners to more aggressively dose IRPA dimer to achieve target goals for control of fasting glucose. Tight control of fasting glucose and HbA1c may allow these molecules to serve as 1) a stand-alone long-acting insulin with an enhanced efficacy and safety profile in Type 2 diabetes mellitus (T2DM) and 2) an improved foundational basal insulin in Type 1 diabetes mellitus (T1DM) (and some T2DM) for use with additional prandial rapid-acting insulin analogs (RAA) doses.

An ideal long-acting insulin provides continuous control of fasting glucose in diabetics with highly stable and reproducible PK/PD. However, currently available basal insulins, even those with improved stability and reproducibility of PK/PD continue to have a narrow therapeutic index and hypoglycemia incidents increase as glucose levels approach euglycemia target. This can often lead to underdosing to avoid hypoglycemia. Treatment with an IRPA of the present invention is expected to alter this efficacy: hypoglycemia relationship by attenuating the rate of change in glucose lowering as dosing is increased.

Insulin A and B Chains

Disclosed herein are insulin or insulin analog dimers that have insulin receptor agonist activity. The level of insulin activity of the dimers is a function of the dimeric structure, the sequence of the insulin analog, the length of the dimerization linker, and the site of dimerization that connects the two insulin polypeptides. The insulin polypeptides of the present invention may comprise the native B and A chain sequences of human insulin (SEQ ID NOs: 1 and 2, respectively) or any of the known analogs or derivatives thereof that exhibit insulin agonist activity when linked to one another in a heteroduplex. Such analogs include, for example, proteins that having an A-chain and a B-chain that differ from the A-chain and B-chain of human insulin by having one or more amino acid deletions, one or more amino acid substitutions, and/or one or more amino acid insertions that do not destroy the insulin activity of the insulin analog.

One type of insulin analog, "monomeric insulin analog," is well known in the art. These are fast-acting analogs of human insulin, including, for example, insulin analogs wherein:

(a) the amino acyl residue at position B28 is substituted with Asp, Lys, Leu, Val, or Ala, and the amino acyl residue at position B29 is Lys or Pro;

(b) the amino acyl residues at any of positions B27 and B30 are deleted or substituted with a nonnative amino acid.

In one embodiment an insulin analog is provided comprising an Asp substituted at position B28 (e.g., insulin aspart (NOVOLOG); see SEQ ID NO:9) or a Lys substituted at position 28 and a proline substituted at position B29 (e.g., insulin lispro (HUMALOG); see SEQ ID NO:6). Additional monomeric insulin analogs are disclosed in Chance, et al., U.S. Pat. No. 5,514,646; Chance, et al., U.S. patent application Ser. No. 08/255,297; Brems, et al., Protein Engineering, 5:527-533 (1992); Brange, et al., EPO Publication No. 214,826 (published Mar. 18, 1987); and Brange, et al., Current Opinion in Structural Biology, 1:934-940 (1991). These disclosures are expressly incorporated herein by reference for describing monomeric insulin analogs.

Insulin analogs may also have replacements of the amidated amino acids with acidic forms. For example, Asn may be replaced with Asp or Glu. Likewise, Gln may be replaced with Asp or Glu. In particular, Asn(A18), Asn(A21), or Asp(B3), or any combination of those residues, may be replaced by Asp or Glu. Also, Gln(A15) or Gln(B4), or both, may be replaced by either Asp or Glu.

As disclosed herein insulin single chain analogs are provided comprising a B chain and A chain of human insulin, or analogs or derivative thereof, wherein the carboxy terminus of the B chain is linked to the amino terminus of the A chain via a linking moiety. In one embodiment the A chain is amino acid sequence GIVEQCCTSICSLY-QLENYCN (SEQ ID NO: 1 and the B chain comprises amino acid sequence FVNQHLCGSH LVEALYL-VCGERGFFYTPKT (SEQ ID NO: 2) or a carboxy shortened sequence thereof having B30 deleted, and analogs of those sequences wherein each sequence is modified to comprise one to five amino acid substitutions at positions corresponding to native insulin positions selected from A5, A8, A9, A10, A14, A15, A17, A18, A21, B1, B2, B3, B4, B5, B9, B10, B13, B14, B20, B22, B23, B26, B27, B28, B29 and B30, with the proviso that at least one of B28 or B29 is lysine. In one embodiment the amino acid substitutions are conservative amino acid substitutions. Suitable amino acid substitutions at these positions that do not adversely impact insulin's desired activities are known to those skilled in the art, as demonstrated, for example, in Mayer, et al., Insulin Structure and Function, Biopolymers. 2007; 88(5):687-713, the disclosure of which is incorporated herein by reference.

In accordance with one embodiment the insulin analog peptides may comprise an insulin A chain and an insulin B chain or analogs thereof, wherein the A chain comprises an amino acid sequence that shares at least 70% sequence identity (e.g., 70%, 75%, 80%, 85%, 90%, 95%) over the length of the native peptide, with GIVEQCCTSICSLY-QLENYCN (SEQ ID NO: 1) and the B chain comprises an amino acid sequence that shares at least 60% sequence identity (e.g., 60%, 65%, 70%, 75%, 80%, 85%, 90%, 95%) over the length of the native peptide, with FVNQHLCG-SHLVEALYLVCGERGFFYTPKT (SEQ ID NO: 2) or a carboxy shortened sequence thereof having B30 deleted.

Additional amino acid sequences can be added to the amino terminus of the B chain or to the carboxy terminus of the A chain of the insulin polypeptides of the present invention. For example, a series of negatively charged amino acids can be added to the amino terminus of the B chain, including for example a peptide of 1 to 12, 1 to 10, 1 to 8 or 1 to 6 amino acids in length and comprising one or more negatively charged amino acids including for example glutamic acid and aspartic acid. In one embodiment the B chain amino terminal extension comprises 1 to 6 charged amino acids. In accordance with one embodiment the insulin polypeptides disclosed comprise a C-terminal amide or ester in place of a C-terminal carboxylate on the A chain.

In various embodiments, the insulin analog has an isoelectric point that has been shifted relative to human insulin. In some embodiments, the shift in isoelectric point is achieved by adding one or more arginine, lysine, or histidine residues to the N-terminus of the insulin A-chain peptide and/or the C-terminus of the insulin B-chain peptide. Examples of such insulin polypeptides include ArgM-human insulin, Arg$^{B31}$Arg$^{B32}$-human insulin, Gly$^{A21}$Arg$^{B31}$Arg$^{B32}$-human insulin, Arg$^{A0}$Arg$^{B31}$Arg$^{B32}$-human insulin, and Arg$^{A0}$Gly$^{A21}$Arg$^{B31}$Arg$^{B32}$human insulin. By way of further example, insulin glargine (LANTUS; see SEQ ID NOs: 7 and 8) is an exemplary long-acting insulin analog in which Asn$^{A21}$ has been replaced by glycine, and two arginine residues have been covalently linked to the C-terminus of the B-peptide. The effect of these amino acid changes was to shift the isoelectric point of the molecule, thereby producing a molecule that is soluble at acidic pH (e.g., pH 4 to 6.5) but insoluble at physiological pH. When a solution of insulin glargine is injected into the muscle, the pH of the solution is neutralized and the insulin glargine forms microprecipitates that slowly release the insulin glargine over the 24 hour period following injection with no pronounced insulin peak and thus a reduced risk of inducing hypoglycemia. This profile allows a once-daily dosing to provide a patient's basal insulin. Thus, in some embodiments, the insulin analog comprises an A-chain peptide wherein the amino acid at position A21 is glycine and a B-chain peptide wherein the amino acids at position B31 and B32 are arginine. The present disclosure encompasses all single and multiple combinations of these mutations and any other mutations that are described herein (e.g., Gly$^{A21}$-human insulin, Gly$^{A21}$Arg$^{B31}$-human insulin, A$^{rg}$B$^{31}$Arg$^{B32}$-human insulin, Arg$^{B31}$-human insulin).

In particular aspects of the insulin receptor partial agonists, one or more amidated amino acids of the insulin analog are replaced with an acidic amino acid, or another amino acid. For example, asparagine may be replaced with aspartic acid or glutamic acid, or another residue. Likewise, glutamine may be replaced with aspartic acid or glutamic acid, or another residue. In particular, AsnA$^{18}$, AsnA$^{21}$, or AsnB$^3$, or any combination of those residues, may be replaced by aspartic acid or glutamic acid, or another residue. GlnA$^{15}$ or GlnB$^4$, or both, may be replaced by aspartic acid or glutamic acid, or another residue. In particular aspects of the insulin receptor partial agonists, the insulin analogs have an aspartic acid, or another residue, at position A21 or aspartic acid, or another residue, at position B3, or both.

One skilled in the art will recognize that it is possible to replace yet other amino acids in the insulin analog with other amino acids while retaining biological activity of the molecule. For example, without limitation, the following modifications are also widely accepted in the art: replacement of the histidine residue of position B10 with aspartic acid (His$^{B10}$ to Asp$^{B10}$); replacement of the phenylalanine residue at position B1 with aspartic acid (PheB1 to AspB1); replacement of the threonine residue at position B30 with alanine (ThrB30 to AlaB30); replacement of the tyrosine residue at position B26 with alanine (TyrB26 to AlaB26); and replacement of the serine residue at position B9 with aspartic acid (SerB9 to AspB9).

In various embodiments, the insulin analog has a protracted profile of action. Thus, in certain embodiments, the insulin analog may be acylated with a fatty acid. That is, an amide bond is formed between an amino group on the insulin analog and the carboxylic acid group of the fatty acid. The amino group may be the alpha-amino group of an N-terminal amino acid of the insulin analog, or may be the epsilon-amino group of a lysine residue of the insulin analog. The insulin analog may be acylated at one or more of the three amino groups that are present in wild-type human insulin may be acylated on lysine residue that has been introduced into the wild-type human insulin sequence. In particular aspects of the insulin receptor partial agonists, the insulin analog may be acylated at position A1, B1, or both A1 and B1. In certain embodiments, the fatty acid is selected from myristic acid ($C_{14}$), pentadecylic acid ($C_{15}$), palmitic acid ($C_{16}$), heptadecylic acid ($C_{17}$) and stearic acid ($C_{18}$).

Examples of insulin analogs can be found for example in published International Application WO9634882, WO95516708; WO20100080606, WO2009/099763, and WO2010080609, U.S. Pat. No. 6,630,348, and Kristensen et al., Biochem. J. 305: 981-986 (1995), the disclosures of which are incorporated herein by reference). In further embodiments, the in vitro glycosylated or in vivo N-glycosylated insulin analogs may be acylated and/or pegylated.

In accordance with one embodiment, an insulin analog is provided wherein the A chain of the insulin peptide comprises the sequence GIVEQCCX$_8$SICSLYQLX$_{17}$NX$_{19}$CX$_{23}$ (SEQ ID NO: 3) and the B chain comprising the sequence X$_{25}$LCGX$_{29}$X$_{30}$LVEALYLVCGERGFFYTX$_{31}$X$_{32}$ (SEQ ID NO: 4) wherein $X_8$ is threonine or histidine;

$X_{17}$ is glutamic acid or glutamine;

$X_{19}$ is tyrosine, 4-methoxy-phenylalanine, or 4-amino phenylalanine;

$X_{23}$ is asparagine or glycine;

$X_{25}$ is histidine or threonine;

$X_{29}$ is alanine, glycine or serine;

$X_{30}$ is histidine, aspartic acid, glutamic acid, homocysteic acid, or cysteic acid;

$X_{31}$ is proline or lysine; and $X_{32}$ is proline or lysine, with the proviso that at least one of $X_{31}$ or $X_{32}$ is lysine.

In a further embodiment, the B chain comprises the sequence $X_{22}$VNQ$X_{25}$LCG$X_{29}X_{30}$LVEALYLVCGERGFFYT-$X_{31}X_{32}X_{33}X_{34}X_{35}$ (SEQ ID NO: 5) wherein $X_{22}$ is or phenylalanine and desamino-phenylalanine;

$X_{25}$ is histidine or threonine;

$X_{29}$ is alanine, glycine, or serine;

$X_{30}$ is histidine, aspartic acid, glutamic acid, homocysteic acid, or cysteic acid;

$X_{31}$ is aspartic acid, proline, or lysine;

$X_{32}$ is lysine or proline;

$X_{33}$ is threonine, alanine, or absent;

$X_{34}$ is arginine or absent; and $X_{35}$ is arginine or absent;

With the proviso at least one of $X_{31}$ or $X_{32}$ is lysine.

Linking Moiety

The insulin dimers disclosed herein are formed between a first and second insulin polypeptide wherein each insulin polypeptide comprises an A chain and a B chain. The first and second insulin polypeptides may be two chain insulin analogs (i.e., wherein the A and B chains are linked only via inter-chain disulfide bonds between internal cysteine residues) wherein the first and second insulin polypeptides are linked to one another to form the dimer by a covalent bond, bifunctional linker, or using copper(I) catalyzed alkyne-azide cycloaddition (CuAAC) click chemistry or copper-free click chemistry to link linking moieties on the respective B chains. In accordance with one embodiment the first and second insulin polypeptides are linked to one another by a bifunctional linker joining the side chain of the B28 or B29 lysine of the B chain of the first insulin polypeptide to the side chain of the B28 or B29 amino acid of the B chain of the second insulin polypeptide.

In particular aspects of the insulin receptor partial agonists, the linking moiety may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-C20 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In one embodiment, the linking moiety comprises a PEG linker, a short linear polymer of about 2-25 ethylene glycol units or 2, 3, 4, 5, 6, 7, 8, 9, 10, 11, 12, 13, 14, 15, 16, or 25 ethylene glycol units and optionally one or more amino acids. In particular aspects of the insulin receptor partial agonists, the PEG linker comprises the structure (PEG)$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_{25}$. The PEG linker may be a bifunctional linker that may be covalently conjugated or linked to epsilon amino group of the position B29 or B28 lysine residues of the first and second insulin polypeptides. The structure of a bifunctional PEG linker conjugated to the epsilon amino group of the lysine groups at position B29 or B28 of the first and second insulin polypeptides may be represented by the following general formula

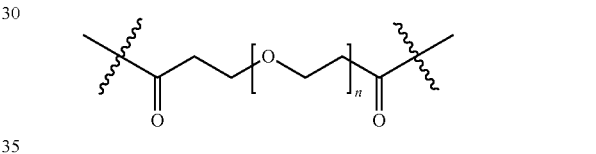

wherein n=1, 2, 3, 4, 5, 6, 7, 8, 9, 10, 11, 12, 13, 14, 15, 16, or 25 and the wavy line indicates the bond between the linker and the epsilon amino group. Methods for conjugating PEG to the epsilon amino group of lysine are well known in the art, see for example, Veronese, Biomaterials 22: 405-417 (2001).

In particular aspects of the insulin receptor partial agonists, PEG linking moiety conjugating the epsilon amino group of the lysine at position B29 or B28 of the first insulin polypeptide to the epsilon amino acid of the lysine at position B29 or B28 of the second insulin polypeptide is

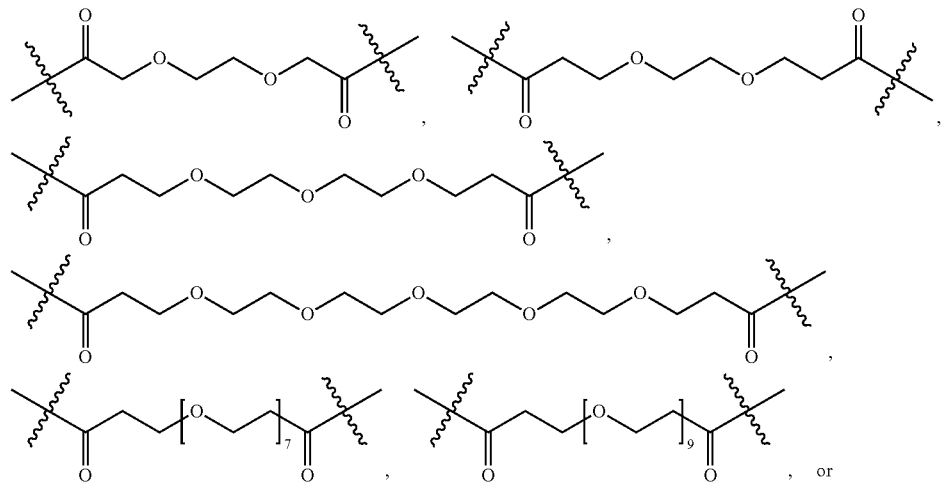

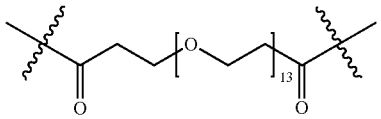

wherein the wavy lines indicate the bond between the linker and the epsilon amino group of the lysine at position B29 or B28 of the insulin polypeptides.

In another embodiment, the linking moiety comprises an acyl moiety comprising 4, 5, 6, 7, 8, 9, 10, 11, 12, 13, 14 15, or 16 carbons. In particular aspects of the insulin receptor partial agonists, the acyl moiety is a succinyl (4), adipoyl (C6), suberyol (C8), or hexadecanedioyl (C16) moiety. The acyl moiety may comprise a bifunctional linker that may be covalently conjugated or linked to epsilon amino group of the position B29 or B28 lysine residues of the first and second insulin polypeptides. The structure of a bifunctional acyl linker conjugated to the epsilon amino group of the lysine group at position B29 or B28 of the first and second insulin polypeptides may be represented by the following general formula

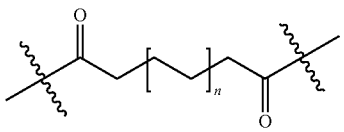

wherein n=0, 1, 2, 3, 4, 5, 6, 7, 8, 9, 10, 11, or 12 and the wavy lines indicate the bond between the linker and the epsilon amino group of the lysine at position B29 or B28 of the insulin polypeptides.

In particular aspects of the insulin receptor partial agonists, acyl linking moiety conjugating the epsilon amino group of the lysine at position B29 or B28 of the first insulin polypeptide to the epsilon amino acid of the lysine at position B29 or B28 of the second insulin polypeptide is

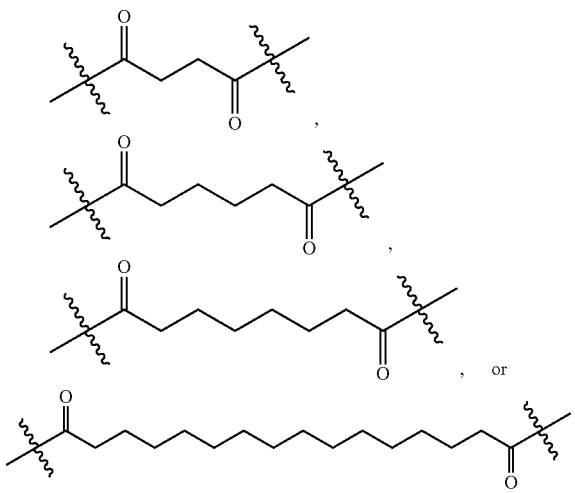

wherein the wavy lines indicate the bond between the linker and the epsilon amino group of the lysine at position B29 or B28 of the insulin polypeptides.

In particular aspects of the insulin receptor partial agonists, the bifunctional acyl linker may further include one or two amino acids at one or both termini of the acyl linker. For example, in particular aspects of the insulin receptor partial agonists, the amino acid at one or both termini of the linker is gamma glutamic acid (γE), which may be represented by the following general formula

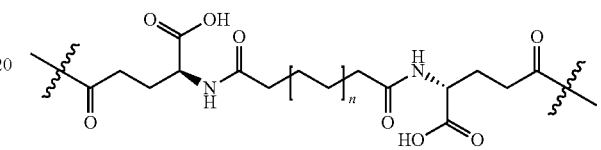

wherein n=0, 1, 2, 3, 4, 5, 6, 7, 8, 9, 10, 11, or 12 and the wavy lines indicate the bond between the linker and the epsilon amino group of the lysine at position B29 or B28 of the insulin polypeptides.

In another embodiment, the linking moiety comprises an amide-containing alkyl chain bifunctional linker that may be covalently conjugated or linked to epsilon amino group of the position B29 or B28 lysine residues of the first and second insulin polypeptides which may be represented by the following general formula

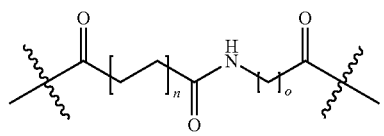

wherein n=1 or 2, o=1, 2, 3, 4, or 5, and the wavy lines indicate the bond between the linker and the epsilon amino group of the lysine at position B29 or B28 of the insulin polypeptides. In a particular embodiment, the linking moiety may have the structure

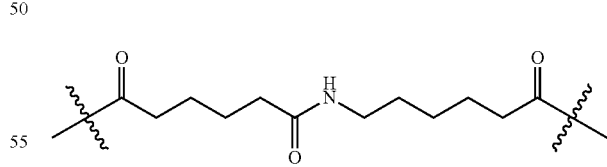

wherein the wavy lines indicate the bond between the linker and the epsilon amino group of the lysine at position B29 or B28 of the insulin polypeptides.

In another embodiment, the linking moiety comprises an amide-containing alkyl chain bifunctional linker that may be covalently conjugated or linked to epsilon amino group of the position B29 or B28 lysine residues of the first and second insulin polypeptides which may be represented by the following general formula

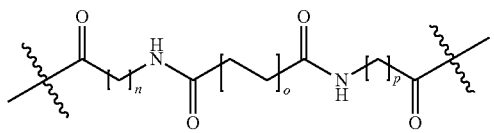

wherein n=1, 2, 3, 4, or 5, o=1 or 2, p=1, 2, 3, 4, or 5, and the wavy lines indicate the bond between the linker and the epsilon amino group of the lysine at position B29 or B28 of the insulin polypeptides. In a particular embodiment, the linking moiety may have the structure

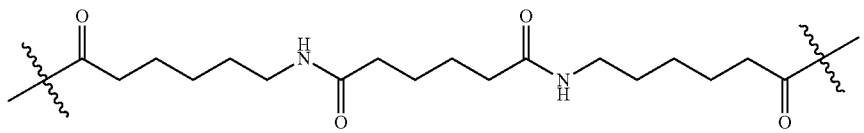 [SMILES: *C(=O)CCCCCNC(=O)CCCCC(=O)NCCCCCC(*)=O]

wherein the wavy lines indicate the bond between the linker and the epsilon amino group of the lysine at position B29 or B28 of the insulin polypeptides.

In another embodiment, the linking moiety comprises an amide-containing alkyl chain bifunctional linker that may be covalently conjugated or linked to epsilon amino group of the position B29 or B28 lysine residues of the first and second insulin polypeptides and which may be represented by the following general formula

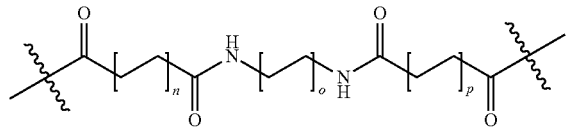

wherein n=1 or 2, o=1, 2, or 3, p=1 or 2, and the wavy lines indicate the bond between the linker and the epsilon amino group of the lysine at position B29 or B28 of the insulin polypeptides. In a particular embodiment, the linking moiety may have the structure

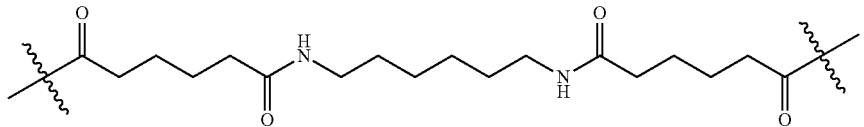 [SMILES: *C(=O)CCCCC(=O)NCCCCCCNC(=O)CCCCC(*)=O]

wherein the wavy lines indicate the bond between the linker and the epsilon amino group of the lysine at position B29 or B28 of the insulin polypeptides.

In particular embodiments, the linking moiety comprises a ring structure, which provides rigidity to the linking moiety. In particular embodiments, the ring structure comprises a benzyl group or a saturated or unsaturated alicyclic group having 3, 4, 5, 6, 7, or 8 carbons. In particular embodiments, the alicyclic group comprises a cyclopropyl, cyclobutyl, cyclopentyl, cyclohexyl, cyclopentyl, or cyclooctyl. In particular embodiments, the unsaturated alicyclic group (cycloalkane) comprises a cyclopropenyl, cyclobutenyl, cyclopentenyl, cyclohexenyl, cycloheptenyl, or cyclooctenyl group. In particular embodiments, the ring structure may further comprise one or more saturated or nonsaturated aliphatic side chains. In particular embodiments, the ring structure may further comprise one or more aliphatic side chains comprising one or more heteroatoms. In particular embodiments, the heteroatom is O, S, or N.

In particular embodiments, the ring structure comprises a heteroatom. In particular embodiments, the heteroatom may be O, S, or N. In particular embodiments, the ring structure comprises a benzyl group or a saturated or unsaturated alicyclic group having 3, 4, 5, 6, 7, or 8 carbons in which one or more carbons are substituted with a heteroatom selected from N, O, and S. Examples of ring structures that include a heteroatom include but are not limited to ethylene oxide, ethylenimime, trimethyloxide, furan, tetrhydrofuran, thiphene, pyrrolidine, pyran, piperidine, imidazole, thiazole, dioxane, morpholine, pyrimidine, triazole, thietane, 1,3-diazetine, 2,3-dihydroazete, 1,2-oxathiolane, isoxazole, oxazole, silole, oxepane, thiepine, 3,4,5,6-tetrahydro-2H-azepine, 1,4-thiazepine, azocane, and thiocane.

In another embodiment, the linking moiety comprises a bifunctional linker that may be covalently conjugated or linked to epsilon amino group of the position B29 or B28 lysine residues of the first and second insulin polypeptides which may be represented by a benzene-1,1 diacyl having the following general formula

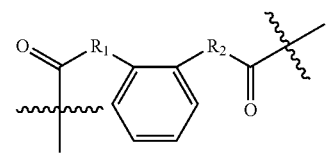

wherein $R_1$ and $R_2$ may be same or different wherein $R_1$ and $R_2$ are independently a bond, a saturated or non-saturated C1-C20 or C1-C6 alkyl chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety, poly(ethylene glycol) (PEG) chain PEG)$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_2$ and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,1 diacyl having the following general formula

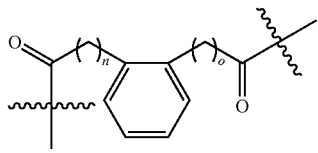

wherein n and o are independently 0, 1, 2, 3, 4, or 5 wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

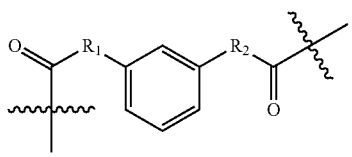

wherein $R_1$ and $R_2$ may be same or different wherein $R_1$ and $R_2$ are independently a bond, a saturated or non-saturated C1-C20 or C1-C6 alkyl chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety, poly(ethylene glycol) (PEG) chain PEG$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_2$ and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

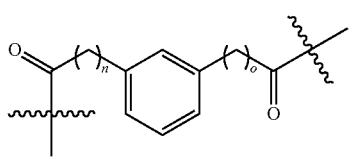

wherein n and o are independently 0, 1, 2, 3, 4, or 5 wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,4 diacyl having the following general formula

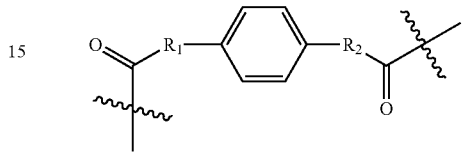

wherein $R_1$ and $R_2$ may be same or different wherein $R_1$ and $R_2$ are independently a bond, a saturated or non-saturated C1-C20 or C1-C6 alkyl chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety, poly(ethylene glycol) (PEG) chain PEG$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_2$ and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,4 diacyl having the following general formula

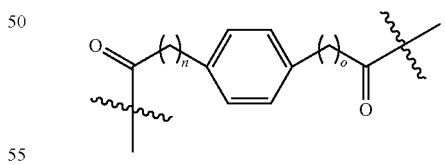

wherein n and o are independently 0, 1, 2, 3, 4, or 5 wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

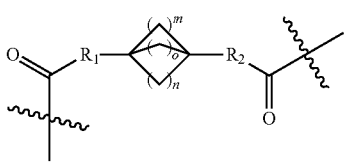

Wherein m, n, and o are each independently 1 or 2; $R_1$ and $R_2$ may be same or different wherein $R_1$ and $R_2$ are independently a bond, a saturated or non-saturated C1-C20 or C1-C6 alkyl chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety, poly(ethylene glycol) (PEG) chain PEG)$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_2$ and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

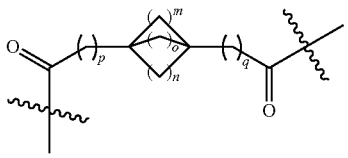

Wherein m, n, and o are each independently 1 or 2; wherein p and q are independently 0, 1, 2, 3, 4, or 5 wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

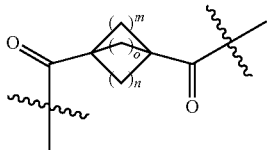

Wherein m, n, and o are each independently 1 or 2; wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a cyclohexane-1,4 diacyl having the following general formula

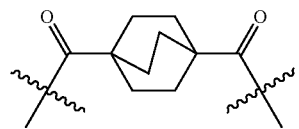

and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a cyclohexane-1,4 diacyl having the following general formula

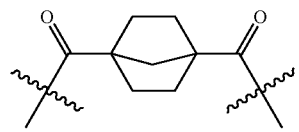

and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

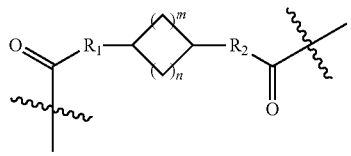

Wherein m and n are each independently 0, 1, or 2 with the proviso that both m and n are not 0; $R_1$ and $R_2$ may be same or different wherein $R_1$ and $R_2$ are independently a bond, a saturated or non-saturated C1-C20 or C1-C6 alkyl chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety, poly(ethylene glycol) (PEG) chain PEG)$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_2$ and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

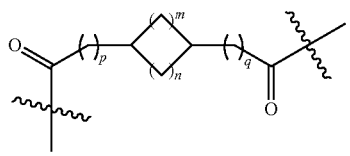

Wherein m and n are each independently 1 or 2; wherein p and q are independently 0, 1, 2, 3, 4, or 5 wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a 1,1 diacyl having the following general formula

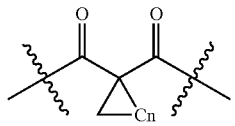

wherein n is 1, 2, 3, or 4 wherein the wavy lines indicate the bond between the linker and the epsilon amino group of the lysine at position B29 or B28 of the insulin polypeptides. In specific embodiments, the 1,1 diacyl may have a structure selected from

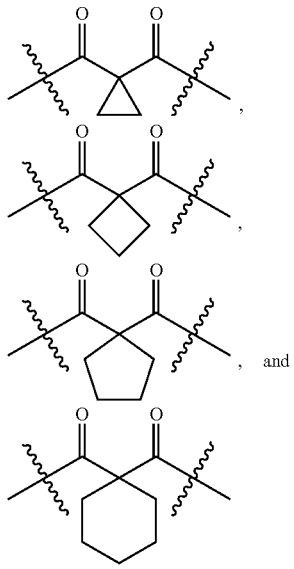

, and (1,1-diacyl-C3; 1,2-diacyl-C4; 1,1-diacyl-C5; and 1,1-diacyl-C6, respectively) wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a 1,2 diacyl having the following general formula

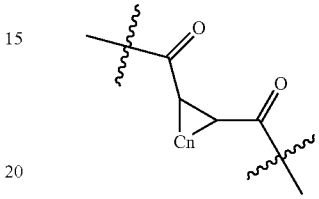

wherein n is 1, 2, 3, or 4 wherein the wavy lines indicate the bond between the linker and the epsilon amino group of the lysine at position B29 or B28 of the insulin polypeptides. In specific embodiments, the 1,2 diacyl may have a structure selected from

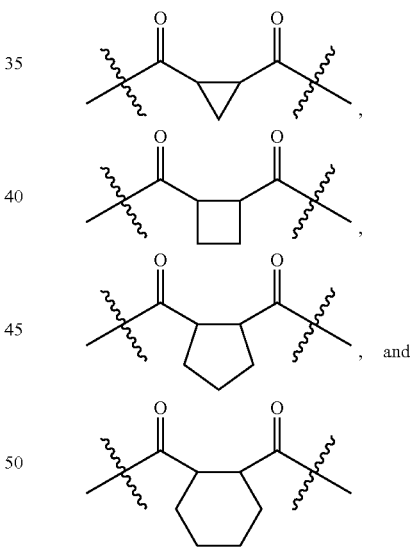

, and (1,2-diacyl-C3; 1,2-diacyl-C4; 1,2-diacyl-C5; and 1,2-diacyl-C6, respectively) wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a 1,3 diacyl having the following general formula

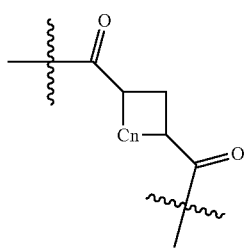

wherein n is 1, 2, or 3 wherein the wavy lines indicate the bond between the linker and the epsilon amino group of the lysine at position B29 or B28 of the insulin polypeptides. In specific embodiments, the 1,3 diacyl may have a structure selected from,

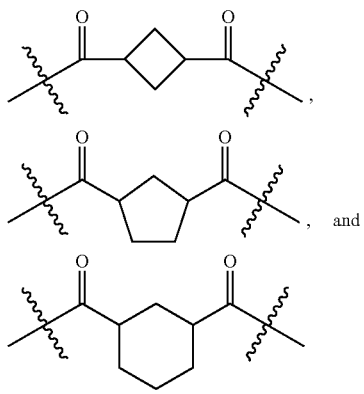

, and (1,3-diacyl-C4; 1,3-diacyl-05; and 1,3-diacyl-C6, respectively) wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a 1,4 diacyl having the following general formula

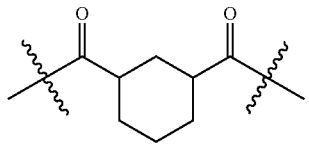

(1,4-diacyl-C6) wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a cyclobutyl-1,3 diacyl having the following general formula

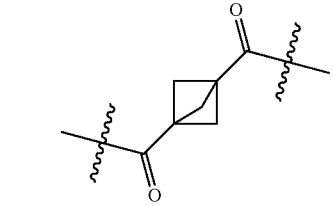

and wherein the wavy lines indicate the bond between the linker and the epsilon amino group of the lysine at position B29 or B28 of the insulin polypeptides.

In a further aspect of the present invention, the first and second insulin polypeptides may be conjugated together using copper-catalyzed Azide-Alkyne Huisgen Cycloaddition (CuAAc), in particular CuAAC click chemistry. In this aspect, the epsilon amino group of the B29 or B28 lysine of the first insulin polypeptide is conjugated to a linker moiety having a proximal end and a distal end wherein the proximal end of the linker moiety is conjugated to the epsilon amino group and the distal comprises an azide group. In this aspect, the epsilon amino group of the B29 or B28 lysine of the second insulin polypeptide is conjugated to a linker moiety having a proximal end and a distal end wherein the proximal end of the linker moiety is conjugated to the epsilon amino group and the distal comprises an alkyne group. In the presence of Cu2+ and a reducing agent, the azide and the alkyne groups will form a contiguous linking moiety comprising a triazole moiety. See U.S. Pat. No. 8,129,542, which is incorporated herein in its entirety, for a description of CuAAC click chemistry.

In particular aspects of the insulin receptor partial agonists, the first insulin polypeptide may have conjugated to the epsilon amino group of the B29 or B28 lysine a linker having the formula

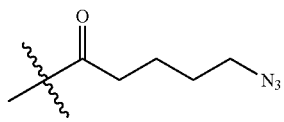 [SMILES: *C(=O)CCCCN=[N+]=[N-]]

and the second insulin polypeptide may have conjugated to the epsilon amino group of the B29 or B28 lysine a linker having the formula

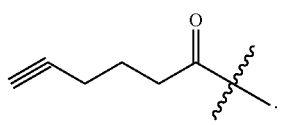 [SMILES: *C(=O)CCCC#C]

In the presence of Cu2+ and a reducing agent, the linkers combine to provide a linking moiety having the structure

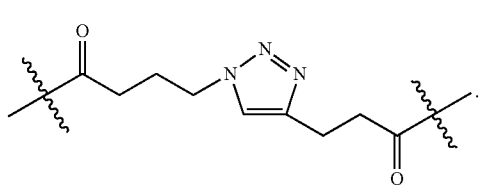 [SMILES: *C(=O)CCCn1cc(CCC(*)=O)nn1]

In particular aspects of the insulin receptor partial agonists, the first insulin polypeptide may have conjugated to the epsilon amino group of the B29 or B28 lysine a linker having the formula

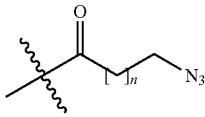

wherein n=1, 2, 3, 4, 5, 6, 7, 8, 9, or 10 and the second insulin polypeptide may have conjugated to the epsilon amino group of the B29 or B28 lysine a linker having the formula

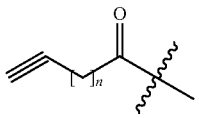

wherein n=1, 2, 3, 4, 5, 6, 7, 8, 9, or 10. In the presence of Cu2+ and a reducing agent, the linkers combine to provide a linking moiety having the structure

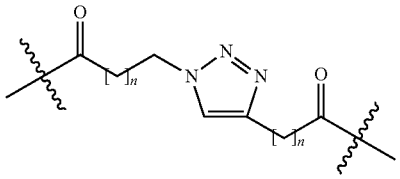

wherein each n independently is 1, 2, 3, 4, 5, 6, 7, 8, 9, or 10.

In a further aspect, both the first insulin polypeptide and the second insulin polypeptide may have conjugated to its respective epsilon amino group of the B29 or B28 lysine a linker having the formula

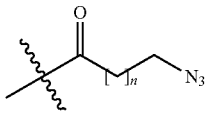

wherein each n is independently 1, 2, 3, 4, 5, 6, 7, 8, 9, or 10. Conjugation of the linkers to form a linking moiety may be achieved by providing a molecule (intermediate or bridging linker) having a structure

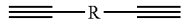

wherein R is a covalent bond, a carbon atom, a phenyl, a heteroatom, or an optionally substituted group selected from the group consisting of acyl, aliphatic, heteroaliphatic, aryl, heteroaryl, and heterocyclic. In particular aspects R is a C2, C3, C4, C6, C7, C8, C9 or C10 acyl group or a PEG2, PEG3, PEG4, PEG5, PEG6, PEG7, PEG8, PEG9, PEG10, PEG11, PEG12, PEG13, or PEG25.

In a further aspect, both the first insulin polypeptide and the second insulin polypeptide may have conjugated to its respective epsilon amino group of the B29 or B28 lysine a linker having the formula

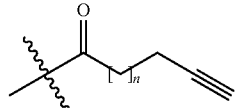

wherein each n is independently 1, 2, 3, 4, 5, 6, 7, 8, 9, or 10. Conjugation of the linkers to form a linking moiety may be achieved by providing a molecule (intermediate or bridging linker) having a structure

wherein R is a covalent bond, a carbon atom, a phenyl, a heteroatom, or an optionally substituted group selected from the group consisting of acyl, aliphatic, heteroaliphatic, aryl, heteroaryl, and heterocyclic. In particular aspects R is a C2, C3, C4, C6, C7, C8, C9 or C10 acyl group or a PEG2, PEG3, PEG4, PEG5, PEG6, PEG7, PEG8, PEG9, PEG10, PEG11, PEG12, PEG13, or PEG 25.

In particular aspects, the first insulin polymer is conjugated at the epsilon amino group of the B29 or B28 lysine to an azide terminated linker as above and the second insulin polypeptide is conjugated at the epsilon amino group of the B29 or B28 lysine to a linker terminated with a cyclooctyne moiety and the linkers are conjugated to form a linker moiety using copper-free cycloaddition click chemistry. See for example, U.S. Pat. No. 7,807,619, which is incorporated herein in its entirety.

The following table shows exemplary linkers, which may be used to construct the dimers of the present invention. The dimers shown comprise 2,5-dioxopyrrolidin-1y groups for conjugating to the epsilon amino group of the B29 or B29 lysine.

-continued
Table of Linkers
| | Linker | Name |
|---|---|---|
| 2 | 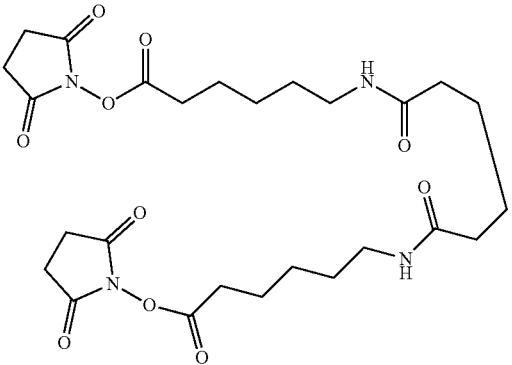 | C6N + C6 + NC6 |
| 3 | 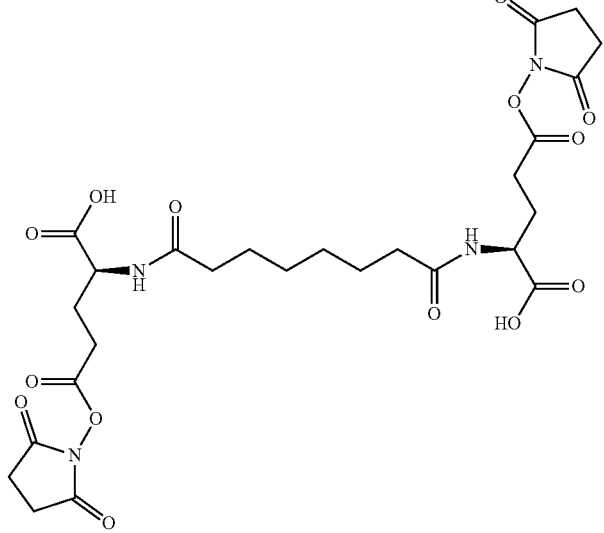 | γE-C8-γE |
| 4 | 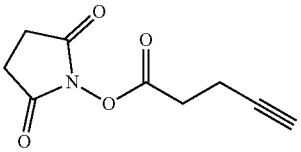 | Click-1 |
| 5 | 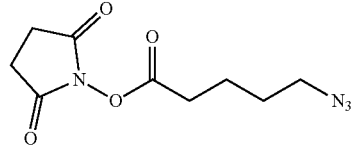 | Click-2 |
| 6 | 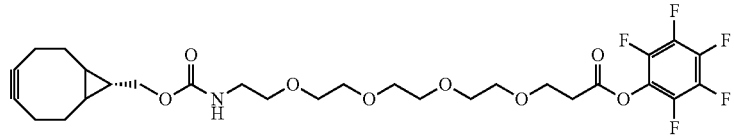 | Click-3 |

-continued

| | Table of Linkers | |
|---|---|---|
| | Linker | Name |
| 7 | [structure: NHS ester-CH2CH2-O-CH2CH2-N3] | Click-4 |
| 8 | [structure: NHS ester-(CH2)4-C≡CH] | Click-5 |
| 9 | [structure: NHS ester-CH2CH2-O-CH2CH2-O-CH2CH2-O-CH2-C≡CH] | Click-6 |
| 10 | [structure: bis-NHS ester, succinate] | C2 |
| 11 | [structure: bis-NHS ester, C4] | C4 |
| 12 | [structure: bis-NHS ester, C6] | C6 |
| 13 | [structure: bis-NHS ester, C8] | C8 |

Table of Linkers

| | Linker | Name |
|---|---|---|
| 14 | | C16 |
| 15 | | PEG2 |
| 16 | | PEG3 |
| 17 | | PEG4 |
| 18 | | PEG5 |

-continued
| Table of Linkers | |
|---|---|
| Linker | Name |
19 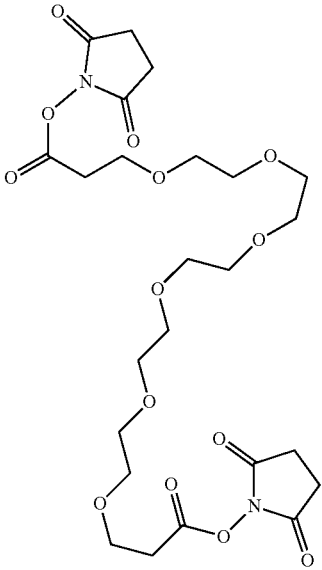 [SMILES: O=C(CCOCCOCCOCCOCCOCCOCCC(=O)ON1C(=O)CCC1=O)ON1C(=O)CCC1=O] PEG6
20 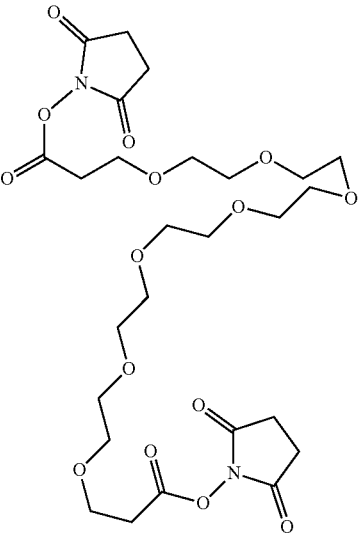 [SMILES: O=C(CCOCCOCCOCCOCCOCCOCCOCCC(=O)ON1C(=O)CCC1=O)ON1C(=O)CCC1=O] PEG7
21 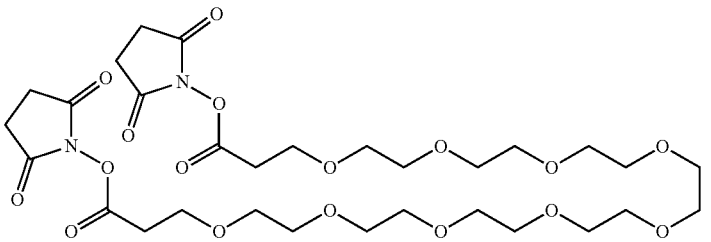 [SMILES: O=C(CCOCCOCCOCCOCCOCCOCCOCCOCCOCCC(=O)ON1C(=O)CCC1=O)ON1C(=O)CCC1=O] PEG9

-continued

| Table of Linkers | |
|---|---|
| Linker | Name |
| 22 | PEG13 |
| 23 | PEG25 |
| 24 | C6-glycine |
| 25 | C6-alanine |
| 26 | C6-isoleucine |

-continued

| | Table of Linkers | |
|---|---|---|
| | Linker | Name |
| 27 | | C6-leucine |
| 28 | | C6-valine |
| 29 | | Dipropyl phenol |
| 30 | | Trans-cyclohexane 1,4-diacid |
| 31 | | Cis-cyclohexane 1,4-diacid |
| 32 | | Tert-butyl-piperidine-tricarb |
| 33 | | C6N-chloro-1,3,5-Triazine-NC6 |

Table of Linkers
| | Linker | Name |
|---|---|---|
| 34 | 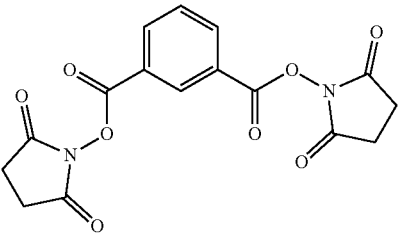 | Terephthalate |
| 35 | 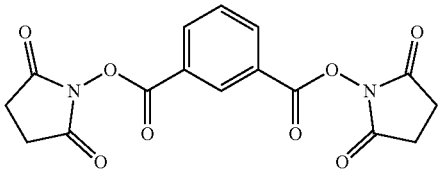 | isophthalate |
| 36 | 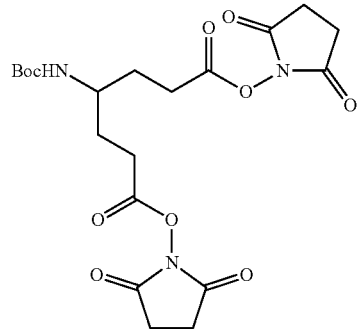 | Heptanedioate |
| 37 | 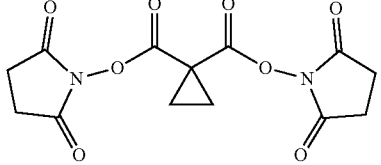 | 1,1-diacyl-C3 |
| 38 | 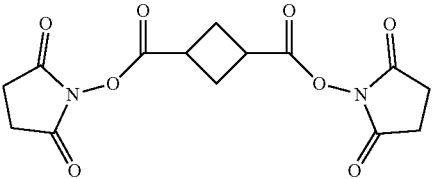 | 1,1-diacyl-C4 |
| 39 | 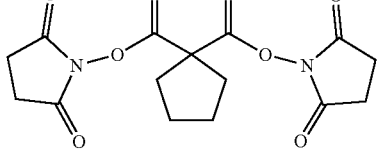 | 1,1-diacyl-C5 |

Table of Linkers

| | Linker | Name |
|---|---|---|
| 40 | (structure: bis-NHS ester of 1,1-dicarboxylic acid cyclopropane with Cn, n = 1, 2, 3, or 4) | 1,1-diacyl-C6 |
| 41 | (structure: bis-NHS ester of cyclopropane-1,2-dicarboxylic acid) | 1,2-diacyl-C3 |
| 42 | (structure: bis-NHS ester of cyclobutane-1,2-dicarboxylic acid) | 1,2-diacyl-C4 |
| 43 | (structure: bis-NHS ester of cyclopentane-1,2-dicarboxylic acid) | 1,2-diacyl-C5 |
| 44 | (structure: bis-NHS ester of cyclohexane-1,2-dicarboxylic acid) | 1,2-diacyl-C6 |

Table of Linkers

| | Linker | Name |
|---|---|---|
| 45 | | 1,3-diacyl-C4 |
| 46 | | 1,3-diacyl-C5 |
| 47 | | 1,3-diacyl-C6 |
| 48 | | 1,4-diacyl-cyclobutyl-C1 |
| 49 | | 1,4-cyclohexyl-C1 |
| 50 | | 1,4-cyclohexyl-C2 |

Conjugation of a bifunctional linker to the epsilon amino group of the lysine residue at position B29 or B28 of the B-chain polypeptide of two insulin or insulin analog molecules to form the insulin dimer linked by a linking moiety may be schematically shown as

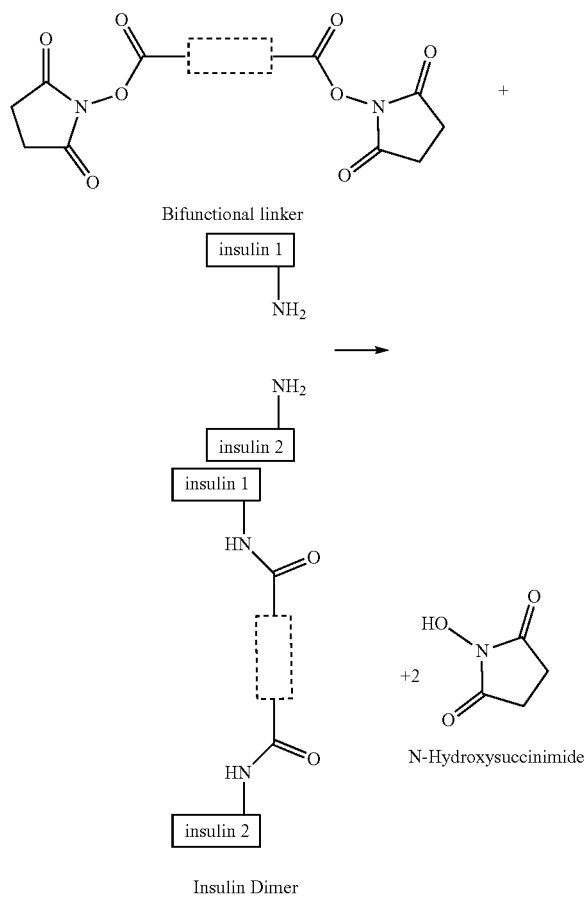

wherein the insulin 1 and insulin 2 molecules may be the same or different and the bifunctional linker and resulting and linking moiety following conjugation may have the structure of any linker and resulting linking moiety disclosed herein.

Modification of Insulin Polypeptides

In some embodiments, at least one of the A-chain polypeptides or B-chain polypeptides of the insulin receptor partial agonist is modified to comprise an acyl group. The acyl group can be covalently linked directly to an amino acid of the insulin polypeptide, or indirectly to an amino acid of the insulin polypeptide via a spacer, wherein the spacer is positioned between the amino acid of the insulin polypeptide and the acyl group. The insulin polypeptide may be acylated at the same amino acid position where a hydrophilic moiety is linked, or at a different amino acid position. For example, acylation may occur at any position including any amino acid of the A- or B-chain polypeptides as well as a position within the linking moiety, provided that the activity exhibited by the non-acylated insulin polypeptide is retained upon acylation. Non-limiting examples include acylation at positions A1 of the A chain and positions position B1 of the B chain.

In one specific aspect of the invention, the first and/or second insulin polypeptide (or derivative or conjugate thereof) is modified to comprise an acyl group by direct acylation of an amine, hydroxyl, or thiol of a side chain of an amino acid of the insulin polypeptide. In some embodiments, the first and/or second insulin polypeptide is directly acylated through the side chain amine, hydroxyl, or thiol of an amino acid. In this regard, an insulin polypeptide may be provided that has been modified by one or more amino acid substitutions in the A- or B-chain polypeptide sequence, including for example at positions A1, A14, A15, B1, B10, or B22 or at any position of the linking moiety with an amino acid comprising a side chain amine, hydroxyl, or thiol.

In some embodiments, the spacer between the first and/or second insulin polypeptide and the acyl group is an amino acid comprising a side chain amine, hydroxyl, or thiol (or a dipeptide or tripeptide comprising an amino acid comprising a side chain amine, hydroxyl, or thiol). In some embodiments, the spacer comprises a hydrophilic bifunctional spacer. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.). In one embodiment, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In some embodiments, the spacer between the first and/or second insulin polypeptide and the acyl group is a hydrophobic bifunctional spacer. Hydrophobic bifunctional spacers are known in the art. See, e.g., Bioconjugate Techniques, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

In accordance with certain embodiments the bifunctional spacer can be a synthetic or naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer attached to the insulin polypeptide can be independently selected from the group consisting of: naturally-occurring and/or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring amino acids selected from the group consisting of: β-alanine (β-Ala), N-α-methyl-alanine (Me-Ala), aminobutyric acid (Abu), α-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O2)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-C1)), 4-fluorophenylalanine (Phe(4-F)), 4-nitrophenylalanine (Phe(4-NO2)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), U-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4-tetrahydro-isoquinoline-3-carboxylic acid (Tic), tetrahydropyranglycine, thienylalanine (Thi), U-Benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), 1-amino-1-cyclohexane carboxylic acid (Acx), aminovaleric acid, beta-cyclopropyl-alanine (Cpa), propargylglycine (Prg), allylglycine (Alg), 2-amino-2-cyclohexyl-propanoic acid (2-Cha), tertbutylglycine (Tbg), vinylglycine (Vg), 1-amino-1-cyclopropane carboxylic acid (Acp), 1-amino-1-cyclopentane carboxylic acid (Acpe), alkylated 3-mercaptopropionic acid, 1-amino-1-cyclobutane carboxylic acid (Acb). In some embodiments the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

The first and/or second insulin polypeptide may be modified to comprise an acyl group by acylation of a long chain alkane. In specific aspects, the long chain alkane comprises an amine, hydroxyl, or thiol group (e.g. octadecylamine, tetradecanol, and hexadecanethiol) which reacts with a carboxyl group, or activated form thereof, of the insulin polypeptide. The carboxyl group, or activated form thereof, of the insulin polypeptide can be part of a side chain of an amino acid (e.g., glutamic acid, aspartic acid) of the insulin polypeptide or can be part of the peptide backbone.

In certain embodiments, the first and/or second insulin polypeptide is modified to comprise an acyl group by acylation of the long chain alkane by a spacer which is attached to the insulin polypeptide. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers. As used herein, the term "activated form of a carboxyl group" refers to a carboxyl group with the general formula R(C=O)X, wherein X is a leaving group and R is the insulin polypeptide or the spacer. For example, activated forms of a carboxyl groups may include, but are not limited to, acyl chlorides, anhydrides, and esters. In some embodiments, the activated carboxyl group is an ester with an N-hydroxysuccinimide (NHS) leaving group.

With regard to these aspects of the invention, in which a long chain alkane is acylated by the peptide, the insulin polypeptide or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane.

In some embodiments, an amine, hydroxyl, or thiol group of the first and/or second insulin polypeptide is acylated with a cholesterol acid. In a specific embodiment, the peptide is linked to the cholesterol acid through an alkylated des-amino Cys spacer, i.e., an alkylated 3-mercaptopropionic acid spacer. Suitable methods of peptide acylation via amines, hydroxyls, and thiols are known in the art. See, for example, Miller, Biochem Biophys Res Commun 218: 377-382 (1996); Shimohigashi and Stammer, Int J Pept Protein Res 19: 54-62 (1982); and Previero et al., Biochim Biophys Acta 263: 7-13 (1972) (for methods of acylating through a hydroxyl); and San and Silvius, J Pept Res 66: 169-180 (2005) (for methods of acylating through a thiol); Bioconjugate Chem. "Chemical Modifications of Proteins: History and Applications" pages 1, 2-12 (1990); Hashimoto et al., Pharmacuetical Res. "Synthesis of Palmitoyl Derivatives of Insulin and their Biological Activity" Vol. 6, No: 2 pp. 171-176 (1989).

The acyl group of the acylated peptide the first and/or second insulin polypeptide can be of any size, e.g., any length carbon chain, and can be linear or branched. In some specific embodiments of the invention, the acyl group is a $C_4$ to $C_{30}$ fatty acid. For example, the acyl group can be any of a $C_4$ fatty acid, $C_6$ fatty acid, $C_8$ fatty acid, $C_{10}$ fatty acid, $C_{12}$ fatty acid, $C_{14}$ fatty acid, $C_{16}$ fatty acid, $C_{18}$ fatty acid, $C_{20}$ fatty acid, $C_{22}$ fatty acid, $C_{24}$ fatty acid, $C_{26}$ fatty acid, $C_{28}$ fatty acid, or a $C_{30}$ fatty acid. In some embodiments, the acyl group is a $C_8$ to $C_{20}$ fatty acid, e.g., a $C_{14}$ fatty acid or a $C_{16}$ fatty acid. In some embodiments, the acyl group is urea.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

The acylated first and/or second insulin polypeptide described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In some embodiments the acylated single chain analog comprises an amino acid selected from the group consisting of a Cys, Lys, Orn, homo-Cys, or Ac-Phe, and the side chain of the amino acid is covalently bonded to a hydrophilic moiety (e.g., PEG). In one embodiment, the acyl group is attached to position A1, A14, A15, B1, B2, B10, or B22 (according to the amino acid numbering of the A and B chains of native insulin), optionally via a spacer comprising Cys, Lys, Orn, homo-Cys, or Ac-Phe.

Alternatively, the acylated first and/or second insulin polypeptide comprises a spacer, wherein the spacer is both acylated and modified to comprise the hydrophilic moiety. Non-limiting examples of suitable spacers include a spacer comprising one or more amino acids selected from the group consisting of Cys, Lys, Orn, homo-Cys, and Ac-Phe.

In some embodiments, the amino terminus of at least one N-terminal amino acid of at least one of the A-chain polypeptides and the B-chain polypeptides of the insulin receptor partial agonist is modified to comprise a substituent. The substituent may be covalently linked directly to the amino group of the N-terminal amino acid or indirectly to the amino group via a spacer, wherein the spacer is positioned between the amino group of the N-terminal amino acid of the insulin polypeptide and the substituent. The substituent may be an acyl moiety as discussed supra. The substituent may have the general formula RC(O)—, where R can be R'CH$_2$, R'NH, R'O, and R' can be H, linear alkyl chain, amino acid, peptide, polyethylene glycol (PEG), saccharides, which in particular aspects RC(O)— may be acetyl, phenylacetyl, carbamoyl, N-alkyl carbamoyl, or alkoxycarbonyl. In particular aspects, the substituent is a carbamoyl group, acetyl group, glycine, methyl group, methoxy group, dimethyl group, isobutyl group, PEG1 group, or PEG2 group (see Examples herein for structures of the substituents). Carbamolyation of insulin has been disclosed by Oimoni et al., Nephron 46: 63-66 (1987) and insulin dimers comprising a carbamoyl groups at the N-terminus has been disclosed in disclosed in published PCT Application No. WO2014052451 (E.g., MIU-90).

In particular embodiments, at least one N-terminal amino acid is conjugated via the N2 nitrogen to a substituent comprising an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides, which in particular aspects RC(O)— may be acetyl, phenylacetyl, carbamoyl, N-alkyl carbamoyl, or alkoxycarbonyl. In particular aspects, the substituent is a carbamoyl group, acetyl group, glycine, methyl group, methoxy group, dimethyl group, isobutyl group, PEG1 group, or PEG2 group.

In particular embodiments, the saccharide covalently linked to one or more amino termini of the first and second insulin polypeptides may be a monosaccharide, see for example Dimer 51. In some embodiments, the saccharide comprises one or more amine groups. In certain embodiments the saccharide and amine group are separated by a C$_1$-C$_6$ alkyl group, e.g., a C$_1$-C$_3$ alkyl group. In some embodiments, the saccharide is aminoethylglucose (AEG). In certain embodiments, a saccharide ligand is of the "D" configuration. In other embodiments, a saccharide ligand is of the "L" configuration. Below we show the structures of these exemplary saccharides. Other exemplary saccharides will be recognized by those skilled in the art.

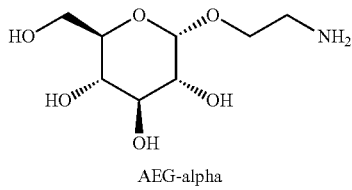

AEG-alpha

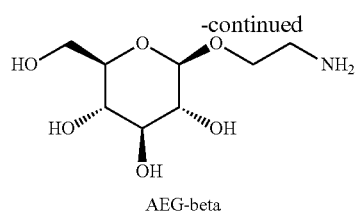

AEG-beta

In general, the saccharides may be directly or indirectly conjugated via a linker to the amino terminus of one or more of the first and second insulin polypeptides. In particular aspects, the linker is an alkyldioyl, —C(O)(CH$_2$)$_n$C(O)—, wherein n=0-45, 0-20, 0-10, or 0-5.

Exemplary substituents conjugated to the N-terminal amino group may be

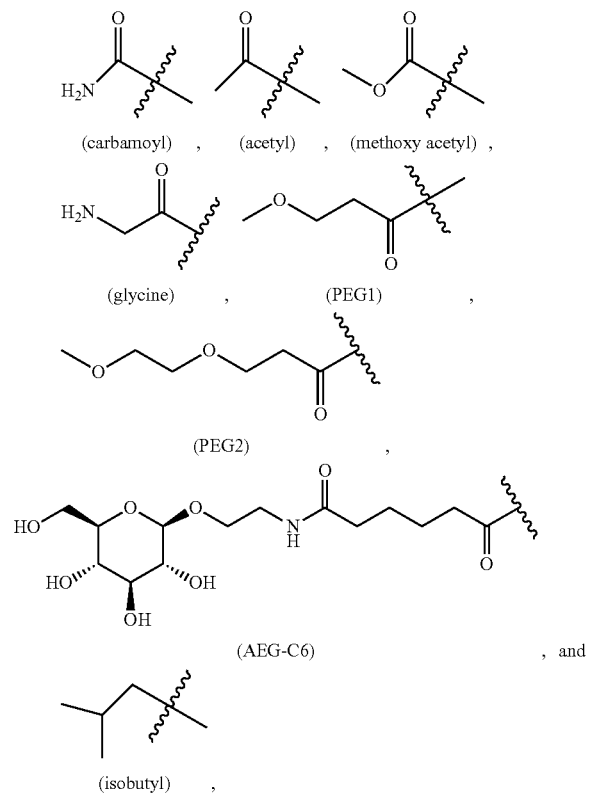

wherein the wavy line indicates the bond between the substituent and the N-terminal amino group. The substituent may also be

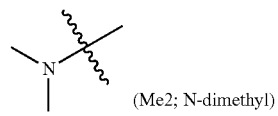 [SMILES: *N(C)C]

wherein the wavy line indicates the bond between Me2 and the alpha carbon of the N-terminal amino acid.

Exemplary Insulin Dimers

In particular embodiments, the present invention provides insulin dimers wherein a first B29 or B28 Lys of a first insulin heterodimer molecule having a first A-chain polypeptide and first B-chain polypeptide and a second B29 or B28 Lys of a second insulin heterodimer having a second A-chain polypeptide and second B-chain polypeptide are conjugated together by a bifunctional linker selected from the group consisting Linker 1, Linker 2, Linker 3, Linker 10, Linker 11, Liner 12, Linker 13, Linker 14, Linker 15, Linker 16, Linker 17, Linker 18, Linker 19, Linker 20, Linker 21, Linker 22, Linker 23, Linker 24, Linker 25, Linker 26, Linker 27, Linker 28, Linker 29, Linker 30, Linker 31, Linker 32, Linker 33, Linker 34, Linker 35, Linker 36, Linker 37, Linker 38, Linker 39, Linker 40, Linker 41, Linker 42, Linker 43, Linker 44, Linker 45, Linker 46, Linker 47, Linker 48, Linker 49, and Linker 50 with the proviso that when the bifunctional linker is Linker 10, Linker 11, Linker 12, Linker 13, or Linker 14, at least one of the first or second A-chain or B-chain polypeptides is conjugated at its N-terminal amino acid to a substituent as disclosed herein or at least the N-terminal amino acids of the first insulin heterodimer molecule are conjugated to a substituent as disclosed herein or the N-terminal amino acids of both the first insulin heterodimer and second insulin heterodimer are conjugated to a substituent. In particular embodiments, the substituent comprises an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides, which in particular aspects RC(O)— may be acetyl, phenylacetyl, carbamoyl, N-alkyl carbamoyl, or alkoxycarbonyl. In particular aspects, the substituent is a carbamoyl group, acetyl group, glycine, methyl group, methoxy group, dimethyl group, isobutyl group, PEG1 group, AEG group, AEG-C6 alkyl group, or PEG2 group.

In particular embodiments, the present invention provides insulin dimers wherein a first B29 or B28 Lys of a first insulin heterodimer molecule having a first A-chain polypeptide and first B-chain polypeptide is conjugated to a first linker selected from the group consisting of Linker 5 and Linker 7 and a second B29 or B28 Lys of a second insulin heterodimer having a second A-chain polypeptide and second B-chain polypeptide is conjugated to a second linker selected from the group consisting of Linker 4, Linker 6, Linker 8, and Linker 9 are conjugated together via the first linker and the second linker. In particular embodiments, at least one of the first or second A-chain or B-chain polypeptides is conjugated at its N-terminal amino acid to a substituent as disclosed herein or at least the N-terminal amino acids of the first insulin heterodimer molecule are conjugated to a substituent as disclosed herein or the N-terminal amino acids of both the first insulin heterodimer and second insulin heterodimer are conjugated to a substituent. In particular embodiments, the substituent comprises an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides, which in particular aspects RC(O)— may be acetyl, phenylacetyl, carbamoyl, N-alkyl carbamoyl, or alkoxycarbonyl. In particular aspects, the substituent is a carbamoyl group, acetyl group, glycine, methyl group, methoxy group, dimethyl group, isobutyl group, PEG1 group, AEG group, AEG-C6 alkyl group, or PEG2 group.

In particular embodiments, the present invention provides insulin dimers wherein a first B29 or B28 Lys of a first insulin heterodimer molecule having a first A-chain polypeptide and first B-chain polypeptide is conjugated to a first linker selected from the group consisting of Linker 5 and Linker 7 and a second B29 or B28 Lys of a second insulin heterodimer having a second A-chain polypeptide and second B-chain polypeptide is conjugated to a second linker selected from the group consisting of Linker 5 and Linker 7, wherein the first and second linkers are conjugated together via a bridging linker having a structure

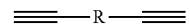

wherein R is a covalent bond, a carbon atom, a phenyl, a heteroatom, or an optionally substituted group selected from the group consisting of acyl, aliphatic, heteroaliphatic, aryl, heteroaryl, and heterocyclic. In particular aspects R is a C2, C3, C4, C6, C7, C8, C9 or C10 acyl group or a PEG2, PEG3, PEG4, PEG5, PEG6, PEG7, PEG8, PEG9, PEG10, PEG11, PEG12, PEG13, or PEG25. In particular embodiments, at least one of the first or second A-chain or B-chain polypeptides is conjugated at its N-terminal amino acid to a substituent as disclosed herein or at least the N-terminal amino acids of the first insulin heterodimer molecule are conjugated to a substituent as disclosed herein or the N-terminal amino acids of both the first insulin heterodimer and second insulin heterodimer are conjugated to a substituent. In particular embodiments, the substituent comprises an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides, which in particular aspects RC(O)— may be acetyl, phenylacetyl, carbamoyl, N-alkyl carbamoyl, or alkoxycarbonyl. In particular aspects, the substituent is a carbamoyl group, acetyl group, glycine, methyl group, methoxy group, dimethyl group, isobutyl group, PEG1 group, AEG group, AEG-C6 alkyl group, or PEG2 group.

In particular embodiments, the present invention provides insulin dimers wherein a first B29 or B28 Lys of a first insulin heterodimer molecule having a first A-chain polypeptide and first B-chain polypeptide is conjugated to a first linker selected from the group consisting of Linker 4, Linker 6, Linker 8, and Linker 9 and a second B29 or B28 Lys of a second insulin heterodimer having a second A-chain polypeptide and second B-chain polypeptide is conjugated to a second linker selected from the group consisting of Linker 4, Linker 6, Linker 8, and Linker 9, wherein the first and second linkers are conjugated together via a bridging linker having a structure

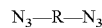

wherein R is a covalent bond, a carbon atom, a phenyl, a heteroatom, or an optionally substituted group selected from the group consisting of acyl, aliphatic, heteroaliphatic, aryl, heteroaryl, and heterocyclic. In particular aspects R is a C2, C3, C4, C6, C7, C8, C9 or C10 acyl group or a PEG2, PEG3, PEG4, PEG5, PEG6, PEG7, PEG8, PEG9, PEG10, PEG11, PEG12, PEG13, or PEG 25. In particular embodiments, at least one of the first or second A-chain or B-chain polypeptides is conjugated at its N-terminal amino acid to a substituent as disclosed herein or at least the N-terminal amino acids of the first insulin heterodimer molecule are conjugated to a substituent as disclosed herein or the N-terminal amino acids of both the first insulin heterodimer and second insulin heterodimer are conjugated to a substituent. In particular embodiments, the substituent comprises an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides, which in particular aspects RC(O)— may be acetyl, phenylacetyl, carbamoyl, N-alkyl carbamoyl, or alkoxycarbonyl. In particular aspects, the substituent is a carbamoyl group, acetyl group, glycine, methyl group, methoxy group, dimethyl group, isobutyl group, PEG1 group, AEG group, AEG-C6 alkyl group, or PEG2 group.

In further embodiments the first and second insulin heterodimers may comprise any of the insulin or insulin analog molecules disclosed herein.

The present invention also provides insulin dimers selected from

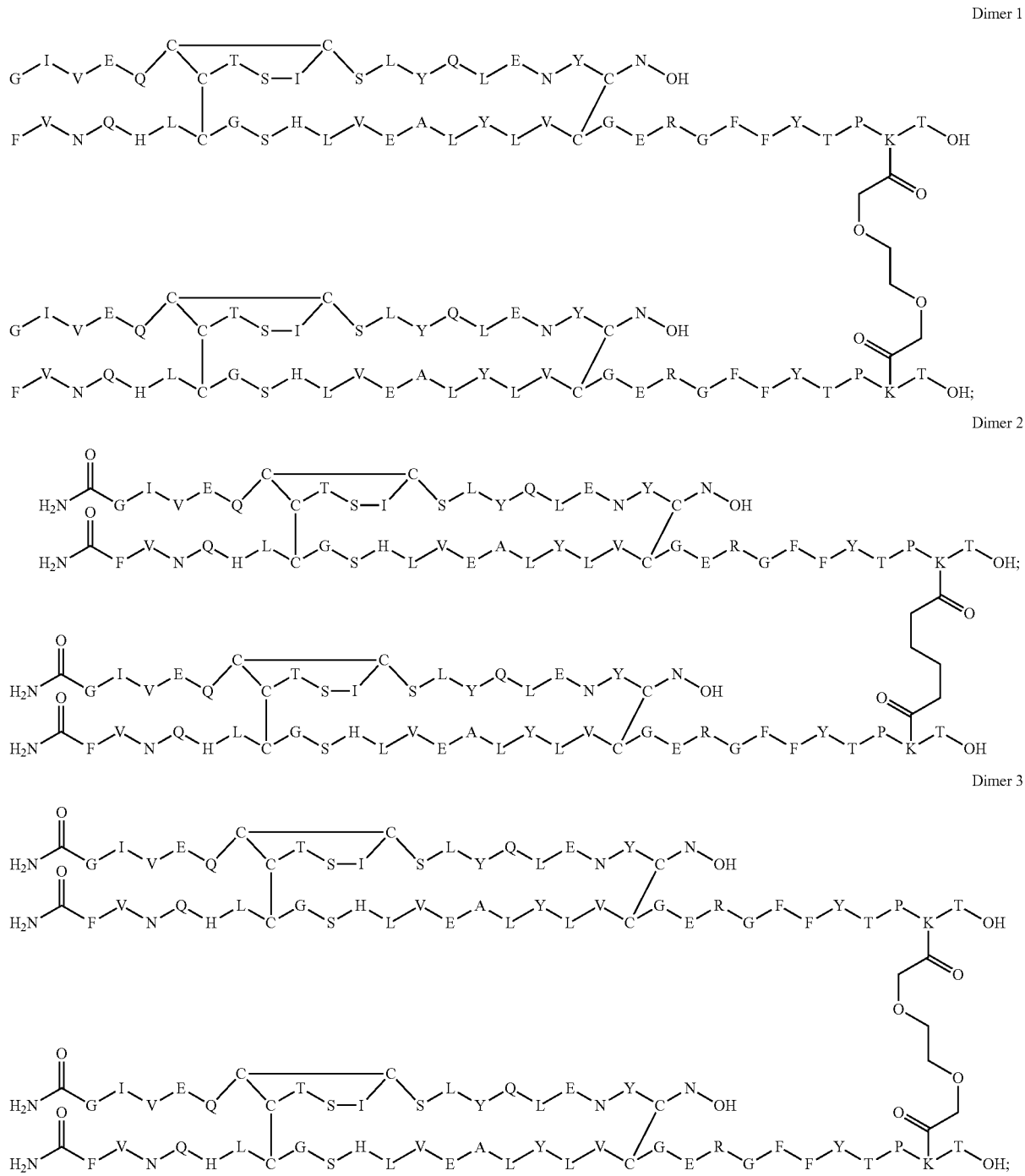

-continued
Dimer 4
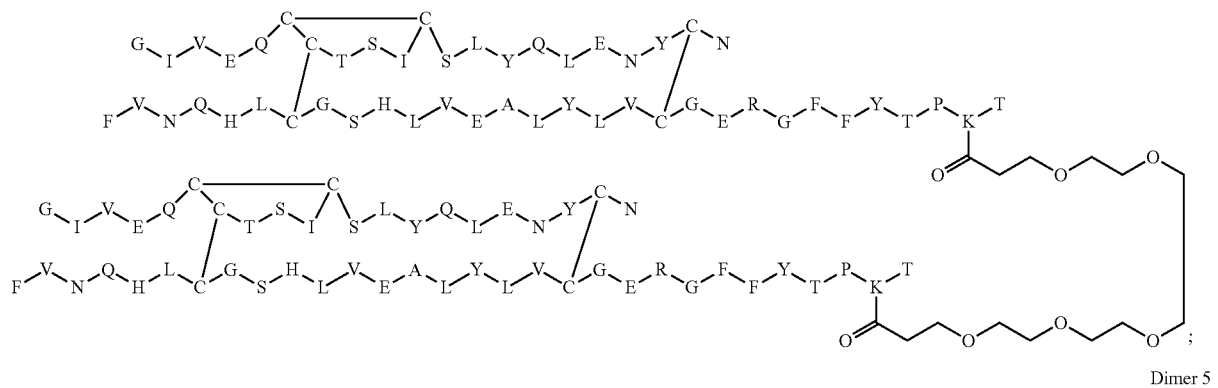
Dimer 5
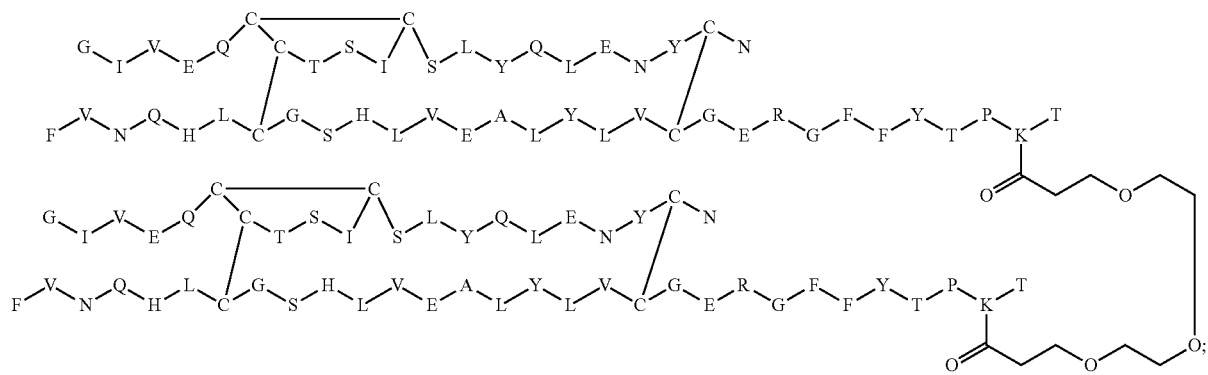
Dimer 6
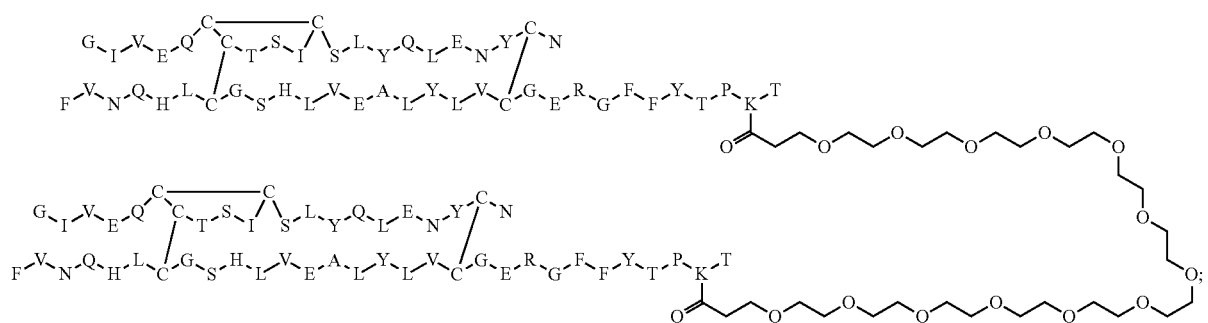
Dimer 7
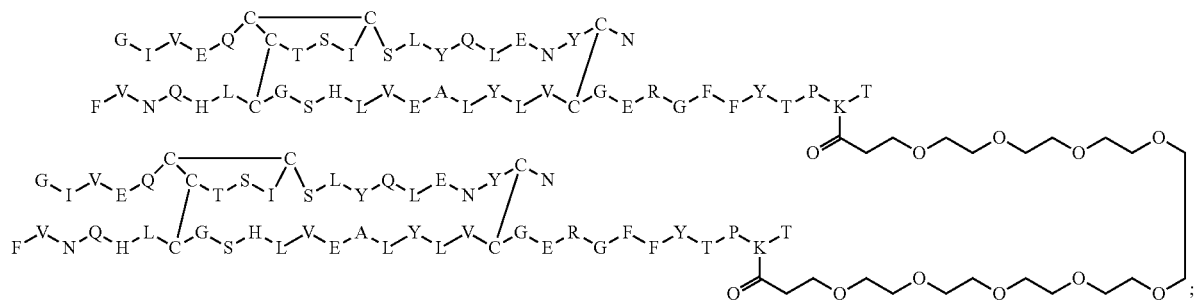

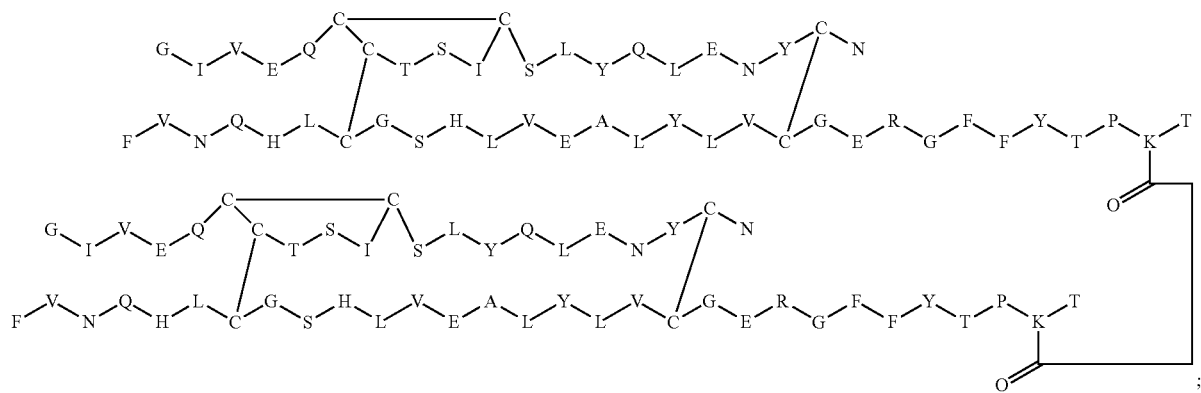
Dimer 8
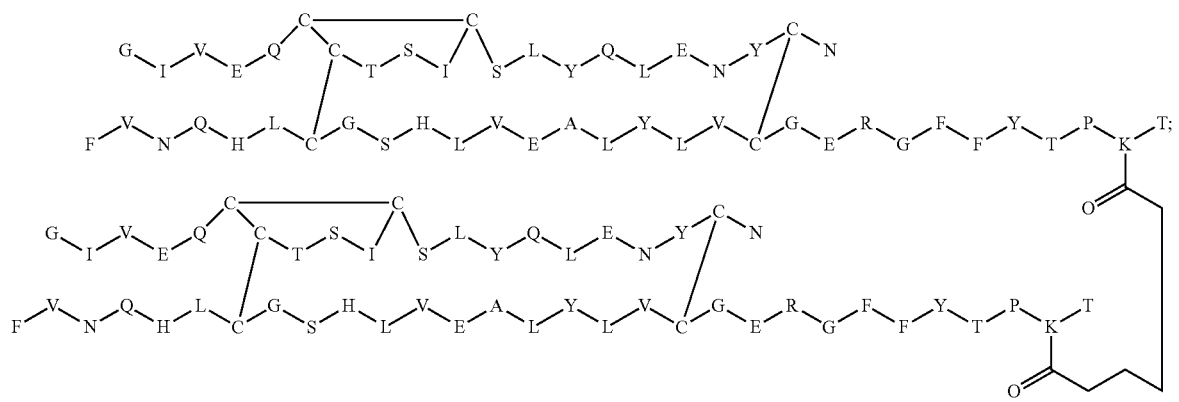
Dimer 9
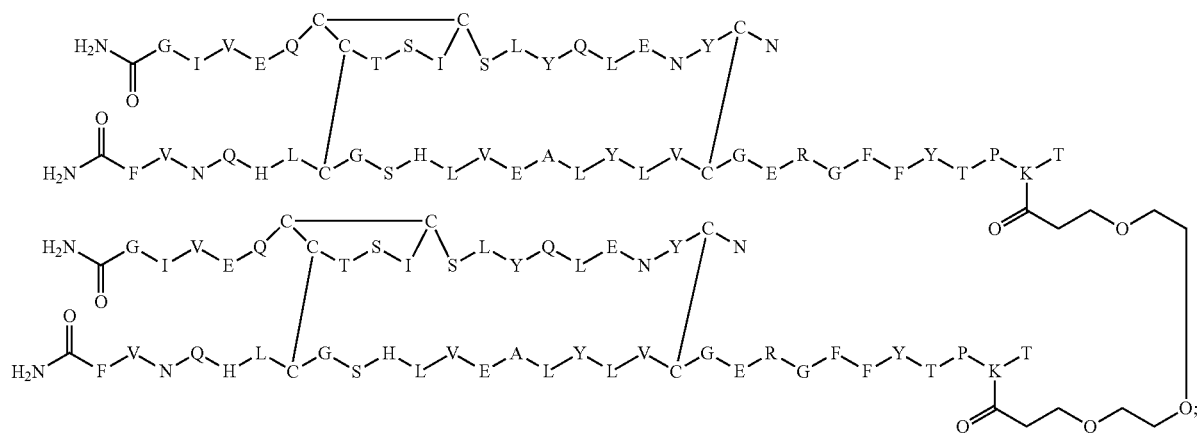
Dimer 10

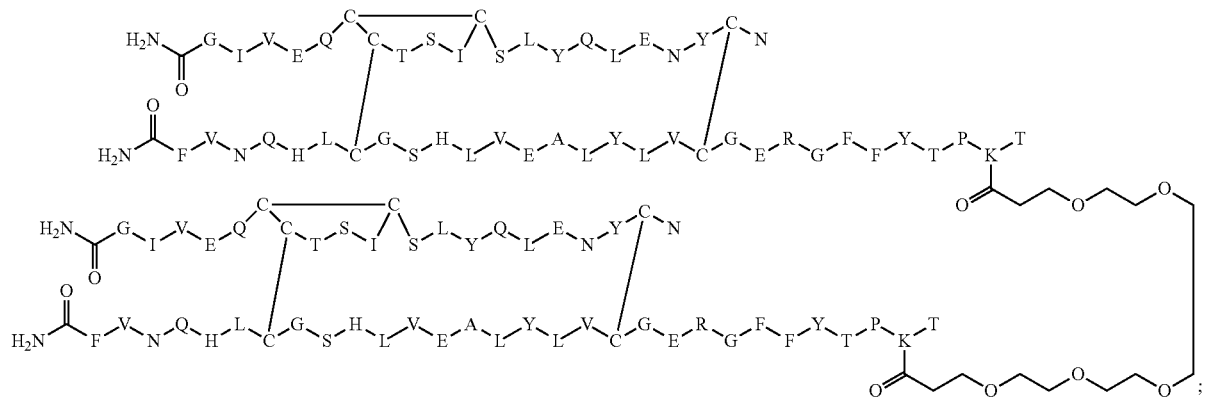
Dimer 11
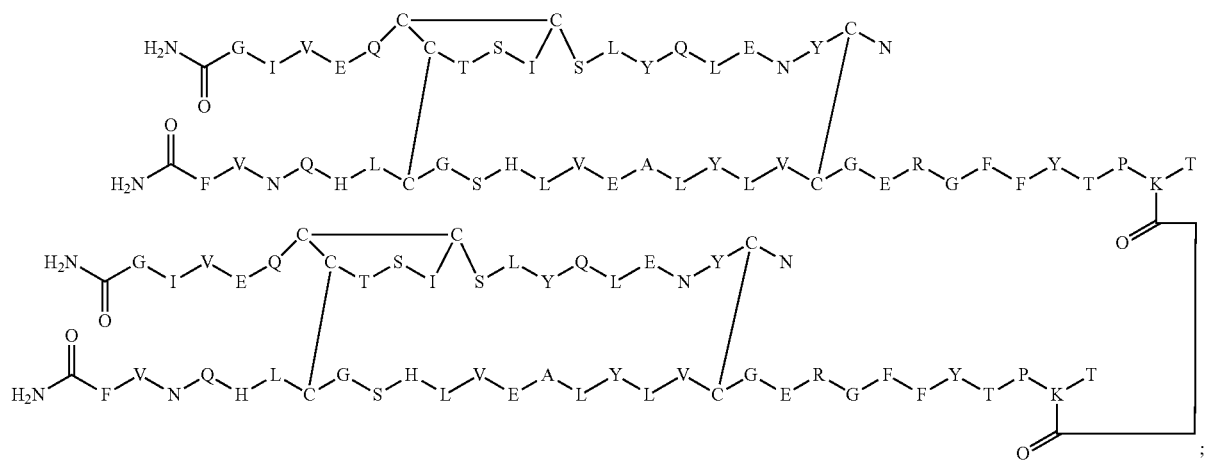
Dimer 12
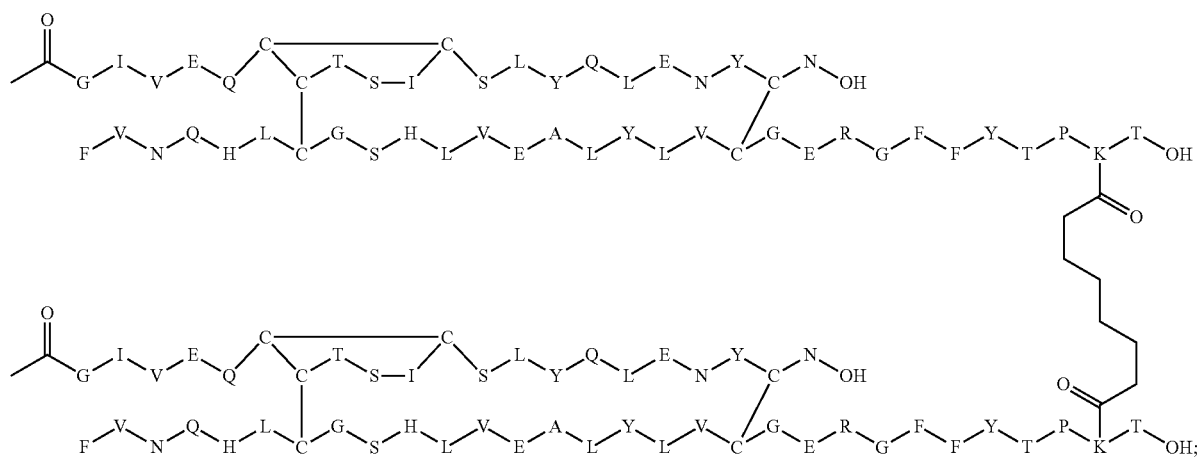
Dimer 13

-continued
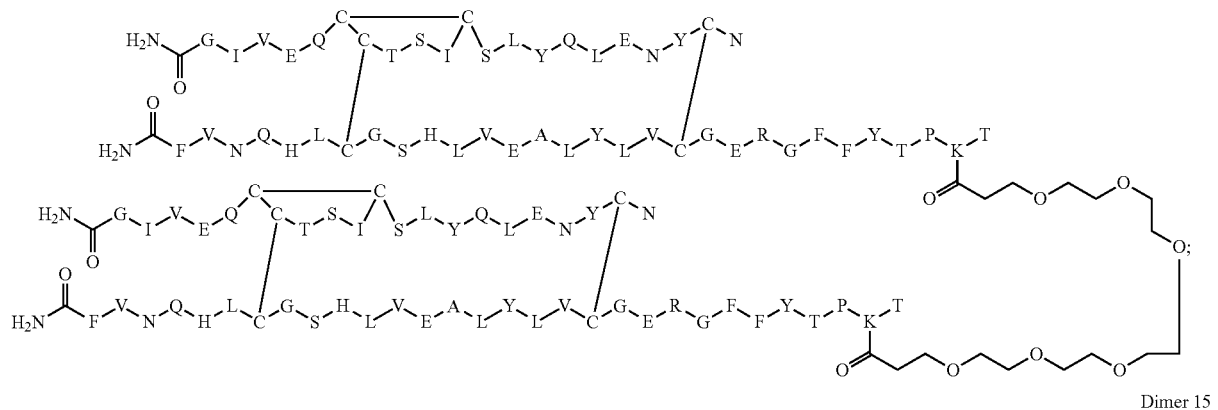
Dimer 14
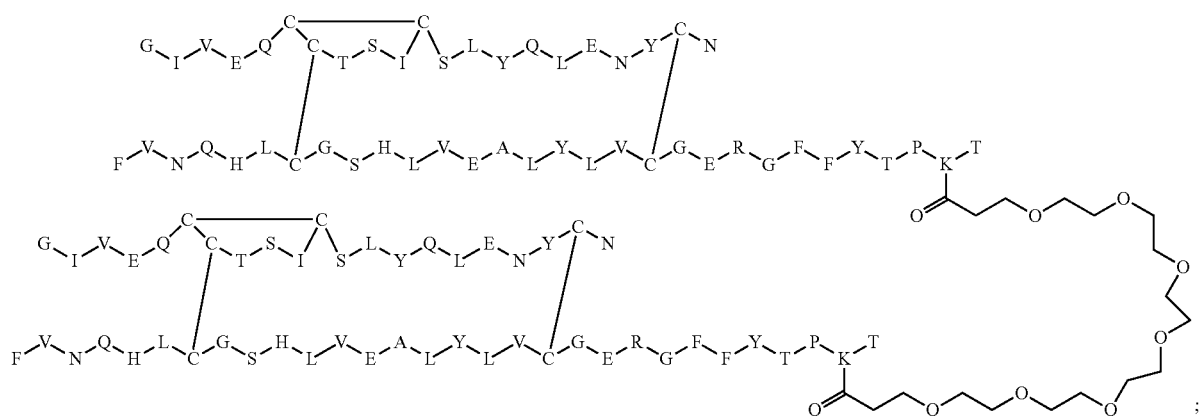
Dimer 15
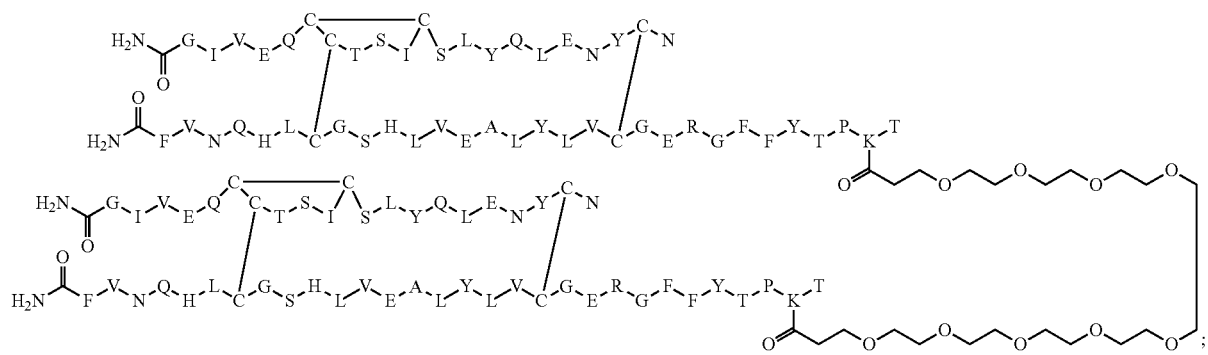
Dimer 16
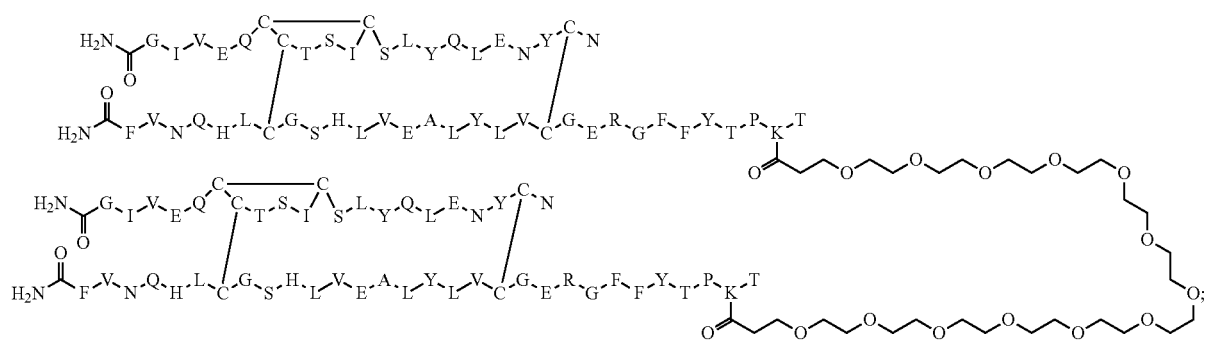
Dimer 17

Dimer 18
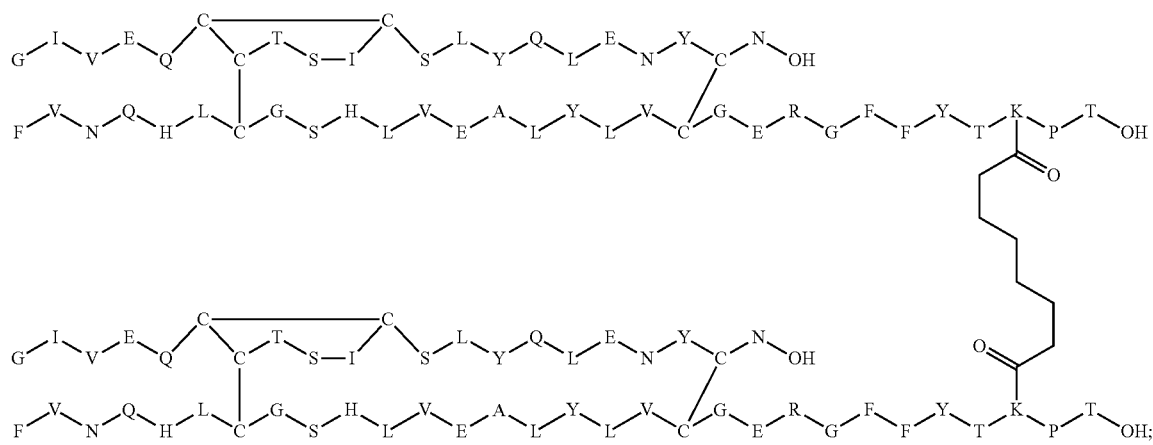
Dimer 19
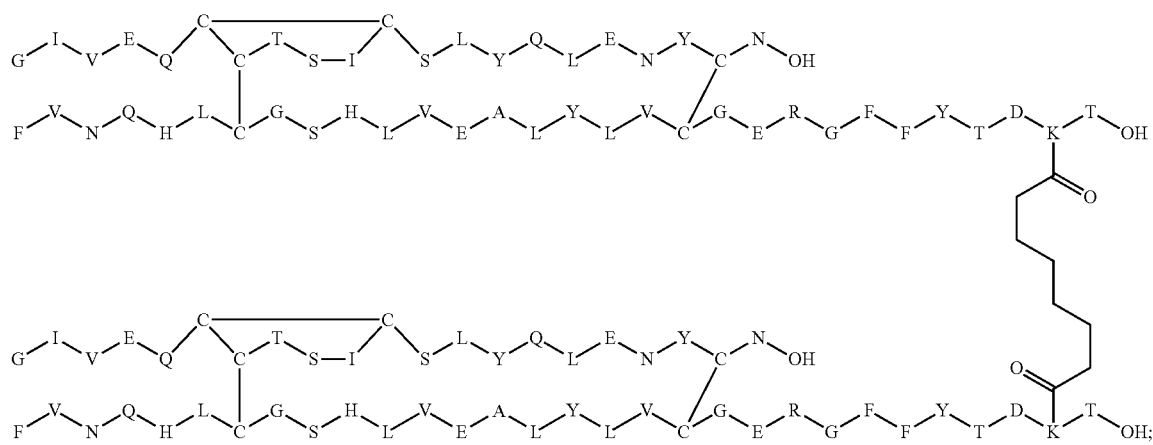
Dimer 20
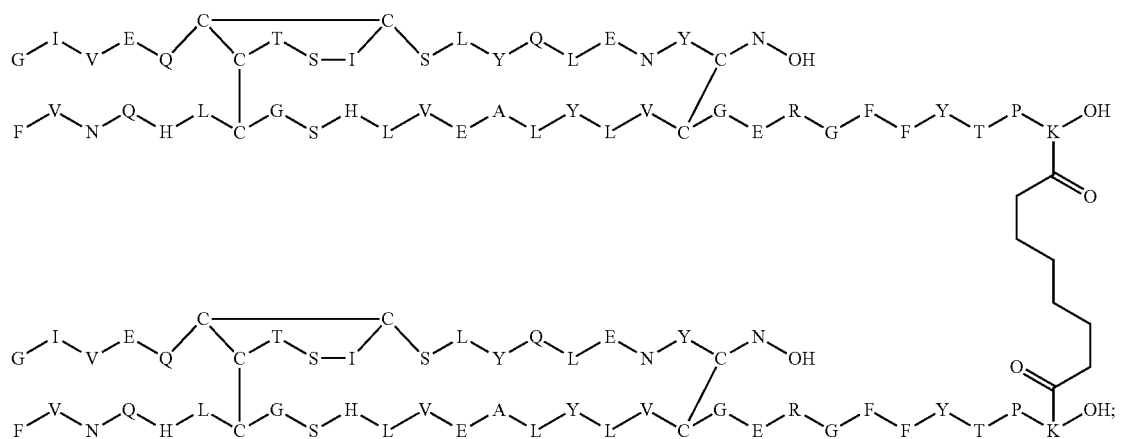

Dimer 21
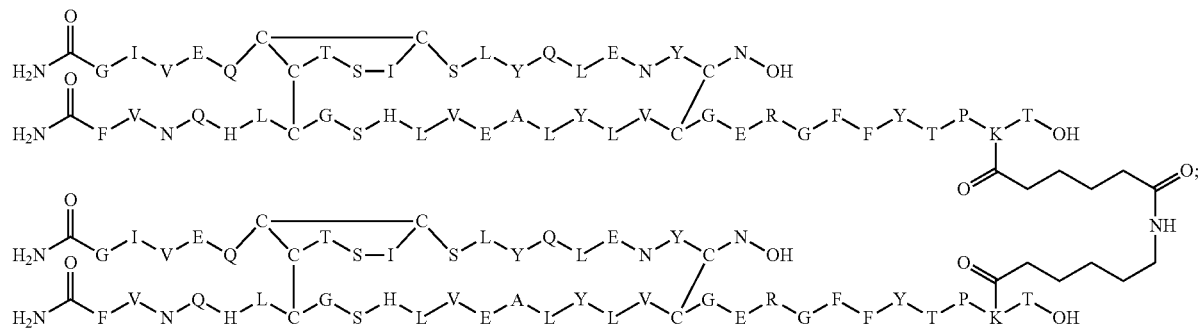
Dimer 22
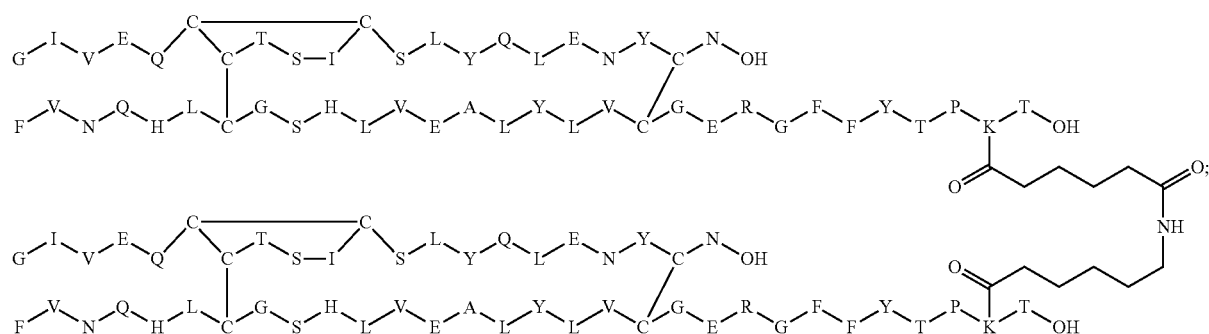
Dimer 23
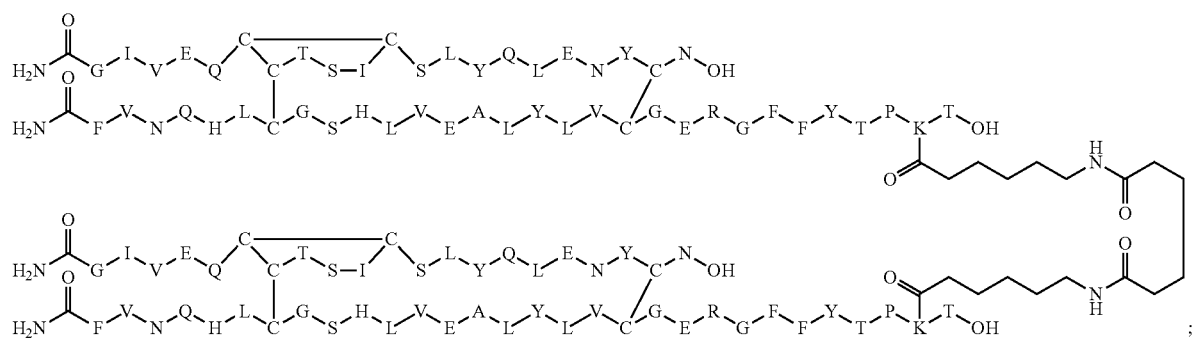
Dimer 24
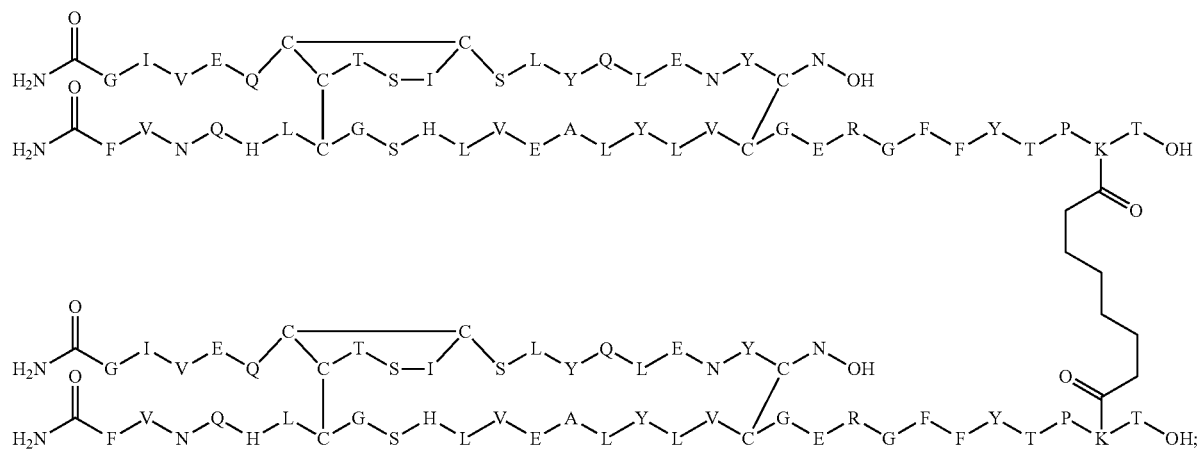

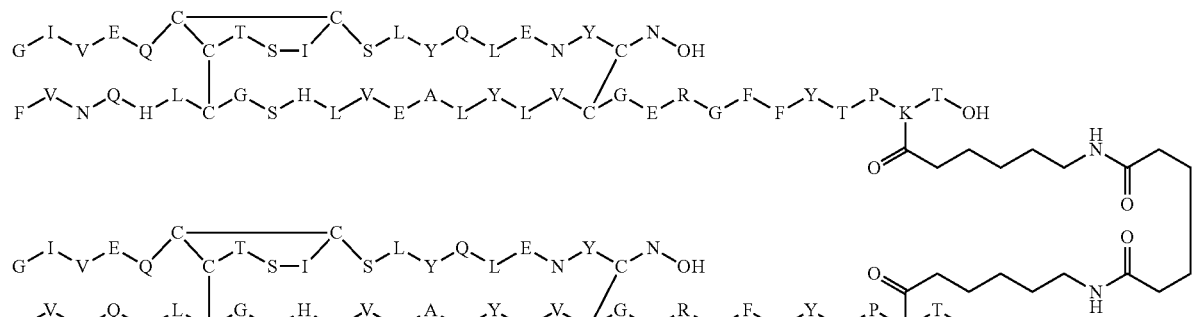
Dimer 25
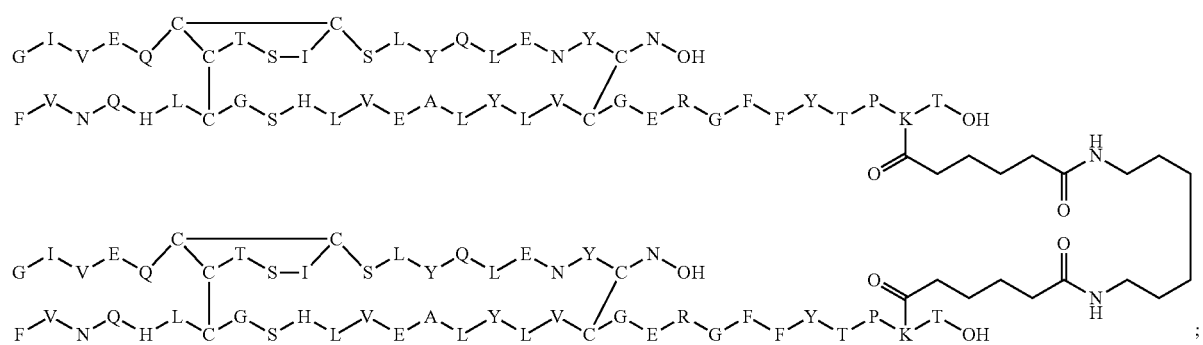
Dimer 26
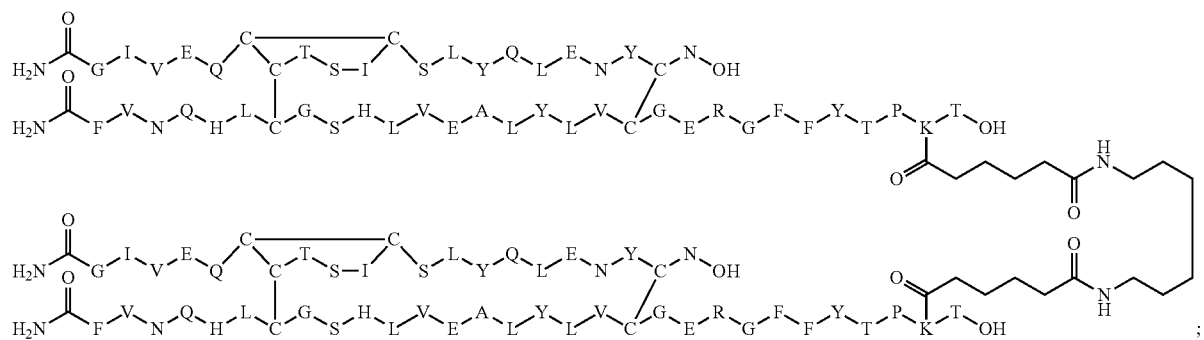
Dimer 27
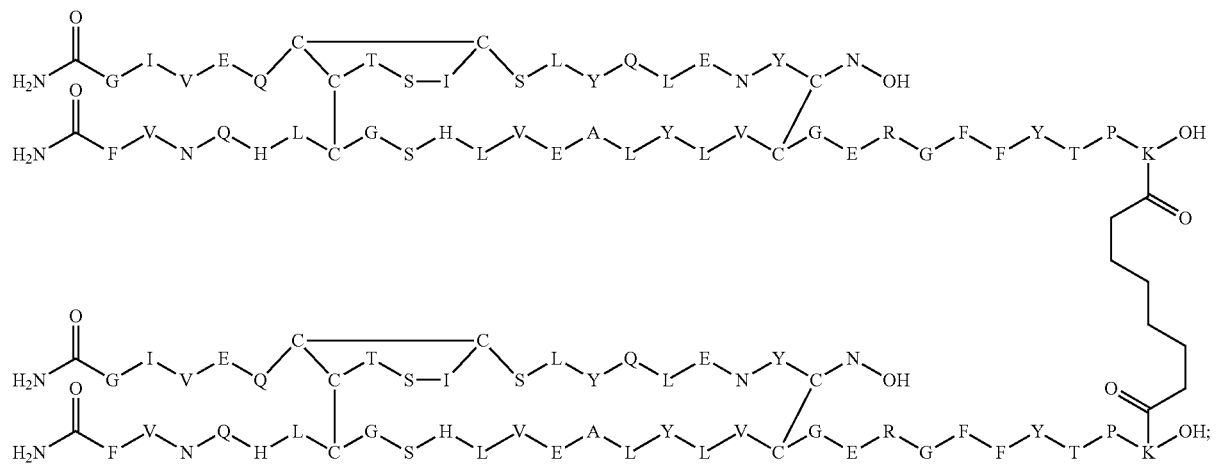
Dimer 28

-continued
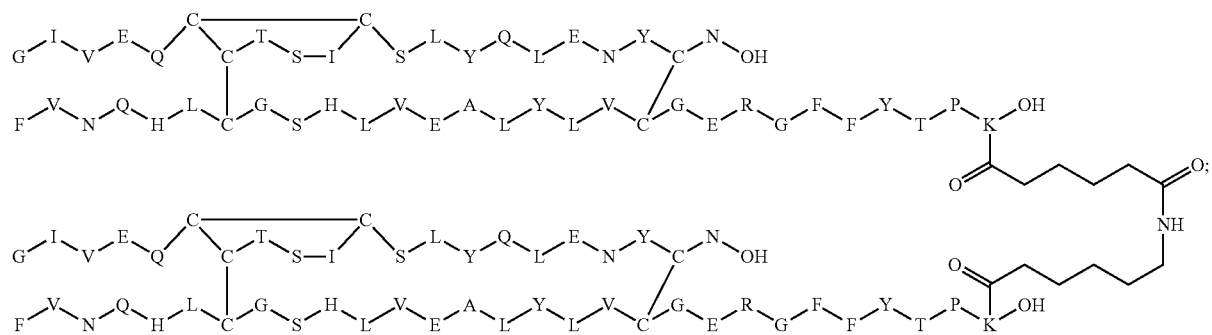
Dimer 29
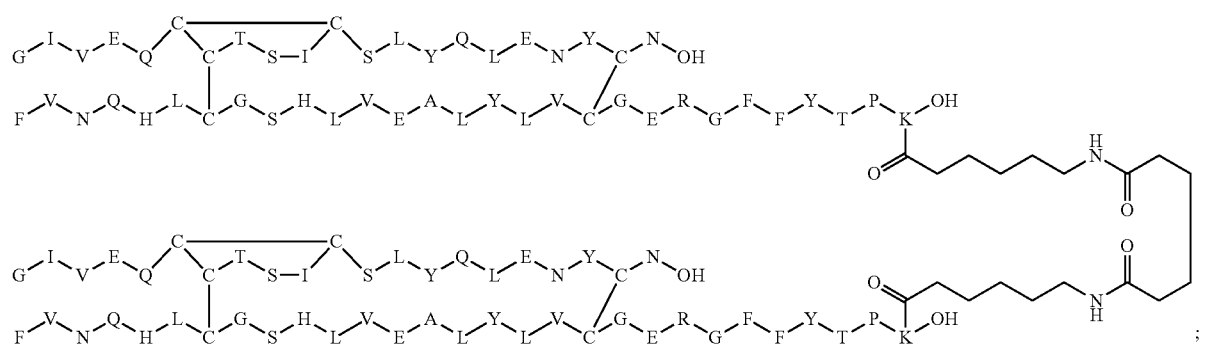
Dimer 30
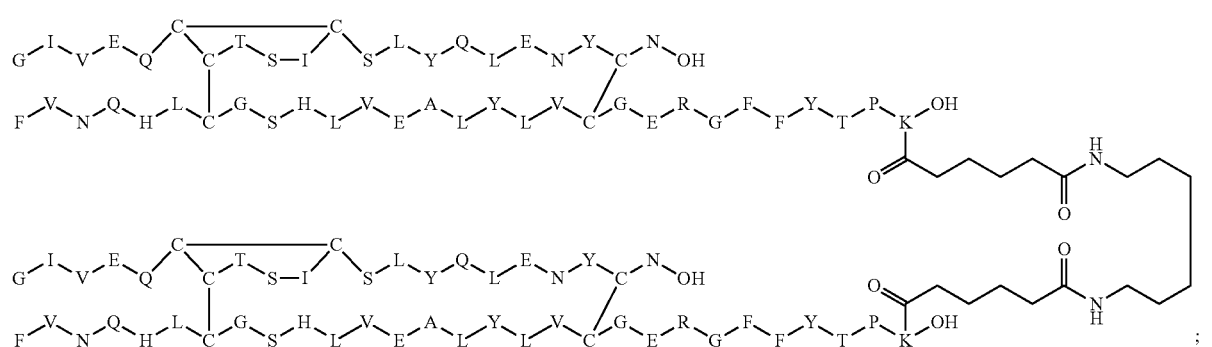
Dimer 31
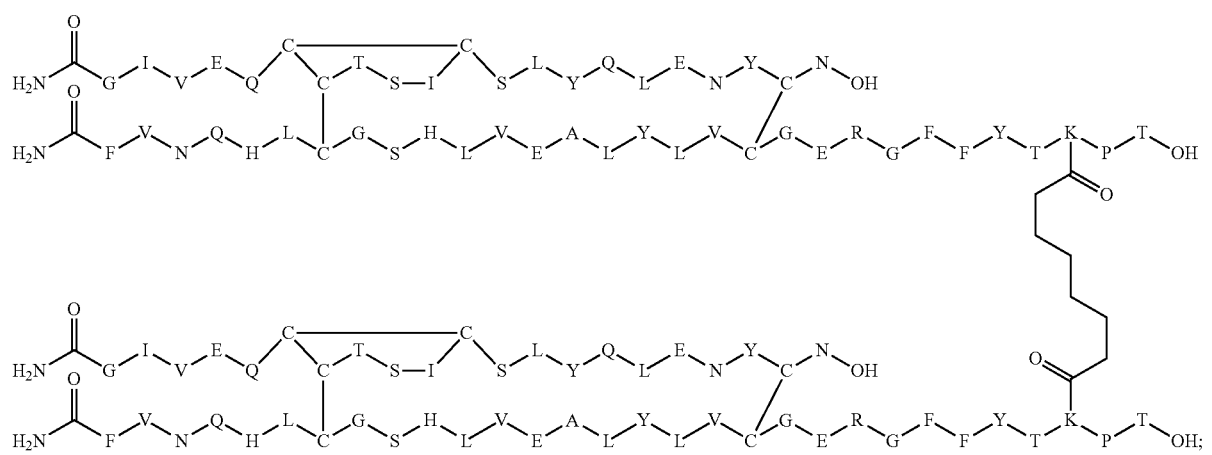
Dimer 32

-continued
Dimer 33
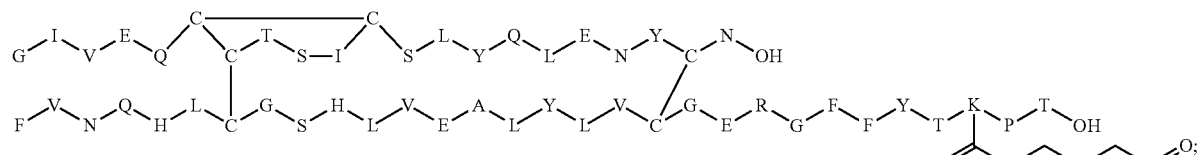
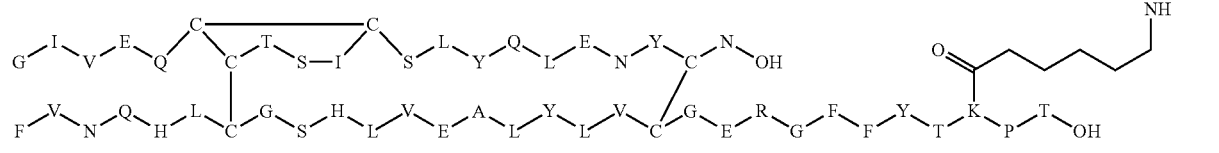
Dimer 34
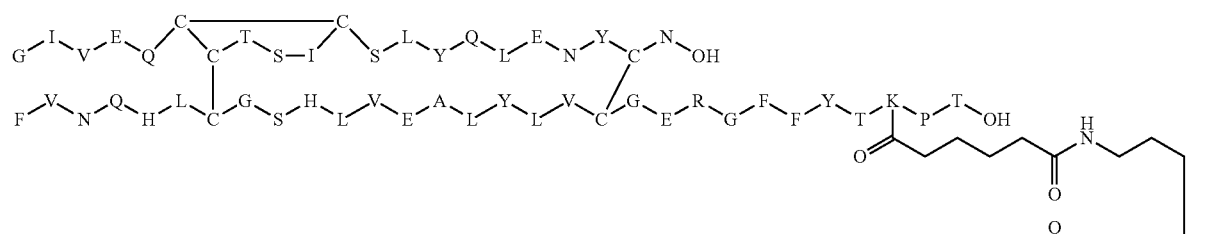
Dimer 35
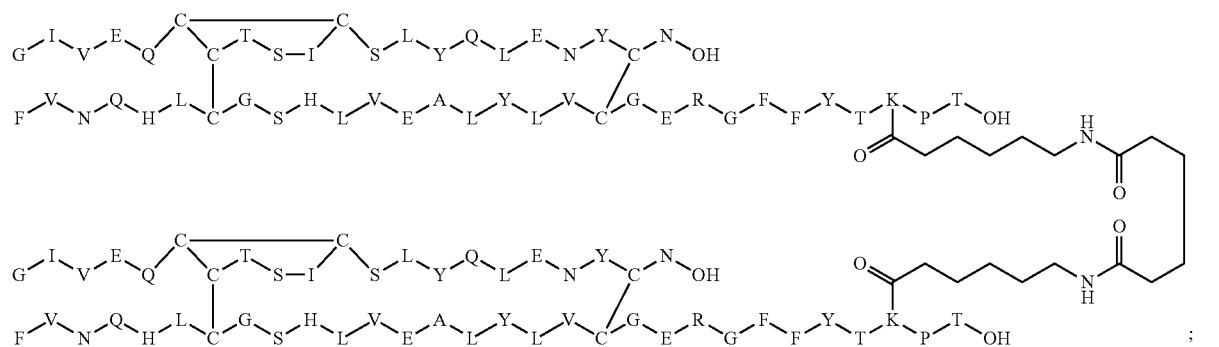
Dimer 36
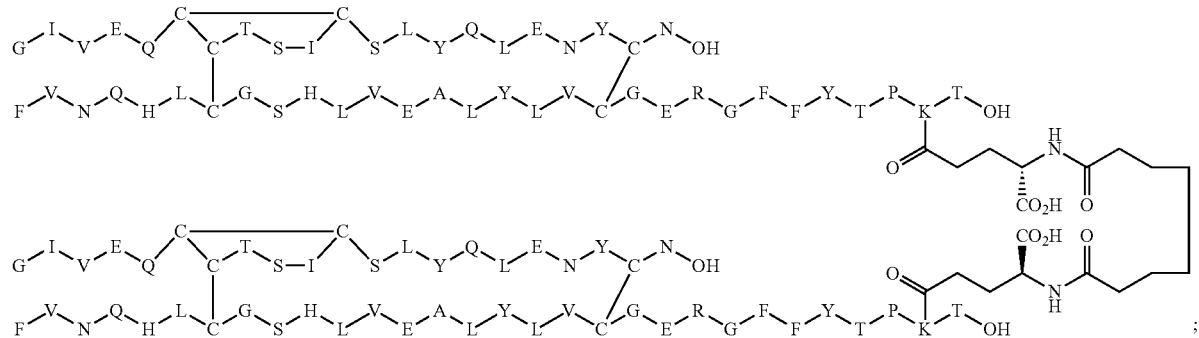

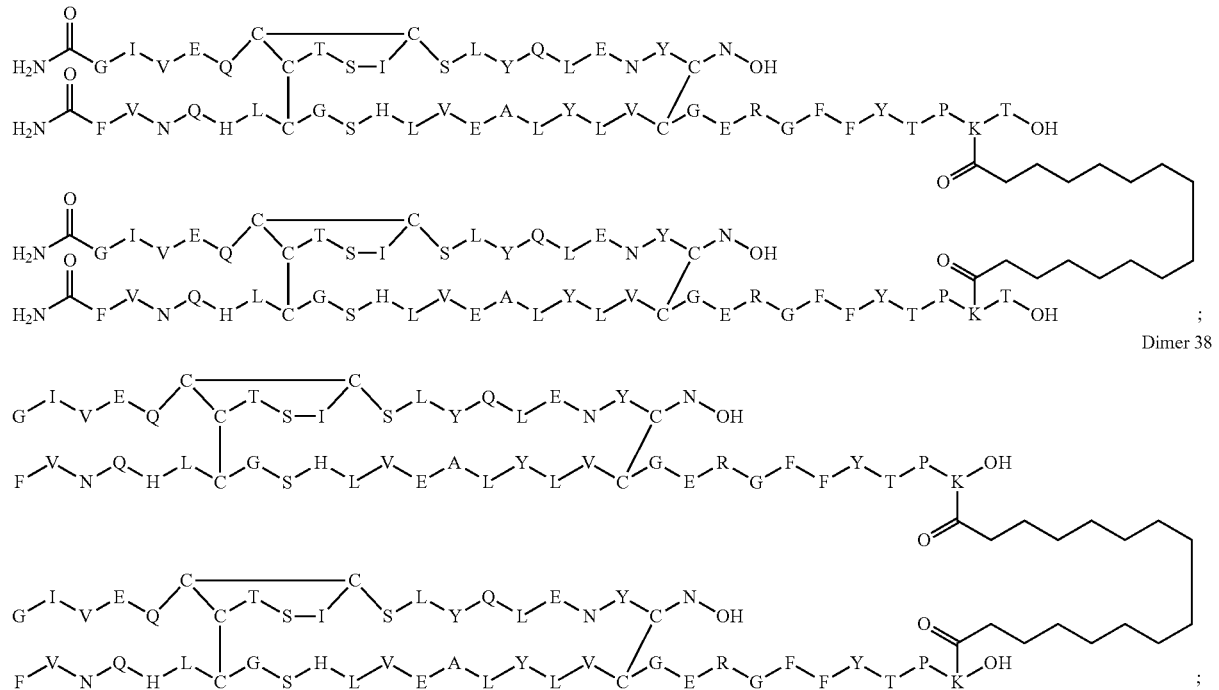
Dimer 37
Dimer 38
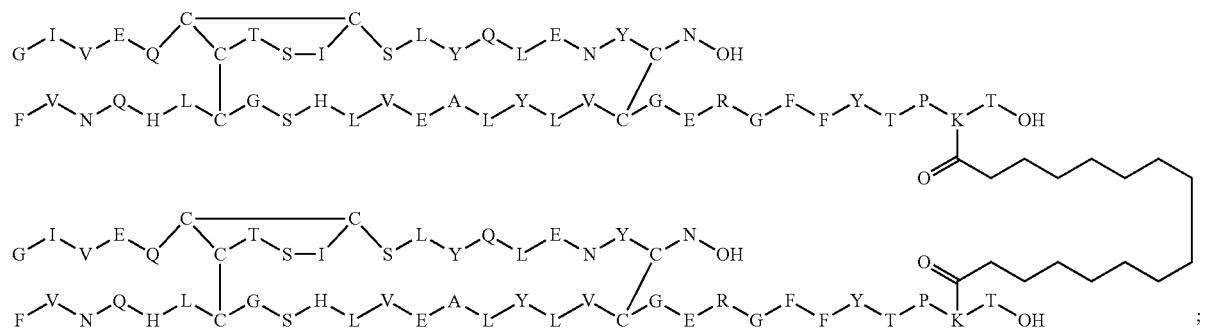
Dimer 39
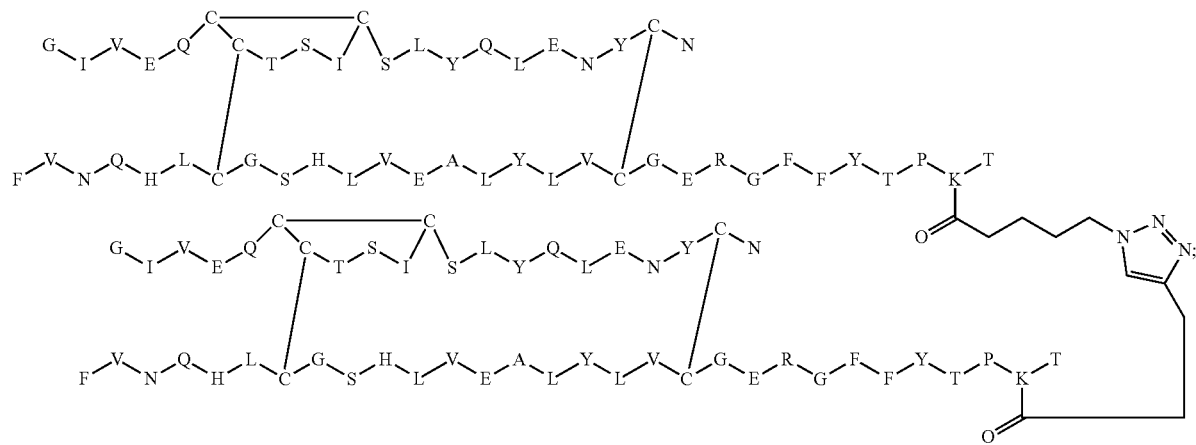
Dimer 40

Dimer 41
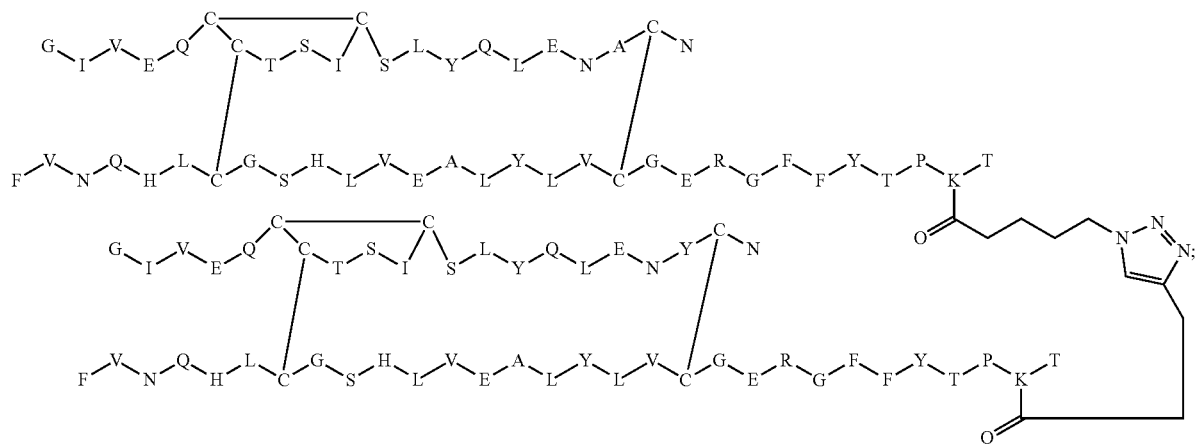
Dimer 42
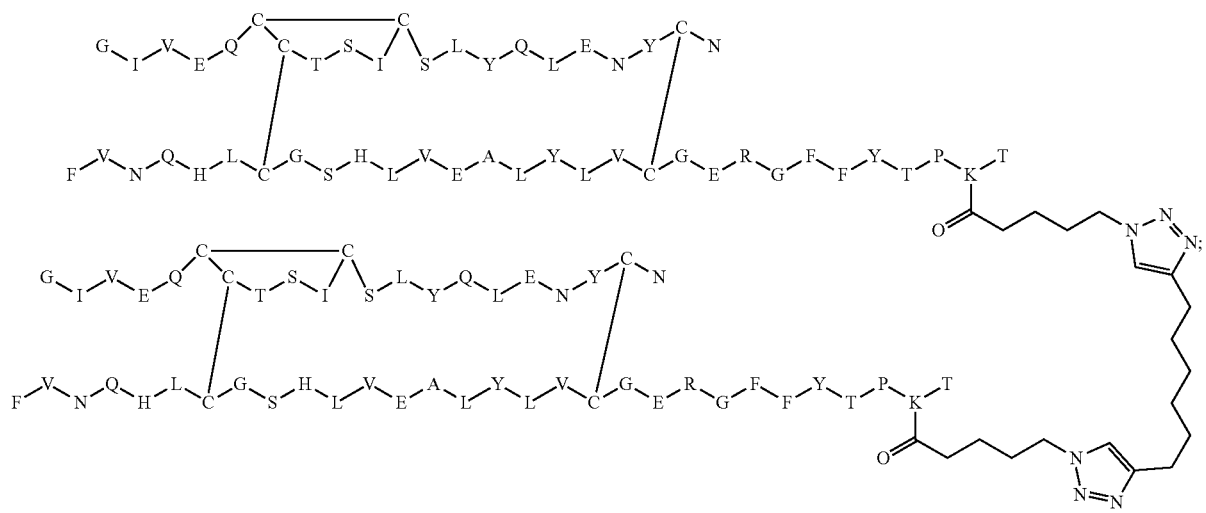
Dimer 43
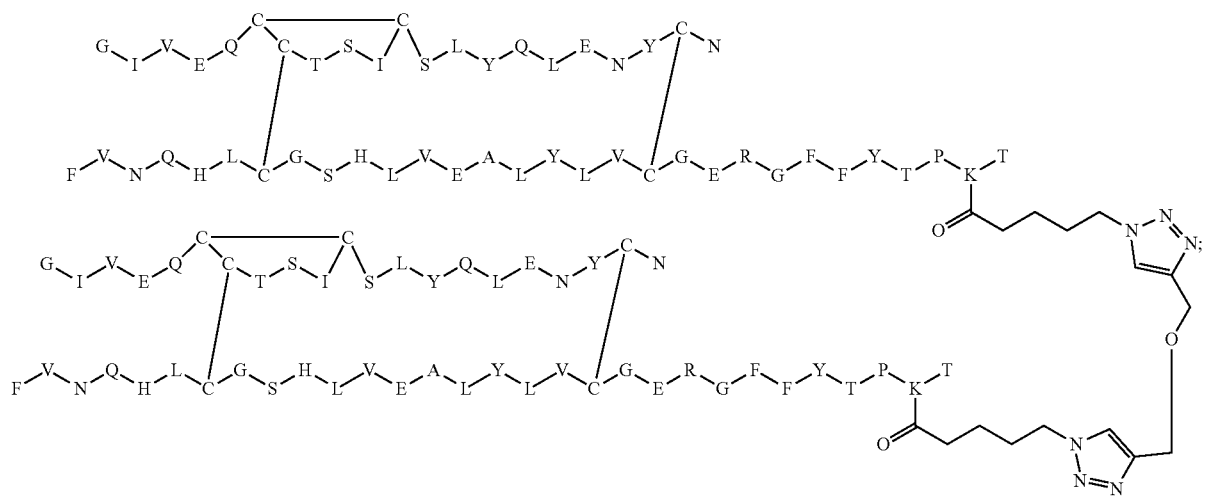

Dimer 44
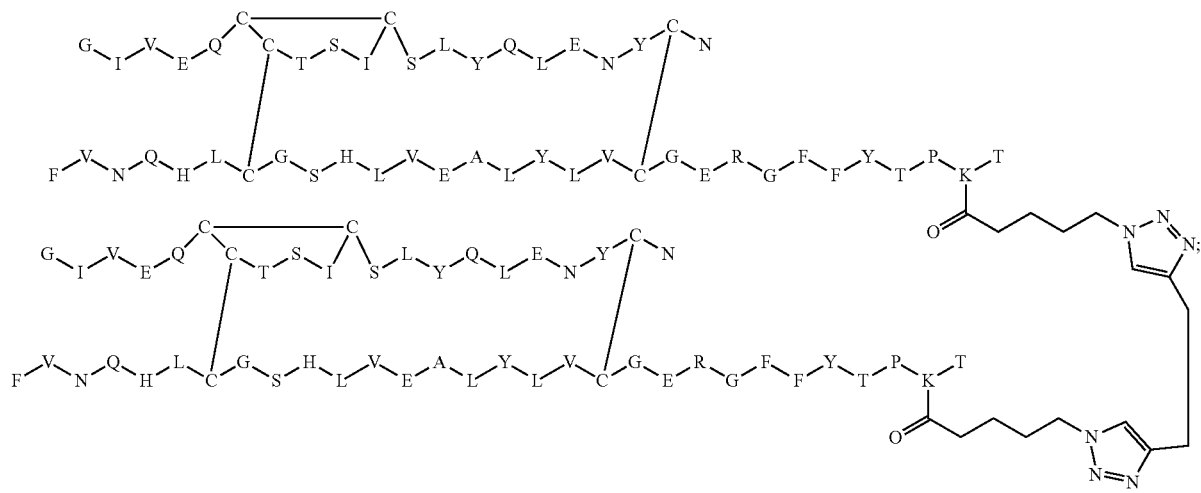
Dimer 45
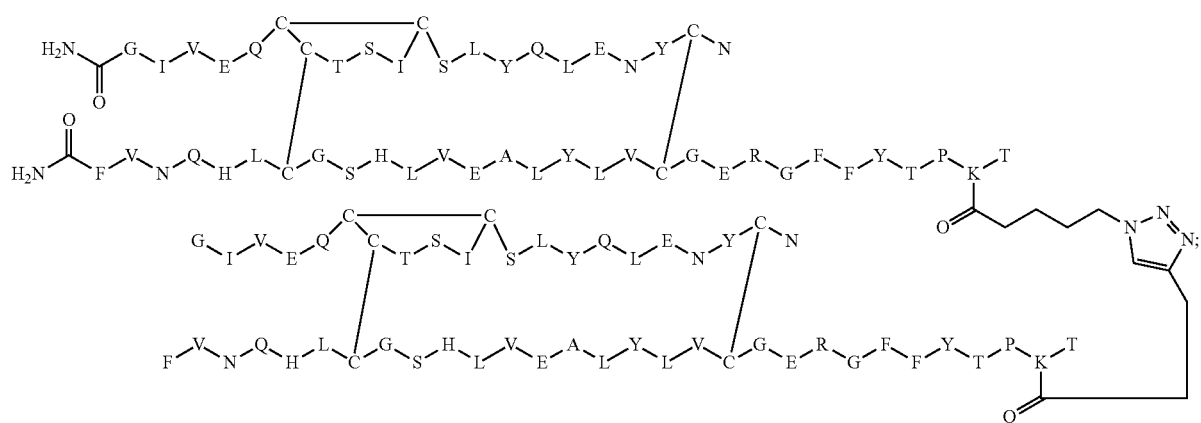
Dimer 46
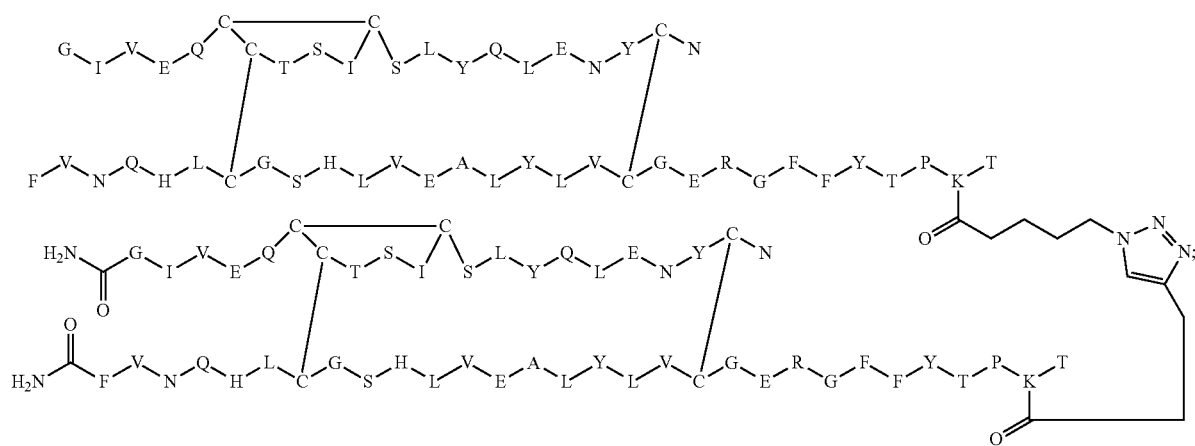

Dimer 47
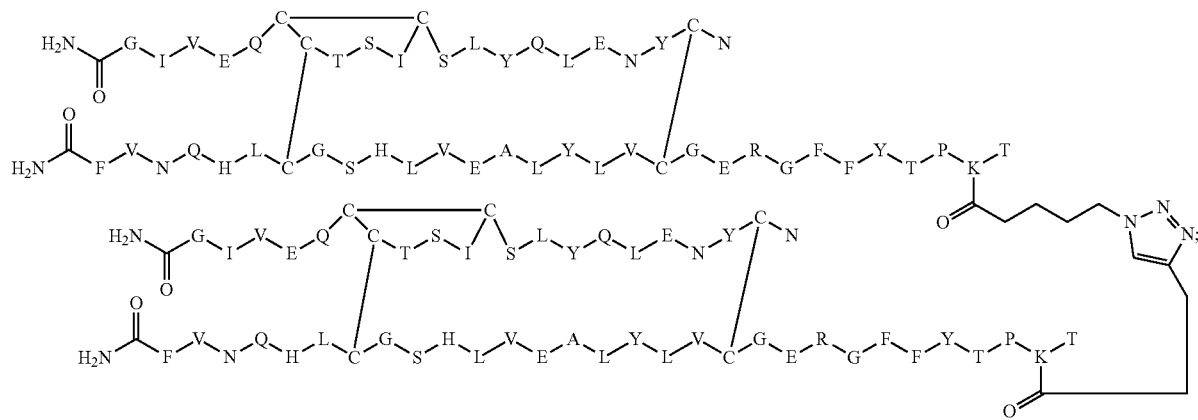
Dimer 48
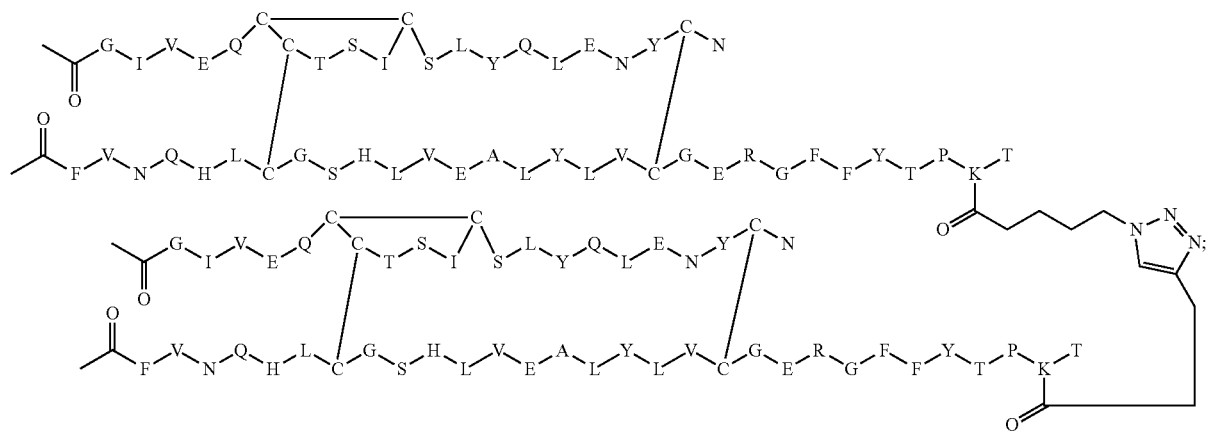
Dimer 49
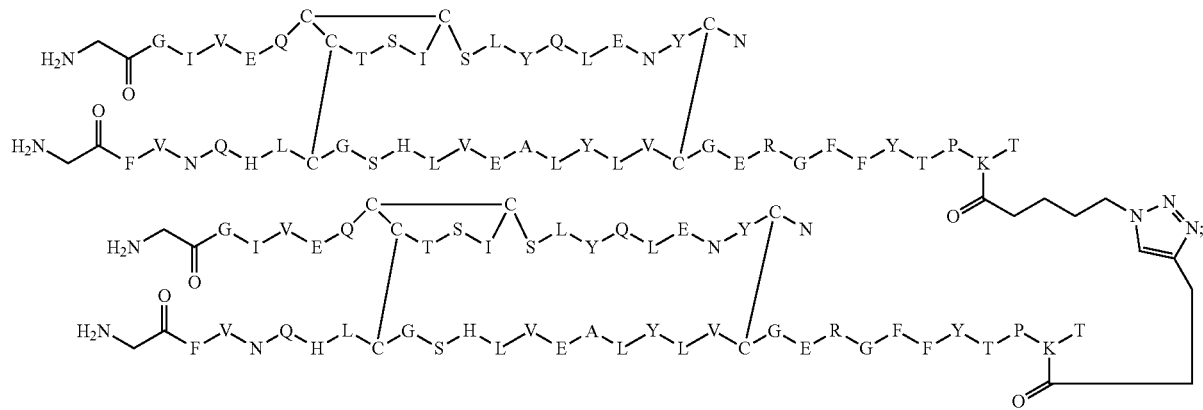

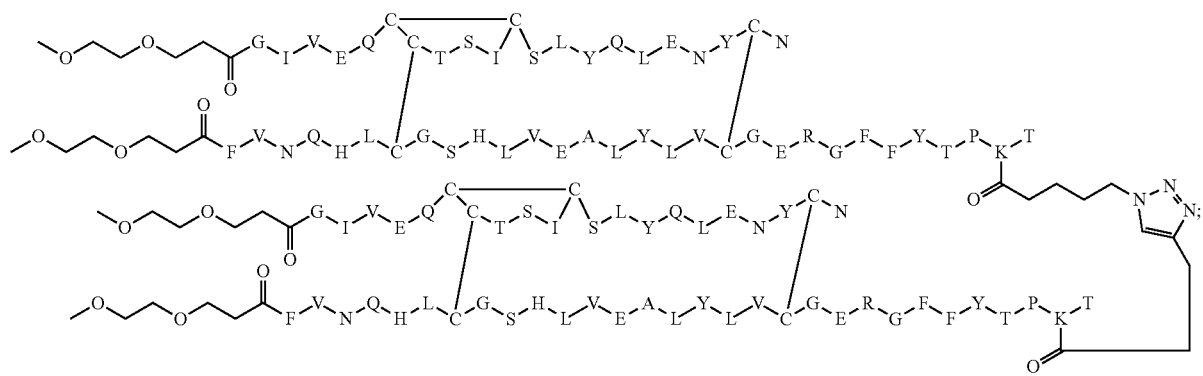
Dimer 50
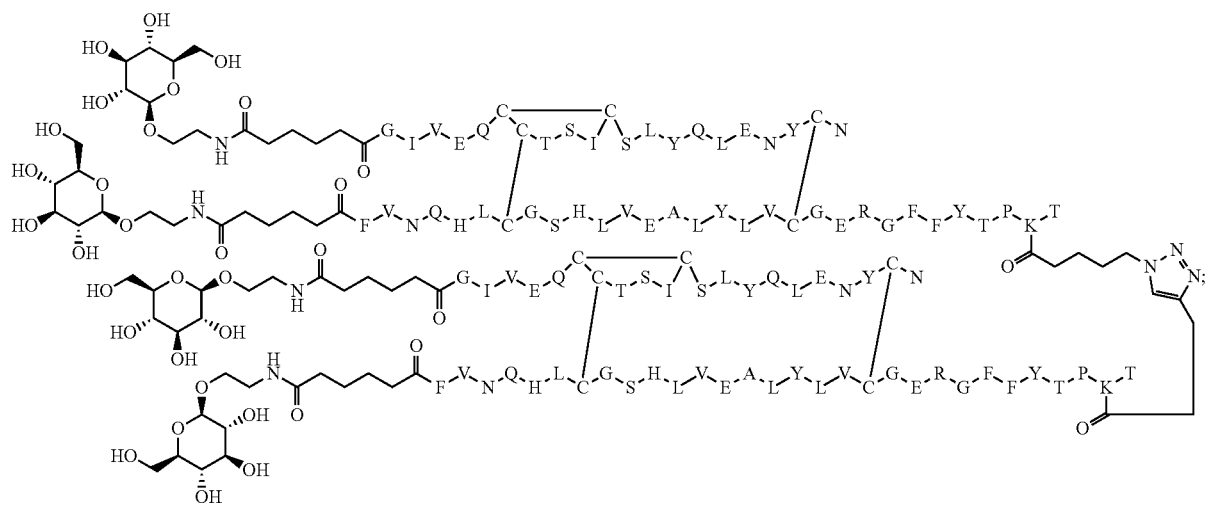
Dimer 51
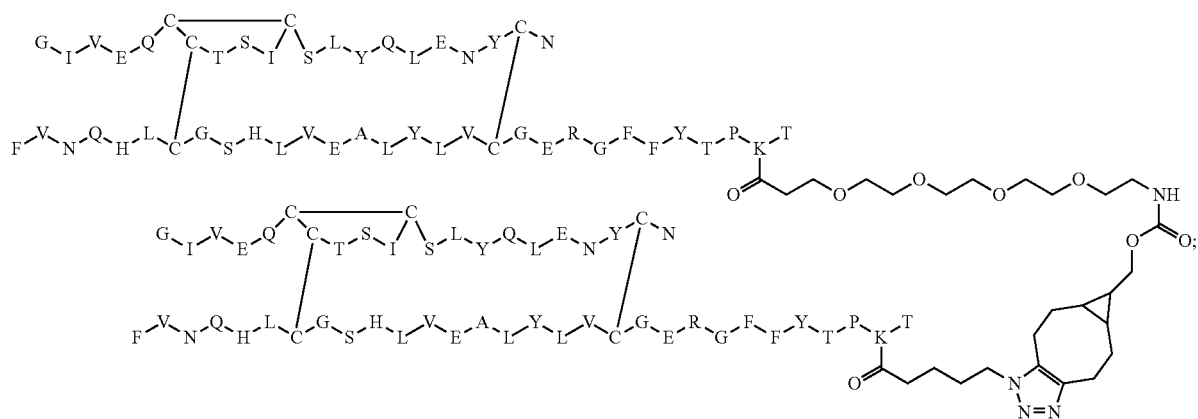
Dimer 52

-continued
Dimer 53
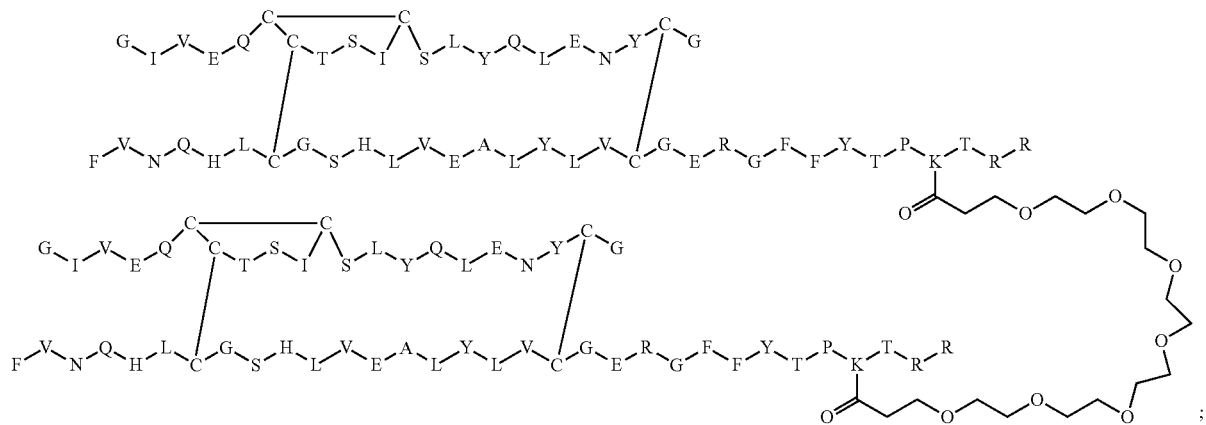
Dimer 54
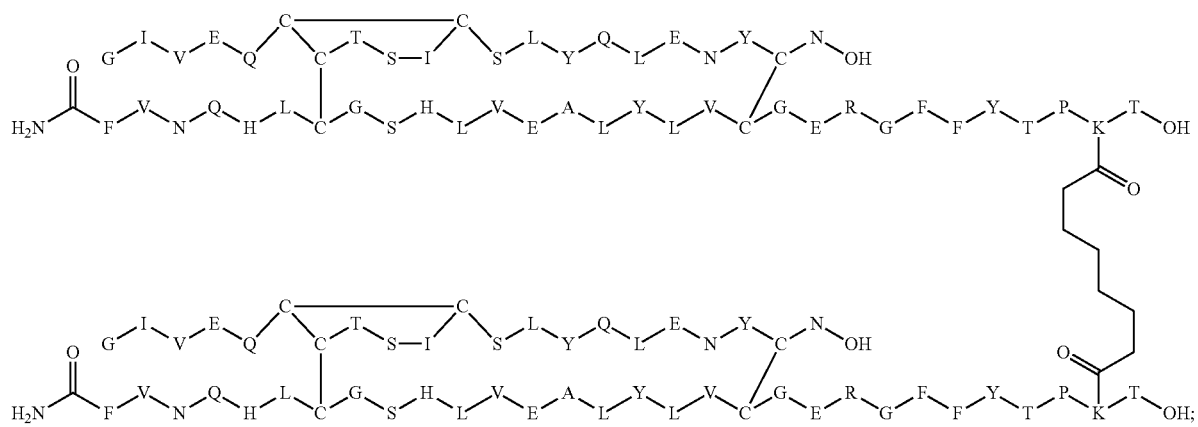
Dimer 55
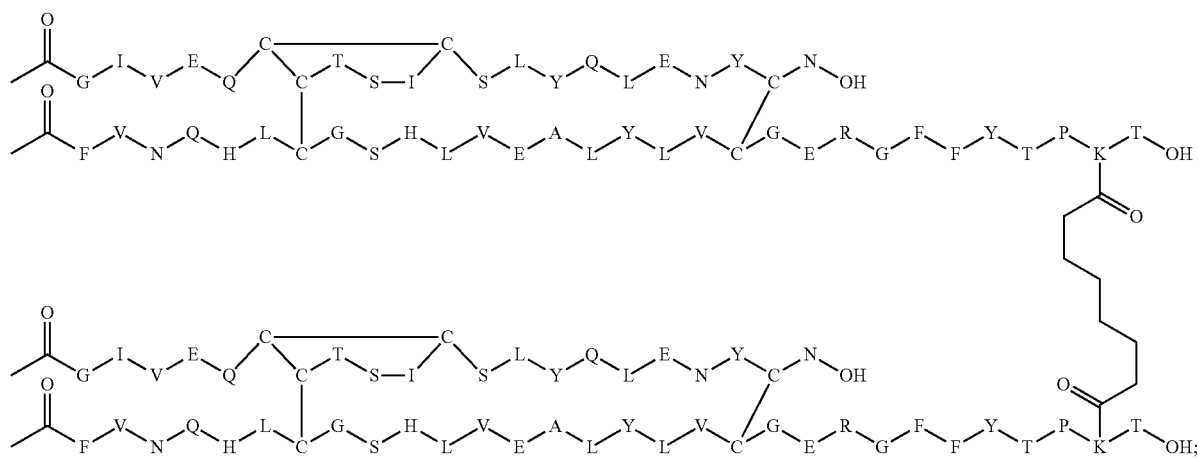

Dimer 56
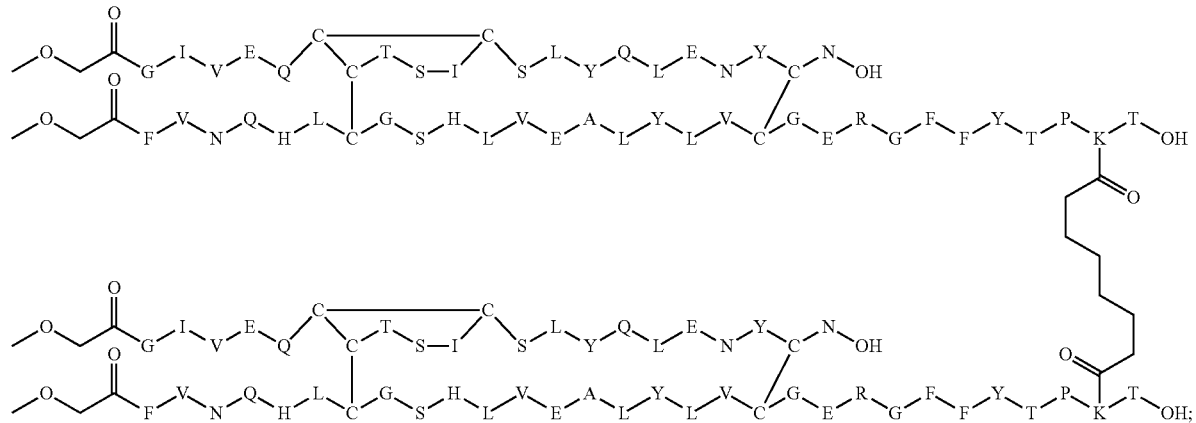
Dimer 57
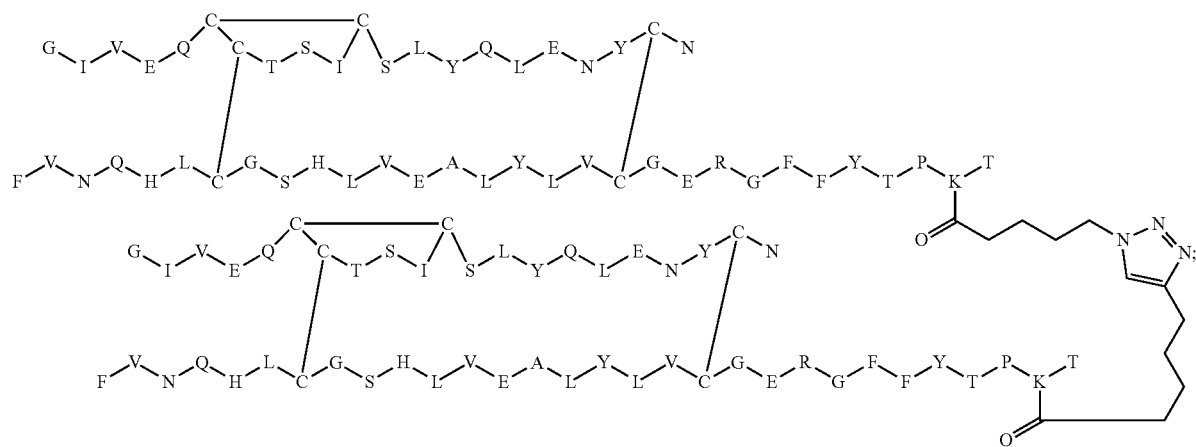
Dimer 58
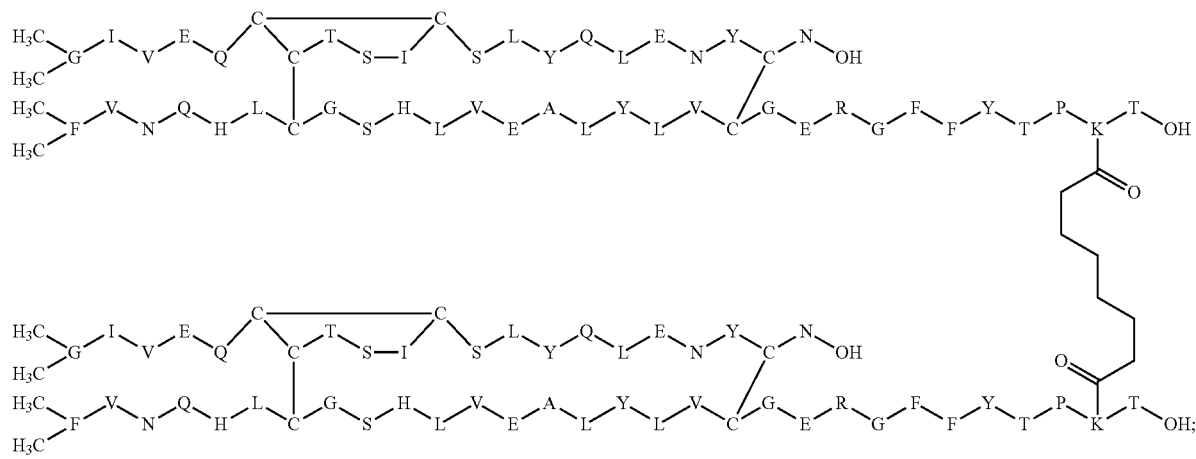

Dimer 59
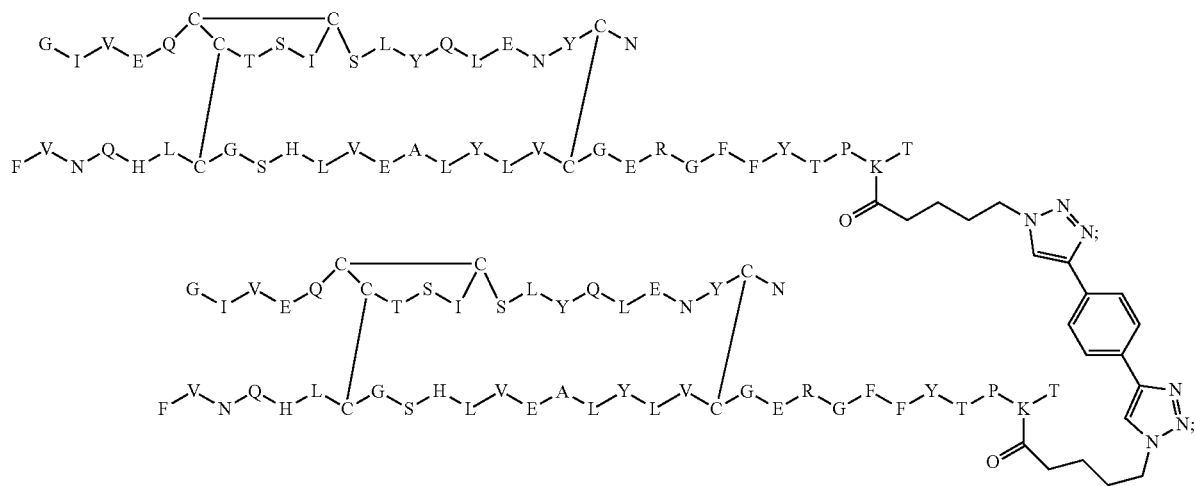
Dimer 60
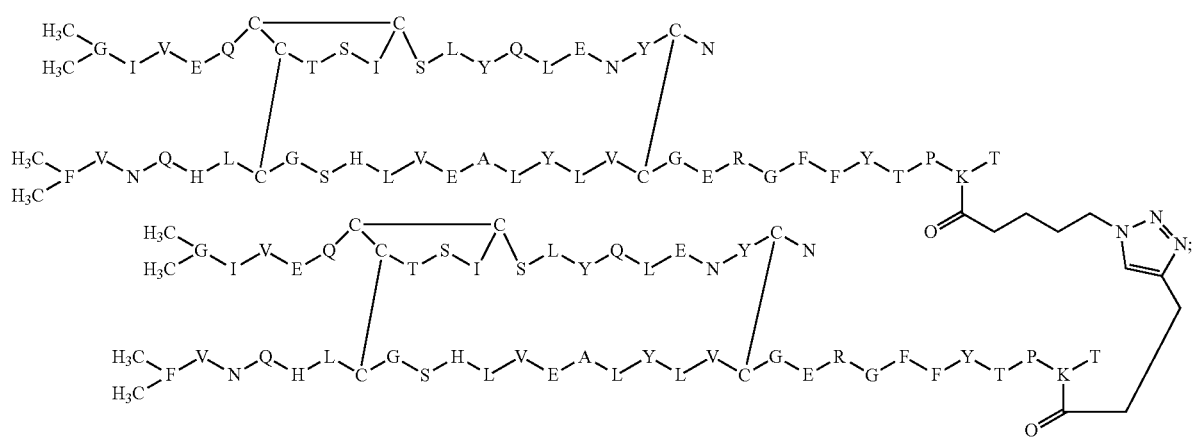
Dimer 61
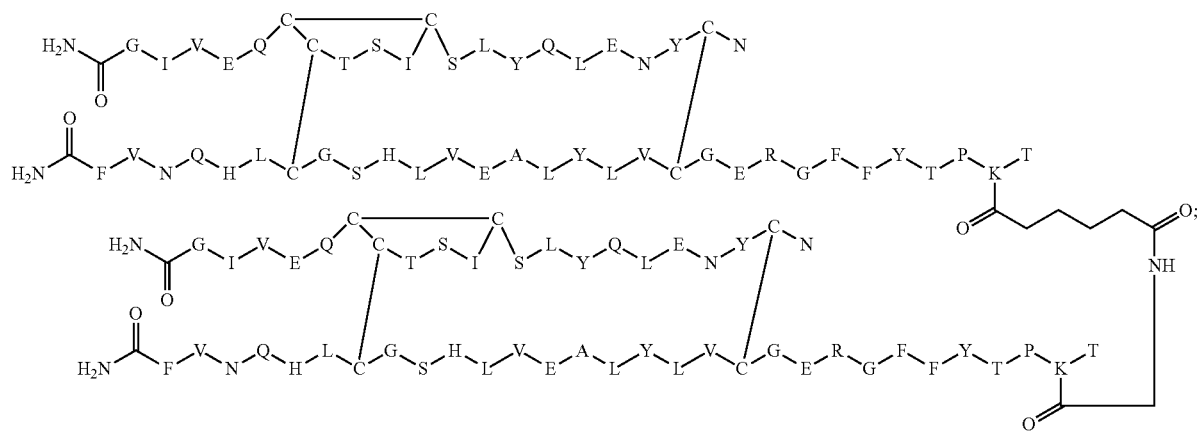

Dimer 62
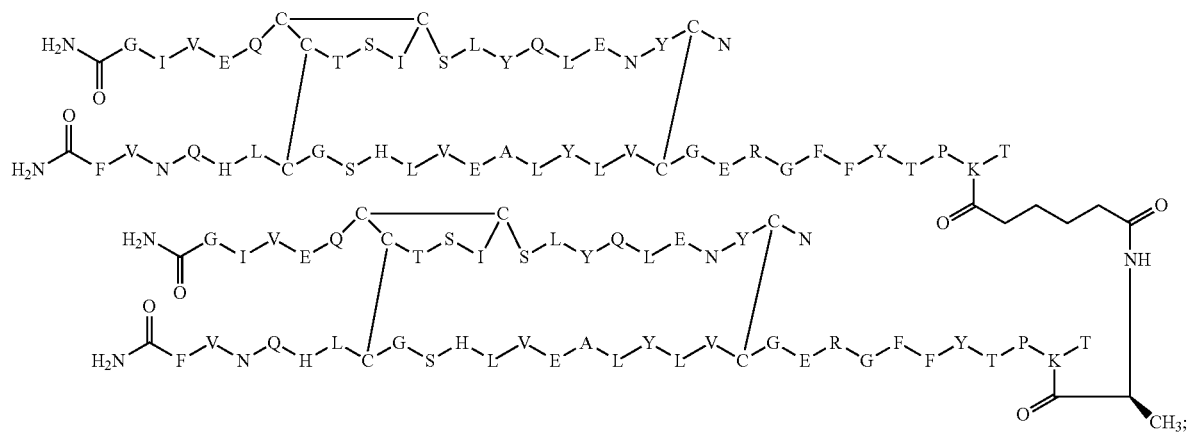
Dimer 63
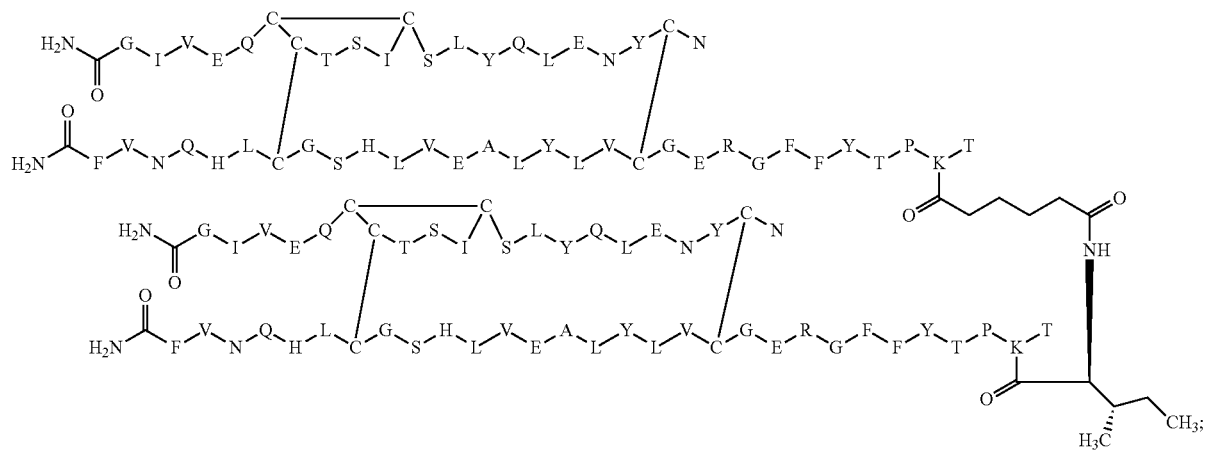
Dimer 64
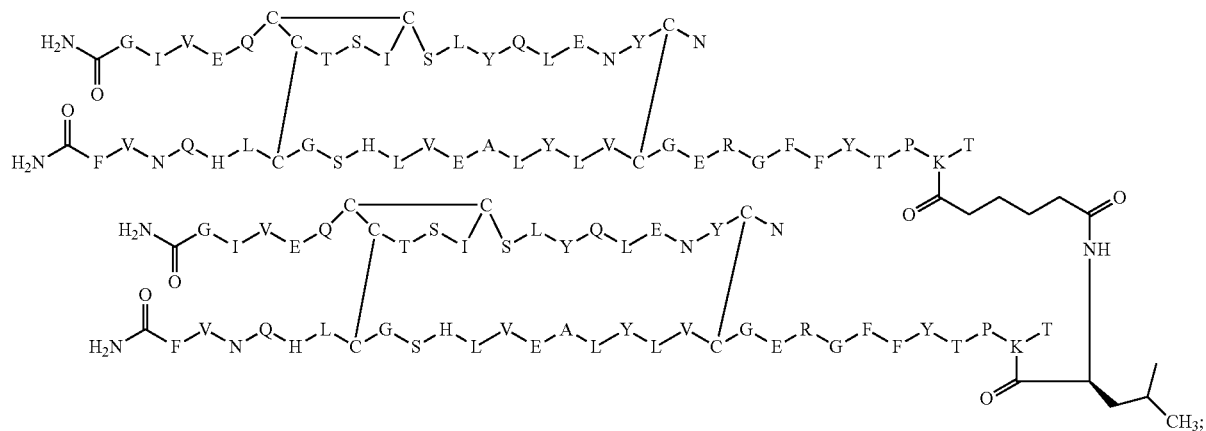

Dimer 65
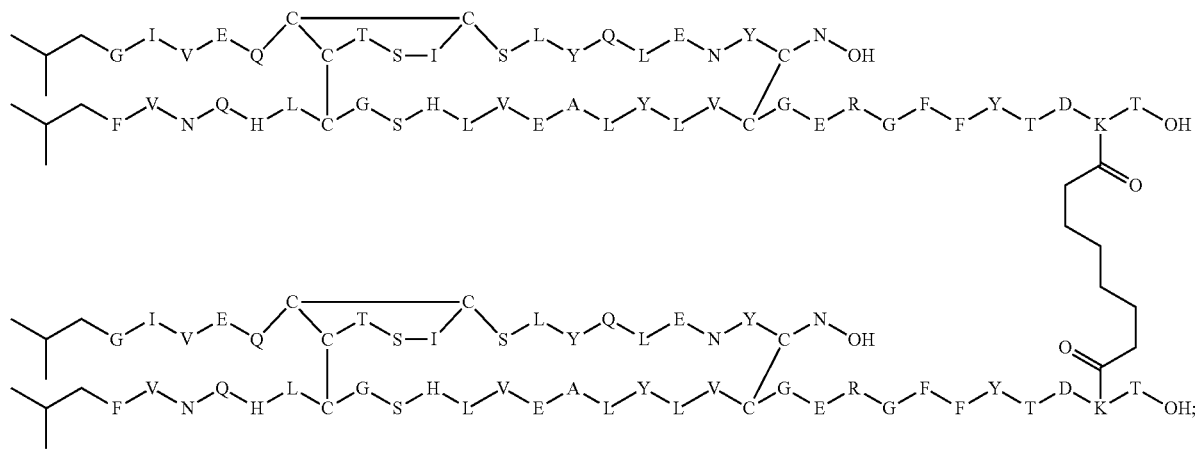
Dimer 66
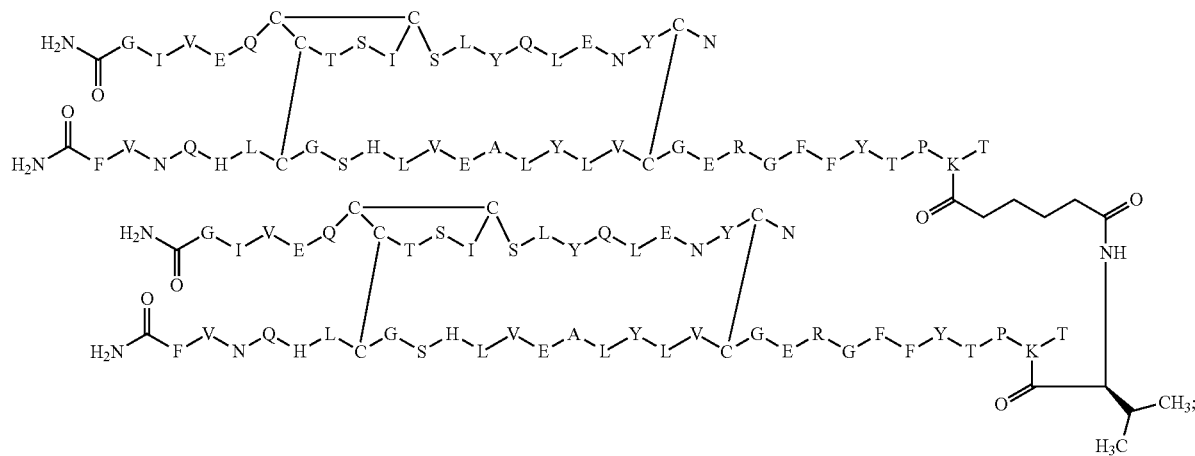
Dimer 67
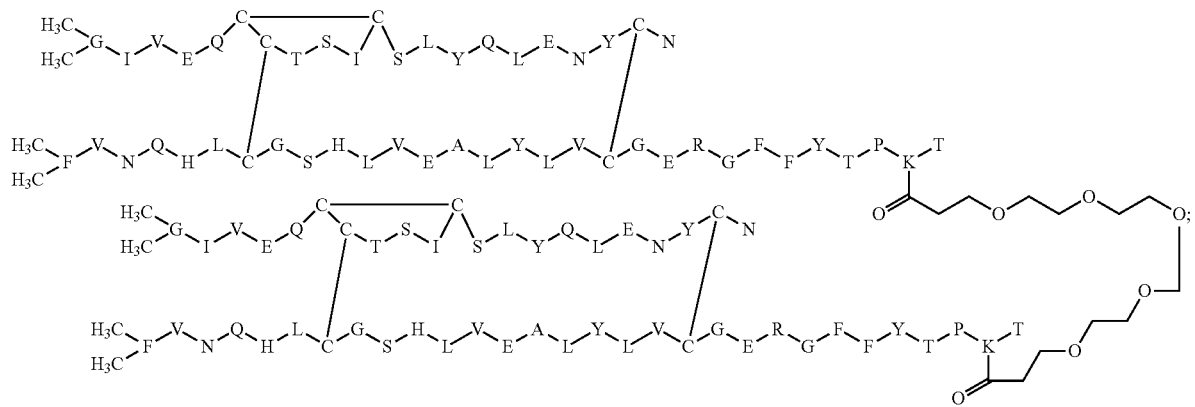

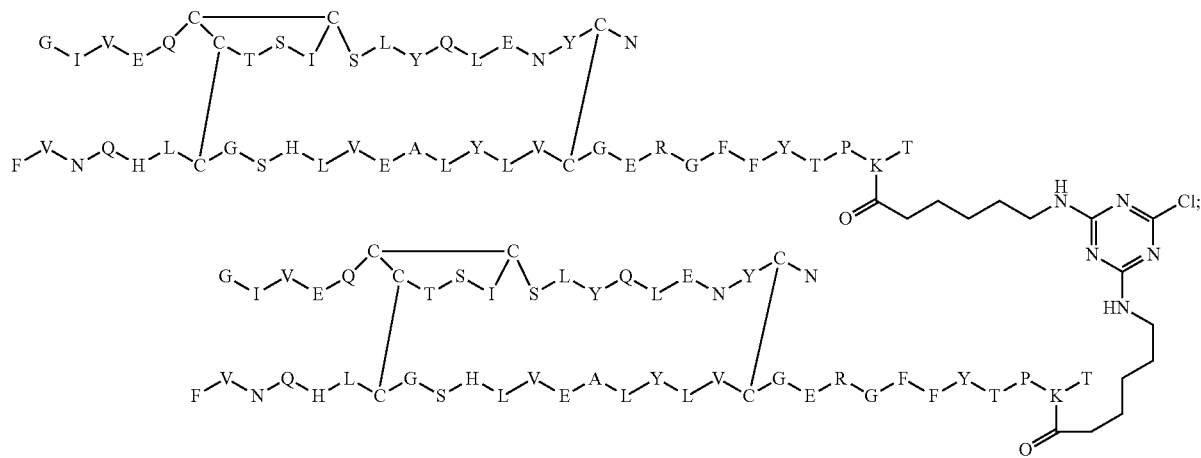
Dimer 68
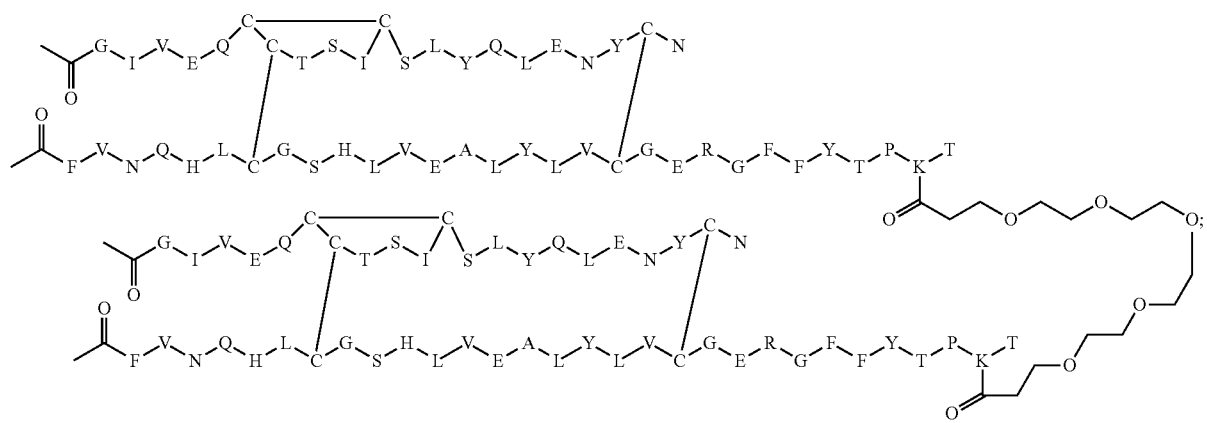
Dimer 69
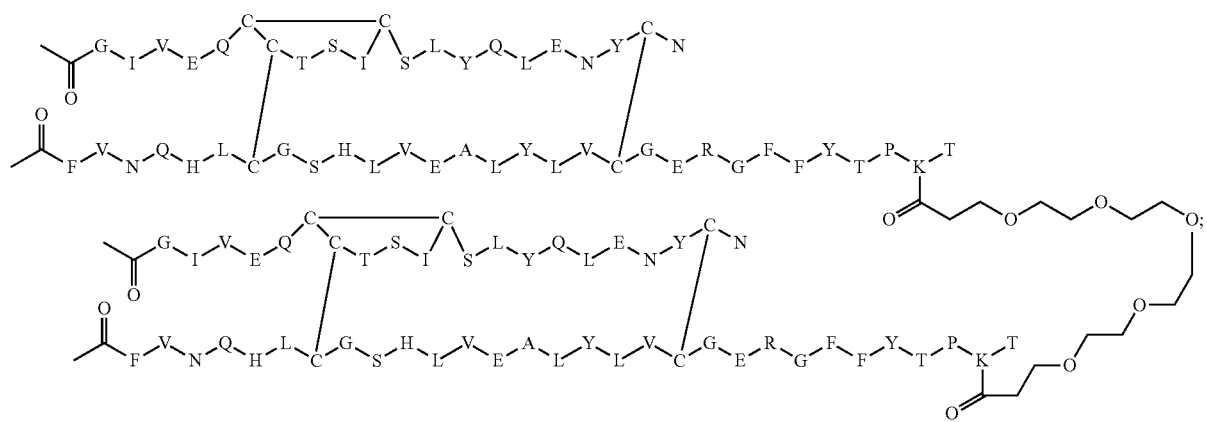
Dimer 70

Dimer 71
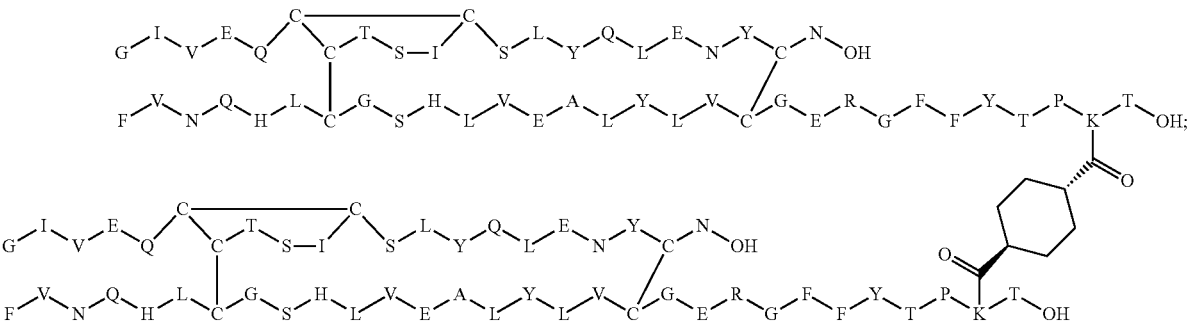
Dimer 72
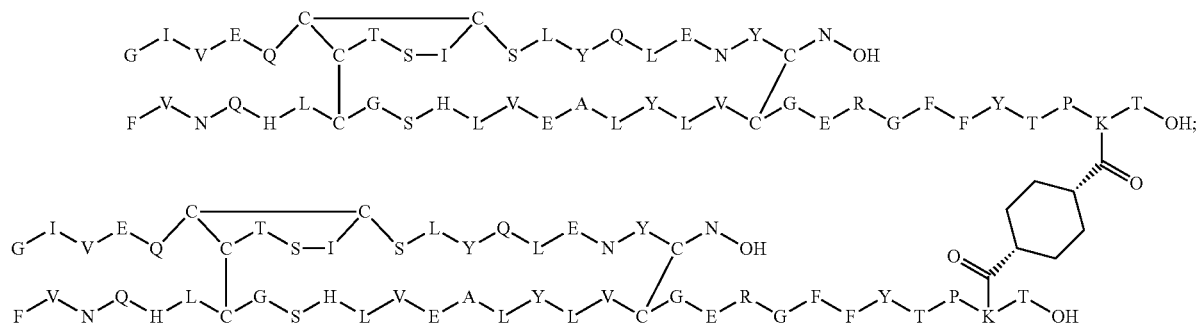
Dimer 73
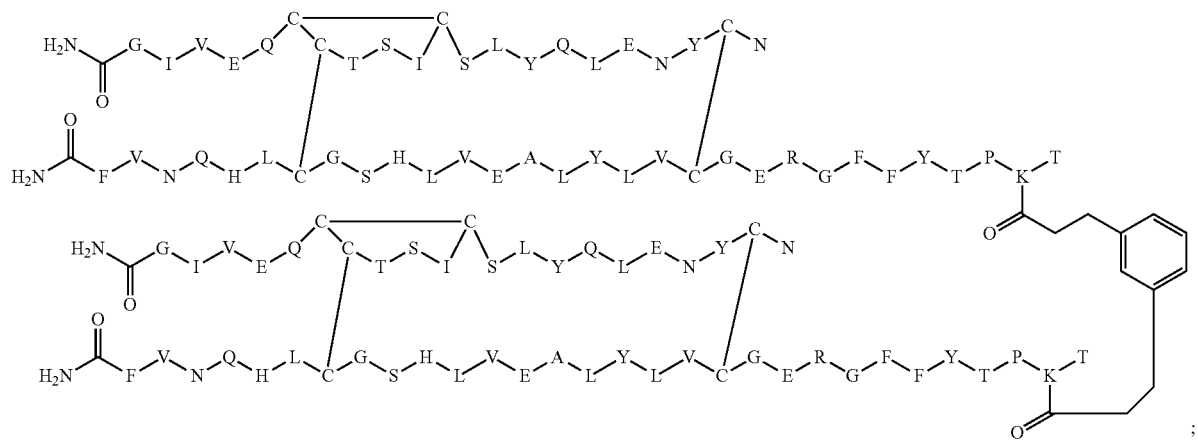
Dimer 74
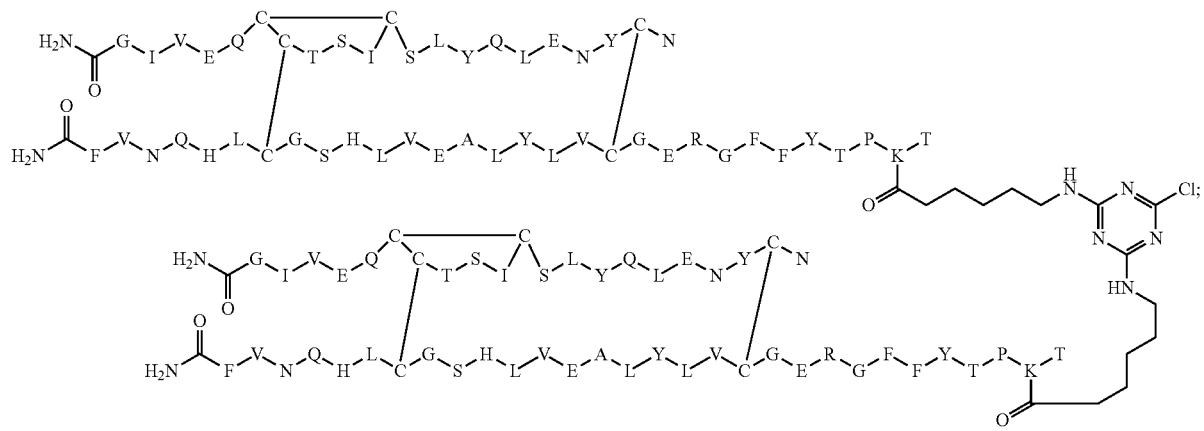

-continued
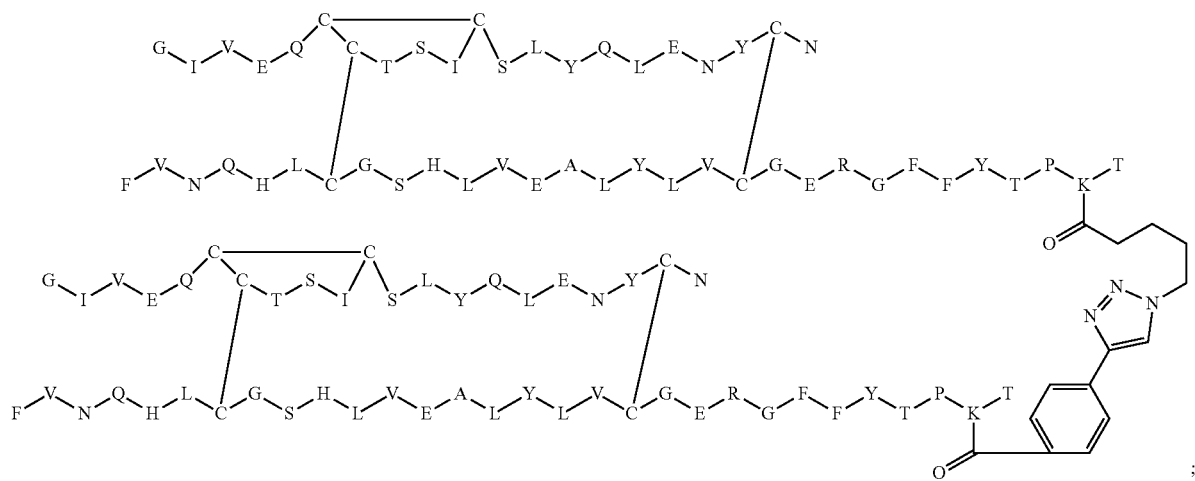
Dimer 75
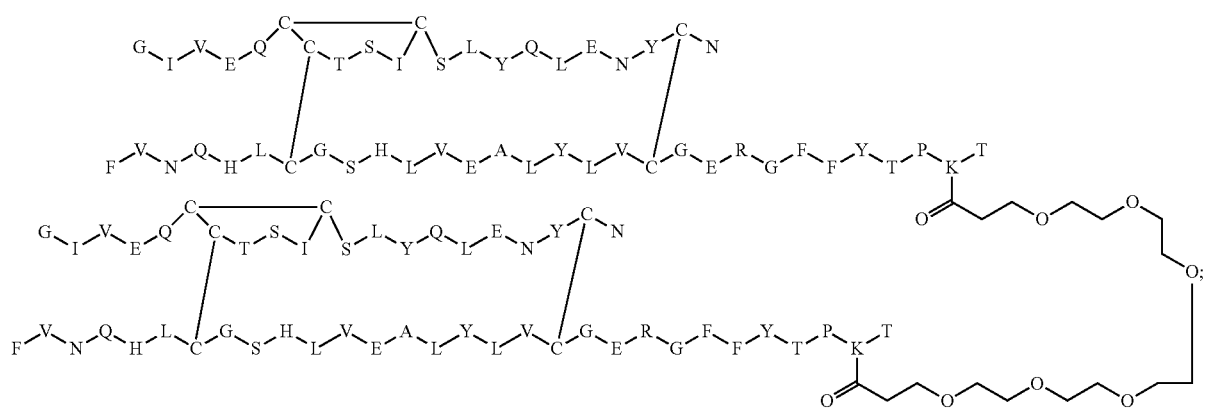
Dimer 76
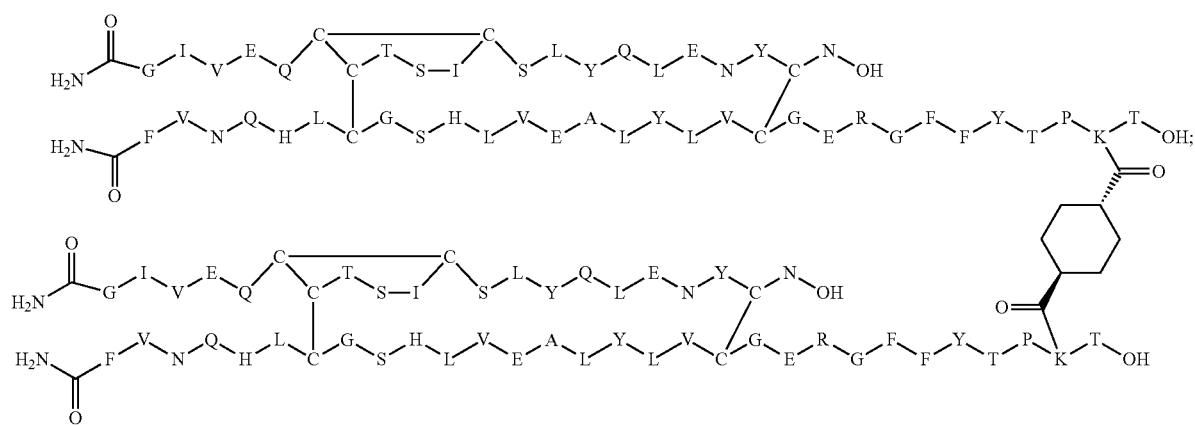
Dimer 77

Dimer 78
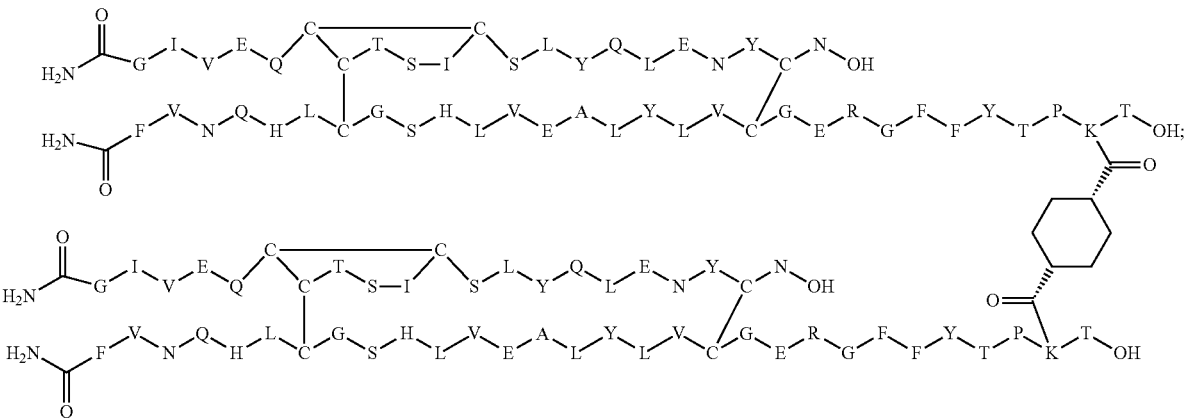
Dimer 79
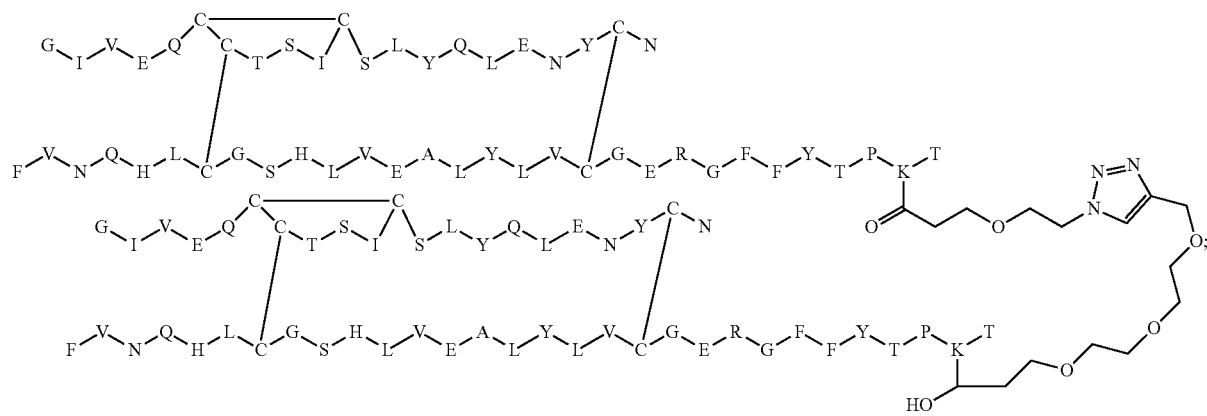
Dimer 80
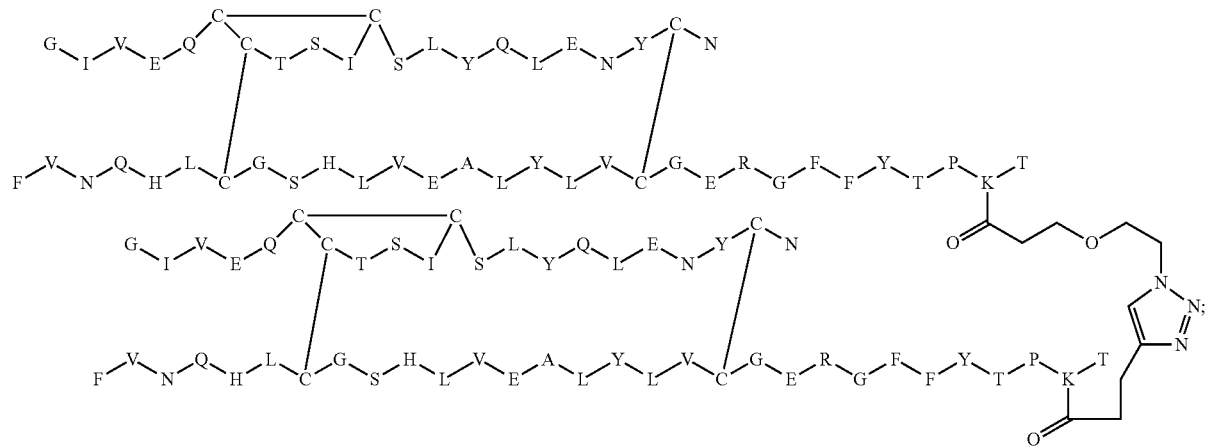

Dimer 81
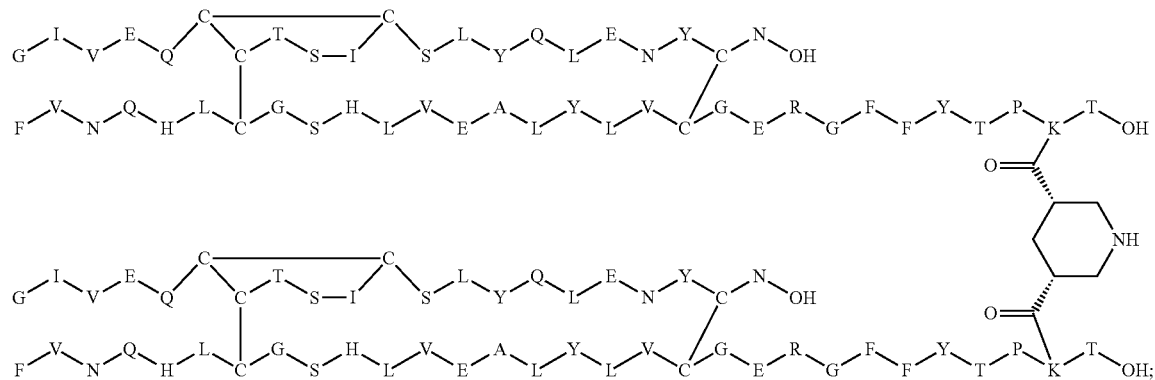
Dimer 82
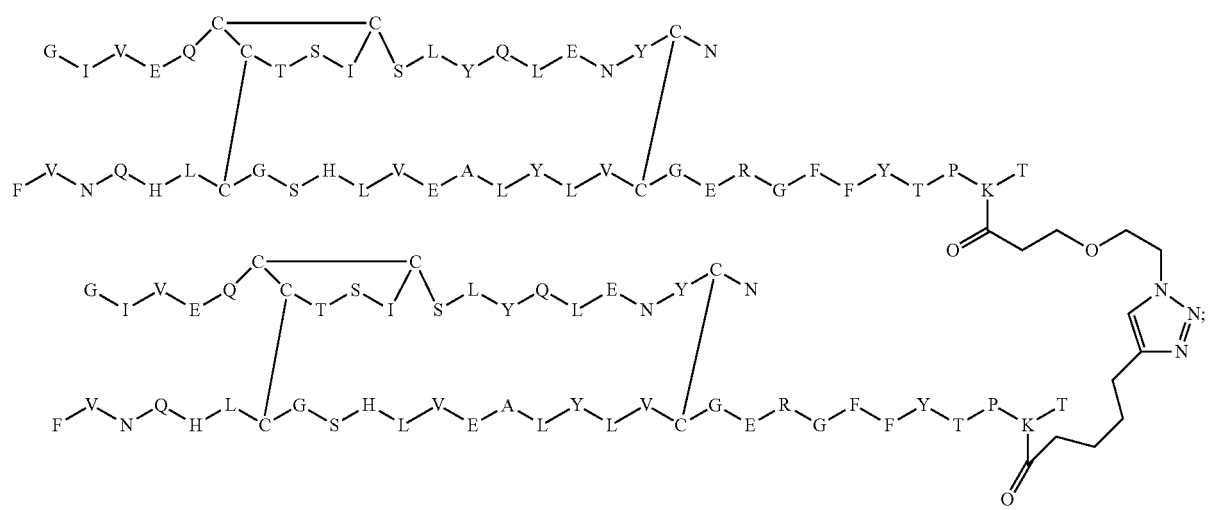
Dimer 83
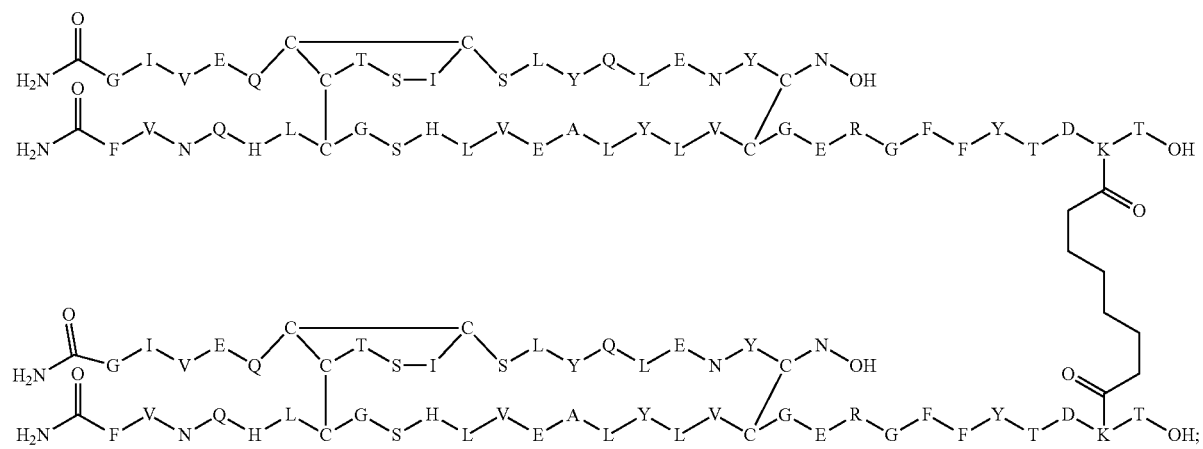

Dimer 84
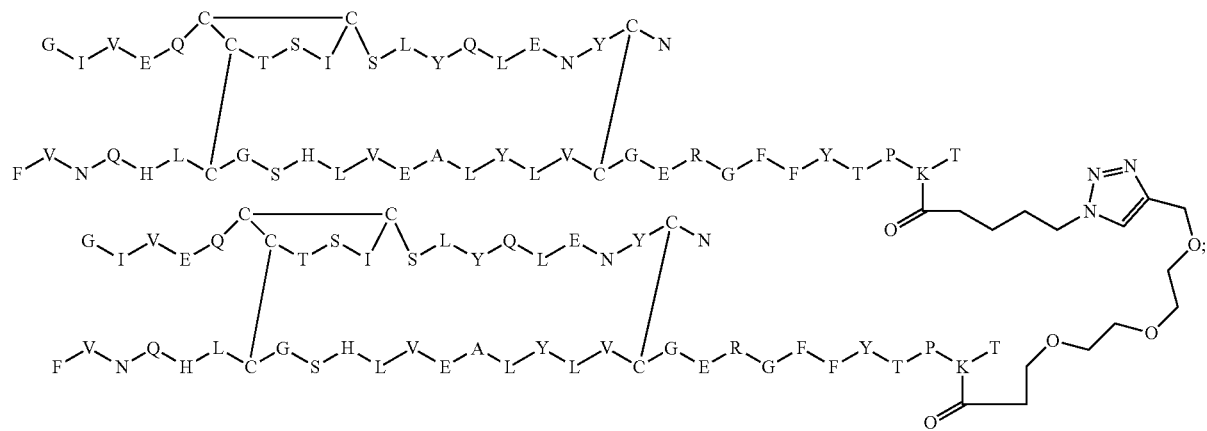
Dimer 85
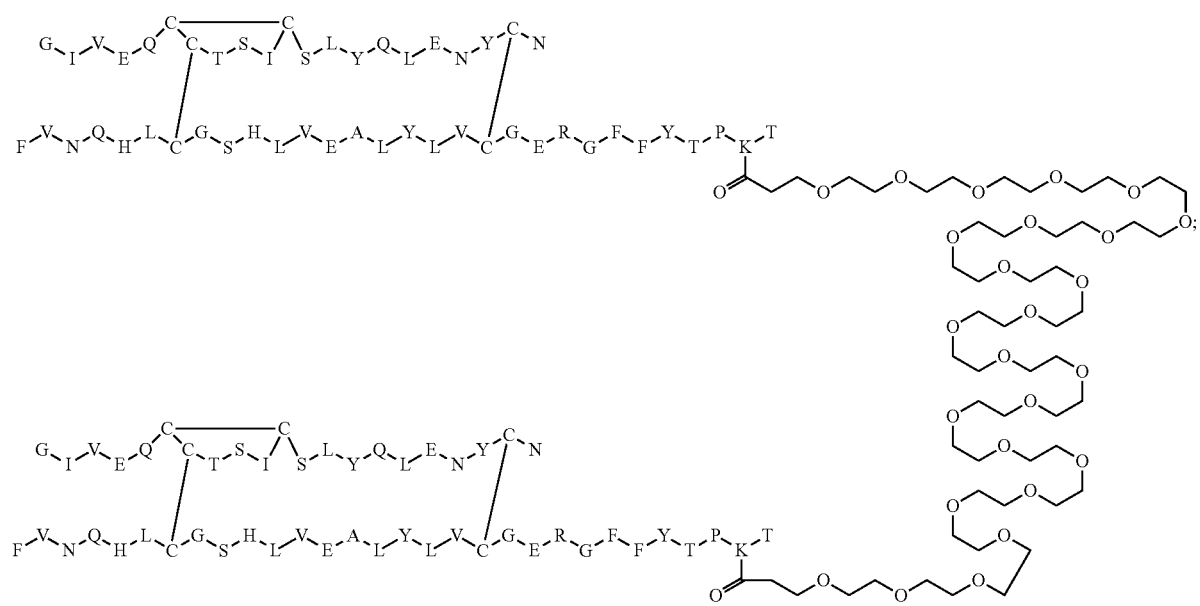
Dimer 86
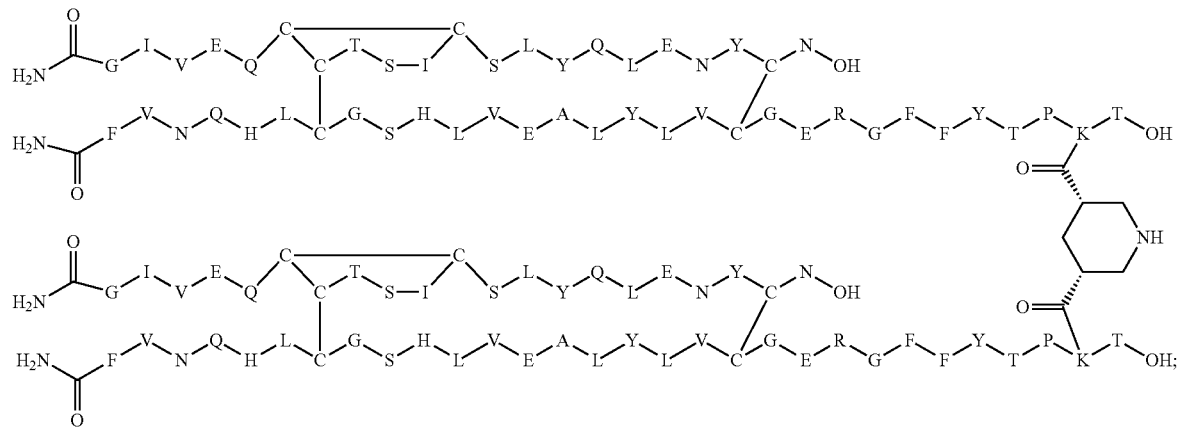

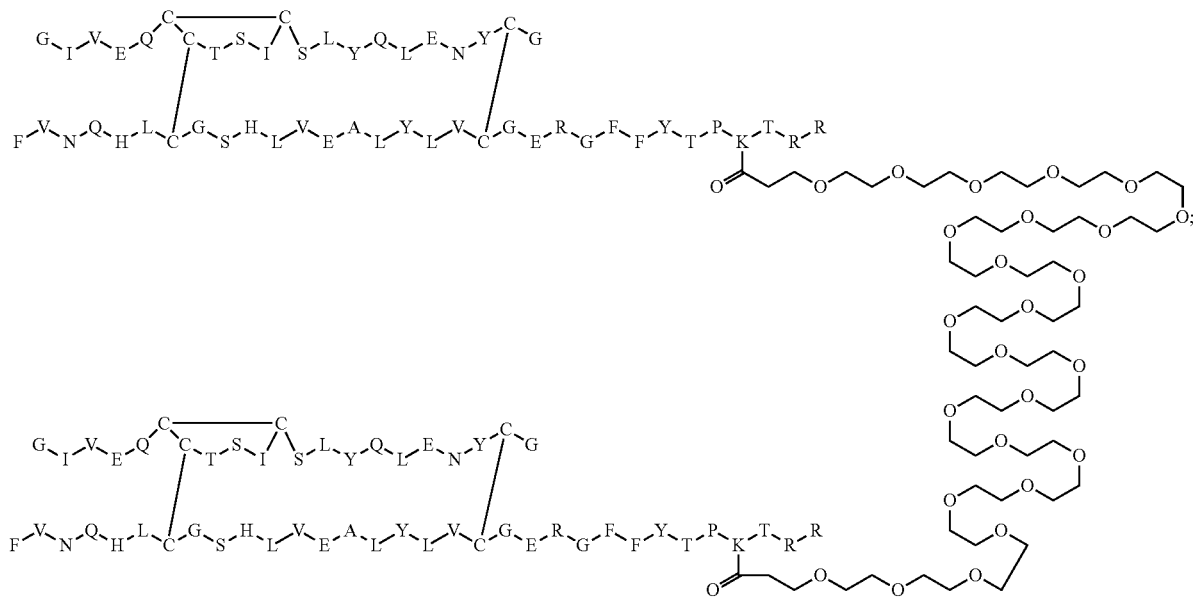
Dimer 87
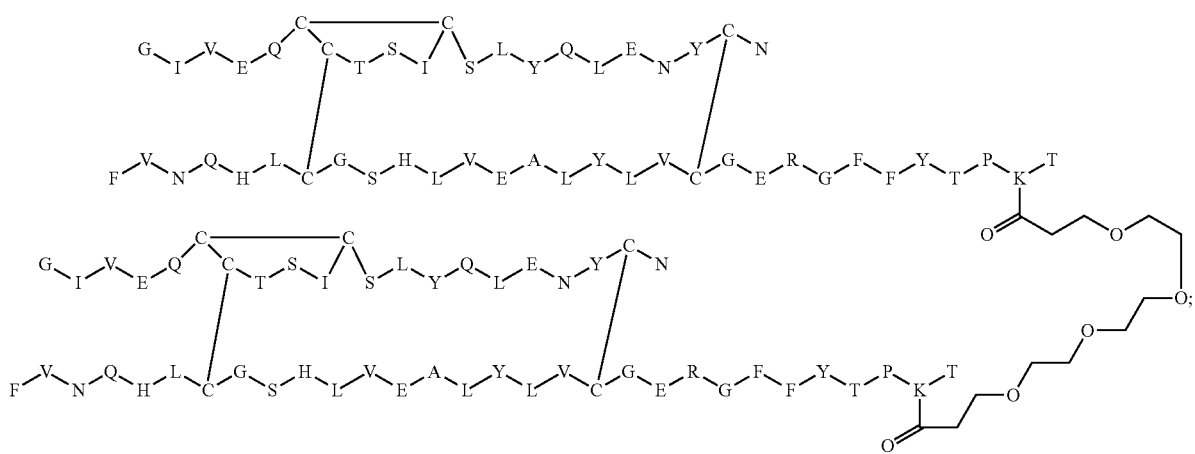
Dimer 88
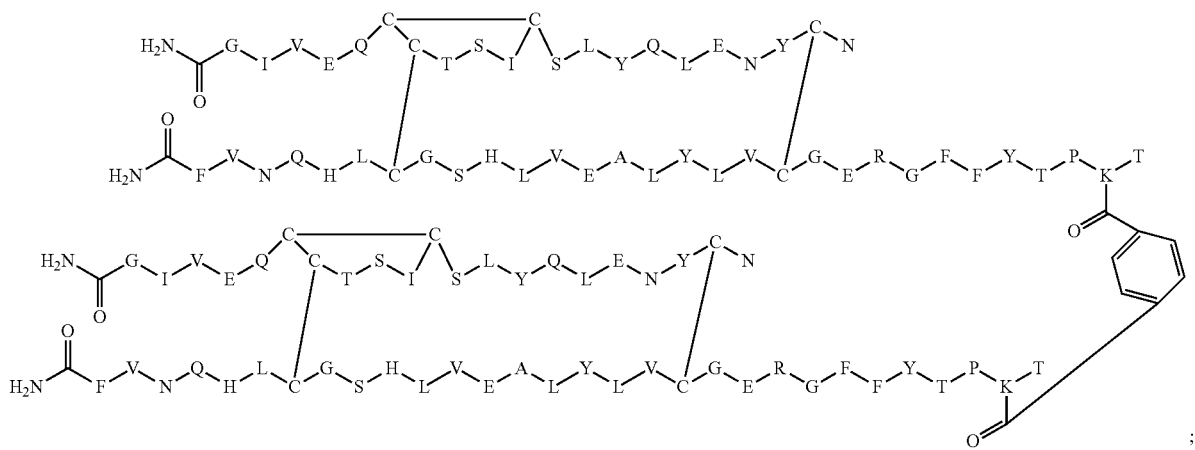
Dimer 89

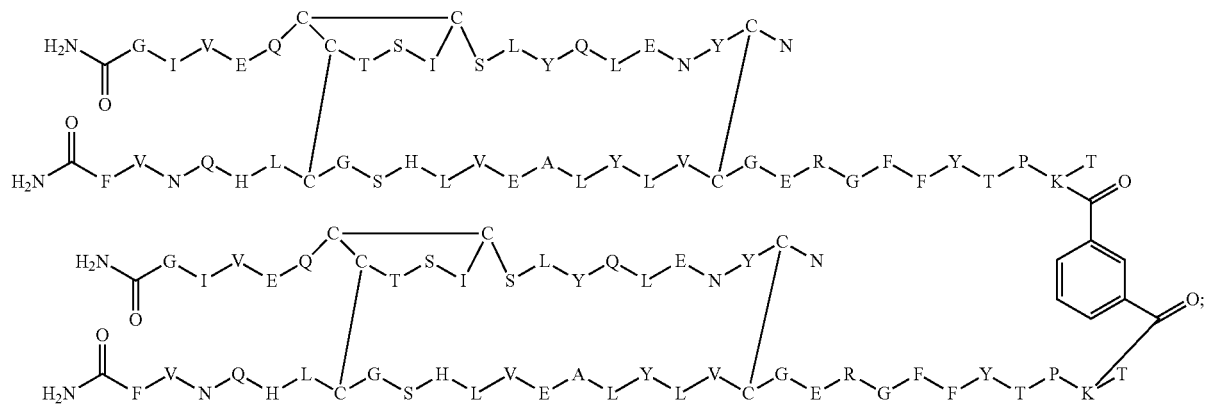
Dimer 90
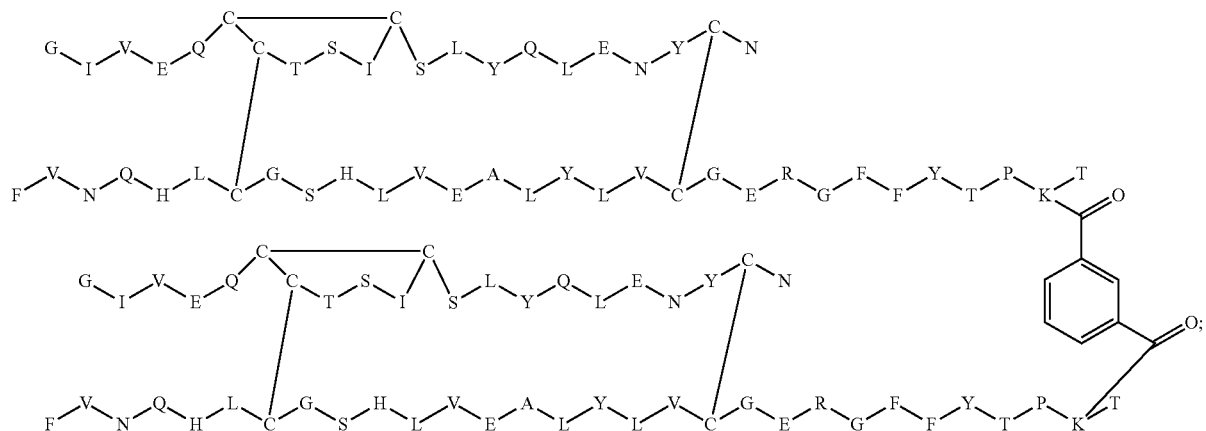
Dimer 91
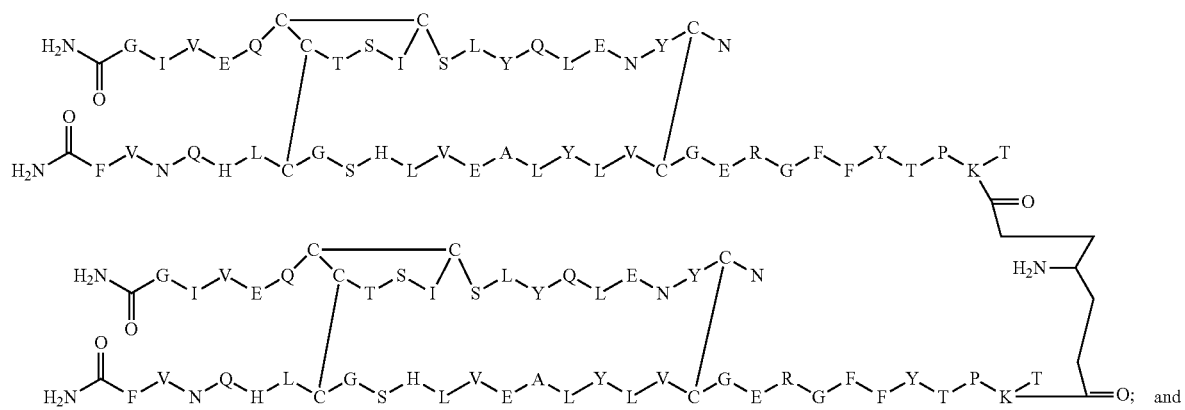
Dimer 93

Dimer 94

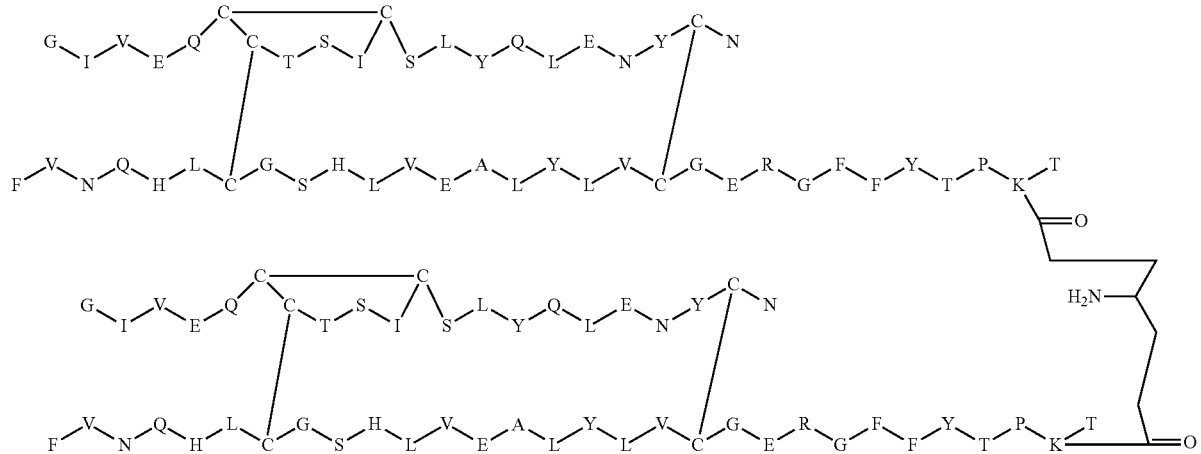

Wherein the disulfide linkages between the $Cys_6$ and Cys residues of the A-chain polypeptide and the disulfide linkages between the $Cys_7$ and $Cys_{20}$ of the A-chain to the $Cys_7$ and $Cys_{19}$ of the B-chain polypeptide, respectively, are represented by the solid line therebetween; wherein the linking moieties are covalently linked to the epsilon amino acid of the shown lysine residue, wherein the A-chain polypeptide for Dimers 1-40, 42-52, 54-86, and 88-94 has the amino acid sequence shown in SEQ ID NO:1; the A-chain polypeptide for Dimer 56 has the amino acid sequence shown for SEQ ID NO:11; the B-chain polypeptide for Dimers 1-17, 21-27, 36, 37, 39-40, and 42-52, 54-82, 84-86, and 88-94 has the amino acid sequence shown in SEQ ID NO:2; the B-chain polypeptide for Dimers 18 and 32-35 has the amino acid sequence shown in SEQ ID NO:6; the B-chain polypeptide for Dimers 19 and 83 has the amino acid sequence shown in SEQ ID NO:9; the B-chain polypeptide for Dimers 20, 28-31, and 38 has the amino acid sequence shown in SEQ ID NO:10; and the A-chain polypeptide and B-chain polypeptide for Dimers 53 and 87 are SEQ ID NO:7 and SEQ ID NO:8, respectively.

Pharmaceutical Compositions

In accordance with one embodiment a pharmaceutical composition is provided comprising any of the novel insulin dimers disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an insulin dimer as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

The disclosed insulin dimers are believed to be suitable for any use that has previously been described for insulin peptides. Accordingly, the insulin dimers disclosed herein can be used to treat hyperglycemia, or treat other metabolic diseases that result from high blood glucose levels. Accordingly, the present invention encompasses pharmaceutical compositions comprising a insulin dimers as disclosed herein and a pharmaceutically acceptable carrier for use in treating a patient suffering from high blood glucose levels. In accordance with one embodiment the patient to be treated using a insulin dimer disclosed herein is a domesticated animal, and in another embodiment the patient to be treated is a human.

One method of treating hyperglycemia in accordance with the present disclosure comprises the steps of administering the presently disclosed insulin dimers to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the insulin polypeptide, or prodrug derivative thereof, is prepackaged in a syringe.

The insulin dimers disclosed herein may be administered alone or in combination with other anti-diabetic agents. Anti-diabetic agents known in the art or under investigation include native insulin, native glucagon and functional analogs thereof, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bisphosphatase) inhibitors.

Pharmaceutical compositions comprising the insulin dimers disclosed herein can be formulated and administered to patients using standard pharmaceutically acceptable carriers and routes of administration known to those skilled in the art. Accordingly, the present disclosure also encompasses pharmaceutical compositions comprising one or more of the insulin dimers disclosed herein, or a pharmaceutically acceptable salt thereof, in combination with a pharmaceutically acceptable carrier. For example, the pharmaceutical compositions comprising the insulin dimers disclosed herein may optionally contain zinc ions, preservatives (e.g., phenol, cresol, parabens), isotonicizing agents (e.g., mannitol, sorbitol, lactose, dextrose, trehalose, sodium chloride, glycerol), buffer substances, salts, acids and alkalis and also further excipients. These substances can in each case be present individually or alternatively as mixtures. Glycerol, dextrose, lactose, sorbitol and mannitol are customarily present in the pharmaceutical preparation in a concentration of 100-250 mM, NaCl in a concentration of up to 150 mM. Buffer substances, such as, for example, phosphate, acetate, citrate, arginine, glycylglycine or TRIS (i.e. 2-amino-2-hydroxymethyl-1,3-propanediol) buffer and corresponding salts, are present in a concentration of 5-250 mM, commonly from about 10-100 mM. Further excipients can be, inter alia, salts or arginine.

In one embodiment the pharmaceutical composition comprises a 1mg/mL concentration of the insulin dimer at a pH of about 4.0 to about 7.0 in a phosphate buffer system. The pharmaceutical compositions may comprise the insulin dimer as the sole pharmaceutically active component, or the insulin dimer can be combined with one or more additional active agents.

All therapeutic methods, pharmaceutical compositions, kits and other similar embodiments described herein contemplate that insulin dimers include all pharmaceutically acceptable salts thereof.

In one embodiment the kit is provided with a device for administering the insulin dimers composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the insulin dimer composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

The following examples are intended to promote a further understanding of the present invention.

EXAMPLES

General Procedures

All chemicals were purchased from commercial sources, unless otherwise noted. Reactions were usually carried out at ambient temperature or at room temperature unless otherwise noted. Reactions sensitive to moisture or air were performed under nitrogen or argon using anhydrous solvents and reagents. The progress of reactions was monitored by analytical thin layer chromatography (TLC), and ultra performance liquid chromatography-mass spectrometry (UPLC-MS). TLC was performed on E. Merck TLC plates precoated with silica gel 60F-254, layer thickness 0.25 mm. The plates were visualized using 254 nm UV and/or by exposure to cerium ammonium molybdate (CAM) or p-anisaldehyde staining solutions followed by charring. Ultra performance liquid chromatography (UPLC) was performed on a Waters Acquity™ UPLC® system.

UPLC-MS Method A: Waters Acquity™ UPLC® BEH C18 1.7 μm 1.0×50 mm column with gradient 10:90-95:5 v/v $CH_3CN/H_2O$+v 0.05% TFA over 2.0 min; flow rate 0.3 mL/min, UV wavelength 215 nm; UPLC-MS;

Method B: Waters Acquity™ UPLC® BEH C18 1.7 μm 2.1×100 mm column with gradient 60:40-100:0 v/v $CH_3CN/H_2O$+v 0.05% TFA over 4.0 min and 100:0-95:5 v/v $CH_3CN/H_2O$+v 0.05% TFA over 40 sec; flow rate 0.3 mL/min, UV wavelength 200-300 nm; UPLC-MS;

Method C: Waters Acquity™ UPLC® BEH C18 1.7 μm 2.1×100 mm column with gradient 20:80-90:10 v/v $CH_3CN/H_2O$+v 0.05% TFA over 4.0 min and 90:10-95:5 v/v $CH_3CN/H_2O$+v 0.05% TFA over 0.5 min; flow rate 0.3 mL/min, UV wavelength 200-300 nm; UPLC-MS;

Method D: Waters Acquity™ UPLC® BEH C8 1.7 μm 2.1×100 mm column with gradient 10:90-55:45 v/v $CH_3CN/H_2O$+v 0.05% TFA over 4.0 min and 55:45-95:5 v/v $CH_3CN/H_2O$+v 0.05% TFA over 40 sec; flow rate 0.3 mL/min, UV wavelength 200-300 nm; UPLC-MS;

Method E: Waters Acquity™ UPLC® BEH300 C4 1.7 μm 2.1×100 mm column with gradient 10:90-50:50 v/v $CH_3CN/H_2O$+v 0.05% TFA over 4.3 min and 50:50-70:30 v/v $CH_3CN/H_2O$+v 0.05% TFA over 0.5 min; flow rate 0.3 mL/min, UV wavelength 200-300 nm; UPLC-MS;

Method F: Waters Acquity™ UPLC® BEH C8 1.7 μm 2.1×100 mm column with gradient 20:80-72.5:27.5 v/v $CH_3CN/H_2O$+v 0.05% TFA over 4.3 min and 72.5:27.5-95:5 v/v $CH_3CN/H_2O$+v 0.05% TFA over 0.5 min; flow rate 0.3 mL/min, UV wavelength 200-300 nm, and UPLC-MS;

Method G: Waters Acquity™ UPLC® BEH C8 1.7 μm 2.1×100 mm column with gradient 20:80-90:10 v/v $CH_3CN/H_2O$+v 0.1% TFA over 4.0 min and 90:10-95:5 v/v $CH_3CN/H_2O$+v 0.1% TFA over 0.4 min; flow rate 0.3 mL/min, UV wavelength 200-300 nm.

Mass analysis was performed on a Waters SQ Detector with electrospray ionization in positive ion detection mode and the scan range of the mass-to-charge ratio was 170-900 or a Waters Micromass® LCT Premier™ XE with electrospray ionization in positive ion detection mode and the scan range of the mass-to-charge ratio was 300-2000. The identification of the produced insulin conjugates or IRPA was confirmed by comparing the theoretical molecular weight to the experimental value that was measured using UPLC-MS. For the determination of the linkage positions, specifically, insulin dimers were subjected to DTT treatment (for a/b chain) or Glu-C digestion (with or without reduction and alkylation), and then the resulting peptides were analyzed by LC-MS. Based on the measured masses, the linkage positions were deduced.

Flash chromatography was performed using either a Biotage Flash Chromatography apparatus (Dyax Corp.) or a CombiFlash® Rf instrument (Teledyne Isco). Normal-phase chromatography was carried out on silica gel (20-70 μm, 60 Å pore size) in pre-packed cartridges of the size noted. Ion exchange chromatography was carried out on a silica-based material with a bonded coating of a hydrophilic, anionic poly(2-sulfoethyl aspartamide) (PolySULFOETHYL A column, PolyLC Inc., 250×21 mm, 5 μm, 1000 Å pore size). Reverse-phase chromatography was carried out on C18-bonded silica gel (20-60 μm, 60-100 Å pore size) in pre-packed cartridges of the size noted. Preparative scale HPLC was performed on Gilson 333-334 binary system using Waters DELTA PAK C4 15 μm, 300 Å, 50×250 mm column or KROMASIL® C8 10 μm, 100 Å, 50×250 mm column, flow rate 85 mL/min, with gradient noted. Concentration of solutions was carried out on a rotary evaporator under reduced pressure or freeze-dried on a VirTis Freezemobile Freeze Dryer (SP Scientific).

Abbreviations: acetonitrile (AcCN), aqueous (aq), N,N-diisopropylethylamine or Hünig's base (DIPEA), N,N-dimethylformamide (DMF), dimethyl sulfoxide (DMSO), ethyl acetate (EtOAc), N-(3-dimethylaminopropyl)-N'-ethylcarbodiimide hydrochloride (EDC), gram(s) (g), 1-hydroxybenzotriazole hydrate (HOBt), hour(s) (h or hr), mass spectrum (ms or MS), microgram(s) (μg), microliter(s) (μL), micromole (μmol), milligram(s) (mg), milliliter(s) (mL), millimole (mmol), minute(s) (min), retention time ($R_t$), room temperature (rt), saturated (sat. or sat' d), saturated aq sodium chloride solution (brine), triethylamine (TEA), trifluoroacetic acid (TFA), and N,N,N',N'-tetramethyl-O—(N-succinimidyl)uronium tetrafluoroborate (TSTU).

The term "RHI" refers to recombinant human insulin and is used to indicate that the insulin has the amino acid sequence characteristic of native, wild-type human insulin. As used herein in the tables, the term indicates that the amino acid sequence of the insulin comprising the dimer is that of native, wild-type human insulin.

After stirring overnight, the reaction mixture was partitioned between sat. $NaHCO_3$ and EtOAc. The organic phase was separated, washed with 1.0 M HCl and brine, dried over $Na_2SO_4$, and concentrated to give the title compound as a semi-solid and used in the next step without further purification. UPLC-MS Method A: Rt=1.26 min, m/z=440.3 [M+1]

Step 2-6-((5-Carboxypentyl)amino)-6-oxohexanoic acid

A suspension of the product of Step 1 (1.08 g, 2.457 mmol) and Pearlman's catalyst (20% wt on carbon, 173 mg, 0.246 mmol) in MeOH (50 mL) was stirred under 50 psi $H_2$ overnight. The catalyst was filtered off and the filtrate was subjected to reverse-phase chromatography on C8 phase (Kromasil, C8 10 μm 100 Å, 250×50 mm; solvent A=water/0.05% TFA, solvent B=AcCN/0.05% TFA), flow rate=85 mL/min, gradient B in A 5-30% in 30 min. UPLC-MS Method A: Rt=0.40 min, m/z=260.15 [M+1].

Step 3 2,5-dioxopyrrolidin-1-yl 6-((6-((2,5-dioxopyrrolidin-1-yl)oxy)-6-oxohexyl)amino)-6-oxohexanoate To a solution of the product of Step 2 (50 mg, 0.193 mmol) in DMF (964 μL) was added TSTU (116 mg, 0.386 mmol). After cooled down to 0° C., to the mixture was added triethylamine (53.8 0.386 mmol). After stirring for 45 minutes, formation of the desired compound was observed: UPLC-MS Method A: Rt=0.71 min, m/z=453.4 [M+1]. The resulting 2,5-dioxopyrrolidin-1-yl 6-((6-((2,5-dioxopyrrolidin-1-yl)oxy)-6-oxohexyl)amino)-6-oxohexanoate was used as 0.2 M solution in DMF without purification.

Example 2

Synthesis of bis(2,5-dioxopyrrolidin-1-yl) 6,6'-(adipoylbis(azanediyl))dihexanoate (Linker 2; C6N+C6+NC6) is Described

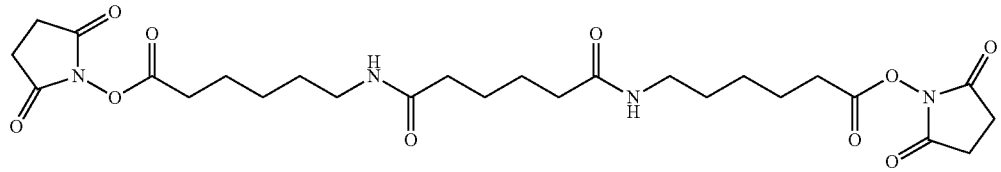

Example 1

Synthesis of 2,5-dioxopyrrolidin-1-yl 6-((6-((2,5-dioxopyrrolidin-1-yl)oxy)-6-oxohexyl)amino)-6-oxohexanoate (Linker 1; C6+NC6) is Described

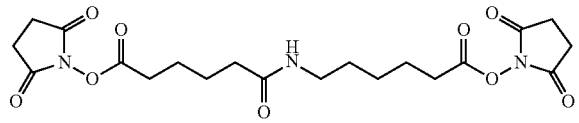 [SMILES: O=C(CCCCC(=O)ON1C(=O)CCC1=O)NCCCCCC(=O)ON1C(=O)CCC1=O]

Step 1 Benzyl 6-((6-(benzyloxy)-6-oxohexyl)amino)-6-oxohexanoate

To a mixture of adipic acid monobenzyl ester (600 mg, 2.54 mmol) and 6-(benzyloxy)-6-oxohexan-1-aminium 4-methylbenzenesulfonate (1.0 g, 2.54 mmol) in DMF (12.71 mL) was added HOBt (584 mg, 3.81 mmol), Hunig's base (888 μL, 5.08 mmol), and EDC (731 mg, 3.81 mmol).

Step 1 dibenzyl 6,6'-(adipoylbis(azanediyl))dihexanoate

To a solution of 6-(benzyloxy)-6-oxohexan-1-aminium 4-methylbenzenesulfonate (2.693 g, 6.84 mmol) and adipic acid (500 mg, 3.42 mmol) in DMF (17.1 mL) was added Hunig's Base (1.793 mL, 10.26 mmol), HOBt (1.572 g, 10.26 mmol), and EDC (1.968 g, 10.26 mmol). After stirring overnight, the reaction mixture was poured into water (500 mL) and stirred for 30 minutes. The title compound was collected through filtration as a solid and dried by air suction. UPLC-MS Method A: Rt=1.23 min, m/z=553.5 [M+1].

Step 2 Bis(2,5-dioxopyrrolidin-1-yl) 6,6'-(adipoylbis(azanediyl))dihexanoate

The title compound was prepared using the procedure analogous to those described for EXAMPLE 1 substituting dibenzyl 6,6'-(adipoylbis(azanediyl))dihexanoate for benzyl 6-((6-(benzyloxy)-6-oxohexyl)amino)-6-oxohexanoate in Step 2. UPLC-MS Method A: Rt=0.74 min, m/z=567.4 [M+1].

Example 3

Synthesis of (2S,2'S)-2,2'-(octanediylbis(azanediyl)) bis(5-(2,5-dioxopyrrolidin-1-yl)oxy)-5-oxopentanoic acid) (Linker 3; gamma-Glu-suberic-gamma-Glu) is Described

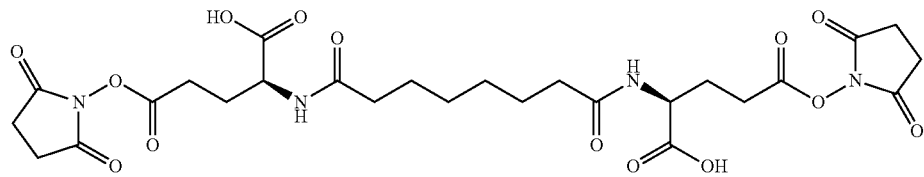 [SMILES: O=C(CCCCCCC(=O)N[C@@H](CCC(=O)ON1C(=O)CCC1=O)C(=O)O)N[C@@H](CCC(=O)ON1C(=O)CCC1=O)C(=O)O]

Step 1 (S)-5-(benzyloxy)-4-(8-(((S)-1-(benzyloxy)-4-carboxy-1-oxobutan-2-yl)amino)-8-oxooctanamide)-5-oxopentanoic acid To a solution of H-GLU-OBZL (1.00 g, 4.21 mmol) in DMF (10.5 mL) was added triethylamine (5.875 mL, 42.1 mmol) followed by disuccinimidyl suberate (776 mg, 2.107 mmol). After stirring for 1 hour, the reaction mixture was concentrated and the resulting residue was purified on C18 column (ISCO 44 g), flow=37 mL/min; gradient AcCN in water with 0.05% TFA: 2%-20% in 20 min followed by hold. After lyophilization, the intermediate bis-carboxylic acid was obtained. UPLC-MS Method B: Rt=2.66 min, m/z=613.3 [M+1].

Step 2 Bis-N-hydroxysuccinimide ester of (S)-5-(benzyloxy)-4-(8-(((S)-1-(benzyloxy)-4-carboxy-1-oxobutan-2-yl)amino)-8-oxooctanamide)-5-oxopentanoic acid To a suspension of the product of Step 1 (455 mg, 0.743 mmol) in acetonitrile (7.4 mL) was added TSTU (492 mg, 1.634 mmol) as a solid followed by triethylamine (228 μL, 1.634 mmol), at which point the suspension dissolved. Stirred the reaction mixture for 1.5 hr and concentrated on the rotovap at room temperature. The product was purified by reverse-phase chromatography on C-8 phase (Column Kromasil, C8 10 μm 100 A, size 250×50 mm; solvent A=water/0.05% TFA, solvent B=AcCN/0.05% TFA), Flow=85 mL/min, gradient B in A 10-80% in 30 min. After lyophilization of fractions, the bis-NHS ester was obtained. UPLC-MS Method B: Rt=2.77 min, m/z=807 [M+1].

Step 3. (2S,2'S)-2,2'-(octanediylbis(azanediyl))bis(5-((2,5-dioxopyrrolidin-1-yl)oxy)-5-oxopentanoic acid)

The product of Step 2 (250 mg, 0.310 mmol) was hydrogenated using palladium on carbon (66.0 mg, 0.031 mmol) as the catalyst, and acetone containing 0.1% TFA as the solvent (6.2 mL) at 1 atm of hydrogen, overnight. Catalyst was filtered off and the filtrate was concentrated to give the title compound. Pumped on high vacuum overnight. UPLC-MS Method C: Rt=3.61 min, m/z=627.3 [M+1].

Example 4

General Method A: Synthesis of $N^{6,B29}$ Insulin Conjugates (Analogs)

In an appropriate sized container, insulin or insulin analog was dissolved, with gentle stirring, at room temperature in a mixed solvent: 2:3 v/v 0.1 M $Na_2CO_3$:AcCN. After the mixture cleared, the pH was adjusted to the value of 10.5-10.8 using alkaline solution, e.g., 0.1 N NaOH. In a separate vial, an activated ester intermediate (linking moiety) was dissolved in an organic solvent, e.g., DMSO, at room temperature. Aliquots of the solution of the activated ester (Linker) was added over a period of time to the solution containing insulin until UPLC chromatogram showed that most of the unmodified insulin had been reacted and that a substantial portion of the reaction mixture had been converted into B29-conjugated insulin. The reaction was quenched by the addition of an amine nucleophile, e.g., 2-aminoethanol. The reaction solution was stirred at room temperature for 30 minutes. The resulting solution was carefully diluted with cold $H_2O$ (20×) at 0° C. and its pH was adjusted to a final pH of 2.5 using 1 N HCl (and 0.1 N NaOH if needed). The solution was first concentrated by ultrafiltration, either through a tangential flow filtration (TFF) system or using Amicon Ultra-15 Centrifugal Units, with 1K, 3K or 10K MWCO membrane. The concentrated solution was usually first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing B29-conjugate with desired purity were combined and concentrated using TFF system or Amicon Ultra-15. The resulting solution was then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in water; Buffer B: 0.05-0.1% TFA in AcCN). Fractions containing the title conjugate were combined and freeze-dried or buffer exchanged using TFF system and/or Amicon Ultra-15 to give the title product.

Example 5

Synthesis of $N^{6,29B}$-5-azido-pentanoyl desB30 Insulin (A:Y19A) (Analog 1) is Described In 20 mL scintillation vial, desB30 A:Y19A insulin (112 mg, 0.020 mmol) was dissolved, with gentle stirring, at room temperature in a mixed solvent (2 mL, 2:3 v/v 0.1 M $Na_2CO_3$:AcCN). After the mixture cleared, the pH was adjusted to the value of 10.5-10.8 using alkaline solution, e.g., 0.1 N NaOH. In a separate 8 mL scintillation vial, 2,5-dioxopyrrolidin-1-yl 5-azidopentanoate (Linker 5; see EXAMPLE 6) (4.79 mg, 0.020 mmol) was dissolved in DMSO (500 μL) at room temperature. Aliquots of the solution of the activated ester was added over a period of time to the solution containing insulin until UPLC chromatogram showed that most of the unmodified insulin had been reacted and that a substantial portion of the reaction mixture had been converted into B29-conjugated insulin. The reaction was quenched by the addition of an amine nucleophile, e.g., 2-aminoethanol. The reaction solution was stirred at room temperature for 30 minutes. The resulting solution was carefully diluted with cold H₂O (20×) at 0° C. and its pH was adjusted to a final pH of 2.5 using 1.0 N HCl (and 0.1 N NaOH if needed). The solution was first concentrated by ultrafiltration using Amicon Ultra-15 Centrifugal Units with 3K or 10K MWCO membrane. The concentrated solution was subjected to reverse phase HPLC (KROMASIL C8 250×50 mm, 10 μm, 100 Å column, 25-35% Buffer B in Buffer A over 20 min; Buffer A: 0.05% TFA in water; Buffer B: 0.05% TFA in AcCN). Fractions containing Analog 1 were combined and then freeze-dried. UPLC-MS Method D: Rt=3.91 min, m/z=1435.86 [(M+4)/4].

Example 6

The $N^{6,29B}$-acylated RHI Analog 2, Analog 3, and Analog 4 were prepared for use in constructing dimers using "click" chemistry and were prepared using General Method A or the procedure analogous to those described for EXAMPLE 4 but substituting recombinant human insulin and either

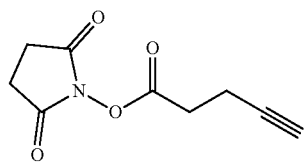

(2,5-dioxopyrrolidin-1-yl pent-4-ynoate; Linker 4);

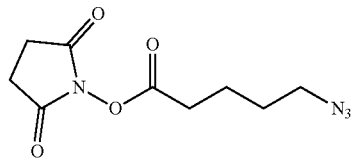 [SMILES: [N-]=[N+]=NCCCCC(=O)ON1C(=O)CCC1=O]

(2,5-dioxopyrrolidin-1-yl-azidopentanoate; Linker 5); or

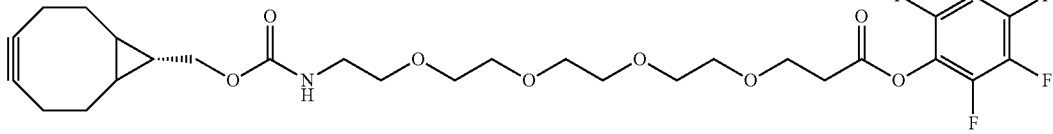

(perfluorophenyl 1-(bicyclo[6.1.0]non-4-yn-9-yl)-3-oxo-2,7,10,13,16-pentaoxa-4-azanonadecan-19-oate) (Linker 6) to make Analog 2, Analog 3, or Analog 4, respectively. The analogs were characterized using UPLC-MS Method D except for Analog 5, which was characterized using UPLC-MS Method F.

TABLE 1

| Analog | Linking moiety | Rt (min) | (M + 4)/4 |
|---|---|---|---|
| 2 | ![alkyne ketone] | 4.08 | 1472.56 |
| 3 | ![azide ketone] | 4.10 | 1483.89 |
| 4 | ![PEG-BCN] | 3.94 | 1558.58 |

The wavy line indicates the bond between the epsilon amino group of the B29 Lys of the insulin molecule.

Example 7

Synthesis of $N^{2,1A},N^{2,1B}$-bis(carbamoyl) Human Insulin (Analog 5) is Described To a suspension of RHI (1 g, 0.172 mmol) in water (50 mL) was added a solution of potassium phosphate, dibasic (0.249 g, 1.429 mmol) in water (5.0 mL). After stirring at room temperature for 30 minutes, to the resulting mixture was added potassium cyanate (0.279 g, 3.44 mmol). The reaction mixture was allowed to stir for 16 hours. To stop the reaction, unreacted potassium cyanate was removed by TFF using MWCO 3K diafiltration device, and the product was isolated as a solid by lyophilization. The product contained about 10-35% of A1/B1/B29-tris-urea-RHI, which optionally could be removed by reverse-phase chromatography on C8 phase (Column KROMASIL, C8 10 µm 100 Å, 250×50 mm; solvent A=water/0.05% TFA, solvent B=AcCN/0.05% TFA), flow rate=85 mL/min, gradient B in A 26-34% over 30 min). UPLC-MS Method D: Rt=4.29 min, m/z=1474.6 (z=4). The N-terminal substituent has the structure

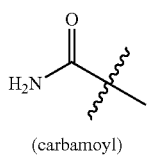

(carbamoyl)

wherein the wavy line indicates the bond between the substituent and the N2 nitrogen of the N-terminal amino acid.

Example 8

Synthesis of $N^{2,1A},N^{2,1B}$-bis(carbamoyl) desB30 Human Insulin (Analog 6) is Described The title compound was prepared using the procedure analogous to those described for EXAMPLE 7 substituting desB30 insulin for RHI. UPLC-MS Method D: Rt=4.10 min, m/z=1448.9 (z=4). The N-terminal substituent has the structure

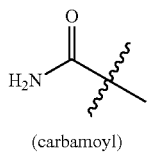

(carbamoyl)

wherein the wavy line indicates the bond between the substituent and the N2 nitrogen of the N-terminal amino acid.

Example 9

Synthesis of $N^{2,1A},N^{2,1B}$-bis(carbamoyl) Insulin lispro (Analog 7) is Described The title compound was prepared using the procedure analogous to those described for EXAMPLE 7 substituting insulin lispro for RHI. UPLC-MS Method D: Rt=4.07 min, m/z=1473.6 (z=4). The N-terminal substituent has the structure

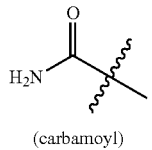

(carbamoyl)

wherein the wavy line indicates the bond between the substituent and the N2 nitrogen of the N-terminal amino acid.

Example 10

Synthesis of $N^{2,1A}$-acetyl Human Insulin (Analog 8) is Described

To a solution of RHI (400 mg, 0.069 mmol) in DMSO (4.6 mL) was added dropwise a solution of 2,5-dioxopyrrolidin-1-yl acetate

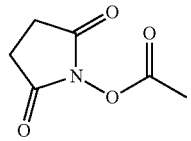

(10.82 mg, 0.069 mmol) in 100 µL of DMSO. After stirring for 3 hours, the reaction mixture was diluted with water (95 mL), acidified until pH of about 3, and then diafiltrated through Amicon Ultra-15 Centrifugal Units with 3 or 10K MWCO membrane to remove most of DMSO. The resulting solution was first subjected to ion exchange chromatography (PolySULFOETHYL A column, PolyLC Inc., 250×21 mm, 5 µm, 1000 Å, flow rate 15 mL/min; Buffer A: 0.1% (v/v) $H_3PO_4$/25% AcCN; Buffer B: 0.1% (v/v) $H_3PO_4$/25% AcCN/0.5M NaCl) using gradient 10-40% of Buffer B in Buffer A over 24 minutes. Fractions containing the desired $N^{2,1A}$-acetyl-RHI was combined and concentrated, and then subjected to reverse phase chromatography on (KROMASIL, C8 10 µm 100 Å, 250×50 mm; solvent A=water/0.05% TFA, solvent B=AcCN/0.05% TFA, gradient 26-30% of B in A). The modification position was confirmed using DTT analysis. UPLC-MS Method D: Rt=3.5 min and m/z=1463.5 (z=4). The N-terminal substituent has the structure

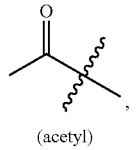

(acetyl)

wherein the wavy line indicates the bond between the substituent and the N2 nitrogen of the N-terminal amino acid.

Example 11

Synthesis of $N^{2,1A},N^{2,1B}$-bis(carbamoyl) $N^{6,29B}$-acylated RHI is Described Analog 5 conjugated to either 2,5-dioxopyrrolidin-1-yl-azidopentanoate (Linker 5) to construct Analog 9 or 2,5- dioxopyrrolidin-1-yl pent-4-ynoate (Linker 4) to construct Analog 10 were prepared using General Method A or the procedure analogous to those described for EXAMPLE 4.

Example 12

The following $N^{6,29B}$-acylated RHI analogs (Analog 11, Analog 12, and Analog 13) were prepared for use in constructing dimers using "click" chemistry. The analogs were prepared using General Method A or the procedure analogous to those described for EXAMPLE 4 but substituting recombinant human insulin (RHI) and the appropriate linking moiety selected from

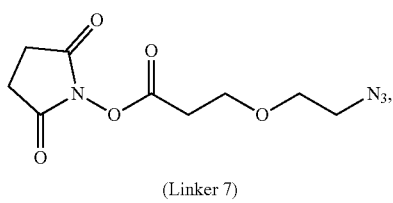

(Linker 7)

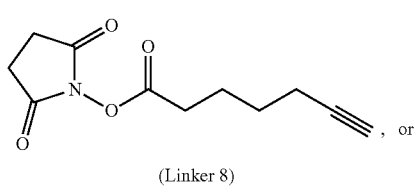

(Linker 8)

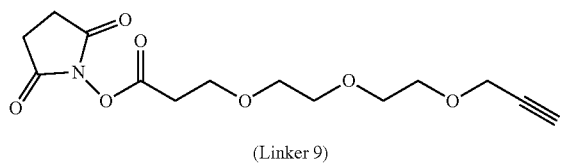

(Linker 9)

to make Analog 11, Analog 12, or Analog 13, respectively. The analogs were characterized using UPLC-MS Method D except for Analog 12, which was characterized using UPLC-MS Method F.

Example 13

General Method B: Synthesis of $N^{6,29B},N^{6,29B'}$-Insulin Dimers Using Organic Base Condition In an appropriate sized container, insulin or insulin analog is suspended at room temperature in an organic solvent or mixed aqueous (aq)/organic solvents, e.g., DMSO, in the presence of a base, e.g., TEA. The mixture is allowed to stir gently until insulin is completely dissolved. To the resulting solution is added an activated ester intermediate (linker) in solution of organic solvents, such as DMSO or DMF. After UPLC chromatogram shows that a substantial portion of the reaction mixture has converted into $N^{6,29B},N^{6,B29B'}$-insulin dimer (or $N^{6,28B},N^{6,28B'}$-insulin lispro dimer). The reaction mixture may be subjected directly to reverse phase HPLC purification (Waters C4 250×50 mm column, 10 μm, 1000 Å column or KROMASIL C8 250×50 mm, 10 μm, 100 Å column; Buffer A: 0.05-0.1% TFA in deionized water; Buffer B: 0.05-0.1% TFA in AcCN), or the reaction may be quenched by careful dilution with cold acidic $H_2O$ (20×, pH about 3.0) at 0° C. and its pH is adjusted to a final pH of 2.5 using 1 N HCl (and 0.1 N NaOH if needed). The solution may first be concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v) H3PO4/25% AcCN; Buffer B: 0.1% (v/v) H3PO4/25% AcCN/0.5 M NaCl). Fractions containing B29-conjugate with desired purity are combined and concentrated using TFF system or Amicon Ultra-15. The concentrated solution is then subjected to reverse phase HPLC purification (Waters C4 250×50 mm column, 10 μm, 1000 Å column or KROMASIL C8 250×50 mm, 10 100 Å column; Buffer A: 0.05-0.1% TFA in deionized water; Buffer B: 0.05-0.1% TFA in AcCN). Fractions containing the desired insulin dimer are combined and freeze-dried or buffer exchanged using TFF system and/or Amicon Ultra-15 to give the $N^{6,29B},N^{6,29B'}$-Insulin dimers.

Example 14

General Method C: Synthesis of $N^{6,29B},N^{6,29B'}$-Insulin Dimers Using Aqueous Base Conditions.

In an appropriate sized container, insulin or insulin analog is dissolved, with gentle stirring, at room temperature in a mixed solvent: 2:3 v/v 0.1 M $Na_2CO_3$:AcCN. After the

TABLE 2

| Analog | Linking moiety | Rt (min) | (M + 4)/4 |
|---|---|---|---|
| 11 | | 3.26 | 1488.11 |
| 12 | | 3.97 | 1479.30 |
| 13 | | 3.27 | 1502.26 |

The wavy line indicates the bond between the epsilon amino group of the B29 Lys of the insulin molecule.

mixture cleared, the pH is adjusted to the value of 10.5-10.8 using alkaline solution, e.g., 0.1 N NaOH. In a separate vial, an activated ester intermediate (linker) is dissolved in an organic solvent, e.g., DMSO, at room temperature. Aliquots of the solution of the activated ester is added over a period of time to the solution containing insulin until UPLC chromatogram shows that most of the unmodified insulin has reacted and that a substantial portion of the reaction mixture has converted into $N^{6,B29}, N^{6,B29'}$-insulin dimer (or $N^{6,28B}$, $N^{6,28B}$-insulin lispro dimer). The reaction is quenched by the addition of an amine nucleophile, e.g., 2-aminoethanol. The reaction solution is stirred at rt for 30 minutes. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing B29-conjugate with desired purity are combined and concentrated using TFF system or Amicon Ultra-15. The resulting solution is then further purified by reverse phase HPLC (Waters C4 250×50 mm column, 10 μm, 1000 Å column or KROMASIL C8 250×50 mm, 10 μm, 100 Å column; Buffer A: 0.05-0.1% TFA in water; Buffer B: 0.05-0.1% TFA in AcCN). Fractions containing the title insulin dimer are combined and freeze-dried or buffer exchanged using TFF system and/or Amicon Ultra-15 to give the $N^{6,29B}, N^{6,29B'}$-Insulin dimers.

Example 15

This example illustrates the synthesis of $N^{6,B29}N^{6,B29'}$-(2, 2'-(ethane-1,2-diylbis(oxy))diacetyl)bis[insulin human] (Dimer 1).

Dissolved RHI (2.6 g, 0.448 mmol) in a mixture of $Na_2CO_3$ (0.1 M) (15.8 mL) and AcCN (10.5 mL) and added 0.895 mL (0.179 mmol) of 0.2M DMF solution of bis(2,5-dioxopyrrolidin-1-yl) 2,2'-(ethane-1,2-diylbis(oxy))diacetate (Linker 8). Stirred the reaction mixture for 30 min and added additional portion of 0.895 mL (0.179 mmol) of 0.2M DMF solution of bis(2,5-dioxopyrrolidin-1-yl) 2,2'-(ethane-1,2-diylbis(oxy))diacetate and stirred the reaction mixture for 30 more min Poured the reaction mixture into 60 mL of 20% AcCN/0.1% TFA/water, adjusted pH to 2.5, and diafiltrated using Amicon Ultra-15 with 10K MWCO membrane to concentrate until the resulting volume was about 10 mL. The resulting solution was subjected to ion-exchange chromatography (PolySULFOETHYL A column, 250×21 mm, 5 μm, 1000 Å, gradient 10-80% of Buffer B in Buffer A over 30 min; Buffer A: 0.1% (v/v) $H_3PO_4$/25% AcCN; Buffer B: 0.1% (v/v) $H_3PO_4$/25% AcCN/0.5M NaCl). Fractions containing the title compound was combined and concentrated. The resulting solution was then subjected to reverse phase chromatography (KROMASIL C8 250×50 mm, 10 μm, 100 Å column; gradient 27-35% of AcCN with 0.05% TFA in water with 0.05% TFA). UPLC-MS Method E: Rt=2.75 min, m/z=1960.4 (z=6), 1680.4 (z=7).

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 1 | 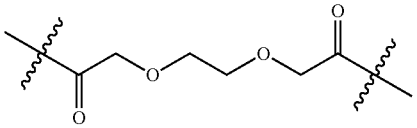 [SMILES: *C(=O)COCCOCC(*)=O] | RHI; A1, A1', B1, B1' = H | 2.75 | 1960.4 |

The wavy line indicates the bond between the epsilon amino group of the B29 Lys and B29' Lys, respectively.

Example 16

This example illustrates the synthesis of $N^{2,1A}, N^{2,1A'}$, $N^{2,1B}, N^{2,1B'}$-Tetrakis(carbamoyl)-$N^{6,B29}, N^{6,B29'}$-(hexanedioyl)bis[insulin human] (Dimer 2).

Dissolved $N^{2,1A}, N^{2,1B}$-bis(carbamoyl) RHI (150 mg, 0.025 mmol) in DMSO (1 mL) and added triethylamine (0.106 mL, 0.764 mmol) followed by dropwise addition of di(N-succinimidyl) adipate (Linker 12) (4.33 mg, 0.013 mmol) dissolved in 100 μL of DMSO. Stirred 1 hour and poured the reaction mixture into 20 mL of water. Acidified to pH=2 and diafiltrated using 10K Amicon Ultra 15. The product was purified by ion-exchange chromatography using gradient 10-40% of Solvent B in Solvent A in 24 minutes, and re-purified by reverse-phase chromatography on C-8 phase gradient B in A 26-36% in 30 minutes. UPLC-MS Method E: Rt=3.75 min, m/z=1983.9, (z=6).

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 2 | 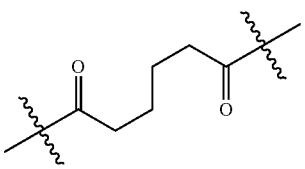 [SMILES: *C(=O)CCCCC(*)=O] | RHI; A1, A1', B1, B1' = carbamoyl | 3.75 | 1983.9 |

The wavy line indicates the bond between the epsilon amino group of the B29 Lys and B29' Lys, respectively.

Examples 17

Table 3 shows dimers that were prepared using appropriate intermediates (linkers) following either General Method B or General Method C as noted using the RHI, DesB30 RHI, insulin lispro, insulin aspart, insulin glargine, or the appropriate analog. For example, for dimers with carbamoylated N-termini, Analog 5 or Analog 6 (DesB30) were used; for dimers with acetylated A1 N-termini, Analog 8 was used. The dimers were characterized using UPLC-MS Method D or UPLC-MS Method E, exhibiting either six charged, i.e. [(M+6)/6], (or seven charged, i.e. [(M+7)/7]) species of parent compound at certain retention time (Rt). The insulin and the insulin's molecules linked together by the linking moiety are the same for each of the dimers shown in Table 3.

TABLE 3

| Dimer No. | Structure of Dimer showing the Linking moiety between the B29 and B29' Lysine residues | Insulin Type; Insulin N termini | Prep. Method | Rt (min) | (M + 6)/6 or (M + 7)/7 |
| --- | --- | --- | --- | --- | --- |
| 3 | | RHI; A1, B1, A1', B1' = carbamoyl | B | 4.41 | 1988.745 |
| 4 | | RHI; A1, B1, A1', B1' = H | C | 3.76 | 1986.88 |
| 5 | | RHI; A1, B1, A1', B1' = H | C | 3.74 | 1972.6 |
| 6 | | RHI; A1, B1, A1', B1' = H | C | 3.80 | 1754.2 |
| 7 | | RHI; A1, B1, A1', B1' = H | C | 3.87 | 1728.8 |
| 8 | | RHI; A1, B1, A1', B1' = H | C | 3.70 | 1950.65 |
| 9 | | RHI; A1, B1, A1', B1' = H | C | 3.70 | 1954.9 |

TABLE 3-continued

| Dimer No. | Structure of Dimer showing the Linking moiety between the B29 and B29' Lysine residues | Insulin Type; Insulin N termini | Prep. Method | Rt (min) | (M + 6)/6 or (M + 7)/7 |
|---|---|---|---|---|---|
| 10 | | RHI; A1, B1, A1', B1' = carbamoyl | B | 3.97 | 1715.3 |
| 11 | | RHI; A1, B1, A1', B1' = carbamoyl | B | 3.98 | 1727.9 |
| 12 | | RHI; A1, B1, A1', B1' = carbamoyl | B | 3.73 | 1978.8 |
| 13 | | RHI; A1, A1' = acetyl, B1, B1' = H | B | 3.83 | 1973.8 |
| 14 | | RHI; A1, B1, A1', B1' = carbamoyl | B | 4.10 | 1740.5 |
| 15 | | RHI; A1, B1, A1', B1' = H | C | 3.97 | 1716.0 |
| 16 | | RHI; A1, B1, A1', B1' = carbamoyl | B | 3.80 | 1752.4 |

TABLE 3-continued

| Dimer No. | Structure of Dimer showing the Linking moiety between the B29 and B29' Lysine residues | Insulin Type; Insulin N termini | Prep. Method | Rt (min) | (M + 6)/6 or (M + 7)/7 |
|---|---|---|---|---|---|
| 17 | [structure] | RHI; A1, B1, A1', B1' = carbamoyl | B | 4.13 | 1778.7 |
| 18 | [structure] | Insulin lispro; A1, B1, A1', B1' = H | C | 3.74 | 1960.54 |
| 19 | [structure] | Insulin aspart; A1, B1, A1', B1' = H | C | 3.74 | 1966.13 |
| 20 | [structure] | RHI desB30; A1, B1, A1', B1' = H | C | 4.57 | 1926.04 |
| 21 | [structure] | RHI; A1, B1, A1', B1' = carbamoyl | B | 4.48 | 1716.7 |
| 22 | [structure] | RHI; A1, B1, A1', B1' = H | C | 4.32 | 1974.06 |
| 23 | [structure] | RHI; A1, B1, A1', B1' = carbamoyl | B | 3.38 | 1733.11 |

TABLE 3-continued

| Dimer No. | Structure of Dimer showing the Linking moiety between the B29 and B29' Lysine residues | Insulin Type; Insulin N termini | Prep. Method | Rt (min) | (M + 6)/6 or (M + 7)/7 |
|---|---|---|---|---|---|
| 24 | | RHI; A1, B1, A1', B1' = carbamoyl | B | 3.59 | 1988.4 |
| 25 | | RHI; A1, B1, A1', B1' = H | C | 4.31 | 1708.35 |
| 26 | | RHI; A1, B1, A1', B1' = H | C | 4.08 | 1993.02 |
| 27 | | RHI; A1, B1, A1', B1' = carbamoyl | B | 4.18 | 1732.48 |
| 28 | | RHI desB30; A1, B1, A1', B1' = carbamoyl | B | 3.86 | 1954.9 |
| 29 | | RHI desB30; A1, B1, A1', B1' = H | C | 3.75 | 1940.76 |
| 30 | | RHI desB30; A1, B1, A1', B1' = H | C | 3.77 | 1959.02 |

TABLE 3-continued

| Dimer No. | Structure of Dimer showing the Linking moiety between the B29 and B29' Lysine residues | Insulin Type; Insulin N termini | Prep. Method | Rt (min) | (M + 6)/6 or (M + 7)/7 |
|---|---|---|---|---|---|
| 31 | | RHI desB30; A1, B1, A1', B1' = H | C | 4.00 | 1959.4 |
| 32 | | Insulin lispro; A1, B1, A1', B1' = carbamoyl | B | 3.81 | 1988.42 |
| 33 | | Insulin lispro; A1, B1, A1', B1' = H | C | 3.70 | 1974.04 |
| 34 | | Insulin lispro; A1, B1, A1', B1' = H | C | 3.80 | 1992.89 |
| 35 | | Insulin lispro; A1, B1, A1', B1' = H | C | 3.76 | 1992.86 |

TABLE 3-continued

| Dimer No. | Structure of Dimer showing the Linking moiety between the B29 and B29' Lysine residues | Insulin Type; Insulin N termini | Prep. Method | Rt (min) | (M + 6)/6 or (M + 7)/7 |
|---|---|---|---|---|---|
| 36 | | RHI; A1, B1, A1', B1' = H | C | 4.29 | 1717.28 |
| 37 | | RHI; A1, B1, A1', B1' = carbamoyl | B | 4.01 | 1720.6 |
| 38 | | RHI desB30; A1, B1, A1', B1' = H | C | 3.88 | 1944.96 |
| 39 | | RHI; A1, B1, A1', B1' = H | C | 3.87 | 1978.88 |
| 88 | | RHI; A1, B1, A1', B1' = H | D | 3.39 | 1697.36 |

TABLE 3-continued

| Dimer No. | Structure of Dimer showing the Linking moiety between the B29 and B29' Lysine residues | Insulin Type; Insulin N termini | Prep. Method | Rt (min) | (M + 6)/6 or (M + 7)/7 |
|---|---|---|---|---|---|
| 76 | | RHI; A1, B1, A1', B1' = H | D | 3.50 | 1709.73 |
| 83 | | Insulin aspart; A1, B1, A1', B1' = carbamoyl | B | 3.50 | 1994.39 |
| 85 | | RHI; A1, B1, A1', B1' = H | D | 3.46 | 1829.31 |

TABLE 3-continued

| Dimer No. | Structure of Dimer showing the Linking moiety between the B29 and B29' Lysine residues | Insulin Type; Insulin N termini | Prep. Method | Rt (min) | (M + 6)/6 or (M + 7)/7 |
|---|---|---|---|---|---|
| 53 | | Insulin glargine; A1, B1, A1', B1' = H | D | 3.37 | 1788.87 |
| 87 | | Insulin glargine; A1, B1, A1', B1' = H | D | 3.43 | 1902.16 |

The wavy line indicates the bond between the epsilon amino group of the B29 Lys and B29' Lys, respectively.

Example 18

General Method D: Synthesis of $N^{6,29B},N^{6,29B'}$-Insulin Dimers Using $Cu^{2+}$-Catalyzed Click Chemistry.

In an appropriate sized container, appropriate acetylene containing insulin intermediate (Analog) was dissolved, with gentle stirring, at room temperature in a mixed solvent of DMSO and aq. triethylammonium acetate buffer (pH 7.0, final concentration 0.2 mM). In another appropriate sized container, appropriate azido containing insulin intermediate (Analog) was dissolved, with gentle stirring, at rt in a mixed solvent of DMSO and water. Both solutions were combined, thoroughly mixed, degassed by gently bubbling $N_2$ through. To the resulting solution was added freshly prepared sodium ascorbate or ascorbic acid solution (final concentration is 0.5 mM) and, after thoroughly mixed, a solution of 10 mM $CuSO_4$ and tris[(1-benzyl-1H-1,2,3-triazol-4-yl)methyl] amine (i.e., TBTA ligand) in 55% DMSO. After degassed by gently bubbling $N_2$ through and mixed thoroughly, the mixture was stored at rt, with occasional mixing, overnight. The reaction mixture was carefully diluted with a mix solvent (v/v 7:3 AcCN/water with 0.05% TFA) at 0° C. and pH was adjusted to 2.50 using 0.1, 1.0 N HCl (and 0.1 N NaOH if needed). The solution was first concentrated by ultrafiltration, either through a tangential flow filtration (TFF) system or using Amicon Ultra-15 Centrifugal Units, with 1K, 3K, or 10K MWCO membrane. The concentrated solution was usually first subjected to ion exchange chromatography (PolySULFOETHYL A column, PolyLC Inc., 250×21 mm, 5 µm, 1000 Å; Buffer A: 0.1% (v/v) H$_3$PO$_4$/ 25% AcCN; Buffer B: 0.1% (v/v) H$_3$PO$_4$/25% AcCN/0.5 M NaCl). Fractions containing desired product with desired purity were combined and concentrated using TFF system or Amicon Ultra-15. The resulting solution was then further purified by reverse phase HPLC (Waters C4 250×50 mm column, 10 µm, 1000 Å column or KROMASIL C8 250×50 mm, 10 µm, 100 Å column; Buffer A: 0.05-0.1% TFA in water; Buffer B: 0.05-0.1% TFA in AcCN). Fractions containing the desired product with desired purity were combined and freeze-dried or buffer exchanged using TFF system and/or Amicon Ultra-15 to give the insulin dimers.

Table 4 lists Dimers 40, 41, 45, 46, 47, 59, 57, 79, 80, 82, and 84, which were prepared using the appropriate intermediates following General Method D. These dimers were characterized using UPLC-MS Method D or UPLC-MS Method E or UPLC-MS Method G, exhibiting either six charged, i.e. [(M+6)/6], (or seven charged, i.e. [(M+7)/7]) species of parent compound at certain retention time (Rt).

TABLE 4

| Dimer No. | First Insulin backbone | Second Insulin (') backbone | Structure of Dimer showing the Linking moiety between the B29 and B29' Lysine residues | Rt (min) | (M + 6)/6 or (M + 7)/7 |
|---|---|---|---|---|---|
| 40 | Analog 3 | Analog 2 | | 3.83 | 1970.38 |
| 41 | Analog 1 | Analog 2 | | 3.88 | 1938.84 |
| 45 | Analog 9 | Analog 2 | | 4.28 | 1985.30 |
| 46 | Analog 3 | Analog 10 | | 4.50 | 1985.43 |
| 47 | Analog 9 | Analog 10 | | 4.59 | 1714.34 |
| 75 | Analog 3 | Analog 2 | | 3.40 | 1696.35 |
| 57 | Analog 3 | Analog 12 | | 3.57 | 1975.90 |

TABLE 4-continued

| Dimer No. | First Insulin backbone | Second Insulin (') backbone | Structure of Dimer showing the Linking moiety between the B29 and B29' Lysine residues | Rt (min) | (M + 6)/6 or (M + 7)/7 |
|---|---|---|---|---|---|
| 79 | Analog 11 | Analog 13 | | 3.38 | 1993.39 |
| 80 | Analog 11 | Analog 2 | | 3.37 | 1973.83 |
| 82 | Analog 11 | Analog 12 | | 3.34 | 1978.33 |
| 84 | Analog 3 | Analog 13 | | 3.40 | 1990.54 |

The wavy line indicates the bond between the epsilon amino group of the B29 Lys and B29' Lys, respectively.

Example 19

General Method E: Synthesis of $N^{6,29B}$, $^{N6,29B'}$-Insulin Dimers Using $Cu^{2+}$-Catalyzed Double Click Chemistry.

In an appropriate sized container, appropriate azido containing insulin intermediate (Analog) was dissolved, with gentle stirring, at room temperature in a mixed solvent of DMSO and aq. triethylammonium acetate buffer (pH 7.0, final concentration 0.2 mM). In another appropriate sized container, appropriate bis-acetylene containing bridging or intermediate linker was dissolved, with gentle stirring, at room temperature in a mixed solvent of DMSO and water. Both solutions were combined, thoroughly mixed, degassed by gently bubbling $N_2$ through. To the resulting solution was added freshly prepared sodium ascorbate or ascorbic acid solution (final concentration is 0.5 mM) and, after thoroughly mixed, a solution of 10 mM $CuSO_4$ and tris[(1-benzyl-1H-1,2,3-triazol-4-yl)methyl]amine (i.e., TBTA ligand) in 55% DMSO. After degassed by gently bubbling $N_2$ through and mixed thoroughly, the mixture was stored at room temperature, with occasional mixing, overnight. The reaction mixture was carefully diluted with a mix solvent (v/v 7:3 AcCN/water with 0.05% TFA) at 0° C. and pH was adjusted to 2.50 using 0.1, 1.0 N HCl (and 0.1 N NaOH if needed). The solution was first concentrated by ultrafiltration, either through a tangential flow filtration (TFF) system or using Amicon Ultra-15 Centrifugal Units, with 1K, 3K, or 10K MWCO membrane. The concentrated solution was usually first subjected to ion exchange chromatography (PolySULFOETHYL A column, PolyLC Inc., 250×21 mm, 5 µm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing desired product with desired purity were combined and concentrated using TFF system or Amicon Ultra-15. The resulting solution was then further purified by reverse phase HPLC (Waters C4 250×50 mm column, 10 µm, 1000 Å column or KROMASIL C8 250×50 mm, 10 µm, 100 Å column; Buffer A: 0.05-0.1% TFA in water; Buffer B: 0.05-0.1% TFA in AcCN). Fractions containing the desired product with desired purity were combined and freeze-dried or buffer exchanged using TFF system and/or Amicon Ultra-15 to give the insulin dimers.

Table 5 lists Dimers 42-44 and 54 that were prepared using the appropriate intermediates following General Method E. The bis-acetylene bridging or intermediate linkers were

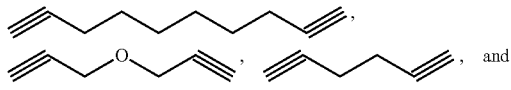, 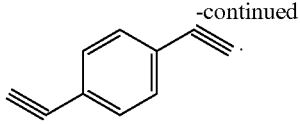

These dimers were characterized using UPLC-MS Method D or UPLC-MS Method E, exhibiting either six charged, i.e. [(M+6)/6], (or seven charged, i.e. [(M+7)/7]) species of parent compound at certain retention time (Rt).

TABLE 5

| Dimer No. | First Insulin backbone | Second Insulin (') backbone | Structure of Dimer showing the Linking moiety between the B29 and B29' Lysine residues | Rt (min) | (M + 6)/6 or (M + 7)/7 |
|---|---|---|---|---|---|
| 42 | Analog 3 | Analog 3 | 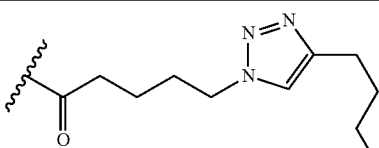 | 4.07 | 1501.00 |
| 43 | Analog 3 | Analog 3 | 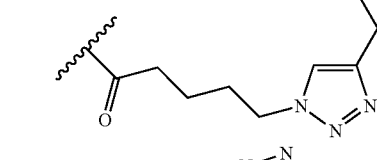 | 4.47 | 1993.95 |
| 44 | Analog 3 | Analog 3 | 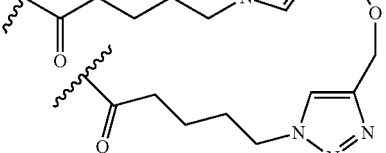 | 4.22 | 1494.14 |
| 59 | Analog 3 | Analog 3 | 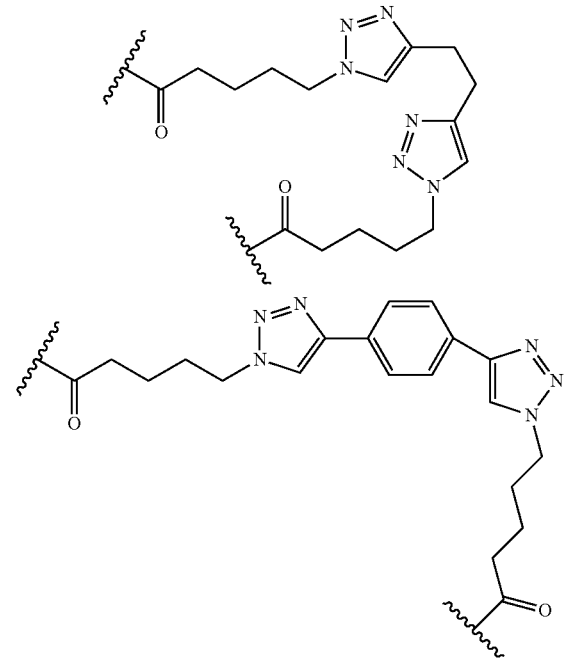 | 3.78 | 1714.17 |

The wavy line indicates the bond between the epsilon amino group of the B29 Lys and B29' Lys, respectively.

Example 20

This example illustrates the synthesis of $N^{2,1A},N^{2,1A'}$, $N^{2,1B},N^{2,1B'}$-Tetrakis(acetyl or PEG1 or methoxy acetyl)-Dimers (Dimer 48, 55, 56, 69, and 70).

To a solution of Dimer 40, 19, or 4 (21 mg, 1.777 μmol) in DMSO (2 mL) at room temperature was added TEA (3.96 μL, 0.028 mmol) and then a solution of 2,5-dioxopyrrolidin-1-yl acetate (2.23 mg, 0.014 mmol) in DMSO (100 μL) or other appropriate N-hydroxysuccinimide activated ester (2,5-dioxopyrrolidin-1-yl methoxy acetate or 2,5-dioxopyrrolidin-1-yl PEG1 acetate) in DMSO (100 μL). After 3 hours, the reaction mixture was diluted with 12 mL of mixture of water/AcCN=7/3 with 0.1% TFA, and pH was adjusted until 2.5. The resulting clear solution was concentrated by Amicon Ultra 15 Centrifuge Filters with 10K MWCO membrane. The resulting solution was first subjected to ion exchange chromatography (PolySULFOETHYL Å, 250×21 mm, 5 μm, 1000 Å, 15 mL/min, gradient from 5% to 45% in 30 min; Buffer A: 0.1% (v/v) $H_3PO_4$/25% Acetonitrile in water; Buffer B: 0.1% (v/v) $H_3PO_4$/25% Acetonitrile/0.5 M NaCl in water). Fractions containing desired product with desired purity were combined and concentrated using Amicon Ultra-15 with 10K MWCO membrane. The resulting solution was then subjected to reverse phase HPLC (KROMASIL C8 250×50 mm, 10 μm, 100 Å column; Buffer A: 0.05% TFA in AcCN/$H_2O$; Buffer B: 0.05% AcCN; flow rate 85 mL/min). The desired fractions were combined and freeze-dried to give Dimer 48, 55, 56, 69, or 70 as shown in Table 6. UPLC-MS Method F or G was used.

The N-terminal substituents have the structure

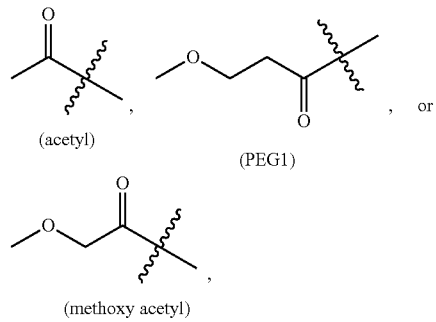

wherein the wavy line indicates the bond between the substituent and the N2 nitrogen of the N-terminal amino acid.

TABLE 6

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 48 | | RHI; A1, B1, A1', B' = acetyl | 4.71 | 1998.93 |
| 55 | | RHI; A1, B1, A', B' = acetyl | 3.61 | 1987.97 |
| 56 | | RHI; A1, B1, A1', B' = PEG1 | 3.53 | 1729.22 |
| 69 | | RHI; A1, B1, A1', B' = acetyl | 3.55 | 1727.31 |
| 70 | | RHI; A1, B1, A1', B' = methoxy acetyl | 3.67 | 1744.71 |

The wavy line indicates the bond between the epsilon amino group of the B29 Lys and B29' Lys, respectively.

Example 21

Table 7 shows Dimers 49, 50, and 51 and shows the acyl groups linked to the amino groups of $N^{2,A1}, N^{2,B1}, N^{2,A1'}$ and $N^{2,B1'}$. These dimers were prepared from Dimer 40 using the procedures analogous to that described for making Dimer 48 but substituting the appropriate N-hydroxysuccinimide activated esters for 2,5-dioxopyrrolidin-1-yl acetate to produce Dimers 49, 50, and 51. The activated esters were 2,5-dioxopyrrolidin-1-yl Fmoc-glycine acetate

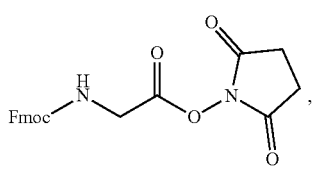

2,5-dioxopyrrolidin-1-yl PEG2 acetate

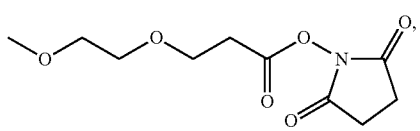 [SMILES: COCCOCCC(=O)ON1C(=O)CCC1=O]

and 2,5-dioxopyrrolidin-1-yl AEG-C6 acetate, wherein AEG is aminoethylglucose

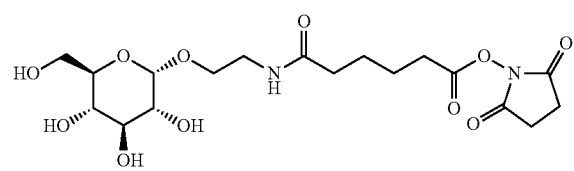 [SMILES: O=C(CCCCC(=O)ON1C(=O)CCC1=O)NCCO[C@H]1O[C@H](CO)[C@@H](O)[C@H](O)[C@H]1O]

These dimers were characterized using either UPLC-MS Method F (Dimers 50 and 51) or UPLC-MS Method G (Dimer 49), exhibiting either six charged, i.e. [(M+6)/6], (or seven charged, i.e. [(M+7)/7]) species of parent compound at certain retention time (Rt). The dimers are shown in Table 7.

The N-terminal substituents have the structure

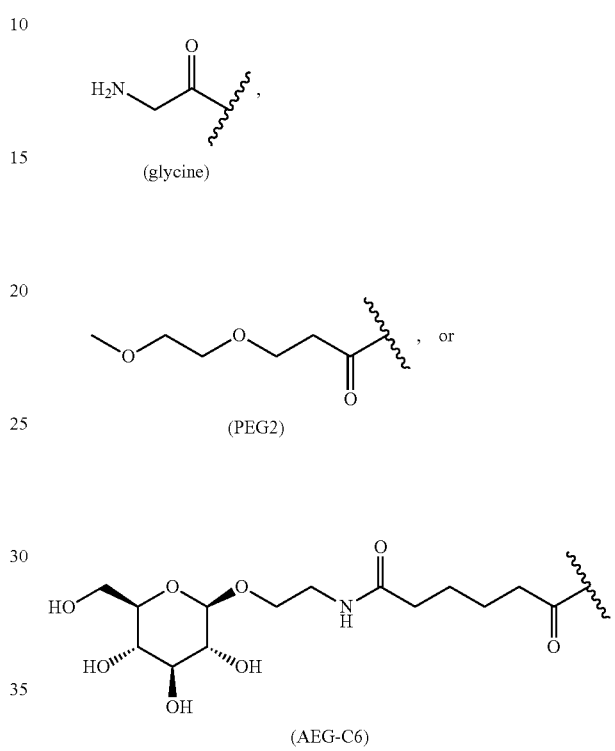

TABLE 7

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 49 | | RHI; A1, A1', B1, B1' = glycine | 3.62 | 1722.06 |
| 50 | | RHI; A1, A1', B1, B1' = PEG2 | 4.85 | 1764.16 |
| 51 | | RHI; A1, A1', B1, B1' = AEM-C6 | 4.06 | 1880.19 |

The wavy line indicates the bond between the epsilon amino group of the B29 Lys and B29' Lys, respectively.

Example 22

This example illustrates the synthesis of Dimer 52 using copper-free click chemistry.

To a solution of Analog 3 (10 mg, 1.686 μmol) in 1.0 mL of 3:2 v/v H$_2$O/AcCN at room temperature was added a solution of Analog 4 (10.5 mg, 1.686 μmol) in 1.0 mL of 3:2 v/v H$_2$O/AcCN. After stirring at room temperature for 2 hours, the reaction mixture was first subjected to ion exchange chromatography (PolySULFOETHYL A, 250×21 mm, 5 μm, 1000 Å, 15 mL/min, gradient from 5% to 45% in 30 min; Buffer A: 0.1% (v/v) H$_3$PO$_4$/25% Acetonitrile in water; Buffer B: 0.1% (v/v) H$_3$PO$_4$/25% Acetonitrile/0.5 M NaCl in water). Fractions containing desired product with desired purity were combined and concentrated using Amicon Ultra-15 with 3K or 10K MWCO membrane. The resulting solution was then subjected to reverse phase HPLC (KROMASIL C8 250×50 mm, 10 μm, 100 Å column; Buffer A: 0.05% TFA in AcCN/H$_2$O; Buffer B: 0.05% AcCN; flow rate 85 mL/min). The desired fractions were combined and freeze-dried to give Dimer 52. UPLC-MS Method F: Rt=3.73 min, m/z=1738.59 [(M+7)/7+1]. The results are shown in Table 8.

stirred. After completion of the reaction about 1 hour, the mixture is carefully acidified by dropwise addition of 1N HCl to pH 2.9. The suspension became clear solution. The mixture were purification by reverse phase prep HPLC (C-8 column, 50×250 cm, 85 ml/min, gradient from 29% to 36% in 25 min). (Water with 0.1% TFA and MeCN with 0.05% TFA). The desired fractions were lyophilyzed to give the dimers (19.9 mg, 1.506 μmol, 17.80% yield). UPLC-MS Method D: Rt=3.31 min, m/z=1989.44 [(M+6)/6+1].

The N-terminal substituents have the structure

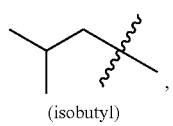 [SMILES: *CC(C)C]

(isobutyl)

wherein the wavy line indicates the bond between the substituent and the N2 nitrogen of the N-terminal amino acid, or

TABLE 8

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 52 | ![structure] | RHI; A1, A1' = H, B1, B1' = carbamoyl | 3.73 | 1738.59 |

The wavy line indicates the bond between the epsilon amino group of the B29 Lys and B29' Lys, respectively.

Example 23

This example illustrates the synthesis of $N^{2,1A}, N^{2,1A'}, N^{2,1B}, N^{2,1B'}$-Tetrakis(dimethyl or isobutyl)-Dimers (Dimers 60, 58, 65, and 67).

Dimer 40, 19, or 4 (100 mg, 8.46 μmol) was dissolved (suspension) in Water (10 ml) and adjusted to pH=4.0 by acetic acid solution, then formaldehyde (0.013 ml, 0.169 mmol) or isobutyraldehyde (0.025 ml, 0.272 mmol) was added, followed by addition of a freshly prepared solution of sodium cyanoborohydride (10.63 mg, 0.169 mmol) in Water (500 μL). The precipitate was formed. The mixture is gently

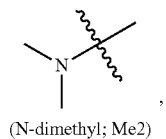

(N-dimethyl; Me2)

wherein the wavy line indicates the bond between the N2 nitrogen and the C2 carbon of the N-terminal amino acid.

The dimers are shown in Table 9.

TABLE 9

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 60 | | RHI; A1, B1, A1', B' = Me2 | 3.31 | 1989.44 |
| 58 | | RHI; A1, B1, A1', B' = Me2 | 3.42 | 1978.48 |
| 65 | | RHI; A1, B1, A1', B' = isobutyl | 4.13 | 1997.04 |
| 67 | | RHI; A1, B1, A1', B' = Me2 | 3.42 | 1719.39 |

The wavy line indicates the bond between the epsilon amino group of the B29 Lys and B29' Lys, respectively.

Example 24

Synthesis of Dimers 61, 62, 63, 64, and 66 was as Follows

The synthesis of 2,5-dioxopyrrolidin-1-yl 6-((2-((2,5-dioxopyrrolidin-1-yl)oxy)-2-oxoethyl)amino)-6-oxohexanoate (C6-glycine linker; Linker 24) is described.

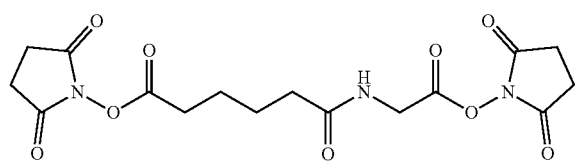 [SMILES: O=C(CCCCC(=O)ON1C(=O)CCC1=O)NCC(=O)ON1C(=O)CCC1=O]

Step 1 Benzyl(2,5-dioxopyrrolidin-1-yl) adipate

To a solution of 6-(benzyloxy)-6-oxohexanoic acid (5 g, 21.16 mmol) in DMF (10 mL) at 0° C. was added N-ethyl-N-isopropylpropan-2-amine (4.44 mL, 25.4 mmol) followed by TSTU (7.01 g, 23.28 mmol). The reaction was stirred at 0° C. for 1 hour and room temperature for 1 hour. The mixture was poured to ice-water/ethyl ether mixture (1/1, 100 mL). The mixture was extracted with ethyl ether (3×50 mL), washed with water (2×10 mL) and brine (10 mL). The organic layer was dried over MgSO$_4$, filtered through a pad of celite and concentrate to give the titled compound as colorless syrup (5.2 g, 15.6 mmol, 74%). LC-MS 2 min: Rt=1.05 min, m/z=334.1 [M+1].

Step 2-((Carboxymethyl)amino)-6-oxohexanoic acid

To a solution of glycine (225 mg, 3.0 mmol) in DMF (2.5 mL) was added the product of Step 1 (1.0 g, 3.0 mmol) in DMF (2.5 mL) drop wise followed by TEA (418 3.0 mmol). The reaction was stirred at room temperature for 18 hr. DMF was removed by under reduced pressure. The crude was purified by C18 reverse phase chromatography (eluted with 0-40% AcCN/water in 16 column volumes (CV)). Fractions containing desired product were combined, concentrated and lyophilized to give intermediate (6-(benzyloxy)-6-oxohexanoyl) glycine. To above intermediate in water (3 mL), was added Pd/C (10%, 160 mg, 0.15 mmol). The reaction was stirred at room temperature under hydrogen balloon for 18 hr. The mixture was filtered through a pad of celite, washed with MeOH/water (1/1, 10 ml). The filtrate was concentrated and lyophilized to give the titled compound (400 mg, 2.2 mmol, 66%). LC-MS 2 min: Rt=0.28 min, m/z=204.03 [M+1].

Step 3. 2,5-dioxopyrrolidin-1-yl 6-((2-((2,5-dioxopyrrolidin-1-yl)oxy)-2-oxoethyl)amino)-6-oxohexanoate To the product of Step 2 (10 mg, 0.049 mmol) in DMF (0.5 mL) at 0° C. was added TEA (0.015 mL, 0.108 mmol)

followed by TSTU (31.1 mg, 0.103 mmol). The reaction was warmed to room temperature and stirred at that temperature for 1 hr. TLC (EtOAc/MeOH/Water/AcCN: 2:1:1:1 (v:v:v:v)) showed formation of desired product (Rf: 0.25) and no starting material left. The crude material was used for constructing dimers without purification.

Linker 25 (C6-alanine), Linker 26 (C6-isoleucine), Linker 27 (C6-leucine), and Linker 28 (C6-valine) wherein the amino acid comprising the C6-amino acid linker is alanine, isoleucine, leucine, and valine, respectively, were synthesized similar to the process shown above. Dimers were constructed using the above linkers using prep. Method D. The results are shown in Table 10.

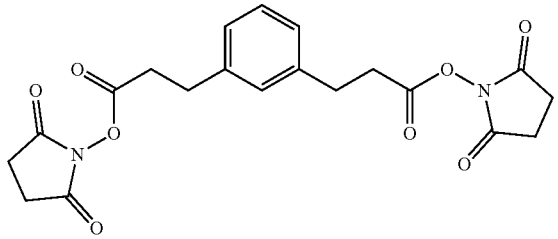 [SMILES: O=C(CCc1cccc(CCC(=O)ON2C(=O)CCC2=O)c1)ON1C(=O)CCC1=O]

TABLE 10

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 61 | | RHI; A1, B1, A1', B1' = Carbamoyl | 3.90 | 1993.24 |
| 62 | | RHI; A1, B1, A1', B1' = Carbamoyl | 3.91 | 1995.62 |
| 63 | | RHI; A1, B1, A1', B1' = Carbamoyl | 4.02 | 1714.70 |
| 64 | | RHI; A1, B1, A1', B1' = Carbamoyl | 3.80 | 1716.61 |
| 66 | | RHI; A1, B1, A1', B1' = Carbamoyl | 3.73 | 1716.93 |

The wavy line indicates the bond between the epsilon amino group of the B29 Lys and B29' Lys, respectively.

Example 25

Synthesis of Dimers 73, 89, 90, 91, 92, and 93 was as Follows

The synthesis of bis 2,5-dioxopyrrolidin-1-yl 3,3'-(1,3-phenylene)dipropionate (dipropyl phenyl; Linker 29) is described.

Step 1. bis 2,5-dioxopyrrolidin-1-yl 3,3'-(1,3-phenylene)dipropionate

To a solution of 3,3'-(1,3-phenylene)dipropionoic acid (21.8 mg, 0.098 mmol) in DMF (0.6 mL) at 0° C. was added TEA (29 mL, 0.206 mmol) followed by TSTU (62.0 mg, 0.206 mmol). The reaction was warmed to room temperature and stirred at that temperature for 1 hour. TLC (EtOAc/MeOH/Water/AcCN: 2/1/1/1) showed formation of desired product (Rf: 0.25) and no starting material left. UPLC-MS Method B: Rt=3.47 min, m/z=417.19 [M+1]. The product was used without further purification to construct Dimer 73 using Analog 5 using Method D.

The synthesis of bis(2,5-dioxopyrrolidin-1-yl) benzene-1,3-dicarboxylate (terephthalate; Linker 34) is described.

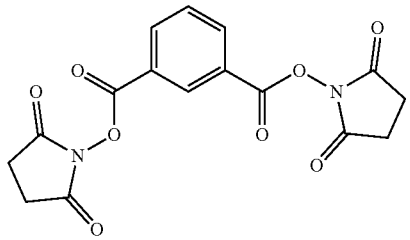 [SMILES: O=C(ON1C(=O)CCC1=O)c1cccc(C(=O)ON2C(=O)CCC2=O)c1]

Step 1. bis(2,5-dioxopyrrolidin-1-yl) benzene-1, 3-dicarboxylate

At 0° C., to a solution of terephthalic acid (100 mg, 0.602 mmol) in THF (2 ml) was added 2-(2,5-dioxopyrrolidin-1-yl)-1,1,3,3-tetramethylisouronium tetrafluoroborate (371 mg, 1.234 mmol) followed by N-ethyl-N-isopropylpropan-2-amine (0.222 ml, 1.234 mmol)). After 30 minutes, the ice bath was removed. The solution was stirred at room temperature for 1 hour. An additional 25 mL THF was added and the reaction was left overnight at room temperature. Product was concentrated down to about 5 mL and a portion was used as is without further purification to construct Dimer 89 using RHI using Method D. Remaining material was diluted with ethylacetate (200 mL) and washed with brine (10 mL), organic layer was dried with Na2SO4, filtered and concentrated.

Synthesis of bis (2,5-dioxopyrrolidin-1-yl) isophthalate (isophthalate; Linker 35) is Described

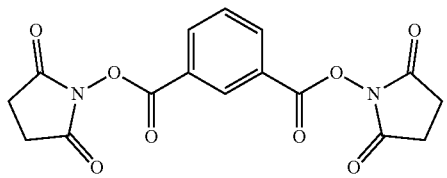 [SMILES: O=C(ON1C(=O)CCC1=O)c1cccc(C(=O)ON2C(=O)CCC2=O)c1]

Step 1. bis (2,5-dioxopyrrolidin-1-yl) isophthalate

To isophthalic acid (54 mg, 0.325 mmol) in DMSO (1 mL) was added TSTU (215 mg, 0.715 mmol) followed by TEA (0.137 mL, 0.975 mmol). LC-MS 2 min: Rt=0.79 min, m/z=721.28 [2M+1]. The product was used without purification to construct Dimer 90 using Analog 5 and Dimer 91 using RHI in Method E.

Synthesis of bis (2,5-dioxopyrrolidin-1-yl) 4-((tert-butoxycarbonyl)amino) heptanedioate (heptanedioate; Linker 36) is Described

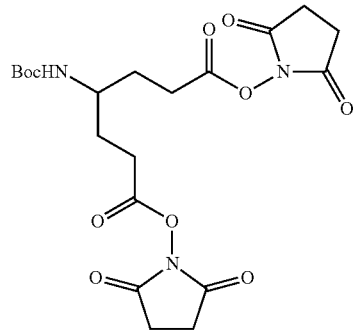 [SMILES: CC(C)(C)OC(=O)NC(CCC(=O)ON1C(=O)CCC1=O)CCC(=O)ON1C(=O)CCC1=O]

Step 1. bis (2,5-dioxopyrrolidin-1-yl) 4-((tert-butoxycarbonyl)amino) heptanedioate To 4-((tert-butoxycarbonyl)amino)heptanedioic acid (16.5 mg, 0.06 mmol) in DMSO (0.5 mL) was added TSTU (39.7 mg, 0.132 mmol) followed by TEA (0.025 mL, 0.180 mmol). LC-MS 2 min: Rt=0.90 min, m/z=470.34 [M+1]. The product was used without purification to construct Dimer 92 using Analog 5 and Dimer 93 using RHI in Method E.

The results are shown in Table 11.

TABLE 11

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 73 | | RHI; A1, B1, A1', B1' = Carbamoyl | 3.55 | 1711.57 |
| 89 | | RHI; A1, B1, A1', B1' = H | 3.43 | 1678.64 |

TABLE 11-continued

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 90 | | RHI; A1, B1, A1', B1' = Carbamoyl | 3.67 | 1703.20 |
| 91 | | RHI; A1, B1, A1', B1' = H | 3.52 | 1678.69 |
| 92 | | RHI; A1, B1, A1', B1' = Carbamoyl | 3.56 | 1704.64 |
| 93 | | RHI; A1, B1, A1', B1' = H | 3.33 | 1680.18 |

The wavy line indicates the bond between the epsilon amino group of the B29 Lys and B29' Lys, respectively.

Example 26

The synthesis of Dimers 71, 72, 77, 78, 81, and 87 was as follows. Synthesis of bis(2,5-dioxopyrrolidin-1-yl) (1S,4S)-cyclohexane-1,4-dicarboxylate (Linker 30; trans-cyclohexane 1,4-diacid) is described.

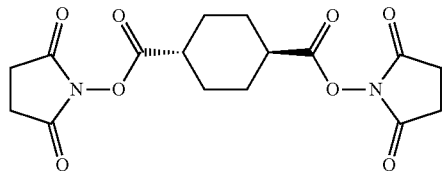 [SMILES: O=C1CCC(=O)N1OC(=O)[C@H]1CC[C@H](C(=O)ON2C(=O)CCC2=O)CC1]

To a solution of (1S,4S)-cyclohexane-1,4-dicarboxylic acid (200 mg, 1.162 mmol) in DCM (11 mL) at 0° C. was added TSTU (734 mg, 2.439 mmol) and DIPEA (0.5 mL, 2.86 mmol). The resulting reaction mixture was stirred at room temperature for 1 hour. The product was crushed out in reaction solution as white solid; filtered and washed with DCM (2×5 ml); and dried in vacuo to obtain the title compound. UPLC-MS calculated for $C_{16}H_{18}N_2O_8$, 366.11, observed m\e: 367.16 (M+H)+, (Rt: 3.20/5.00 minutes). UPLC-MS Method A. $^1$H NMR (500 MHz, DMSO): δ 2.81-2.89 (m; 2 H); 2.80 (s; 8 H); 2.02-2.10 (m; 4 H); 1.57-1.63 (m; 4 H).

Synthesis of bis(2,5-dioxopyrrolidin-1-yl) (1R,4R)-cyclohexane-1,4-dicarboxylate (Linker 31; cis-cyclohexane 1,4-diacid) is Described

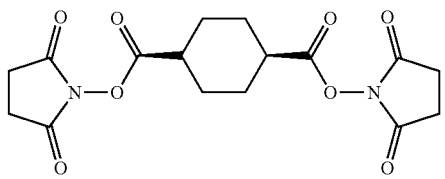

To a solution of (1R,4R)-cyclohexane-1,4-dicarboxylic acid (200 mg, 1.162 mmol) in DCM (11 mL) at 0° C. was added TSTU (734 mg, 2.439 mmol) and DIPEA (0.5 mL, 2.86 mmol). The resulting reaction mixture was stirred at room temperature for 1 hour. The residue was purified by silica gel chromatography (0-100% EtOAc/Hexanes) to provide the title compound. UPLC-MS calculated for $C_{16}H_{18}N_2O_8$, 366.11, observed m/z: 367.17 (M+H)+, (Rt: 3.17/5.00 minutes). UPLC-MS Method A. $^1$H NMR (500 MHz, DMSO): δ 3.02-3.08 (m; 2 H); 2.80 (s; 8 H); 1.80-1.90 (m; 8 H).

Synthesis of 1-(tert-butyl) 3,5-bis(2,5-dioxopyrrolidin-1-yl) (3R,5S)-piperidine-1,3,5-tricarboxylate (Linker 32) is Described

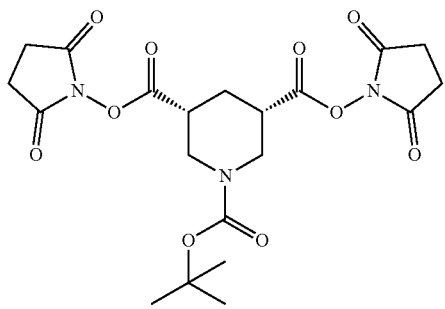 [SMILES: CC(C)(C)OC(=O)N1C[C@H](C(=O)ON2C(=O)CCC2=O)C[C@H](C(=O)ON2C(=O)CCC2=O)C1]

To a solution of (3R,5S)-1-(tert-butoxycarbonyl)piperidine-3,5-dicarboxylic acid (200 mg, 0.734 mmol) in DMF (7 mL) at 0° C. was added TSTU (485 mg, 1.611 mmol) and DIPEA (0.3 mL, 1.718 mmol). The resulting reaction mixture was stirred at room temperature for 2 hour. The residue was purified by silica chromatography (0-100% EtOAc/Hexanes) to provide the title compound. UPLC-MS calculated for $C_{20}H_{25}N_3O_{10}$, 467.15, observed m\e: 468.30 (M+H)+, (Rt: 0.98/2.00 minutes). UPLC-MS Method A.

General Method F: Synthesis of $N^{6,29}B,N^{6,29}B'$-Insulin Dimers Using Organic Base Condition In an appropriate sized container, insulin or insulin analog is suspended at room temperature in an organic solvent or mixed aq/organic solvents, e.g., DMSO, in the presence of a base, e.g., TEA, or 1,1,3,3-tetramethylguanidine (TMG). The mixture is allowed to stir gently until insulin is completely dissolved. To the resulting solution is added an activated ester intermediate in solution of organic solvents, such as DMSO or DMF. After UPLC, chromatogram shows that a substantial portion of the reaction mixture has converted into $N^{6,29}B, N^{6,B29B'}$-insulin dimer (or $N^{6,28B},N^{6,28B'}$-insulin lispro dimer), the reaction solution was transfered, via autopipette, to a 50 mL centrifuge tube containing IPAc/MTBE (v/v 4:1) (45 mL). The addition was made dropwise. The resulting white suspension was centrifuged (3000 rpm, 15 minutes, at 4 C) to generate a clear supernatant and a white pellet. The supernatant was drawn off and white pellet was dried in vacuo. The white pellet containing crude intermediate was then dissolved in 2 mL of TFA at 0 C and stirred for 10 minutes at same temperature. Upon completion of the de-boc reaction, the reaction solution was transferred, via autopipette, to a 50 mL centrifuge tube containing MTBE (45 mL). The addition was made dropwise. The resulting white suspension was centrifuged (3000 rpm, 15 minutes, at 4° C.) to generate a clear supernatant and a white pellet. The supernatant was drawn off and white pellet was dried in vacuo. and re-dissolved in $CH_3CN/H_2O$ (v/v 1:4) solution. Reaction mixture may be subjected directly to reverse phase HPLC purification (Waters C4 250×50 mm column, 10 μm, 1000 Å column or KROMASIL C8 250×50 mm, 10 μm, 100 Å column; Buffer A: 0.05-0.1% TFA in deionized water; Buffer B: 0.05-0.1% TFA in AcCN), or the reaction may be quenched by careful dilution with cold acidic $H_2O$ (20×, pH~3.0) at 0° C. and its pH is adjusted to a final pH of 2.5 using 1 N HCl (and 0.1 N NaOH if needed). The solution may first be concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing B29-conjugate with desired purity are combined and concentrated using TFF system or Amicon Ultra-15. The concentrated solution is then subjected to reverse phase HPLC purification (Waters C4 250× 50 mm column, 10 μm, 1000 Å column or KROMASIL C8 250×50 mm, 10 μm, 100 Å column; Buffer A: 0.05-0.1% TFA in deionized water; Buffer B: 0.05-0.1% TFA in AcCN). Fractions containing the desired insulin dimer are combined and freeze-dried or buffer exchanged using TFF system and/or Amicon Ultra-15 to give the $N^{6,29B},N^{6,29B'}$-Insulin dimers.

Table 12 lists Dimers 71, 72, 77, 78, 81, and 87, which were prepared using the appropriate linker following either General Method B (Dimers 77 and 78), General Method C (Dimers 71 and 72) or General Method F (Dimers 81 and 87). These dimers were characterized using UPLC-MS Method D or UPLC-MS Method E, exhibiting either six charged, i.e. [(M+6)/6], (or seven charged, i.e. [(M+7)/7]) species of parent compound at certain retention time (Rt).

TABLE 12

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 71 | | RHI; A1, B1, A1', B1' = H | 3.05 | 1959.33 1679.86 |
| 72 | | RHI; A1, B1, A1', B1' = H | 3.07 | 1959.33 1679.86 |

TABLE 12-continued

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 81 | ![structure] | RHI; A1, B1, A1', B1' = H | 3.37 | 1959.48 1679.74 |
| 77 | ![structure] | RHI; A1, B1, A1', B1' = carbamoyl | 3.50 | 1988.07 1704.29 |
| 78 | ![structure] | RHI; A1, B1, A1', B1' = carbamoyl | 3.52 | 1988.08 1704.35 |
| 86 | ![structure] | RHI: A1, B1, A1', B1' = carbamoyl | 3.48 | 1988.18 1704.24 |

The wavy line indicates the bond between the epsilon amino group of the B29 Lys and B29' Lys, respectively.

Example 27

Synthesis of Dimer 68 and Dimer 74 was as Follows

Synthesis of bis(2,5-dioxopyrrolidin-1-yl) 6,6'-((6-chloro-1,3,5-triazine-2,4-diyl)bis(azanediyl))dihexanoate (Linker 33; C6N-chloro-1,3,5-Triazine-NC6) is Described

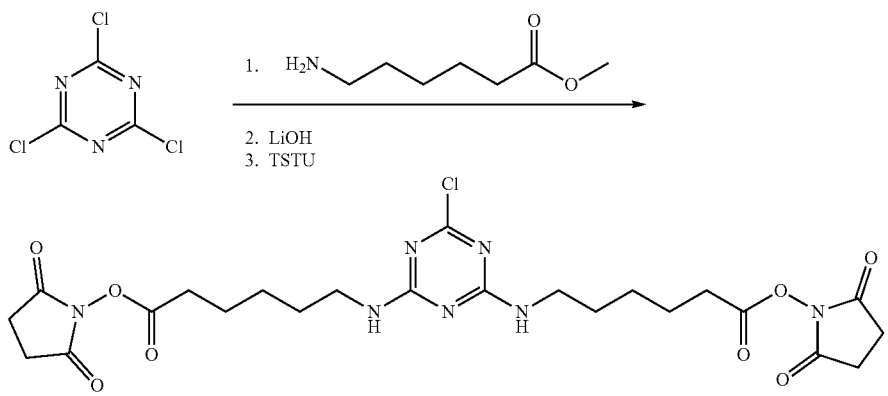

The solution of 2,4,6-trichloro-1,3,5-triazine (80 mg, 0.434 mmol) and methyl 6-aminohexanoate (129 mg, 0.889 mmol) HCl salt in $CH_2Cl_2$ (1 mL) was cooled to −30° C. A solution of DIPEA (0.379 mL, 2.169 mmol) in $CH_2Cl_2$ (1 mL) was added dropwise. The mixture was stirred at −30° C.-room temperature for 5 hours. Then added $CH_2Cl_2$ (20 mL) and washed with aqueous HCl (1 M) (2×10 mL), aqueous $NaHCO_3$ (10 ml) and brine (10 mL). The organic layer dried over sodium sulfate and filtered, concentrated by vacuum to furnish dimethyl 6,6'-((6-chloro-1,3,5-triazine-2,4-diyl)bis(azanediyl))dihexanoate (135 mg, 0.336 mmol).

To the solution of dimethyl 6,6'-((6-chloro-1,3,5-triazine-2,4-diyl)bis(azanediyl))dihexanoate (135 mg, 0.336 mmol) in THF (0.5 ml) and methanol (0.5 mL) was added aqueous (2M) LiOH (504 1.008 mmol). The mixture was stirred at room temperature for 1 hour and then concentrated in vacuo to produce a dried residue. Dissolved the residue in water and neutralized with aq HCl. Collected the precipitate by filtration and washed it with water. Dried the solid in vacuo to furnish of 6,6'-((6-chloro-1,3,5-triazine-2,4-diyl)bis(azanediyl))dihexanoic acid.

To a solution of 6,6'-((6-chloro-1,3,5-triazine-2,4-diyl)bis(azanediyl))dihexanoic acid (108 mg, 0.289 mmol) in DMF (2889 µl) was added TSTU (174 mg, 0.578 mmol) followed by triethylamine (81 µl, 0.578 mmol). Stirred the reaction 1 hour. UPLC indicates formation of desired material UPLC-MS Method C: Rt=0.99 min, m/z=568.2 [M+1]. This reagent (0.1M/DMF) was used without further purification.

The dimers were prepared using either General Method B (Dimer 74) or General Method C (Dimer 68). These dimers were characterized using UPLC-MS Method D or UPLC-MS Method E, exhibiting either six charged, i.e. [(M+6)/6], (or seven charged, i.e. [(M+7)/7]) species of parent compound at certain retention time (Rt). Dimer 68 was constructed using Linker 33 and RHI. Dimer 74 was constructed using Linker 33 and Analog 5. The results are shown in Table 13.

mixture containing water (5 mL) and potassium phosphate dibasic (24.49 mg, 0.141 mmol) (pH of resulting solution is about 0.4). Added potassium cyanate (27.5 mg, 0.339 mmol) and stirred overnight. The product was purified by reverse-phase chromatography on C-8 phase (Column KROMASIL, C8 10 uM 100 A, size 250×50 mm; solvent A=water/0.05% TFA, solvent B=AcCN/0.05% TFA), Flow=85 mL/min, gradient B in A 26-34% in 30 min. UPLC-MS Method F: Rt=4.48 min, m/z=1486.9 [(M+4)/4+1].

Dissolved the above product (60 mg, 10.09 µmol) in DMSO (594 µl) and added triethylamine (28.1 µl, 0.202 mmol) followed by solution of linker disuccinimidyl suberate (1.858 mg, 5.04 µmol) dissolved in 100 µL of DMSO. Stirred for 3 hours. UPLC indicates reaction complete. Added the whole reaction mixture into ammonium hydroxide (2105 µl, 15.13 mmol) (dropwise, exotherm expected). Stirred gently for 2 hours and confirmed deprotection of the TFA group. Diluted the mixture by 20 mL of water and removed most of ammonium hydroxide by diafiltration using 10K Amicon tubes. Adjusted pH to about 3 and removed the salts by diafiltration. The product was purified by ion-exchange chromatography (PolySULFOETHYL A column, PolyLC Inc., 250×21 mm, 5 µm, 1000 Å; Buffer A: 0.1% (v/v) H₃PO₄/25% AcCN; Buffer B: 0.1% (v/v) H₃PO₄/

TABLE 13

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 68 | 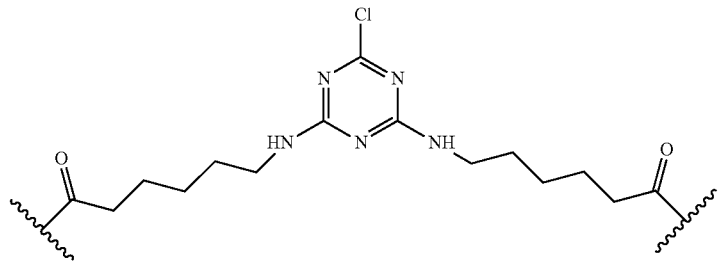 [SMILES: *C(=O)CCCCCNc1nc(Cl)nc(NCCCCCC(*)=O)n1] | A1, B1, A1', B1' = H | 3.48 | 1993.09 |
| 74 | 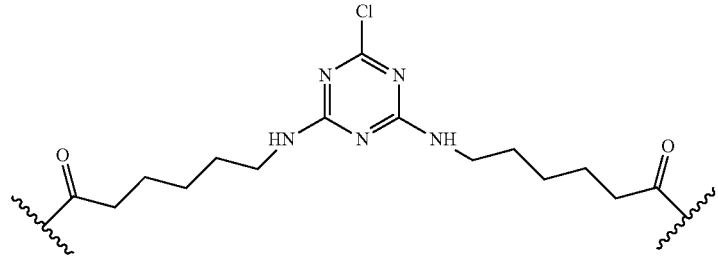 [SMILES: *C(=O)CCCCCNc1nc(Cl)nc(NCCCCCC(*)=O)n1] | A1, B1, A1', B1' = carbamoyl | 3.56 | 1733.20 |

The wavy line indicates the bond between the epsilon amino group of the B29 Lys and B29' Lys, repectively.

Example 28

The synthesis of Dimer 54 was as follows.

Dissolved A1-TFA-RHI (D. Liu et. al., Journal of Peptide Sci., 2012, 18, 336-341) (100 mg, 0.017 mmol) in a pre- 25% AcCN/0.5 M NaCl). The product was re-purified by reverse-phase chromatography on C-8 phase (Column KROMASIL, C8 10 µM 100 A, size 250×50 mm; solvent A=water/0.05% TFA, solvent B=AcCN/0.05% TFA). The result is shown below. Results are shown in Table 14.

TABLE 14

| Dimer No. | Structure of Dimer showing the Linking moiety between the B29 and B29' Lysine residues | Insulin Type; Insulin N termini | Rt (min) | (M + 6)/6 or (M + 7)/7 |
|---|---|---|---|---|
| 54 | (structure: diketone linker with carbonyl groups at each end connected by an alkyl chain) | RHI; A1, A1' = H, B1, B1' = carbamoyl | 4.57 | 1974.45 |

The wavy line indicates the bond between the epsilon amino group of the B29 Lys and B29' Lys, respectively.

Example 29

Insulin Receptor Binding Assays were performed as follows.

IR binding assay was run in a scintillation proximity assay (SPA) in 384-well format using cell membranes prepared from CHO cells overexpressing human IR(B) grown in F12 media containing 10% FBS and antibiotics (G418, Penicillin/Strepavidin). Cell membranes were prepared in 50 mM Tris buffer, pH 7.8 containing 5 mM $MgCl_2$. The assay buffer contained 50 mM Tris buffer, pH 7.5, 150 mM NaCl, 1 mM $CaCl_2$, 5 mM $MgCl_2$, 0.1% BSA and protease inhibitors (Complete-Mini-Roche). Cell membranes were added to WGA PVT PEI SPA beads (5 mg/mL final concentration) followed by addition of insulin dimer molecules at appropriate concentrations. After 5-15 min incubation at room temperature, $^{125}$[I]-insulin was added at 0.015 nM final concentration for a final total volume of 50 µL. The mixture was incubated with shaking at room temperature for 1 to 12 hours followed by scintillation counting to determine $^{125}$[I]-insulin binding to IR and the titration effects of insulin dimer molecules on this interaction.

Example 30

Insulin Receptor (IR) AKT-Phosphorylation Assays were performed as follows.

IR AKT-Phosphorylation Assay: Insulin receptor activation can be assessed by measuring phosphorylation of the Akt protein, a key step in the insulin receptor signaling cascade. CHO cell lines overexpressing human IR were utilized in an HTRF sandwich ELISA assay kit (Cisbio "Phospho-AKT(Ser473) and Phospho-AKT(Thr308) Cellular Assay Kits"). Cells were grown in F12 media supplemented with 10% FBS, 400 µg/mL G418 and 10 mM HEPES. Prior to assay, the cells were incubated in serum free media for 2 to 4 hr. Alternatively, the cells could be frozen and aliquoted ahead of time in media containing 20% DMSO and used in the assay upon thawing, spin down and re-suspension. Cells were plated at 10,000 cells per well in 20 µL of the serum free F12 media in 384-well plates. Humulin and insulin glargine controls were run on each plate of test compounds. The titrated compounds were added to the cells (2 µL per well, final concentrations=1000 nM titrated down to 0.512 pM in 1:5 fold dilutions) and incubated at 37° C. for 30 min. The cells were lysed with 8 µL of the prepared lysis buffer provided in the CisBio kit and incubated at 25° C. for 1 hr. The diluted antibody reagents (anti-AKT-d2 and anti-pAKT-Eu3/cryptate) were prepared according to the kit instructions and then 10 µL was added to each well of cell lysate followed by incubation at 25° C. for 3.5 to 5 hr. The plate was read by in an Envision plate reader (Excitation=320 nm; Emission=665 nm) to determine the IR pAkt agonist activity with regard to both potency and maximum response for each compound. Alternatively, the compounds were tested in the same manner in the presence of 1.6 nM of Humulin to determine how each compound was able to compete against the full agonist activity of insulin.

Example 31

Table 15 shows the in vitro biological activity of the insulin dimers towards the insulin receptor (IR). The activities were measured by either ligand competition assays as described in EXAMPLE 29 or functional Akt-phosphorylation assays as described in EXAMPLE 30.

TABLE 15

| Dimer No. | IR Binding $IC_{50}$ (nM) | IR pAkt % Max |
|---|---|---|
| 1 | 1.50 | 50.5 |
| 2 | 3.77 | 33 |
| 3 | 1.38 | 59.5 |
| 4 | 1.62 | 47.5 |
| 5 | 2.42 | 43 |
| 6 | 1.00 | 83 |
| 7 | 3.19 | 60 |
| 8 | 7.15 | 47.5 |
| 9 | 3.29 | 42 |
| 10 | 3.59 | 34 |
| 11 | 1.37 | 32 |
| 12 | 13.1 | 41 |
| 13 | 2.51 | 36 |
| 14 | 4.42 | 38 |
| 15 | 2.53 | 49 |
| 16 | 4.76 | |
| 17 | 5.27 | 62 |
| 18 | 5.23 | 36 |
| 19 | 1.40 | 25 |
| 20 | 0.62 | 36 |
| 21 | 1.88 | 41 |
| 22 | 1.85 | 41.5 |
| 23 | 2.48 | 39 |
| 24 | 4.29 | 29.3 |
| 25 | 1.82 | 46 |
| 26 | 3.74 | 44 |
| 27 | 3.98 | 31 |
| 28 | 1.96 | 25 |
| 29 | 1.18 | 30 |
| 30 | 1.79 | 30 |
| 31 | 1.36 | 31 |
| 32 | 21.6 | 33 |
| 33 | 2.41 | 38 |
| 34 | 0.57 | 67 |
| 35 | 1.17 | 66 |
| 36 | 0.53 | 28 |
| 37 | 3.52 | 42 |
| 38 | 2.18 | 45 |
| 39 | 3.17 | 45 |
| 40 | 2.03 | 41 |
| 41 | 0.64 | 35 |
| 42 | 2.97 | 49 |
| 43 | 2.02 | 35 |
| 44 | 1.18 | 33 |

TABLE 15-continued

| Dimer No. | IR Binding IC$_{50}$ (nM) | IR pAkt % Max |
|---|---|---|
| 45 | 4.00 | 38 |
| 46 | 0.38 | 25 |
| 47 | 4.56 | 30 |
| 48 | 5.09 | 35 |
| 49 | 5.16 | 58 |
| 50 | 3.61 | 39 |
| 51 | 0.59 | 27 |
| 52 | 3.93 | 67 |
| 54 | 0.49 | 26 |
| 55 | 2.02 | 28 |
| 56 | 2.94 | 33 |
| 57 | 2.02 | 26 |
| 58 | 0.61 | 34 |
| 59 | 0.97 | 53 |
| 60 | 1.81 | 60 |
| 61 | 20.3 | 33 |
| 62 | 5.01 | 32 |
| 63 | 26.7 | 41 |
| 64 | 15.7 | 34 |
| 65 | 3.05 | 42 |
| 66 | 34.5 | 33 |
| 67 | 0.54 | 24 |
| 68 | 4.81 | 34 |
| 69 | 4.99 | 18 |
| 70 | 14.8 | 21 |
| 71 | 2.28 | 45 |
| 72 | 2.35 | 42 |
| 73 | 37.8 | 35 |
| 74 | 73.8 | 33 |
| 75 | 1.85 | 52 |
| 76 | 1.87 | 35 |
| 77 | 42.1 | 23 |
| 78 | 167 | 22 |
| 79 | 1.47 | 42 |
| 80 | 5.48 | 39 |
| 81 | 0.3 | 40 |
| 82 | 1.73 | 50 |
| 83 | 558 | 21 |
| 84 | 2.19 | 50 |

Example 32

In this example, in vivo effects of several insulin receptor partial agonists of the present invention were compared to Compound A (insulin dimer MIU-90 disclosed in published PCT application No. WO2014052451) and compound B (B29,B29'-suberoyl-(insulin)$_2$) disclosed in Deppe et al., Nauyn-Schmiedeberg's Arch. Pharmacol. 350: 213-217 (1994) but using RHI instead of bovine insulin in an Intraperitoneal Insulin Tolerance Test (IP-ITT) assay performed in adult male, lean C57BL/6NTac mice.

Groups of N=6-8 animals per group were randomized by weight (average about 30 grams). Two days prior to study, the mice were conditioned to dosing with an intraperitoneal injection of 0.9% Sodium Chloride solution at 5 ml/kg dosing volume. On the morning of the study, food was removed two or four hours prior to the study. Blood glucose concentrations were determined at T=0 min (baseline) using a Glucometer. Mice were then dosed with vehicle, Dimer 24, Dimer 55, Dimer 58, Dimer 60, Dimer 67, Compound A, Compound B, or Humulin (RHI) at 5 mL/kg via intraperitoneal injection (see Table 16 for doses used). Blood glucose levels were determined from tail bleeds taken between 30 to 360 minutes after dose.

TABLE 16

| Compound | Doses |
|---|---|
| A | 72 nmol/Kg |
|   | 300 nmol/Kg |
| B | 72 nmol/Kg |
|   | 300 nmol/Kg |
| Dimer 24 | 72 nmol/Kg |
|   | 300 nmol/Kg |
| Dimer 55 | 120 nmol/Kg |
|   | 300 nmol/Kg |
| Dimer 58 | 60 nmol/Kg |
|   | 300 nmol/Kg |
| Dimer 60 | 120 nmol/Kg |
|   | 300 nmol/Kg |
| Dimer 67 | 60 nmol/Kg |
|   | 300 nmol/Kg |
| Humulin | 18 nmol/Kg |
|   | 72 nmol/Kg |

The results are shown in FIGS. 2A, 2B, 2C, 2D, 2E, 2F and 2G. The results show that the glucose profile for Dimer 24, Dimer 55, Dimer 58, Dimer 60, and Dimer 67 were substantially the same at both doses tested whereas increasing the dosage of compounds A and B caused an increased glucose lowering potency, indicating a lessor potential for hyperglycemic risk for the dimers compared to RHI or compounds A and B.

Example 33

The glucose lowering effect of Dimers 24, 18, and 40 were compared to RHI in Diabetic Yucatan miniature pigs (D minipigs) as follows.

Yucatan minipigs were rendered Type 1 diabetic by Alloxan injections following a proprietary protocol developed by Sinclair Research Center (Auxvasse, Mo.). Induction is considered successful if basal glucose levels exceed 150 mg/dL. D minipigs with plasma glucose levels of approximately 300 mg/dl were utilized in these experiments.

Male Yucatan minipigs, instrumented with two Jugular vein vascular access ports (VAP), were used in these studies. On the day of the study after an overnight fast, minipigs were placed in slings, and VAPs were accessed for infusion and sampling. At t=0 min, and after collecting two baseline blood samples for plasma glucose measurement (t=−30 minutes and t=0 minutes), minipigs were administered Humulin (recombinant human insulin, RHI) or IRPA as a single bolus IV, at 0.69 nmol/kg. Humulin and IRPA were formulated at 69 nmol/ml in a buffer containing Glycerin, 16 mg/mL; Metacresol, 1.6 mg/mL; Phenol, 0.65 mg/mL; Anhydrous Sodium Phosphate, Dibasic, 3.8 mg/mL; pH adjusted to 7.4 with HCl. After dosing, sampling continued for 480 minutes; time points for sample collection were −30 min, 0 min, 8 min, 15 min, 30 min, 45 min, 60 min, 90 min, 120 min, 150 min, 180 min, 210 min, 240 min, 270 min, 300 min, 330 min, 360 min, 420 min, 480 min. Blood was collected in K3-EDTA tubes, supplemented with 10 µg/mL aprotinin, and kept on ice until processing, which occurred within 30 minutes of collection. After centrifugation at 3000 rpm, 4° C., for 8 min, plasma was collected and aliquoted for glucose measurement using a Beckman Coulter AU480 Chemistry analyzer and for compound levels measurement.

FIG. 1 shows that at 0.69 nmol/kg concentration, RHI reduced serum glucose levels below 50 mg/dL whereas the insulin dimers did not. This result shows that the insulin dimers present less risk of promoting hypoglycemia than RHI.

Example 34

The glucose lowering effect of Dimers 4, 5, 7, 8, 9, 18-29, 32, 37-41, 43, 44, 48, 55, 57, 58, 60, 61, 62, 64, 67, 69, 71, 72, 77, and 78 were compared to RHI in Diabetic Yucatan miniature pigs (D minipigs) as follows.

Yucatan minipigs were rendered Type 1 diabetic by Alloxan injections following a proprietary protocol developed by Sinclair Research Center (Auxvasse, Mo.). Induction is considered successful if basal glucose levels exceed 150 D minipigs with plasma glucose levels of approximately 300-400 mg/dl and instrumented with two Jugular vein vascular access ports (VAP), were used in these studies.

On the day of the study, after an overnight fast, minipigs were placed in slings, and VAPs were accessed for infusion and sampling. At t=0 min, and after collecting two baseline blood samples for plasma glucose measurement (t=−30 minutes and t=0 minutes), minipigs were administered Humulin (recombinant human insulin, RHI) or other dimer as a single bolus IV, at 0.69 nmol/Kg (0.35 nmol/kg for compound#78). Humulin and dimers were formulated at 69 nmol/mL in a buffer containing Glycerin, 16 mg/mL; Meta-cresol, 1.6 mg/mL; Phenol, 0.65 mg/mL; Anhydrous Sodium Phosphate, Dibasic, 3.8 mg/mL, pH adjusted to 7.4 with HCl. After dosing, sampling continued for 480 minutes; time points for sample collection were −30 minutes, 0 minutes, 8 minutes, 15 minutes, 30 minutes, 45 minutes, 60 minutes, 90 minutes, 120 minutes, 150 minutes, 180 minutes, 210 minutes, 240 minutes, 270 minutes, 300 minutes, 330 minutes, 360 minutes, 420 minutes, and 480 minutes. Blood was collected in K3-EDTA tubes, supplemented with 10 µg/mL aprotinin, and kept on ice until processing, which occurred within 30 minutes of collection. After centrifugation at 3000 rpm, 4° C., for 8 minutes, plasma was collected and aliquoted for glucose measurement using a Beckman Coulter AU480 Chemistry analyzer. The results are shown FIG. 7A-7H. The Figures show that at 0.69 nmol/kg concentration, RHI reduced serum glucose levels below 50 mg/dL whereas the insulin dimers did not. This result shows that the insulin dimers present less risk of promoting hypoglycemia than RHI.

Example 35

This experiment compared the stability of the disulfide linking moiety of Compound A to the suberyol (C8) linking moiety of Dimer 24.

1 µM Compound A and Dimer 24 were each separately incubated in Rat Kidney Cell Membranes (RKCM) with or without 5 mM glutathione (GSH). Time 0 and Time 2 hour samples were obtained and the reaction quenched with 1 volume of 10% MeOH in AcCN with 0.1% Formic Acid. The quenched samples were then centrifuged and frozen prior to analysis. The samples were then thawed and analyzed using the Thermo Orbi Velos system. Targeted MetID analysis was performed with Extracted Ion Chromatograms (XICs) using 3 isotopes from 2 charge states at 10 ppm window.

Figure 3:
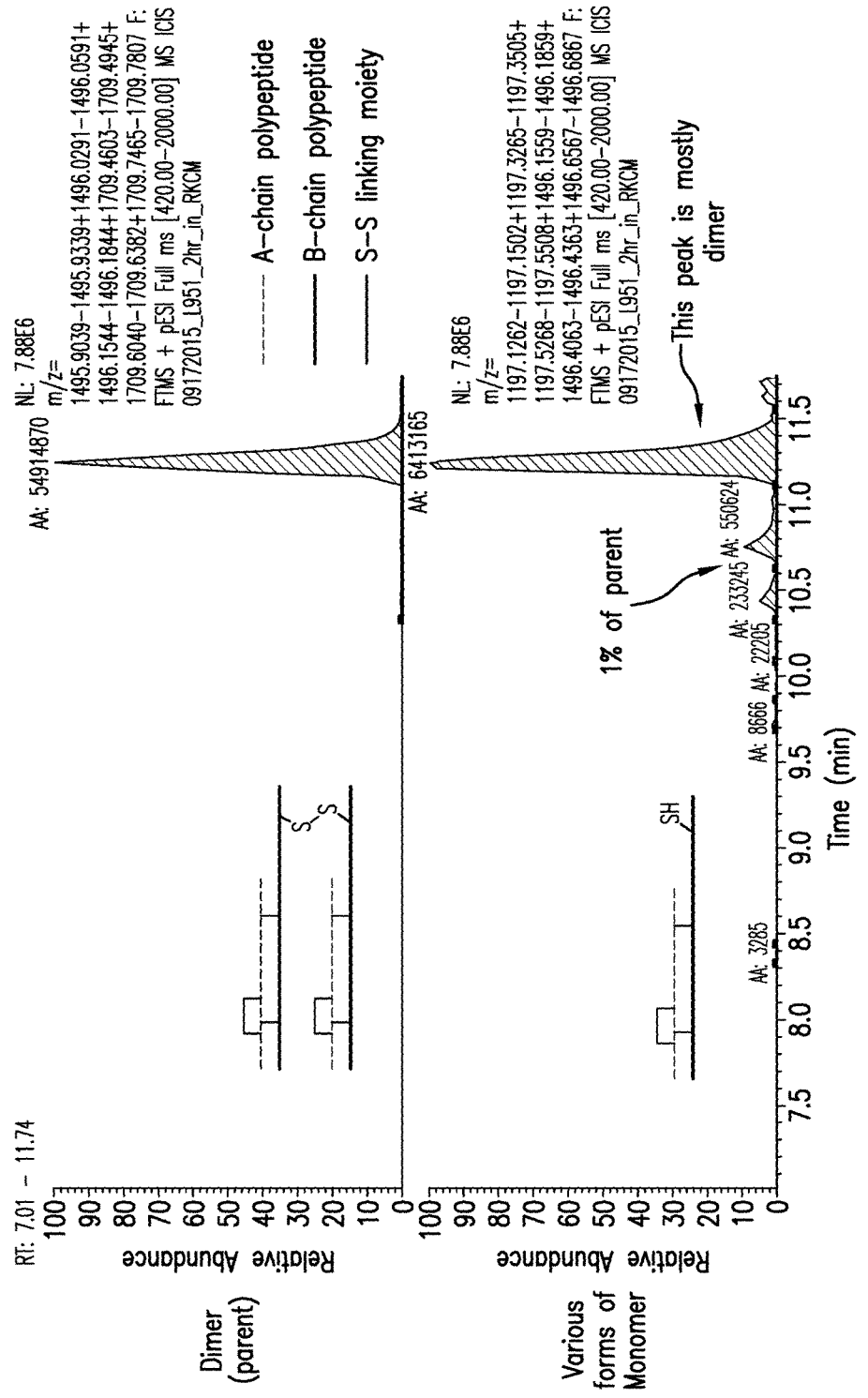
FIG. 3 shows that Compound A insulin dimer was degrading to insulin monomers by 2 hour incubation with rat kidney cell membranes (RKCMs) without glutathione (GSH). The % of parent values are semi-quantitative only due to potential differences in ionization efficiencies.
Figure 4:
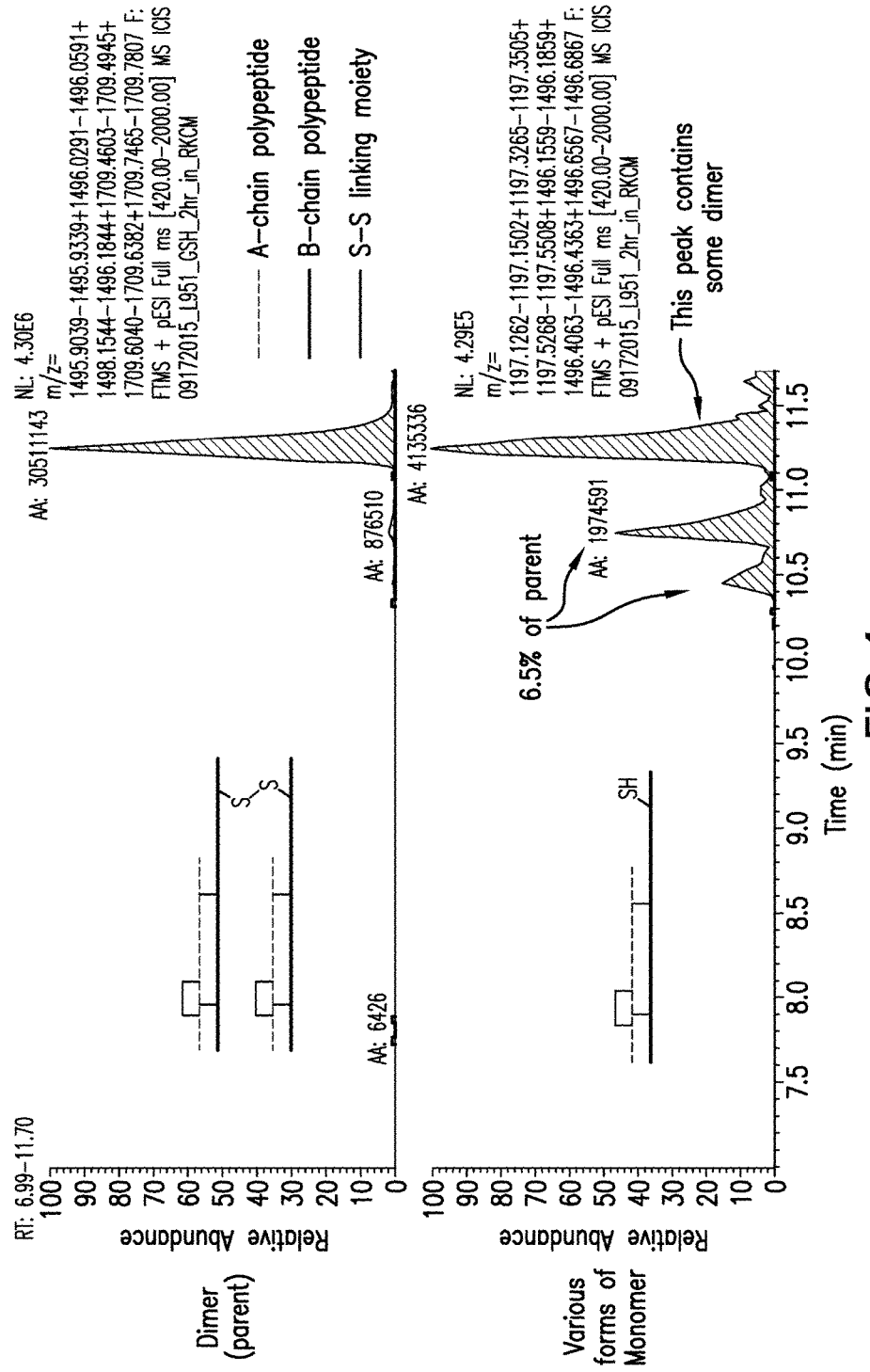
FIG. 4 shows that Compound A insulin dimer was degrading to insulin monomers by 2 hour incubation with rat kidney cell membranes (RKCMs) with glutathione (GSH). The % of parent values are semi-quantitative only due to potential differences in ionization efficiencies.

Compound A metabolites were detected in RKCM both without GSH and with GSH. As shown in FIG. 3, monomer was about 1% of parent (stock solution of Compound A) by 2 hours incubation. As shown in FIG. 4, monomer was about 6.5% of parent (stock solution of Compound A) by 2 hours incubation. The results show the disulfide linkage was breaking over time. No metabolites observed in 0 hour controls for Compound A or in the stock solutions.

Figure 5:
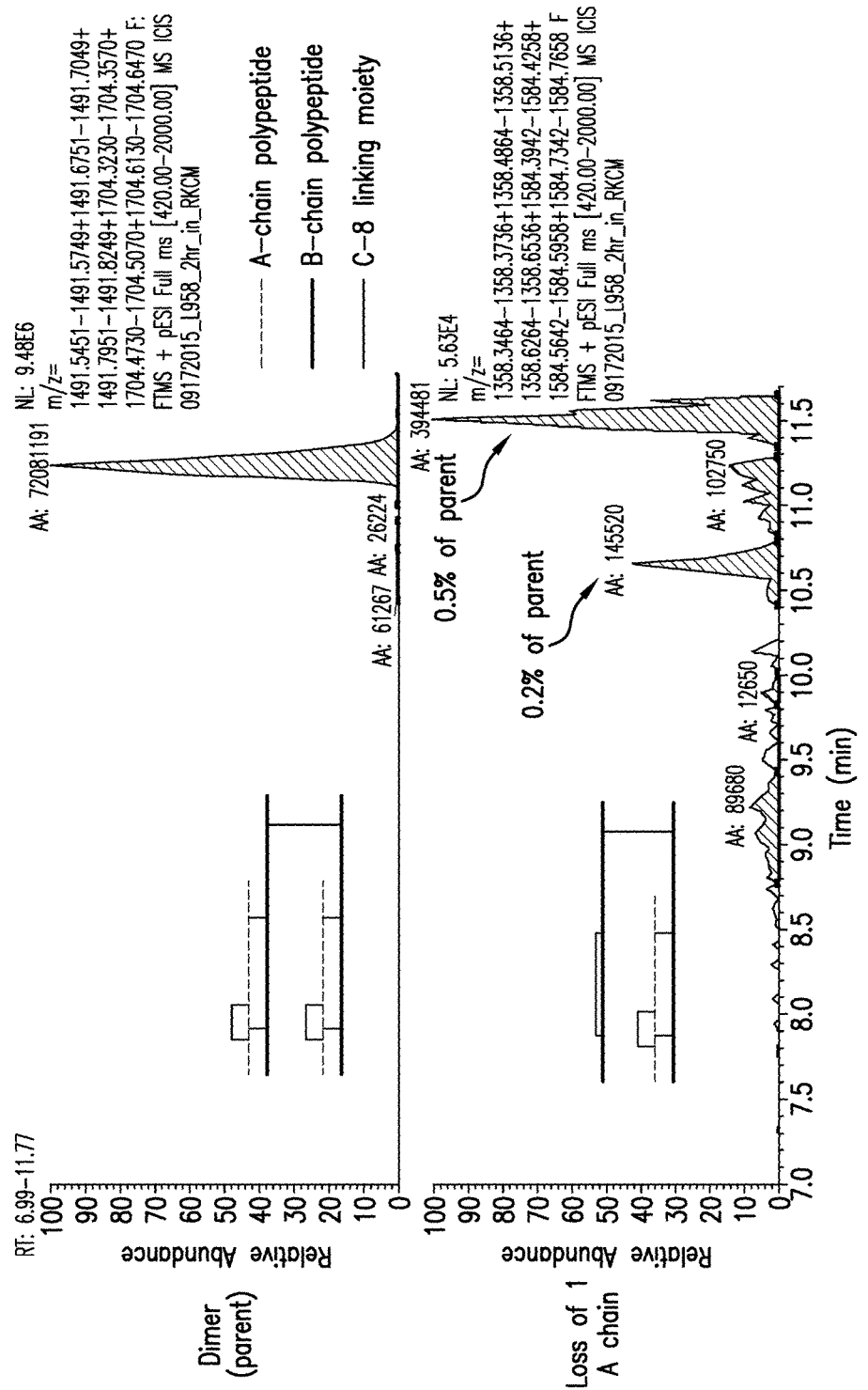
FIG. 5 shows that Dimer 24 lost some A-chain polypeptide but did not degrade to monomers by 2 hour incubation with rat kidney cell membranes (RKCMs) without glutathione (GSH). The % of parent values are semi-quantitative only due to potential differences in ionization efficiencies.
Figure 6:
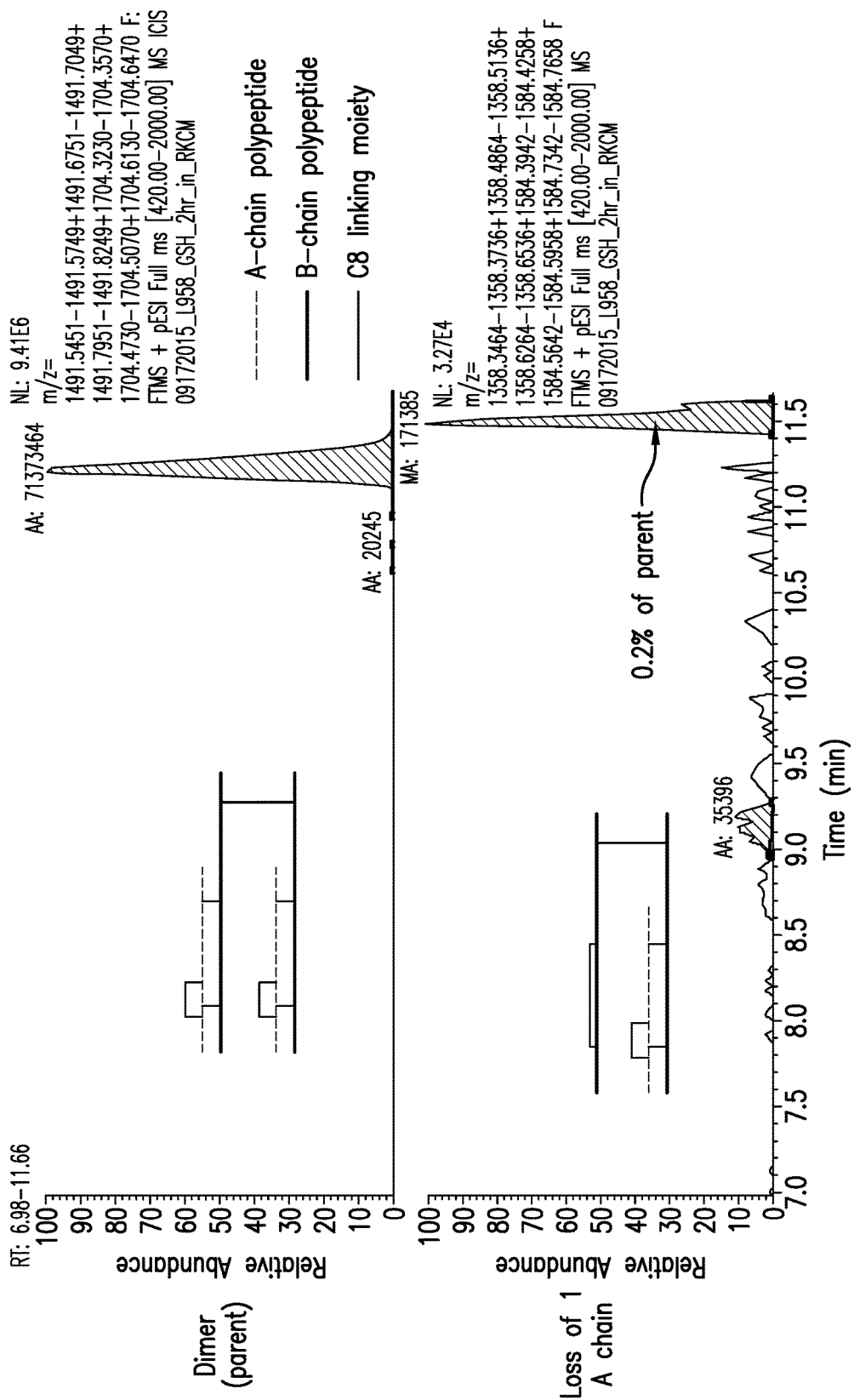
FIG. 6 shows that Dimer 24 lost some A-chain polypeptide but did not degrade to monomers by 2 hour incubation with rat kidney cell membranes (RKCMs) with glutathione (GSH). The % of parent values are semi-quantitative only due to potential differences in ionization efficiencies.
Figure 7A:
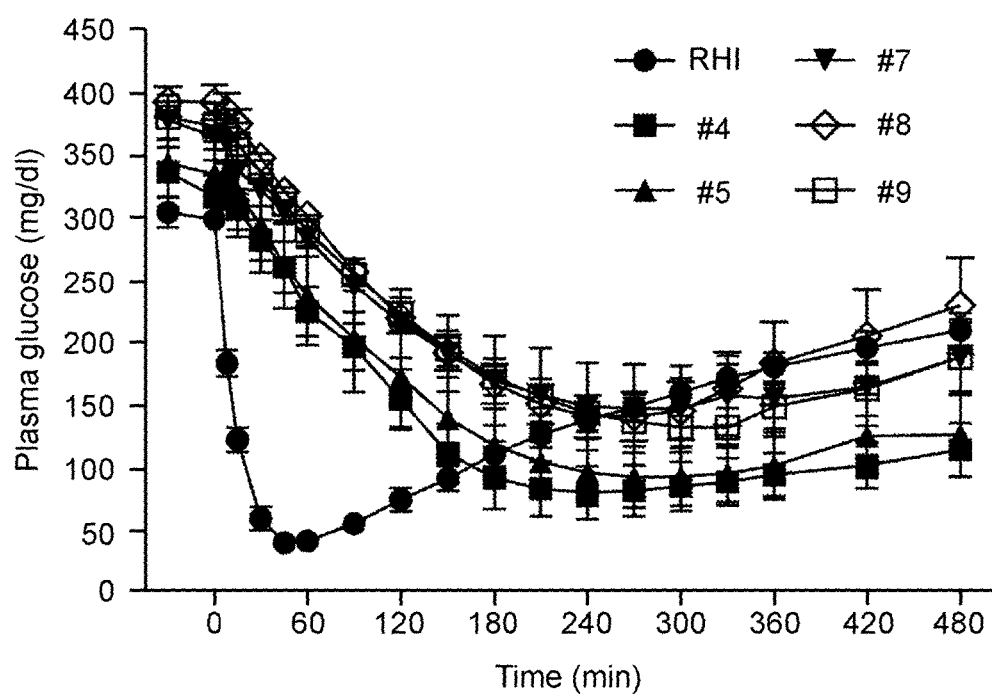
FIG. 7A shows the glucose lowering effect of Dimers 4, 5, 7, 8, and 9 compared to RHI when administered to diabetic minipigs at 0.69 nmol/kg.
Figure 7B:
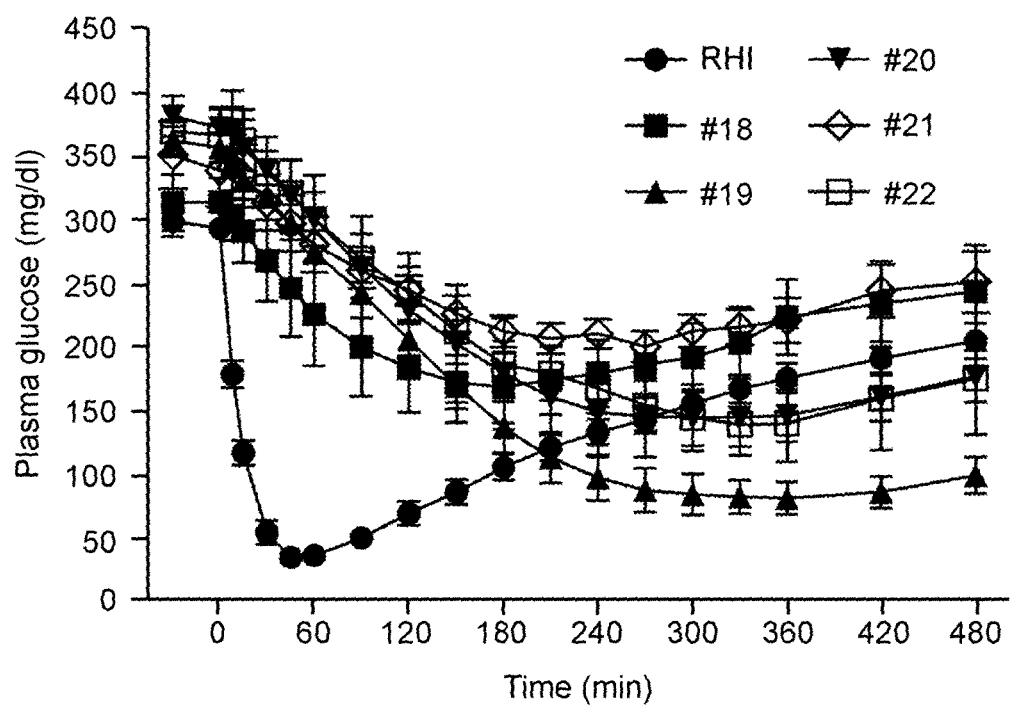
FIG. 7B shows the glucose lowering effect of Dimers 18, 19, 20, 21, and 22 compared to RHI when administered to diabetic minipigs at 0.69 nmol/kg.
Figure 7C:
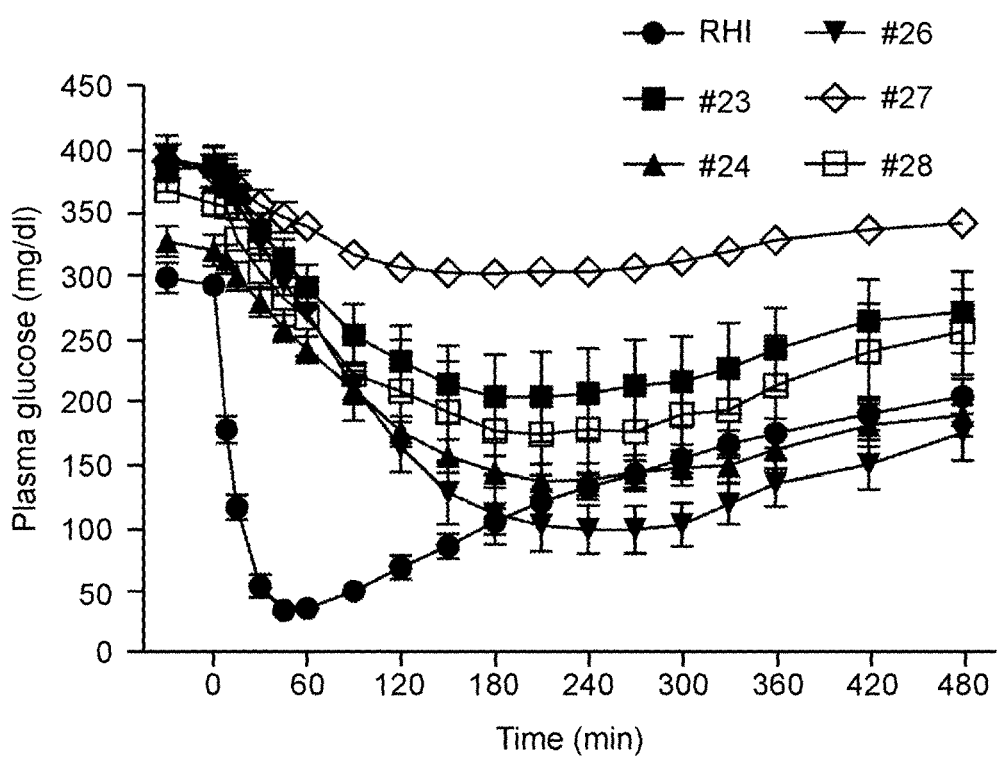
FIG. 7C shows the glucose lowering effect of Dimers 23, 24, 26, 27, and 28 compared to RHI when administered to diabetic minipigs at 0.69 nmol/kg.
Figure 7D:
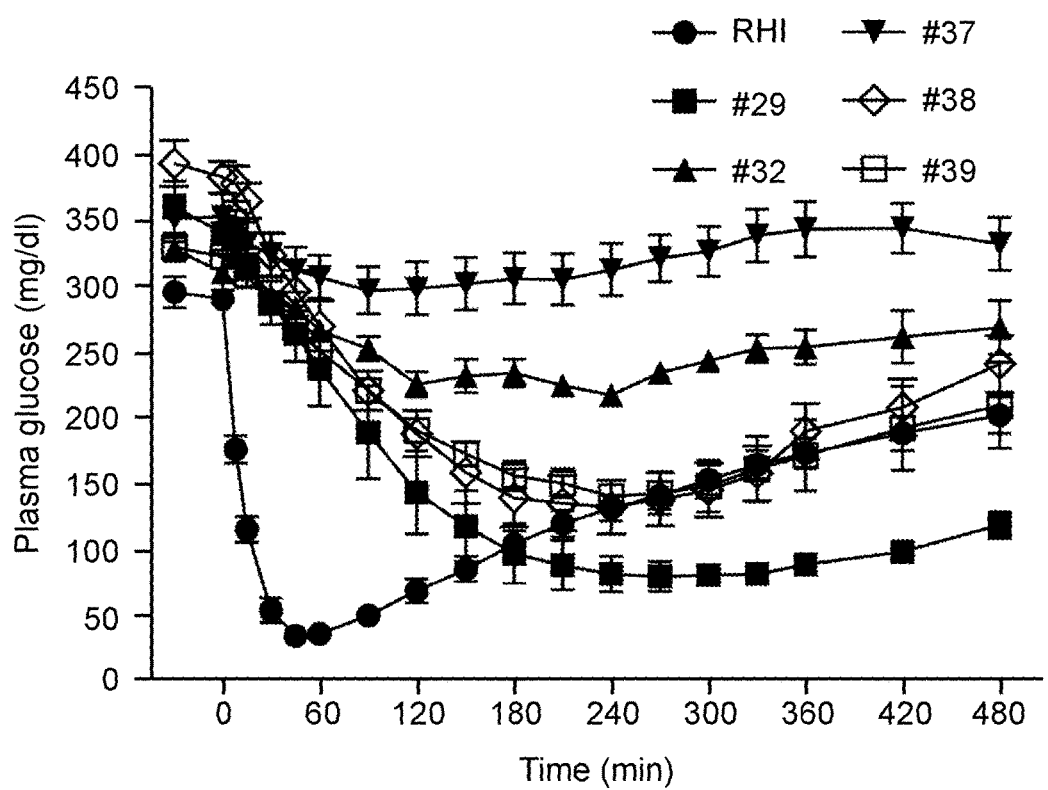
FIG. 7D shows the glucose lowering effect of Dimers 29, 32, 37, 38, and 39 compared to RHI when administered to diabetic minipigs at 0.69 nmol/kg.
Figure 7E:
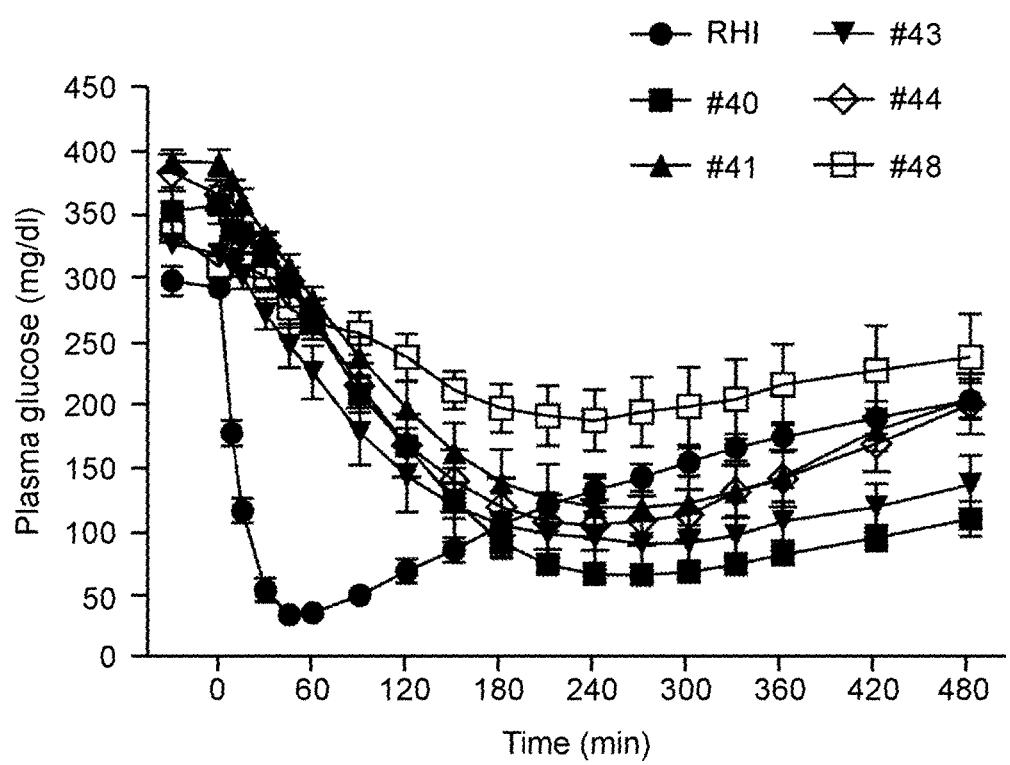
FIG. 7E shows the glucose lowering effect of Dimers 40, 41, 43, 44, and 48 compared to RHI when administered to diabetic minipigs at 0.69 nmol/kg.
Figure 7F:
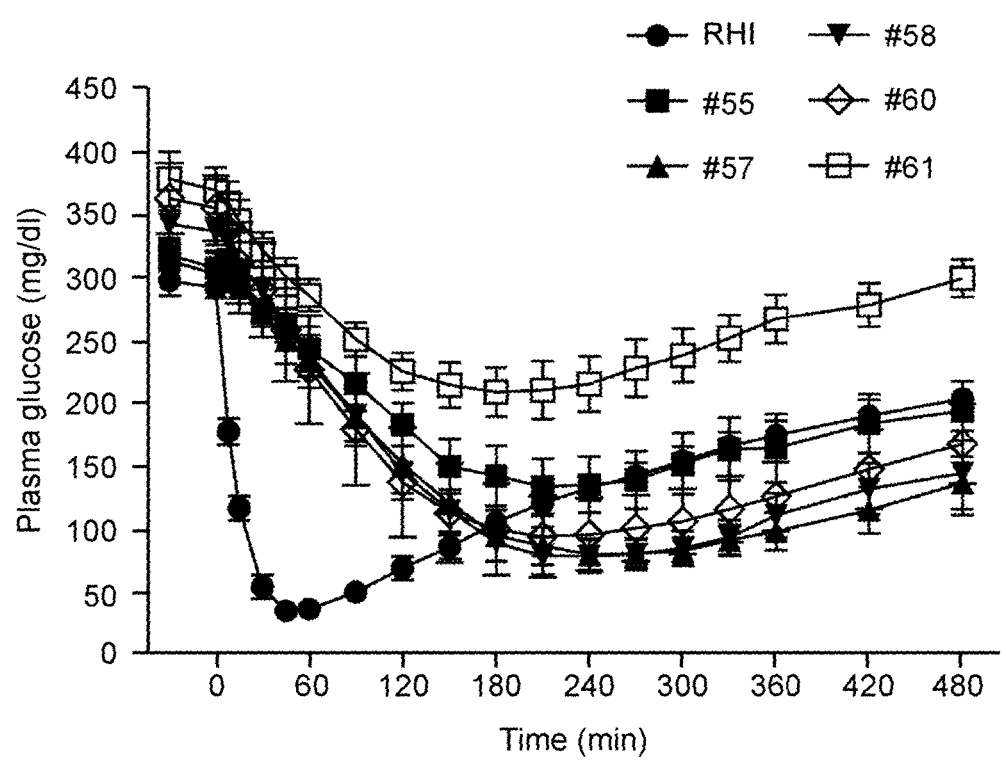
FIG. 7F shows the glucose lowering effect of Dimers 55, 57, 58, 60, and 61 compared to RHI when administered to diabetic minipigs at 0.69 nmol/kg.
Figure 7G:
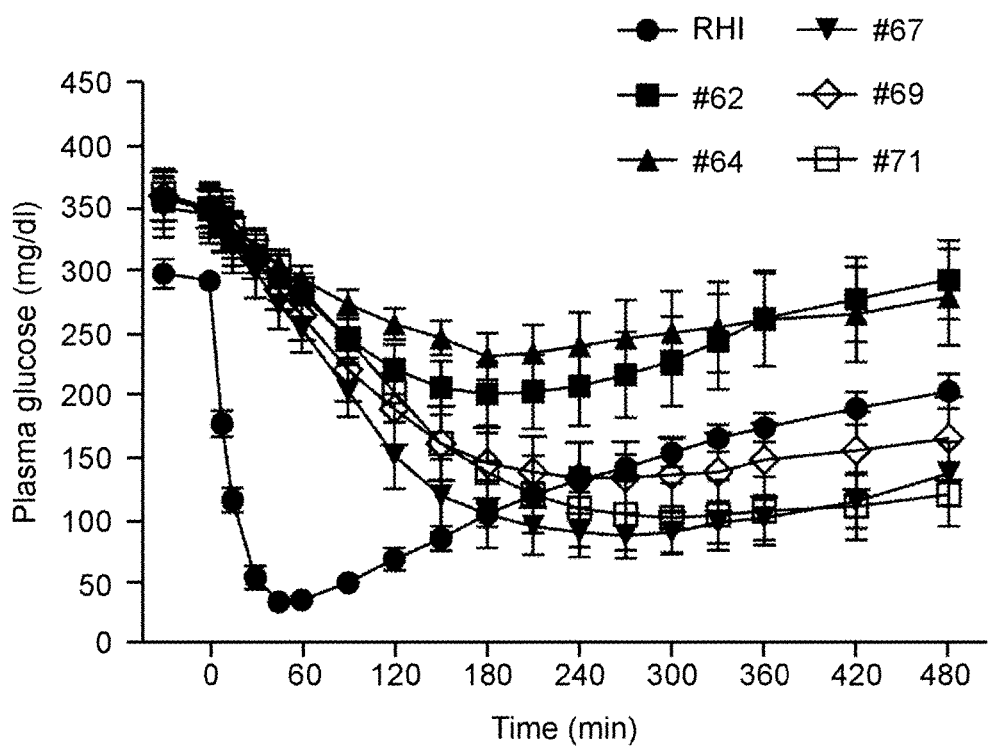
FIG. 7G shows the glucose lowering effect of Dimers 62, 64, 67, 69, and 71 compared to RHI when administered to diabetic minipigs at 0.69 nmol/kg.
Figure 7H:
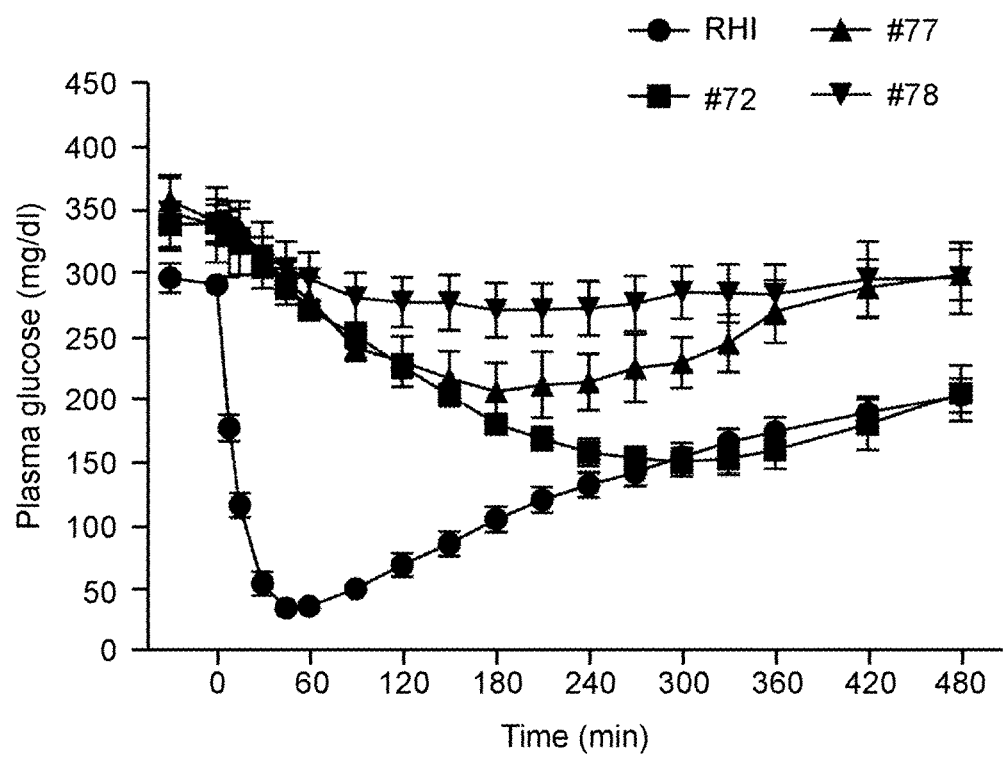
FIG. 7H shows the glucose lowering effect of Dimers 72, 77, and 78 compared to RHI when administered to diabetic minipigs at 0.69 nmol/kg.

Dimer 24 produced metabolites that were detected in RKCM, however, while loss of the A-chain polypeptide due to breakage of the disulfide bonds between the A-chain polypeptide and the B-chain polypeptide was observed, no monomers were detected. FIG. 5 shows that without GSH, loss of A-chain polypeptide was less than1 % of parent (stock solution of Dimer 24). FIG. 6 shows that with GSH, loss of A-chain polypeptide was less than1 % of parent (stock solution of Dimer 24). No metabolites observed in 0 hour controls for Dimer 24 or in the stock solutions. The new quenching procedure with acidic conditions properly halted disulfide exchange.

Table of Sequences

| SEQ. ID NO: | Description | Sequence |
|---|---|---|
| 1 | *Homo sapiens* insulin A chain | GIVEQCCTSICSLYQLENYCN |
| 2 | *Homo sapiens* insulin B chain | FVNQHLCGSHLVEALYLVCGERGFFYTPKT |
| 3 | Artificial sequence insulin A chain<br>$X_2$ is isoleucine or threonine;<br>$X_3$ is valine, glycine, or leucine;<br>$X_8$ is threonine or histidine;<br>$X_{17}$ is glutamic acid or glutamine;<br>$X_{19}$ is tyrosine, 4-methoxy-phenylalanine, alanine, or 4-amino phenylalanine;<br>$X_{23}$ is asparagine or glycine; | $GX_2X_3EQCCX_8SICSLYQLX_{17}NX_{19}CX_{23}$ |
| 4 | Artificial sequence insulin B chain<br>$X_{25}$ is histidine or threonine;<br>$X_{29}$ is alanine, glycine or serine;<br>$X_{30}$ is histidine, aspartic acid, glutamic acid, homocysteic acid, or cysteic acid;<br>$X_{31}$ is proline or lysine; and<br>$X_{32}$ is proline or lysine, with the proviso that at least one of $X_{31}$ or $X_{32}$ is lysine | $X_{25}LCGX_{29}X_{30}LVEALYLVCGERGFX_{27}YTX_{31}X_{32}$ |

-continued

Table of Sequences

| SEQ. ID NO: | Description | Sequence |
|---|---|---|
| 5 | $X_{22}$ is phenylalanine or desamino-phenylalanine; $X_{25}$ is histidine or threonine; $X_{26}$ is glycine or leucine; $X_{27}$ is phenylalanine or aspartic acid; $X_{29}$ is alanine, glycine, or serine; $X_{30}$ is histidine, aspartic acid, glutamic acid, homocysteic acid, or cysteic acid; $X_{31}$ is aspartic acid, proline, or lysine; $X_{32}$ is lysine or proline; $X_{33}$ is threonine, alanine, or absent; $X_{34}$ is arginine or absent; and $X_{35}$ is arginine or absent; With the proviso at least one of $X_{31}$ or $X_{32}$ is lysine | $X_{22}$VNQX$_{25}$X$_{26}$CGX$_{29}$X$_{30}$LVEALYLVCGERGFX$_{27}$YTX$_{31}$X$_{32}$X$_{33}$X$_{34}$X$_{35}$ |
| 6 | Artificial sequence insulin lispro B chain | FVNQHLCGSHLVEALYLVCGERGFFYTKPT |
| 7 | Artificial sequence insulin glargine A chain | GIVEQCCTSICSLYQLENYCG |
| 8 | Artificial sequence Insulin glargine B chain | FVNQHLCGSHLVEALYLVCGERGFFYTPKTRR |
| 9 | Artificial sequence Insulin aspart B chain | FVNQHLCGSHLVEALYLVCGERGFFYTDKT |
| 10 | Artificial sequence B: des30 | FVNQHLCGSHLVEALYLVCGERGFFYTPK |
| 11 | Artificial sequence A: Y19A | GIVEQCCTSICSLYQLENACN |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A compound selected from the group consisting of

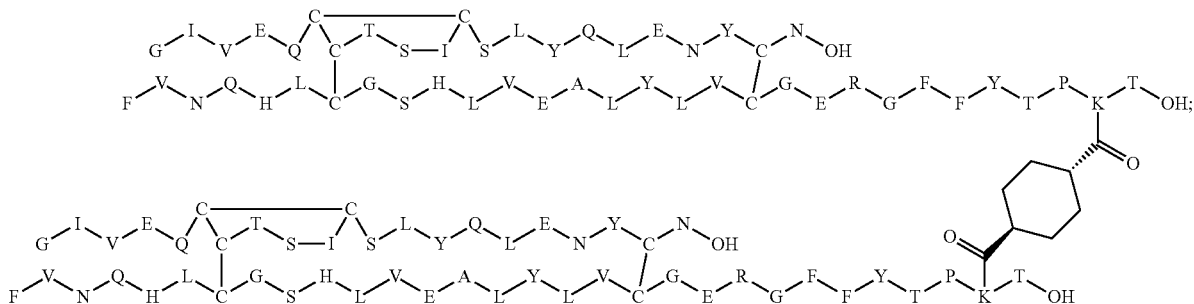

Dimer 71

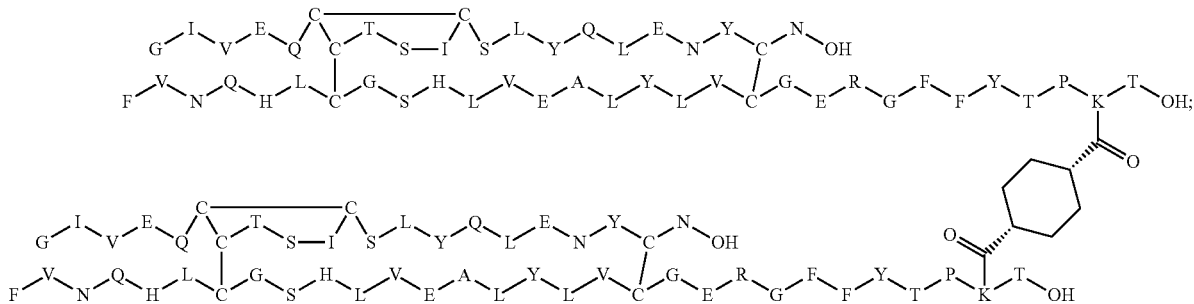

Dimer 72

Dimer 77

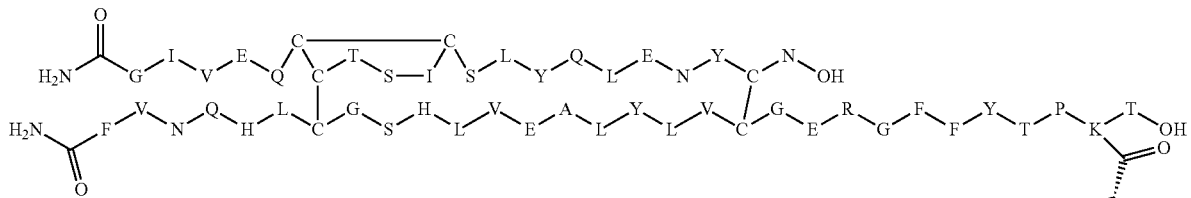

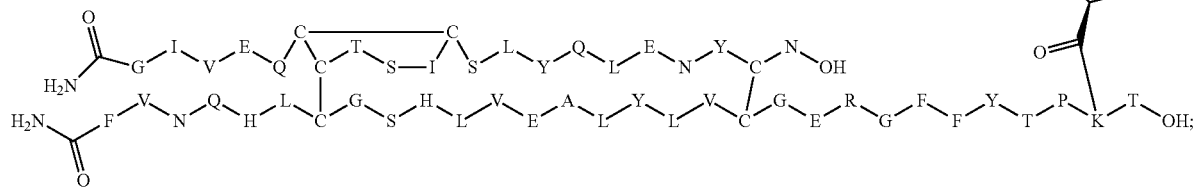

Dimer 78

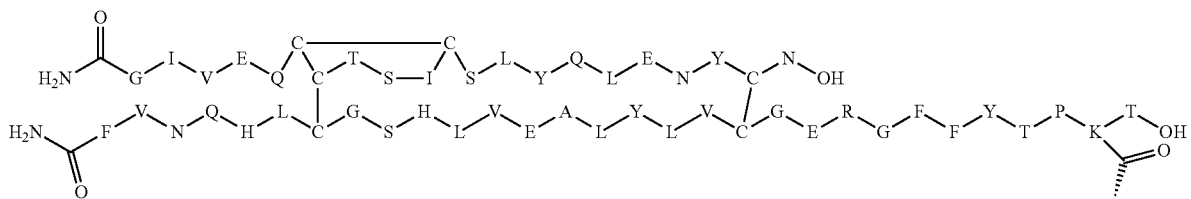

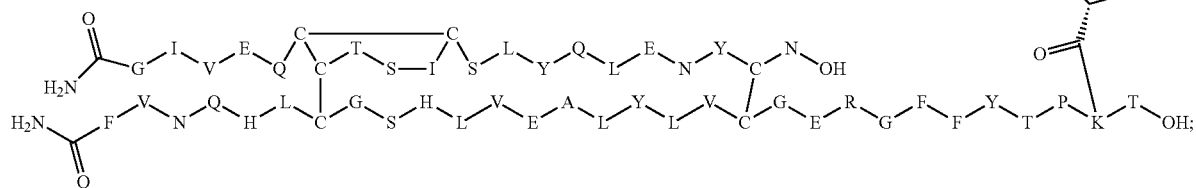

wherein the disulfide linkages between the Cys$_6$ and Cys$_{11}$ residues of the A-chain polypeptide and the disulfide linkages between the Cys$_7$ and Cys$_{20}$ of the A-chain to the Cys$_7$ and Cys$_{19}$ of the B-chain polypeptide, respectively, are represented by the solid line therebetween; wherein the bifunctional linkers are covalently linked to the epsilon amino group of the respective B29 lysine residue, wherein the A-chain polypeptide for Dimers 71, 72, 77 and 78 has the amino acid sequence shown in SEQ ID NO:1; and the B-chain polypeptide for Dimers 71, 72, 77 and 78 has the amino acid sequence shown in SEQ ID NO:2, respectively.

2. A composition comprising one or more compounds of claim 1 and a pharmaceutically acceptable carrier.

3. A method for treating diabetes comprising administering to an individual with diabetes a therapeutically effective amount of a composition comprising the insulin receptor partial agonist of claim 2.

4. The method of claim 3, wherein the diabetes is Type 1 diabetes, Type 2 diabetes, or gestational diabetes.

5. An insulin dimer comprising:
a first B29 or B28 Lys of a first insulin heterodimer molecule having a first A-chain polypeptide and first B-chain polypeptide and a second B29 or B28 Lys of a second insulin heterodimer having a second A-chain polypeptide and second B-chain polypeptide conjugated together by a bifunctional linker selected from the group consisting of:

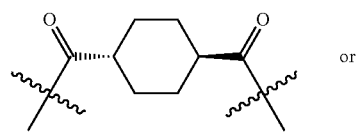 or

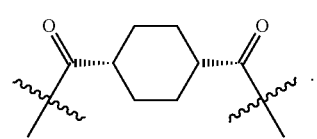

6. A compound having the following formula
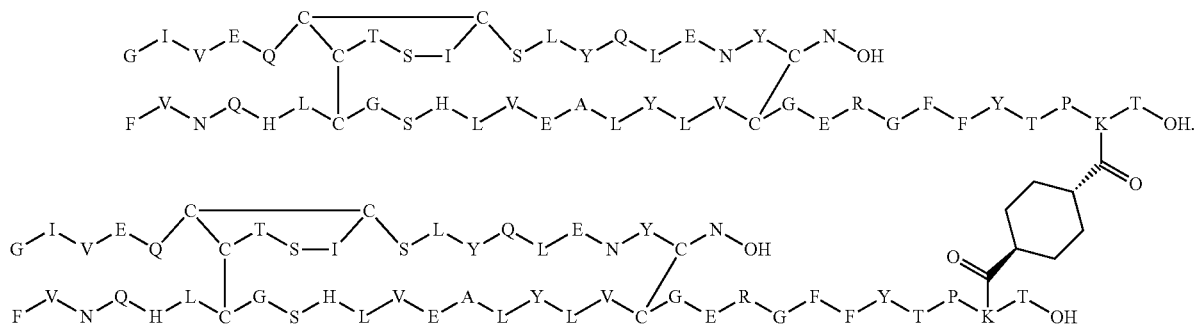
Dimer 71
* * * * *

SEQUENCE LISTING

<160> NUMBER OF SEQ ID NOS: 11

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Insulin A chain mutiens
<220> FEATURE:
<221> NAME/KEY: MISC_FEATURE
<222> LOCATION: (2)..(2)
<223> OTHER INFORMATION: Xaa is isoleucine or threonine
<220> FEATURE:
<221> NAME/KEY: MISC_FEATURE
<222> LOCATION: (3)..(3)
<223> OTHER INFORMATION: Xaa is valine, glycine, or leucine
<220> FEATURE:
<221> NAME/KEY: MISC_FEATURE
<222> LOCATION: (8)..(8)
<223> OTHER INFORMATION: Xaa is threonine or histidine
<220> FEATURE:
<221> NAME/KEY: MISC_FEATURE
<222> LOCATION: (17)..(17)
<223> OTHER INFORMATION: Xaa is glutamic acid or glutamine
<220> FEATURE:
<221> NAME/KEY: MISC_FEATURE
<222> LOCATION: (19)..(19)
<223> OTHER INFORMATION: Xaa is tyrosine, 4-methoxy-phenylalanine,
      alanine, or 4-amino phenylalanine
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: MISC_FEATURE
<222> LOCATION: (23)..(23)
<223> OTHER INFORMATION: Xaa is asparagine or glycine

<400> SEQUENCE: 3

Gly Xaa Xaa Glu Gln Cys Cys Xaa Ser Ile Cys Ser Leu Tyr Gln Leu
1               5                   10                  15

Xaa Asn Xaa Cys Xaa
            20

<210> SEQ ID NO 4
<211> LENGTH: 25
<212> TYPE: PRT
<213> ORGANISM: Artificial Sequence
<220> FEATURE:
<223> OTHER INFORMATION: Insulin B chain variants
<220> FEATURE:
<221> NAME/KEY: MISC_FEATURE
<222> LOCATION: (1)..(1)
<223> OTHER INFORMATION: Xaa is histidine or threonine
<220> FEATURE:
<221> NAME/KEY: MISC_FEATURE
<222> LOCATION: (1)..(25)
<223> OTHER INFORMATION: With the proviso that at least one of 24 or 25
      is lysine
<220> FEATURE:
<221> NAME/KEY: MISC_FEATURE
<222> LOCATION: (5)..(5)
<223> OTHER INFORMATION: Xaa is alanine, glycine, or serine
<220> FEATURE:
<221> NAME/KEY: MISC_FEATURE
<222> LOCATION: (6)..(6)
<223> OTHER INFORMATION: Xaa is histidine, aspartic acid, glutamic acid,
      homocysteic acid, or cysteic acid

```
<220> FEATURE:
<221> NAME/KEY: MISC_FEATURE
<222> LOCATION: (21)..(21)
<223> OTHER INFORMATION: Xaa is proline or lysine
<220> FEATURE:
<221> NAME/KEY: MISC_FEATURE
<222> LOCATION: (24)..(24)
<223> OTHER INFORMATION: Xaa is proline or lysine
<220> FEATURE:
<221> NAME/KEY: MISC_FEATURE
<222> LOCATION: (25)..(25)
<223> OTHER INFORMATION: Xaa is proline or lysine

<400> SEQUENCE: 4

Xaa Leu Cys Gly Xaa Xaa Leu Val Glu Ala Leu Tyr Leu Val Cys Gly
 1               5                  10                  15

Glu Arg Gly Phe Xaa Tyr Thr Xaa Xaa
            20                  25

<210> SEQ ID NO 5
<211> LENGTH: 32
<212> TYPE: PRT
<213> ORGANISM: Artificial Sequence
<220> FEATURE:
<223> OTHER INFORMATION: Insulin B chain variants
<220> FEATURE:
<221> NAME/KEY: MISC_FEATURE
<222> LOCATION: (1)..(1)
<223> OTHER INFORMATION: Xaa is phenylalanine or desamino-phenylalanine
<220> FEATURE:
<221> NAME/KEY: MISC_FEATURE
<222> LOCATION: (1)..(32)
<223> OTHER INFORMATION: With the proviso that at least one of 28 or 29
      is lysine
<220> FEATURE:
<221> NAME/KEY: MISC_FEATURE
<222> LOCATION: (5)..(5)
<223> OTHER INFORMATION: Xaa is histidine or threonine
<220> FEATURE:
<221> NAME/KEY: MISC_FEATURE
<222> LOCATION: (6)..(6)
<223> OTHER INFORMATION: Xaa is glycine or leucine
<220> FEATURE:
<221> NAME/KEY: MISC_FEATURE
<222> LOCATION: (9)..(9)
<223> OTHER INFORMATION: Xaa is alanine, glycine, or serine
<220> FEATURE:
<221> NAME/KEY: MISC_FEATURE
<222> LOCATION: (10)..(10)
<223> OTHER INFORMATION: Xaa is histidine, aspartic acid, glutamic acid,
      homocysteic acid, or cysteic acid
<220> FEATURE:
<221> NAME/KEY: MISC_FEATURE
<222> LOCATION: (25)..(25)
<223> OTHER INFORMATION: Xaa is phenyalanine or aspartic acid
<220> FEATURE:
<221> NAME/KEY: MISC_FEATURE
<222> LOCATION: (28)..(28)
<223> OTHER INFORMATION: Xaa is aspartic acid, proline, or lysine
<220> FEATURE:
<221> NAME/KEY: MISC_FEATURE
<222> LOCATION: (29)..(29)
<223> OTHER INFORMATION: Xaa is lysine or proline
<220> FEATURE:
<221> NAME/KEY: MISC_FEATURE
<222> LOCATION: (30)..(30)
<223> OTHER INFORMATION: Xaa is threonine, alanine, or absent
<220> FEATURE:
<221> NAME/KEY: MISC_FEATURE
<222> LOCATION: (31)..(31)
<223> OTHER INFORMATION: Xaa is arginine or absent
<220> FEATURE:
<221> NAME/KEY: MISC_FEATURE
<222> LOCATION: (32)..(32)
<223> OTHER INFORMATION: Xaa is arginine or absent
```

```
<400> SEQUENCE: 5

Xaa Val Asn Gln Xaa Xaa Cys Gly Xaa Xaa Leu Val Glu Ala Leu Tyr
1               5                   10                  15

Leu Val Cys Gly Glu Arg Gly Phe Xaa Tyr Thr Xaa Xaa Xaa Xaa
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Insulin lispro B chain

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 7
<211> LENGTH: 21
<212> TYPE: PRT
<213> ORGANISM: Artificial Sequence
<220> FEATURE:
<223> OTHER INFORMATION: Insulin glargine A chain

<400> SEQUENCE: 7

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 8
<211> LENGTH: 32
<212> TYPE: PRT
<213> ORGANISM: Artificial Sequence
<220> FEATURE:
<223> OTHER INFORMATION: Insulin glargine B chain

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Insulin aspart B chain

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 10
<211> LENGTH: 29
<212> TYPE: PRT
<213> ORGANISM: Artificial Sequence
<220> FEATURE:
<223> OTHER INFORMATION: Des30 B chain
```

```
<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 11
<211> LENGTH: 21
<212> TYPE: PRT
<213> ORGANISM: Artificial Sequence
<220> FEATURE:
<223> OTHER INFORMATION: A chain Y19A

<400> SEQUENCE: 11

Gly Ile Val Glu Gln Cys Cys Thr Ser Ile Cys Ser Leu Tyr Gln Leu
1               5                   10                  15

Glu Asn Ala Cys Asn
            20
```